US012738275B2

(12) United States Patent
Chang et al.

(10) Patent No.: US 12,738,275 B2
(45) Date of Patent: Sep. 15, 2026

(54) METHOD OF CONTEXTUAL SPEECH DECODING FROM THE BRAIN

(71) Applicant: The Regents of the University of California, Oakland, CA (US)

(72) Inventors: Edward F. Chang, Oakland, CA (US); David A. Moses, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 1136 days.

(21) Appl. No.: 17/626,256

(22) PCT Filed: Jul. 27, 2020

(86) PCT No.: PCT/US2020/043706
§ 371 (c)(1),
(2) Date: Jan. 11, 2022

(87) PCT Pub. No.: WO2021/021714
PCT Pub. Date: Feb. 4, 2021

(65) Prior Publication Data

US 2022/0301563 A1 Sep. 22, 2022

Related U.S. Application Data

(60) Provisional application No. 62/879,957, filed on Jul. 29, 2019.

(51) Int. Cl.
*G10L 15/24* (2013.01)
*A61F 4/00* (2006.01)
(Continued)

(52) U.S. Cl.
CPC ................ *G10L 15/24* (2013.01); *A61F 4/00* (2013.01); *G06F 3/015* (2013.01); *G10L 13/02* (2013.01);
(Continued)

(58) Field of Classification Search
None
See application file for complete search history.

(56) References Cited

U.S. PATENT DOCUMENTS 4,084,583 A 4/1978 Hjort
4,709,702 A 12/1987 Sherwin
(Continued)

FOREIGN PATENT DOCUMENTS

WO 2014138925 9/2014

OTHER PUBLICATIONS

Ajmone-Marsan, (1998) "Electrocorticography: Historical Comments on its Development and the Evolution of its Practical Applications," Electroencephalography: Current Trends and Future Perspectives, Suppl. 48, pp. 10-16.
(Continued)

*Primary Examiner* — Jay B Shah
(74) *Attorney, Agent, or Firm* — Edward J. Baba; Michael J. Blessent; Bozicevic, Field & Francis LLP

(57) ABSTRACT

Provided are methods of contextual decoding and/or speech decoding from the brain of a subject. The methods include decoding neural or optical signals from the cortical region of an individual, extracting context-related features and/or speech-related features from the neural or optical signals, and decoding the context-related features and/or speech-related features from the neural or optical signals. Contextual decoding and speech decoding systems and devices for practicing the subject methods are also provided.

24 Claims, 50 Drawing Sheets

(51) Int. Cl.

| | |
|---|---|
| ***G06F 3/01*** | (2006.01) |
| ***G10L 13/02*** | (2013.01) |
| ***G10L 15/14*** | (2006.01) |
| ***G10L 15/22*** | (2006.01) |
| ***G10L 25/18*** | (2013.01) |
| ***G10L 25/24*** | (2013.01) |
| ***G10L 25/63*** | (2013.01) |

(52) U.S. Cl.

CPC ............ *G10L 15/142* (2013.01); *G10L 15/22* (2013.01); *G10L 25/63* (2013.01); *G10L 2015/227* (2013.01); *G10L 25/18* (2013.01); *G10L 25/24* (2013.01)

(56) References Cited

U.S. PATENT DOCUMENTS

| | | | |
|---|---|---|---|
| 4,967,038 | A | 10/1990 | Gevins et al. |
| 5,038,782 | A | 8/1991 | Gevins et al. |
| 5,119,816 | A | 6/1992 | Gevins |
| 5,291,888 | A | 3/1994 | Tucker |
| 5,361,773 | A | 11/1994 | Ives |
| 5,479,934 | A | 1/1996 | Imran |
| 5,724,984 | A | 3/1998 | Arnold et al. |
| 5,817,029 | A | 10/1998 | Gevins et al. |
| 6,154,669 | A | 11/2000 | Hunter et al. |
| 6,256,531 | B1 | 7/2001 | Ilmoniemi et al. |
| 6,334,778 | B1 | 1/2002 | Brown |
| 6,381,481 | B1 | 4/2002 | Levendowski et al. |
| 6,510,340 | B1 | 1/2003 | Jordan |
| 7,031,923 | B1 | 4/2006 | Chaudhari et al. |
| 7,239,910 | B2 | 7/2007 | Tanner |
| D565,735 | S | 4/2008 | Washbon |
| D603,051 | S | 10/2009 | Causevic et al. |
| 7,715,607 | B2 | 5/2010 | Hu et al. |
| 7,908,009 | B2 | 3/2011 | Wyler et al. |
| D641,886 | S | 7/2011 | Causevic et al. |
| 8,019,142 | B2 | 9/2011 | Nowinski et al. |
| D647,208 | S | 10/2011 | Rothman et al. |
| 8,045,775 | B2 | 10/2011 | Volkau et al. |
| 8,671,069 | B2 | 3/2014 | Chang et al. |
| 9,905,239 | B2 | 2/2018 | Chang et al. |
| 2007/0093706 | A1 | 4/2007 | Gevins et al. |
| 2009/0281408 | A1 | 11/2009 | Lee et al. |
| 2010/0130844 | A1 | 5/2010 | Williams et al. |
| 2010/0198042 | A1 | 8/2010 | Popescu et al. |
| 2011/0046502 | A1 | 2/2011 | Pradeep et al. |
| 2011/0046503 | A1 | 2/2011 | Pradeep et al. |
| 2011/0046504 | A1 | 2/2011 | Pradeep et al. |
| 2011/0237923 | A1 | 9/2011 | Picht et al. |
| 2011/0282231 | A1 | 11/2011 | Pradeep et al. |
| 2011/0282232 | A1 | 11/2011 | Pradeep et al. |
| 2014/0108013 | A1 | 4/2014 | Di Cristo et al. |
| 2014/0112556 | A1 | 4/2014 | Kalinli-Akbacak |
| 2014/0257807 | A1 | 9/2014 | Mauro et al. |
| 2015/0338917 | A1 | 11/2015 | Steiner et al. |
| 2017/0085547 | A1 | 3/2017 | De Aguiar et al. |
| 2018/0239501 | A1 | 8/2018 | Reddy et al. |

OTHER PUBLICATIONS

Chartier et al., (2018) "Encoding of articulatory kinematic trajectories in human speech sensorimotor cortex," Neutron, vol. 98, No. 5, pp. 1042-1054.

Kumar et al, (2018) Envisioned speech recognition using EEG sensors; Pers Ubiquit Comput, 22:185-199.

"Gregory and Tom chose to watch cartoons in the afternoon."
Original Speech
"Ship building is a most fascinating process."
Frequency (kHz)
0
2
4
6
8
0
1
2
3
4
5
6
7
8
MCD: 5.07 dB
Time (s)
MCD: 4.66 dB "Gregory and Tom chose to watch cartoons in the afternoon."
Decoded Speech
"Ship building is a most fascinating process."
Frequency (kHz)
0
2
4
6
8
0
1
2
3
4
5
6
7
8
MCD: 5.07 dB
Time (s)
MCD: 4.66 dB Median Original Phonemes
High vowel /i/
Fricative /z/
Plosive /p/
Low vowel /æ/
Frequency (kHz)
8
6
4
2
0
-0.1
0
0.1
0.2
Time relative to onset(s)
Median Decoded Phonemes
High vowel /i/
Fricative /z/
Plosive /p/
Low vowel /æ/
Frequency (kHz)
Time relative to onset(s)

f0, Envelope
EMA
Manner
Correlation (r)
1.0
0.8
0.6
0.4
0.2
0.0
Kinematic feature
1 2 3 4 5 6 7 8 9 10 11 12 13 14 15 16 17 18 19 20 21 22 23 24 25 26 27 28 29 30 31 32 33

Decoding accuracy rate (%)
100
75
50
25
0
Question
Answer
*
Question
Prediction
Chance
Answer
- context
+ context
Chance Classification accuracy (%)
100
75
50
25
0
Question
Answer
Question
Prediction
Chance
Answer
- context
+ context
Chance Cross entropy (bits)
6
4.5
3
1.5
0
Question
Answer
Question
Prediction
Chance
Answer
- context
+ context
Chance Single set of hyperparameters
Optimal set of hyperparameters Classification accuracy (%)
100
75
50
25
0
Question
Answer Cross entropy (bits)
300
100
10
1
0.5
Question
Answer Performance relative to high resolution results (%)
125
100
75
50
25
0
* * *
* * *
*
Decoding accuracy
Classification accuracy
Detection score
Question
Answer (- context)
Answer (+ context)
700
500
300
100
0
* * *
Cross
Question
Answer (- context)
Answer (+ context)

Sliding window
Speech event probability
1
0
Time
S

S
After sliding window average
Probability threshold
Time
P
P

P
P
After probability thresholding
Time threshold
T
T

T
T
After time thresholding
Detected onset
E
Detected offset

E
Neural data
Event-related time window

FIG. 14A
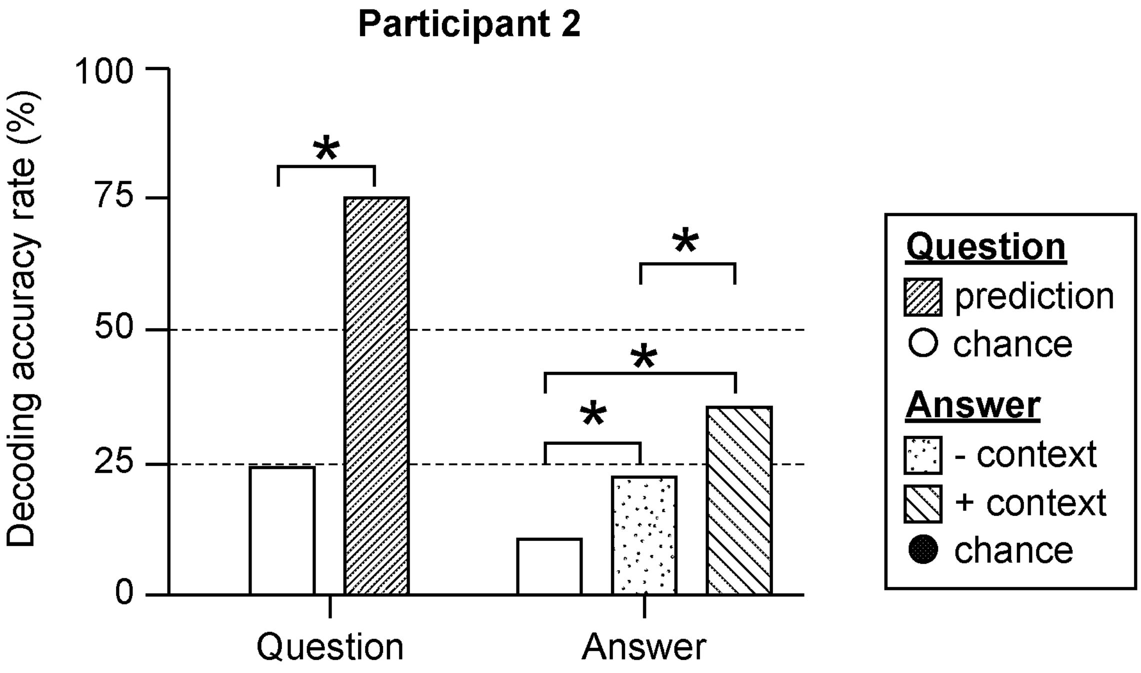
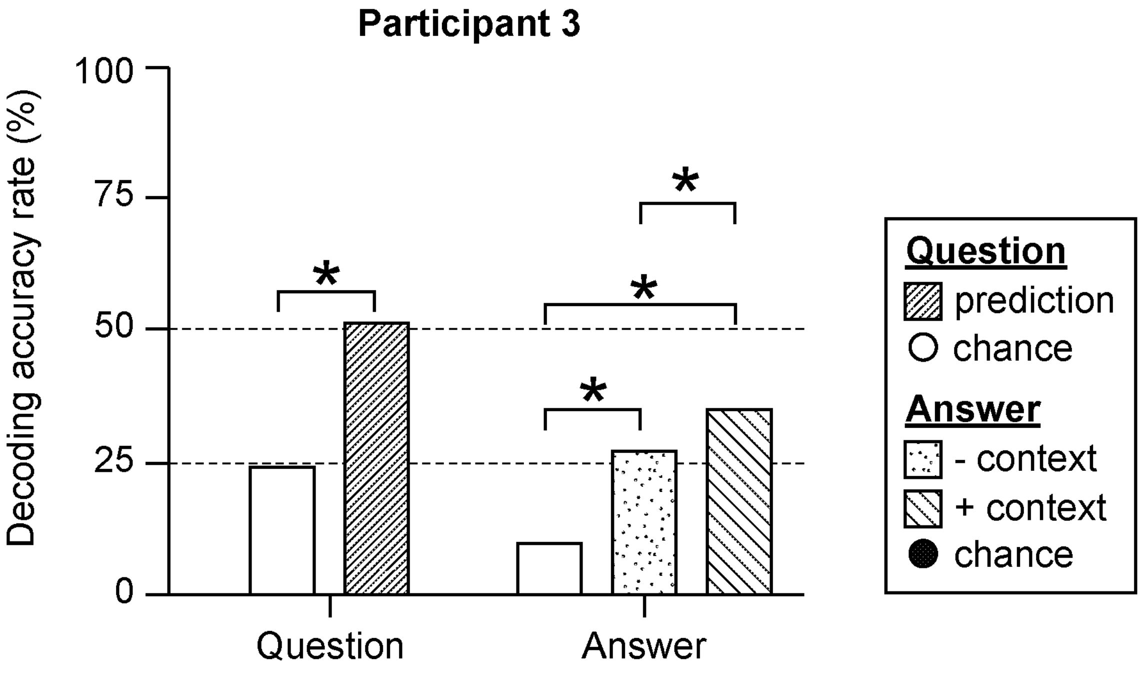

FIG. 14C
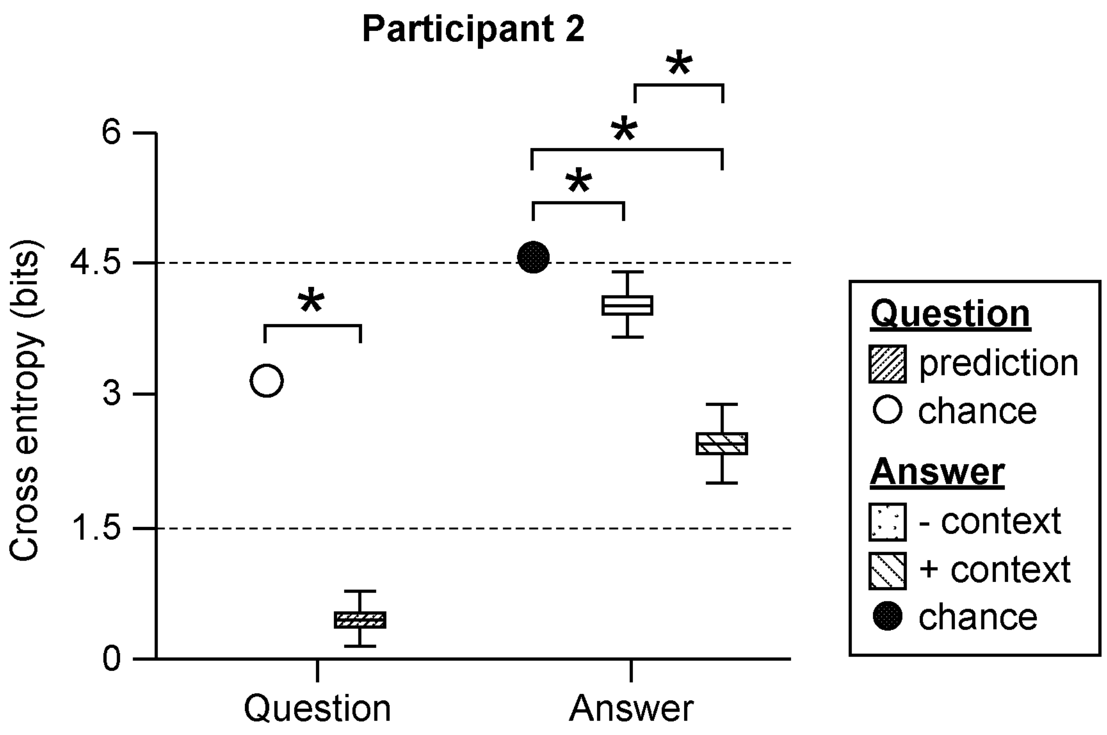
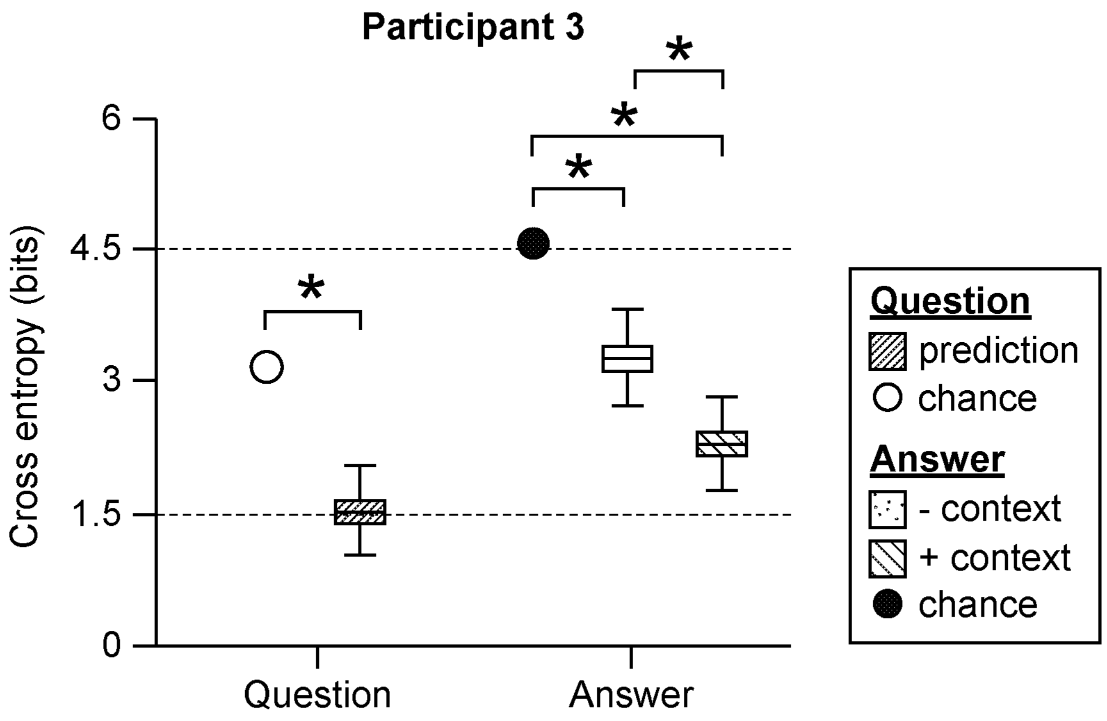

FIG. 14E
Participant 2
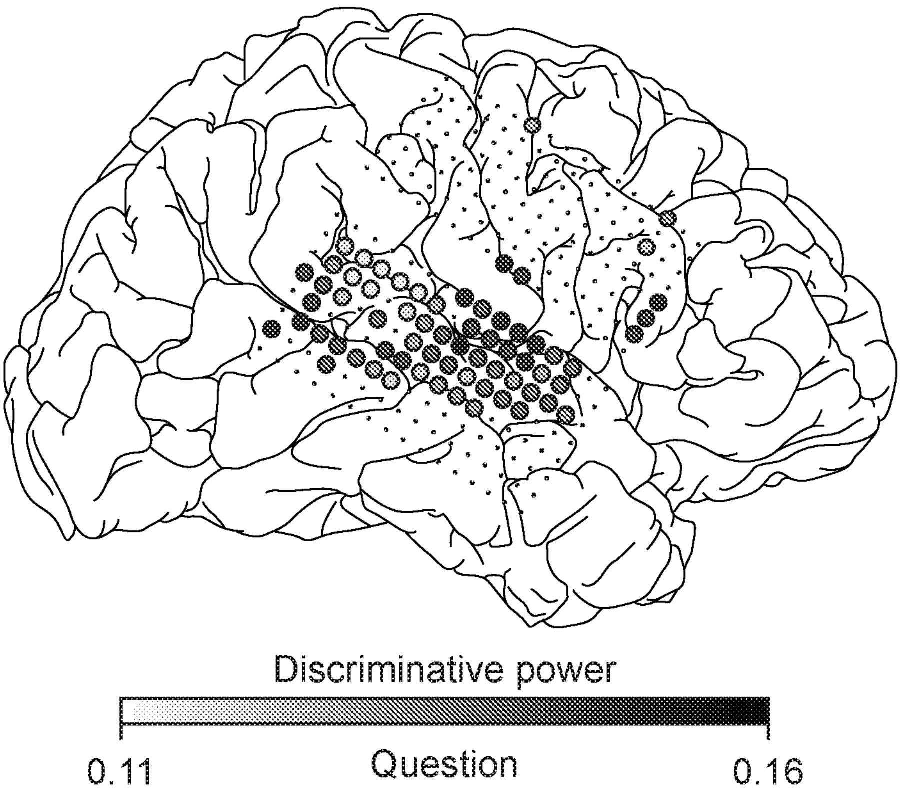
Participant 3
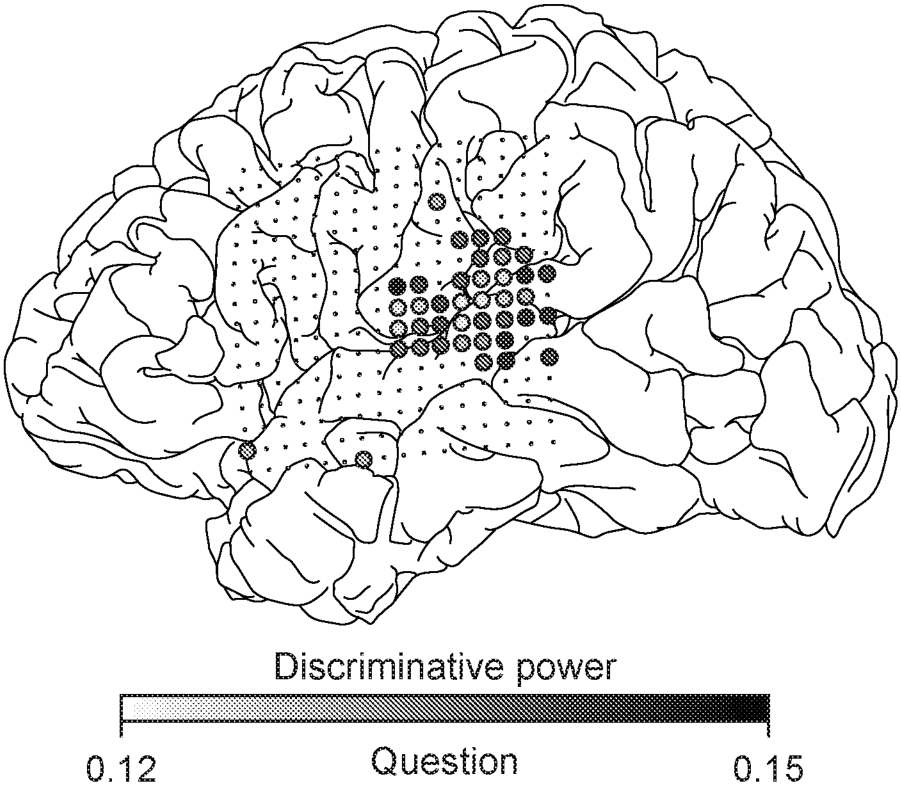

FIG. 14F
Participant 2
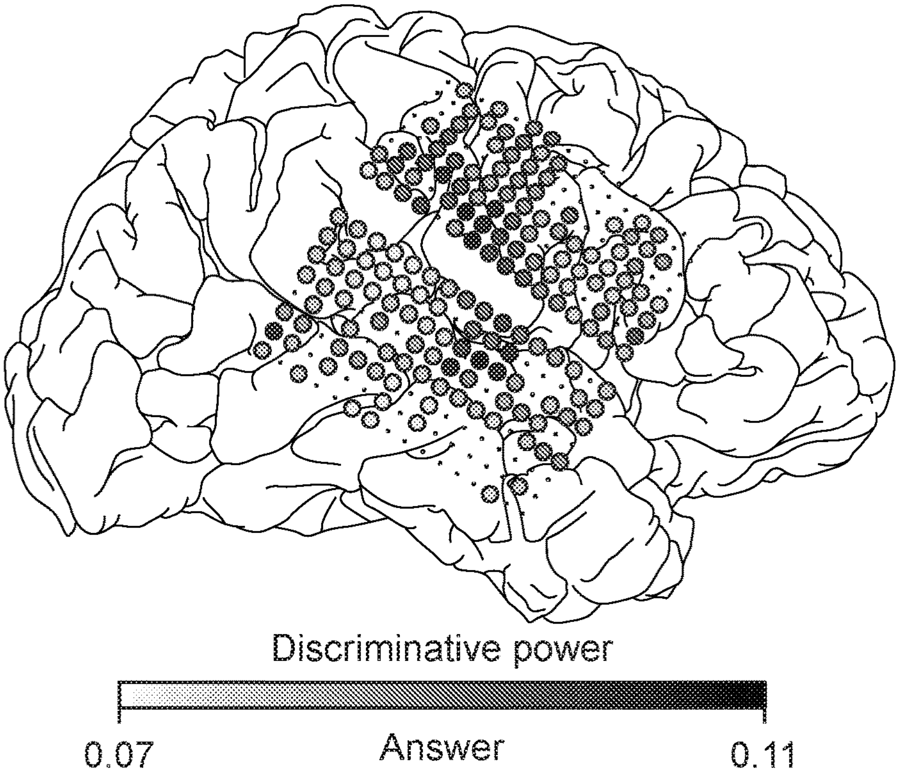
Participant 3
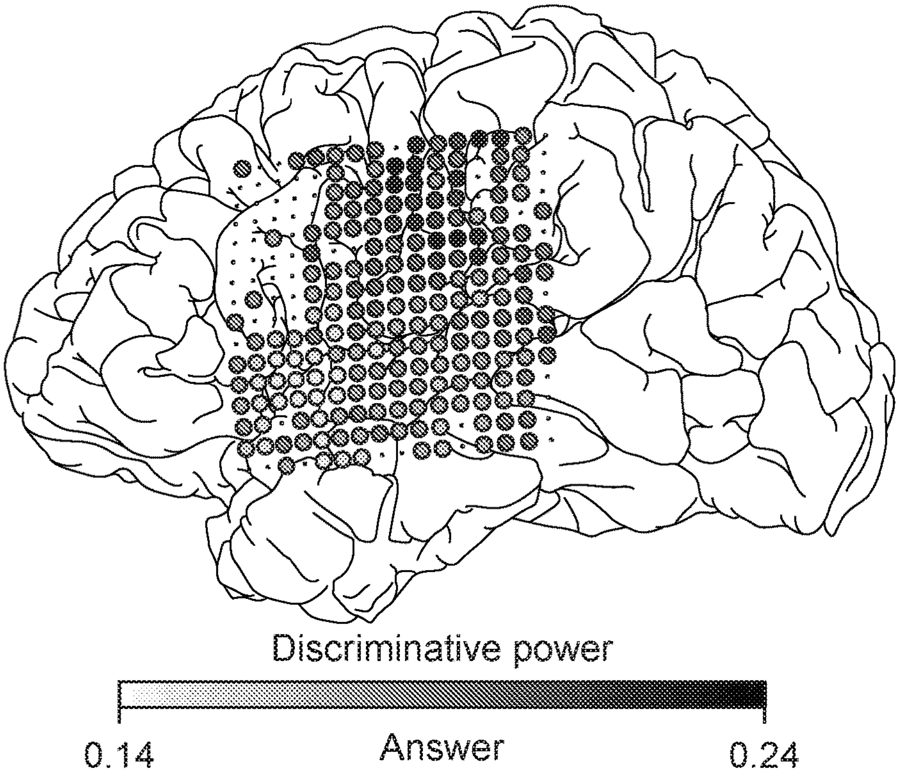

FIG. 14G
Participant 2
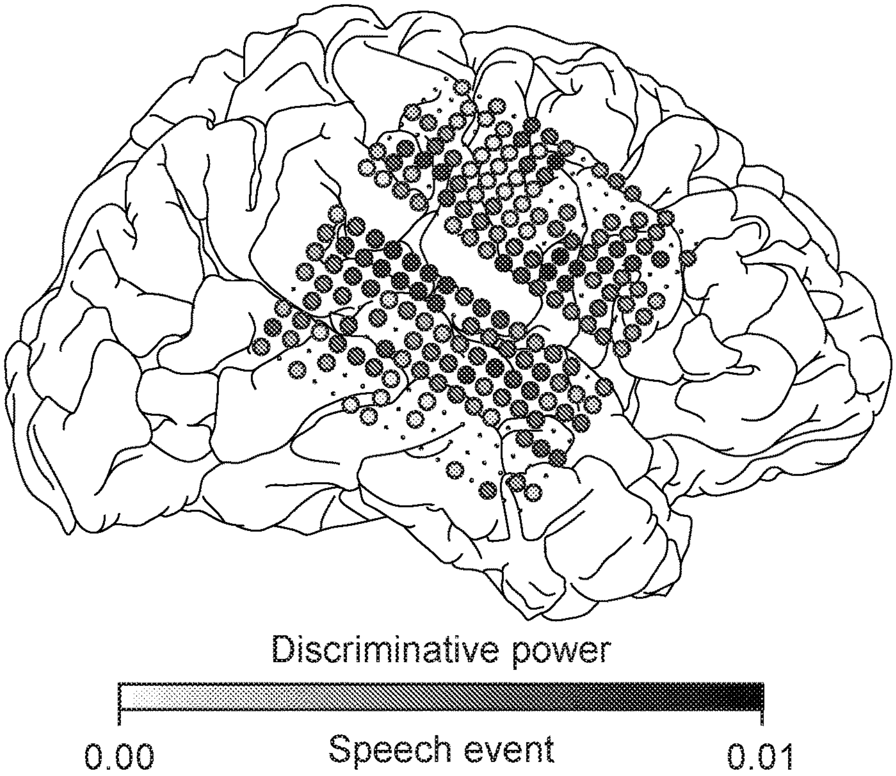
Participant 3
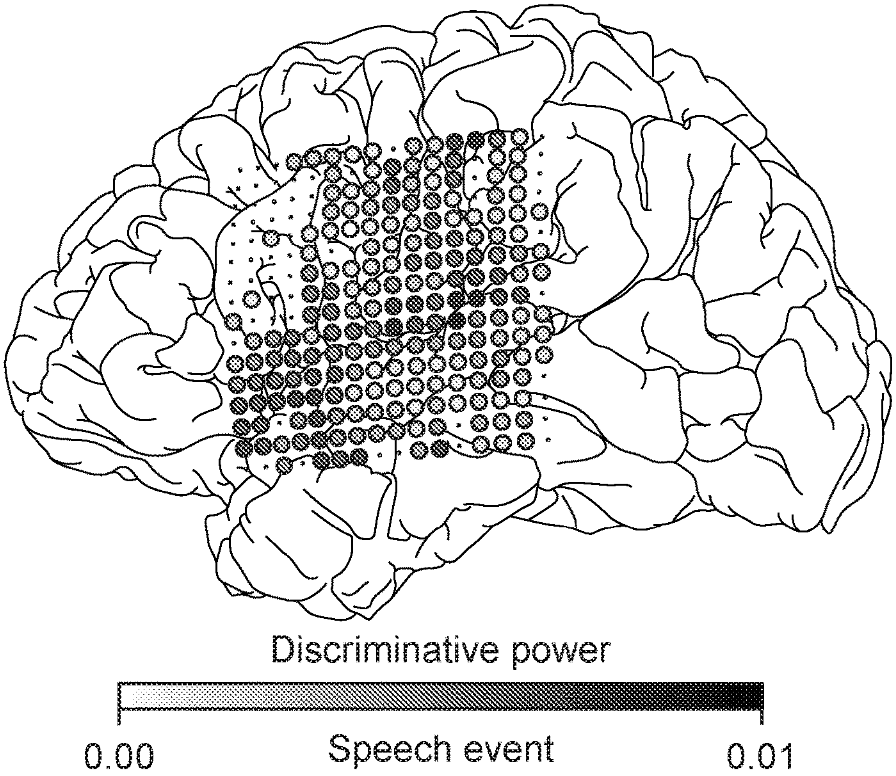

States (phones)

Violin

| | 0 | 1 | 2 | ... | T |
|---|---|---|---|---|---|
| sp | 0 | -2.2 | -5.8 | ... | -612 |
| v | - | -1.8 | -4.6 | ... | -586 |
| aɪ | -ı | - | -6.2 | ... | -561 |
| ʌ | - | - | - | ... | -544 |
| l | - | - | - | ... | -510 |
| ɪ | - | - | - | ... | -501 |
| n | - | - | - | ... | -489 |
| sp | - | - | - | ... | **-464** |

Time point

Cold

| | 0 | 1 | 2 | ... | T |
|---|---|---|---|---|---|
| sp | 0 | -2.2 | -5.8 | ... | -612 |
| k | - | -2.8 | -6.1 | ... | -598 |
| ˈoʊ | - | - | -8.5 | ... | -588 |
| l | - | - | - | ... | -549 |
| d | - | - | - | ... | -533 |
| sp | - | - | - | ... | **-512** |

Eight

| | 0 | 1 | 2 | ... | T |
|---|---|---|---|---|---|
| sp | 0 | -2.2 | -5.8 | ... | -612 |
| eɪ | - | -4.8 | -7.5 | ... | -601 |
| t | - | - | -8.1 | ... | -590 |
| sp | - | - | - | ... | **-565** |

FIG. 20

| Participant | Data type | Total data | Question (perception) data[1] | Answer (production) data[1] |
|---|---|---|---|---|
| 1 | Training | 3 task blocks, 941 seconds | 90 trials, 189 seconds | 240 trials, 134 seconds |
| | Testing | 2 task blocks, 421 seconds | 52 trials, 104 seconds | 52 trials, 26 seconds |
| 2 | Training | 9 task blocks, 2776 seconds | 270 trials, 565 seconds | 720 trials, 525 seconds |
| | Testing | 4 task blocks, 1146 seconds | 104 trials, 208 seconds | 140 trials, 62 seconds |
| 3 | Training | 6 task blocks, 1898 seconds | 180 trials, 376 seconds | 480 trials, 280 seconds |
| | Testing | 3 task blocks, 875 seconds | 78 trials, 156 seconds | 78 trials, 40 seconds |

[1]Each trial corresponds to one utterance, and the durations given here only consider time points that occured during speech (silence time points are excluded).

FIG. 21

| Metric | Metric | Participant | Prediction type | *P*-value | Number of samples[1] |
|---|---|---|---|---|---|
| Decoding accuracy rate | One-tailed boostrap test, performance vs. chance | 1 | Question | $< 1 \times 10^{-50}$ | 54 |
| | | | Answer without context | $< 1 \times 10^{-50}$ | 53 |
| | | | Answer with context | $< 1 \times 10^{-50}$ | |
| | | 2 | Question | $< 1 \times 10^{-50}$ | 119 |
| | | | Answer without context | $2.3 \times 10^{-10}$ | 105 |
| | | | Answer with context | $< 1 \times 10^{-50}$ | |
| | | 3 | Question | $< 1 \times 10^{-50}$ | 81 |
| | | | Answer without context | $2.1 \times 10^{-14}$ | 78 |
| | | | Answer with context | $< 1 \times 10^{-50}$ | |
| | One-tailed permutation test, with VS. without context | 1 | Answer (with vs. wihtout context) | $1.9 \times 10^{-3}$ | 53 |
| | | 2 | Answer (with vs. wihtout context) | $7.9 \times 10^{-5}$ | 105 |
| | | 3 | Answer (with vs. wihtout context) | 0.029 | 78 |

[1]The reported number of samples were the number of detected events for the decoding accuracy rate metric and the number of actual trials for the other two metrics.

FIG. 21 (Cont.)

| Metric | Metric | Participant | Prediction type | *P*-value | Number of samples[1] |
|---|---|---|---|---|---|
| Classification accuracy | One-tailed boostrap test, performance vs. chance | 1 | Question | $1.7 \times 10^{-10}$ | 52 |
| | | | Answer without context | $5.9 \times 10^{-7}$ | |
| | | | Answer with context | $5.9 \times 10^{-10}$ | |
| | | 2 | Question | $< 1 \times 10^{-50}$ | 101 |
| | | | Answer without context | $4.1 \times 10^{-7}$ | |
| | | | Answer with context | $9.7 \times 10^{-14}$ | |
| | | 3 | Question | $4.0 \times 10^{-14}$ | 75 |
| | | | Answer without context | $2.3 \times 10^{-8}$ | |
| | | | Answer with context | $2.7 \times 10^{-13}$ | |
| | One-tailed exact McNemar's test, with vs. without context | 1 | Answer (with vs. wihtout context) | 0.033 | 52 |
| | | 2 | Answer (with vs. wihtout context) | $1.9 \times 10^{-6}$ | 101 |
| | | 3 | Answer (with vs. wihtout context) | $9.2 \times 10^{-4}$ | 75 |
| Cross entropy | One-tailed boostrap test, performance vs. chance | 1 | Question | $5.6 \times 10^{-16}$ | 52 |
| | | | Answer without context | $3.3 \times 10^{-3}$ | |
| | | | Answer with context | $1.3 \times 10^{-5}$ | |
| | | 2 | Question | $< 1 \times 10^{-50}$ | 101 |
| | | | Answer without context | $1.0 \times 10^{-5}$ | |
| | | | Answer with context | $< 1 \times 10^{-50}$ | |
| | | 3 | Question | $< 1 \times 10^{-50}$ | 75 |
| | | | Answer without context | $3.7 \times 10^{-11}$ | |
| | | | Answer with context | $< 1 \times 10^{-50}$ | |
| | One-tailed Wilcoxon signed-rank test, with vs. without context | 1 | Answer (with vs. wihtout context) | $7.6 \times 10^{-6}$ | 52 |
| | | 2 | Answer (with vs. wihtout context) | $2.6 \times 10^{-17}$ | 101 |
| | | 3 | Answer (with vs. wihtout context) | $3.1 \times 10^{-11}$ | 75 |

[1] The reported number of samples were the number of detected events for the decoding accuracy rate metric and the number of actual trials for the other two metrics.

FIG. 22

| Participant | Context integration | ITR using full task block durations[1] | ITR using answer speech times[1] | ITR using combined question and answer speech times[1] |
|---|---|---|---|---|
| 1 | Without conext | 0.13 | 0.90 | - |
| | With context | 0.21 | 1.4 | 0.43 |
| 2 | Without conext | 0.045 | 0.37 | - |
| | With context | 0.11 | 0.94 | 0.30 |
| 3 | Without conext | 0.085 | 0.77 | - |
| | With context | 0.14 | 1.3 | 0.38 |

[1]All speech times were determined from the acoustic transcriptions, and each task block duration was computed as time interval between the transcribed speech onset time for the first question in the block and the transcribed speech offset time for the final answer in that block.

FIG. 23

| Participant | No context(%)[1] | Soft context(%)[1] | Hard context(%)[1] | True context(%)[1] |
|---|---|---|---|---|
| 1 | 42.31 (-13.46) | 55.77 (+0.00) | 51.92 (-3.85) | 67.31 (+11.54) |
| 2 | 27.18 (-18.45) | 45.63 (+0.00) | 44.66 (-0.97) | 45.63 (+0.00) |
| 3 | 38.96 (-15.58) | 54.55 (+0.00) | 48.05 (-6.49) | 59.74 (+5.19) |

[1]Each entry specifies the classification accuracy on the answer classification test trials followed by the difference between this accuracy and the corresponding accuracy with soft contexts in parentheses.

FIG. 24

| Optimization | Hyperparameter description | Search space type | Value range or choices |
|---|---|---|---|
| Speech Detection | Electrode relevance *P*-vlue threshold | Logarithmically uniform | $[10^{-50}, 10^{-3}]$ |
| | Duration before *t* to include in the spatiotemporal neural feature vector $y_t$ (in ms) | Uniform | [1,300] |
| | Duration after *t* to include in the spatiotemporal neural feature vector $y_t$ (in ms) | Uniform | [1,300] |
| | Minimum amount of variance the principal components should explain when fitting the PCA model | Uniform | [0.01,0.99] |
| | Question perception averaging window size (in samples) | Uniform (integer) | [80,160] |
| | Question perception probability threshold | Uniform | [0.4,0.9] |
| | Question perception time threshold (in samples) | Uniform (integer) | [5,60] |
| | Question perception onset index shift (in samples) | Uniform (integer) | [-100,100] |
| | Question perception offset index shift (in samples) | Uniform (integer) | [-100,300] |
| | Answer production averaging window size (in samples) | Uniform (integer) | [20,80] |
| | Answer production probability threshold | Uniform | [0.4,0.9] |
| | Answer production time threshold (in samples) | Uniform (integer) | [2,10] |
| | Answer production onset index shift (in samples) | Uniform (integer) | [-100,0] |
| | Answer production offset index shift (in samples) | Uniform (integer) | [-100,50] |
| Utterance classification (for questions and answers) | Electrode relevence *P*-value threshold | Logarithmically uniform | $[10^{-50}, 10^{-3}]$ |
| | Set of hidden states for the HMMs (*S*) | Choice | Phones or phonemes[1] |
| | HMM self-transition probability ($P_{self}$) | Uniform | [0.1,0.9] |
| | Shift relative to *t* specifying the first data point in the spatiotemporal neural feature vector $y_t$ (in ms) | Uniform | [-200,200] |
| | Duration of each spatiotemporal neural feature vector (in ms) | Uniform | [10,400] |
| | Minimum amount of variance the principal components should explain when fitting the PCA model | Uniform | [0.01,0.99] |
| | Number of samples of each phone to include when training the phone likelihood models[2] | Uniform (integer) | [50,3000] |
| | HMM emission probability scaling factor ($\omega_e$) | Uniform | [0.1,5.0] |
| | Log likelihood smoothing factor ($\omega$) | Uniform | [0.0001,1.0] |
| Context integration | Context prior scaling factor (*m*) | Logarithmically uniform | [0.1,10] |

[1] Phoneme labels were simply the phone labels without stress markings. Across all test bocks and participants, phoneme labels were only deemed optimal for one question classifier and one answer classifier.

[2] This restriction on the number of available samples for each phone was primarily used to allow the optimizer to limit the number of silence tokens included during training (there were much more silence data points than data points for any other phone).

ENCODER

DECODER

<MFCC$_1$> <MFCC$_2$> <MFCC$_3$> <MFCC$_4$> <MFCC$_5$>

<OUT$_1$>

<IN$_4$> <IN$_3$> <IN$_2$> <IN$_1$> <EOS>

<OUT$_2$> <OUT$_3$> <OUT$_4$> <EOS>

<OUT$_1$> <OUT$_2$> <OUT$_3$> <OUT$_4$>

FIG. 27B (Cont.)
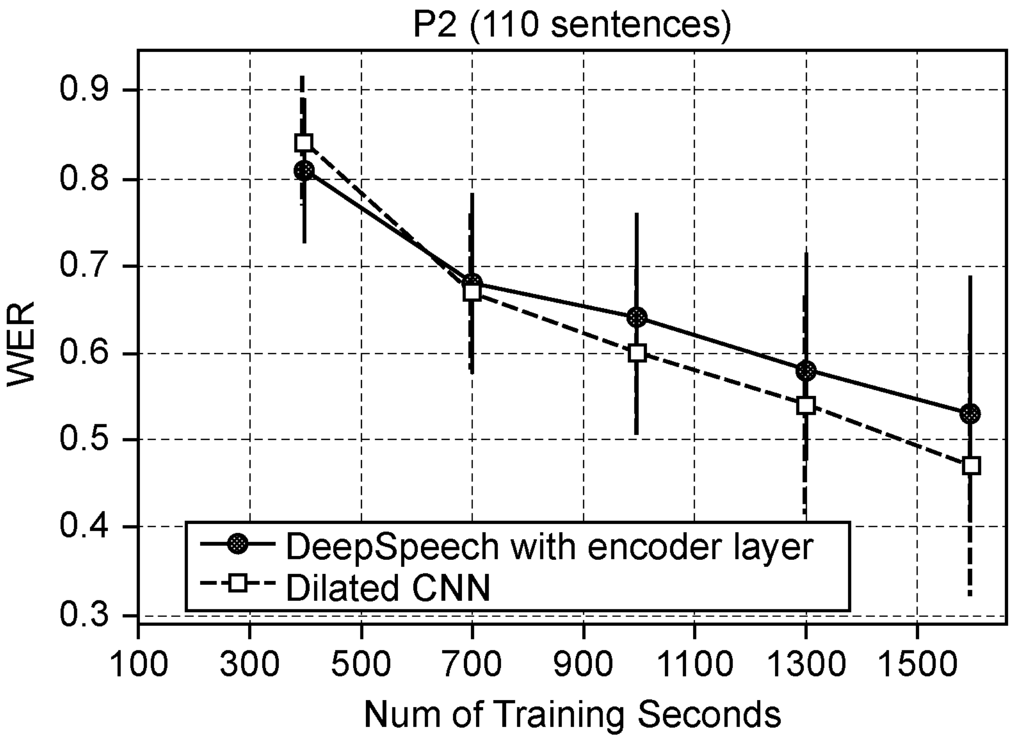
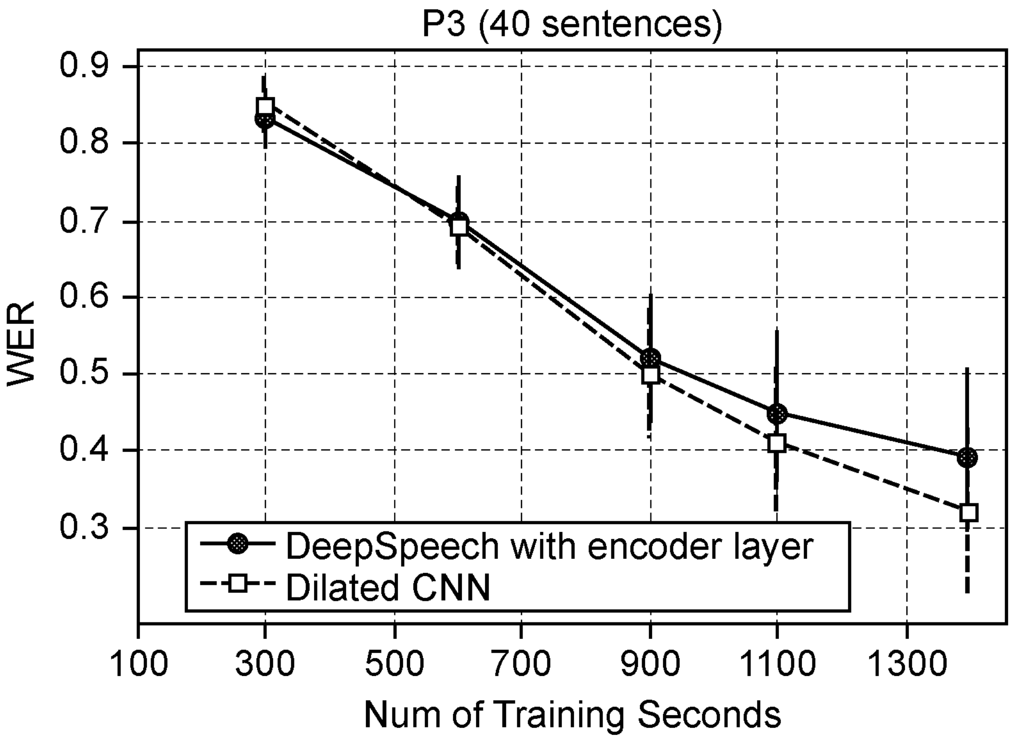

FIG. 27C

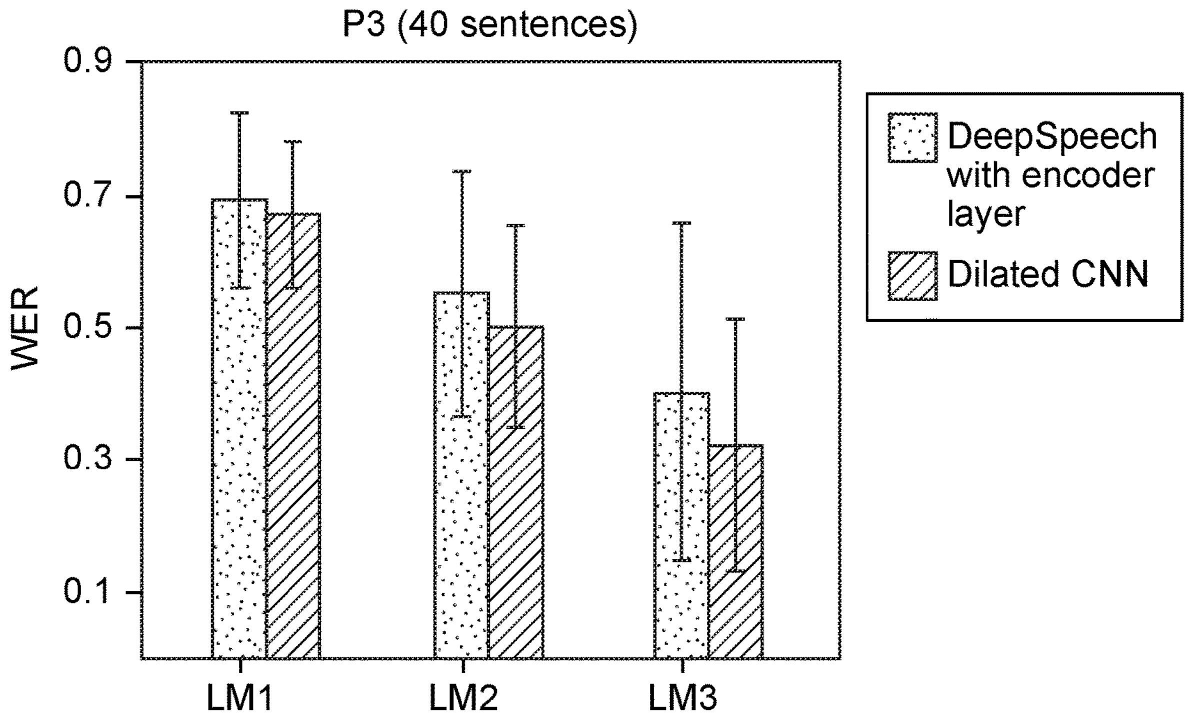

FIG. 27D the guests arrived with hesren (WER: 0.2)
*the guests arrived with presents* the cat does not want to come off the tree (WER:0.09)
*the cat does not want to come off the tree branch* there is a partially eaten cake on the large tale (WER:0.1)
*there is a partially eaten cake on the large table* if only the mother could pay ate her childn (WER:0.4)
*if only the mother could pay attention to her children* mumstrikgangus like a appitazers (WER:1.0)
*mum strongly dislikes appetizers* catastrophic acinoiccutbacksaneclactetohar (WER:0.8)
*catastrophic economic cutbacks neglect the poor*

Decoded
*Ground Truth*

METHOD OF CONTEXTUAL SPEECH DECODING FROM THE BRAIN

CROSS-REFERENCE TO RELATED APPLICATION

This application is a U.S. National Stage Entry of International Application PCT/US2020/043706, filed on Jul. 27, 2020, which claims the benefit of priority under 35 U.S.C. § 119 (e) of U.S. provisional patent application Ser. No. 62/879,957, filed Jul. 29, 2019. The disclosures of the provisional and international patent applications are hereby incorporated by reference in their entirety.

STATEMENT REGARDING FEDERALLY SPONSORED RESEARCH

This invention was made with government support under Grant No. OD008627 and U01 NS098971 awarded by the National Institutes of Health. The government has certain rights in the invention.

INTRODUCTION

Neurological conditions that result in the loss of communication are devastating. Many patients rely on alternative communication devices that measure residual nonverbal movements of the head or eyes, or brain-computer interfaces (BCIs) to control a cursor to select letters one-by-one to spell out words. While these systems can enhance a patient's quality of life, most users struggle to transmit more than 10 words/minute, a rate far slower than the average of 150 words/min in natural speech. A major hurdle is how to overcome the constraints of current spelling-based approaches to enable far higher or even natural communication rates.

Technology that translates neural activity into speech would be transformative for people unable to communicate as a result of neurological impairment. Decoding speech from neural activity is challenging because speaking requires such precise and rapid multi-dimensional control of vocal tract articulators.

There is a need for a recurrent neural network that decodes kinematic and sound representations in human cortical activity into intelligible synthesized speech at the rate of a fluent speaker.

Context can be used to improve speech decoding. Because decoding (e.g. attempted or intended) speech from brain activity is a difficult task, alternative signal sources of information should be considered in an attempt to improve decoding. There is a need for decoding contextual information such as thoughts, sounds heard by an individual, and/or internal states of the individual, such as, pain, anxiety, emotion, and/or mood from brain activity or from peripheral sensors/equipment in order to help facilitate decoding of perceived, attempted, or intended speech.

SUMMARY

Provided are methods of contextual decoding and/or speech decoding from the brain of a subject. The methods include decoding neural or optical signals from the cortical region of an individual, extracting context-related features and/or speech-related features from the neural or optical signals, and decoding context and/or speech from context-related and/or speech-related features. Contextual decoding and speech decoding systems and devices for practicing the subject methods are also provided.

Contextual decoding of the present invention is that context can be used to improve speech decoding. The present invention demonstrates that perceived questions can be decoded in real-time and used as a proxy for context.

Decoding (e.g. attempted or intended) speech from brain activity is a difficult task. Alternative signal sources of information should be considered in an attempt to improve speech decoding. Speech recognition is often contextual. For example, in a conversation, the content of any given sentence is typically dependent on the content of previous sentences. In this example, the previous sentences represent a description of the "context", and knowledge of this context can be used to inform a speech decoder, encouraging it to make predictions that are relevant to the current context. However, it is not just the current conversational state that can be used to inform context; various signal sources can provide contextual information.

In a clinical speech decoding application, a camera could be used to provide information about nearby objects that the patient would like to interact with (light switches, water, computers, etc.). The emotional state of the patient could also be inferred and used to influence the speech decoder. The time of day can be used to inform the decoder too (e.g. one would be far more likely to say "good morning" if it is, in fact, morning time and not evening time). Therefore, speech decoding of the present invention is not limited to decoding speech from brain activity, but also using all available information to inform and assist the decoder. This meta-data can be explicit (eg. time, location, etc) vs implicit (e.g. what someone heard, as inferred from brain activity, or how someone feels).

The mathematical representation of these forms of context is referred to as "context priors" of the present invention, which is used in a statistical and/or probabilistic approach with a decoder to improve predictions.

BRIEF DESCRIPTION OF THE DRAWINGS

FIG. 1A, The neural decoding process begins by extracting high-gamma amplitude (70-200 Hz) and low frequency (1-30 Hz) ECoG activity. FIG. 1B, A 3-layer bi-directional long short term memory (bLSTM) neural network learns to decode kinematic representations of articulation from filtered ECoG signals. FIG. 1C, An additional 3-layer bLSTM learns to decode acoustics from the previously decoded kinematics. Acoustics are represented as spectral features (e.g. Mel-frequency cepstral coefficients (MFCCs)) extracted from the speech waveform. FIG. 1D, Decoded signals are synthesized into an acoustic waveform. FIG. 1E, Spectrogram shows the frequency content of two sentences spoken by a participant. FIG. 1F, Spectrogram of synthesized speech from brain signals recorded simultaneously with the speech in e. Mel97 cepstral distortion (MCD), a metric for assessing the spectral distortion between two audio signals, was computed for each sentence between the original and decoded audio. FIG. 1G-1H 300 ms long, median spectrograms that were time-locked to the acoustic onset of phonemes from original (FIG. 1G) and decoded (FIG. 1H) audio. Medians were computed from phonemes in 100 sentences that were withheld during decoder 101 training (n: /i/=112, /z/=102 115, /p/69, /ae/=86). These phonemes represent the diversity of spectral features. Original and decoded median phoneme spectrograms were well correlated ($r>0.9$ for all 104 phonemes, $p=1e-18$).

FIG. 2A, Spectral distortion, measured by Mel-Cepstral Distortion (MCD) (lower values are better), between original spoken sentences and neurally decoded sentences that were held out from model training (n=100). Reference MCD refers to the MCD resulting from the synthesis of original kinematics without neural decoding and provides an upper bound for performance. MCD scores were compared to chance-level MCD scores obtained by shuffling data before decoding. FIG. 2B, Decoded sentence intelligibility was assessed by asking naïve participants to identify the sentence they heard from 10 choices. Each sample (n=60) represents the percentage of correctly identified trials for one sentence. The median sentence was correctly identified 83% of the time. FIG. 2C, Correlation of original and decoded spectral features. Values represent the mean correlation 166 of the 32 spectral features for each sentence (n=100). Correlation performance for individual spectral features is reported in extended data FIG. 1*b*. FIG. 2D, Correlations between original and decoded intelligibility-relevant features. Kinematic values represent the mean correlation of the 33 kinematic features (the intermediate representation) for each sentence (n=100). Correlation performance for individual kinematic features is reported in FIG. 5A. Box plots depict median (horizontal line inside box), 25th and 75th percentiles (box), 25/75th percentiles ±1.5× interquartile range (whiskers), and outliers (circles). Distributions were compared with each as other as indicated or with chance-level distributions using two-tailed Wilcoxon signed-rank tests ($p<1e-10$, n=100, for all 176 tests).

FIG. 3A-3B, Mean correlation of original and decoded spectral features (FIG. 3A) and mean spectral distortion (MCD) (FIG. 3B) for model trained on varying amounts of training data. Training data was split according to recording session boundaries resulting the following sizes: 2.4, 5.2, 12.6, 25.3, 44.9, 55.2, 77.4, and 92.3 minutes of speaking data. The neural decoding approach that included an articulatory intermediate stage (purple) performed significantly better with every size of training data than direct ECoG to acoustics decoder (grey) (all: $p<1e-5$, n=100; Wilcoxon signed-rank test, error bars=SE). FIG. 3C, Acoustic similarity matrix compares acoustic properties of decoded phonemes and originally spoken phonemes. Similarity is computed by first estimating a gaussian kernel density for each phoneme (both decoded and original) and then computing the Kullback-Leibler (KL) divergence between a pair of decoded and original phoneme distributions. Each row compares the acoustic properties of a decoded phoneme with originally spoken phonemes (columns). Hierarchical clustering was performed on the resulting similarity matrix. FIG. 3D, Anatomical reconstruction of a single participant's brain with the following regions used for neural decoding: ventral sensorimotor cortex (vSMC), superior temporal gyms (STG), and inferior frontal gyrus (IFG). FIG. 3E-3F, Difference in spectral distortion (MCD) (FIG. 3E), and difference in correlation (Pearson's r) performance (FIG. 3F) between decoder 248 trained on all regions and decoders trained on all-but-one region. Exclusion of any region resulted in decreased performance ($p<3e-4$, n=100; Wilcoxon signed-rank test). Box plots as described in FIG. 2.

FIGS. 4A-FC, Spectrograms of original spoken sentence (a), neural decoding from audible production (FIG. 4B), and neural decoding from silently mimed production (c). FIG. 4D-4E, Spectral distortion (MCD) (FIG. 4D) and correlation of original and decoded spectral features (FIG. 4E) for audibly and silently produced speech. Since correlations are with respect to original audibly produced sentences, decoded sentences that were silently mimed were dynamically time-warped according to their spectral features. Decoded sentences were significantly better than chance-level decoding for both speaking conditions ($p<1e-11$, for all comparisons, n=58; Wilcoxon signed-rank test). Box plots as described in FIG. 2.

FIG. 5A Correlations of all 33 decoded articulatory kinematic features with ground-truth. EMA features represent X and Y coordinate traces of articulators (lips, jaw, and three points of the tongue) along the midsagittal plane of the vocal tract. Manner features represent complementary kinematic features to EMA that further describe acoustically consequential movements. FIG. 5B, Correlations of all 32 decoded spectral features with ground-truth. MFCC features are 25 mel-frequency cepstral coefficients that describe power in perceptually relevant frequency bands. Synthesis features describe glottal excitation weights necessary for speech synthesis.

FIG. 7A, On each trial, participants hear a question and see a set of possible answer choices on a screen. FIG. 7B, Participants are instructed to freely choose and verbally produce one of the answers when a green response cue appears on the screen. FIG. 7C, Simultaneously, cortical activity is acquired from ECoG electrodes implanted across temporal and frontal cortex and then filtered in real-time to extract high gamma activity. FIG. 7D, A speech detection model uses the spatiotemporal pattern of high gamma activity to predict whether a question is being heard or an answer is being produced (or neither) at each time point. FIG. 7E, When the speech detection model detects a question event, that time window of high gamma activity is passed to a question classifier that uses phone-level Viterbi decoding to compute question utterance likelihoods. FIG. 7F, The question with the highest likelihood is output as the decoded question. FIG. 7G, To integrate questions and answers, the stimulus set was designed such that each answer was only likely for certain questions (context priors). FIG. 7H, These context priors are combined with the predicted question likelihoods to obtain answer priors. FIG. 7I, When the speech detection model detects an answer event, that time window of neural activity is passed to an answer classifier that uses phone-level Viterbi decoding to compute answer utterance likelihoods. FIG. 7J, The context integration model combines these answer likelihoods with the answer priors to yield answer posterior probabilities (purple). FIG. 7K, The answer with the highest posterior probability is output as the decoded answer.

FIG. 8A, Decoding accuracy rate, which measures the full performance of the system, is significantly above chance for questions and answers (without and with context; * all P<0:05, 4-way Holm-Bonferroni correction). Answer decoding accuracy rate is significantly higher with context compared to without context. FIG. 8B, Classification accuracy (the percent of correctly classified speech events, using true event times) mirrors decoding accuracy rate. FIG. 8C, Cross entropy for utterance classification demonstrates similar patterns of better-than-chance performance and improvement with context (lower values indicate better performance). In FIG. 8B-8C, values were computed by bootstrapping across trials. Each boxplot depicts a line marking the median value, box heights representing the interquartile range, and whiskers extending beyond the box edges by 1:5 times the interquartile range. FIG. 8D, Event detection scores demonstrate near-ceiling performance of the speech detection model for both questions and answers. FIG. 8G-8E, MRI brain reconstructions with electrode locations and discriminative power for each electrode used by e question, f answer, and g speech event discriminative models. Electrodes that were not relevant are depicted as small black dots. See FIG. 14 for other participants.

FIG. 9A, Classification accuracy and cross entropy as a function of the amount of training data (mean with standard error). FIG. 9B, Variability in classification value, box heights representing the interquartile range, and whiskers extending beyond the box edges by 1:5 times the interquartile range. Each blue and red dot shows the performance on the test block using a single set of hyperparameters chosen for one epoch during optimization on a separate validation set. Each green dot marks the performance on the test block using the hyperparameters that minimized cross entropy on the validation set (the hyperparameter values used in the main results). See FIG. 15 for other participants.

FIG. 11A, Viterbi path probabilities during production of the utterance \Fine" demonstrate how the classifier uses phone-level information to predict answers as speech unfolds over time. Each curve depicts the probability of an answer given the neural data at each time point. The probabilities at the final time point represent the answer likelihoods that are passed to the context integration model. Only the five most likely utterances are labeled and colored for visualization purposes. The time at which the correct utterance becomes more likely than the other utterances (and remains more likely throughout the remainder of the decoding window) is marked as the "Decision finalization" time. FIG. 11B, Decision finalization times for answer classification using neural data and the phonetic transcriptions across all participants and test blocks. Each red dot represents the decision finalization time for a correctly-predicted trial (percent of the utterance relative to the actual speech onset and offset for that trial). Each boxplot depicts a line marking the median value, box heights representing the interquartile range, and whiskers extending beyond the box edges by 1:5 times the interquartile range. The observed finalization times typically occurred before speech offset (*$P<10^{-14}$), indicating that the classifiers were able to predict the identity of an utterance before processing all time points in the neural (or phonetic) time window associated with an utterance. This characteristic is only partially explained by the stimuli and transcribed vocalizations (*$P<10^{-9}$). FIG. 11C, Phone confusion matrix using the answer phone likelihood model for every time point in each test block across all participants. Colored squares indicate phonetic classes organized by place of articulation. /sp/ is the silence phone. This matrix illustrates reliable discrimination between the majority of the phones and intuitive confusions within articulatory classes (e.g., /s/ vs. /z/).

FIG. 13A, Speech event probabilities are computed by the detection model for each time point. The plotted curve depicts example event probabilities for one of the utterance types (for either question or answer events). FIG. 13B, Speech event probabilities are smoothed using a sliding window average. FIG. 13C, These smoothed probabilities are thresholded to be either 1 or 0. FIG. 13D, These binary values are then thresholded in time. Sometimes referred to as debouncing, this step prevents false switches between binary states due to noise and the particular threshold chosen. A transition from 0 to 1 in the time-thresholded values signifies a speech onset, and a transition from 1 to 0 signifies a speech offset. FIG. 13E, The neural data are segmented by the detected speech onset and offset, including some padded time points before and after the detected window (controlled by hyperparameters), and passed to the appropriate utterance classification model.

FIGS. 14A-14G: Speech decoding and classification results for participants 2 and 3 (participant 1 shown in FIG. 8). FIG. 14A, Decoding accuracy rate, which measures the full performance of the system, is significantly above chance for questions and answers (without and with context; * all $P<0:05$, 4-way Holm-Bonferroni correction). Answer decoding accuracy rate is significantly higher with context compared to without context. FIG. 14B, Classification accuracy (the percent of correctly classified speech events, using true event times) mirrors decoding accuracy rate. FIG. 14C, Cross entropy for utterance classification demonstrates similar patterns of better-than-chance performance and improvement with context (lower values indicate better performance). In FIG. 14B-14C, values were computed by bootstrapping across trials. Each boxplot depicts a line marking the median value, box heights representing the interquartile range, and whiskers extending beyond the box edges by 1:5 times the interquartile range. FIG. 14D, Event detection scores demonstrate near-ceiling performance of the speech detection model for both questions and answers. FIG. 14E-14G, MRI brain reconstructions with electrode locations and discriminative power for each electrode used by e question, f answer, and g speech event discriminative models. Electrodes that were not relevant are depicted as small black dots.

FIG. 15A, Classification accuracy and cross entropy as a function of the amount of training data (mean with standard error). FIG. 15B, Variability in classification performance across hyperparameter optimization epochs for one test block with each participant. Each boxplot depicts a line marking the median value, box heights representing the interquartile range, and whiskers extending beyond the box edges by 1:5 times the interquartile range. Each blue and red dot shows the performance on the test block using a single set of hyperparameters chosen for one epoch during optimization on a separate validation set. Each green dot marks the performance on the test block using the hyperparameters that minimized cross entropy on the validation set (the hyperparameter values used in the main results).

FIG. 20: Table 3 showing the amount of training and testing data collected with each participant.

FIG. 21: Table 4 showing significant testing statistics for question and answer decoding and classification performance.

FIG. 22: Table 5 showing answer classification information transfer rates (ITR; given in bits per second) for each participant.

FIG. 23: Table 6 showing context integration effects on answer classification accuracy for each participant.

FIG. 24: Table 7 showing the description and optimization search space for each hyperparameter.

FIGS. 27A-27D: FIG. 27A shows a schematic architecture for decoding models. FIG. 27B shows performance comparisons in three participants. FIG. 27C shows language model comparison on Participant P3. FIG. 27D shows examples of decoding results against ground truth.

DEFINITIONS

Figure 1A:
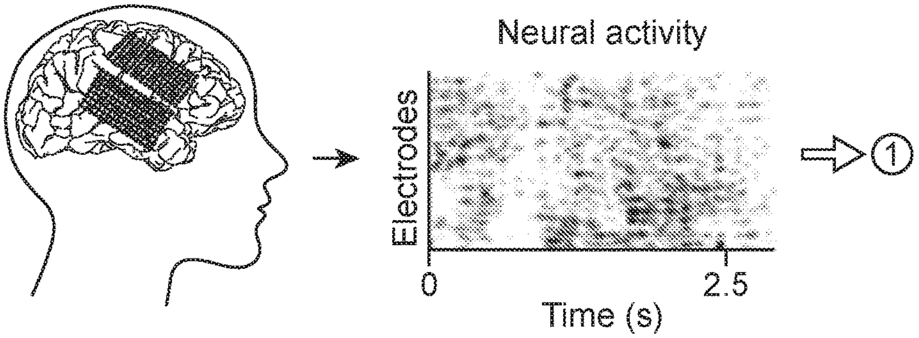
FIGS. 1A-1H: Speech Synthesis from neurally decoded spoken sentences.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a signal" includes a plurality of such signals and reference to "the electrode" includes reference to one or more electrodes and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the apparatus and method has or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

Provided are methods of contextual decoding and/or speech decoding from the brain of a subject. The methods include decoding neural or optical signals from the cortical region of an individual, extracting context-related features and/or speech-related features from the neural or optical signals, and decoding the context-related features and/or speech-related features from the neural or optical signals. Contextual decoding and speech decoding systems and devices for practicing the subject methods are also provided.

Methods—Decoding Contextual Information

Provided are methods of decoding contextual information from the brain of a subject. Aspects of the present disclosure include a method of decoding context-related events in an individual. In some embodiments, the method includes extracting context-related features from a plurality of signals from the brain of an individual with or without one or more external context-related cues; and decoding the one or more context-related features from the plurality of signals. In some embodiments, the method further comprises analyzing one or more external context-related cues. In some embodiments, analyzing one or more external context-related cues is configured to inform and assist a speech decoder in improving speech decoding from brain activity.

Aspects of the present disclosure include methods of decoding context events. In some embodiments, the method includes extracting one or more of: one or more context-related features from a plurality of signals from the brain of an individual, and one or more external context-related features from an external source; and decoding into one or more context priors, one or more of: the one or more context-related features from the plurality of signals, and the one or more external context-related features from the external source.

Aspects of the present methods include decoding neural signals detected from electrodes operably coupled to the motor cortex of an individual and extracting context-related features from the neural signals when an individual in order to decode the context-related feature output from the neural signals.

Aspects of the present methods includes methods of decoding context events in an individual, where the method includes extracting one or more of: one or more context-related features from a plurality of signals from the brain of an individual, and one or more external context-related features from an external source; and decoding one or more of: the one or more context-related features from the plurality of signals, and the one or more external context-related features from the external source.

The term "context" as used, herein, refers to information pertaining to the setting, circumstances, and events, that precede, are simultaneous, or following the speech decoding. Such context could be inferred from machines that interpret speech or text, or visual information from images. Context can also be obtained by decoding the information from neural activity in the brain. For example, "thoughts" or "feelings" of the individual and/or "sounds" heard and interpreted by the individual through brain activity. Non-limiting examples of "context" include pain; anxiety; depression; any emotional state; mood; sound (e.g. sound decoded from an audio device or from a telephone, cellphone, tablet, computer, radio, television, and the like); external contextual features such as, but not limited to, environmental objects or information in physical proximity to the individual, decoded from a camera input); locational data such as, but not limited to, location data decoded a global positioning system (GPS) or any other equivalent location tracker device; time of day; weather; any alternative signal source of information; or a combination thereof. An example of an "internal" context-related feature includes any emotional context (e.g. pain, thoughts, feelings, anxiety, depression). An example of an external context-related feature includes environmental context (e.g. proximal objects), acoustic context (e.g. conversation state), and the like.

Decoding context-related features of the present invention can include, but is not limited to decoding thoughts, language-related features, pain-related features, anxiety-related features, mood-related features, emotional state-related features, speech-related features, sound-related features, or a combination thereof, through a plurality of signals (e.g. optical signals, neural signals, electrical signals) from the brain and/or from the external context-related features. In some embodiments, "context" decoding does not include decoding context-related events associated with articulatory movement or produced sound or speech. In some embodiments, an external context-related feature comprises non-neural external context-related features.

The term "context prior", refers to herein as a mathematical representation of forms context, used in a statistical and/or probabilistic approach with a context decoder to improve predictions. Thus, "context prior" can refer the probability of thinking of a context-related event, responding to a context-related event, and/or hearing a sound. For example, if an individual has just heard a specific question (or any speech targets, including single-word targets, and "continuous" sentences of arbitrary lengths with large vocabulary sizes), that question (or any speech targets, including single-word targets, and "continuous" sentences of arbitrary lengths with large vocabulary sizes) represents the "context". The "context priors" refers to the probability distribution that is used to represent the context of the individual given the current question (or any speech targets, including single-word targets, and "continuous" sentences of arbitrary lengths with large vocabulary sizes). These "context priors" are used in conjunction with decoder outputs to improve decoding compared to using only the decoder outputs directly.

Aspects of the present disclosure further include methods of decoding context-related features in an individual, the method comprising: contacting an electrode array with the cortical region of the brain in the individual; conducting context perception training (e.g. via one or more external context-related cues) on the individual or analyzing one or more external context-related cues, wherein context perception training comprises at least one of: listening to a sound, responding to a sound, thinking about a sound (e.g. a speech event), thinking about a context-related feature, reading, or a combination thereof; recording neural or optical signals during context perception training; analyzing the neural or optical signals in one or more regions of the brain; and decoding the neural or optical signals into a context output. In some embodiments, the context perception training comprises one or more external context-related cues (e.g. non-neural external context-related cues). In some embodiments, the method further comprises decoding one or more external context-related features from an external source in the form of external signals during. In some embodiments, decoding the one or more external context-related features from the external source in the form of external signals occurs during the context training on the individual (e.g. in real-time) or offline. In some embodiments, the context perception training comprises one or more context-related features from brain activity of the individual (e.g. plurality of signals from the brain). In some embodiments, the method further comprises decoding a speech-related feature from a speech decoder comprising the context output and/or the external context output.

In some embodiments, the one or more external context-related features of the present disclosure comprises non-neural external context-related cues. In some embodiments, the one or more external context-related features comprises one or more of a sound, visual environmental cues, and location data. In some embodiments, the one or more external context-related cues comprises sound decoded from an audio device (e.g. a microphone, audio recording device, a sound amplifier, and the like). In some embodiments, the sound is from a telephone, cellphone, tablet, computer, radio, television, and the like. In some embodiments, the one or more external context-related features is the time of day, weather, and/or location. In some embodiments, the one or more external context-related features includes contextual information about objects (e.g. chairs, doors, light switches, computers, water, food, etc.) in the proximity of the individual. In some embodiments, the one or more external context-related features includes contextual information about objects in the proximity of the individual in which the individual interacts with (e.g. chairs, doors, light switches, computers, water, food, etc.).

In some embodiments, the external source comprises semantics or other linguistics attributes from text or language, an acoustic device, an imaging device, a time tracking device, a heart monitoring device, a computer, a telecommunication device, a GPS, a radio, a television, or a combination thereof. In some embodiments, the time tracking device is a clock. In some embodiments, an imaging device is a charge-coupled device. In some embodiments, the charge-coupled device is a camera.

In some embodiments, the one or more external context-related features comprises semantics or other linguistics attributes from text or language, visual environmental objects in physical proximity to the individual, locational data of the individual, the time of day, weather, heart rate, sound, or a combination thereof. In some embodiments, the external context-related features are decoded from the external source. For example, in a clinical speech decoding application, a camera could be used to provide information about nearby objects that the patient would like to interact with (light switches, water, computers, etc.). The emotional state of the patient could also be inferred and used to influence the speech decoder. The time of day can be used to inform the decoder too (e.g. one would be far more likely to say 'good morning' if it is, in fact, morning time and not evening time). Therefore, speech decoding of the present invention is not limited to decoding speech from brain activity, but also using all available information to inform and assist the decoder. This meta-data can be explicit (eg. time, location, etc) vs implicit (e.g. what someone heard, as inferred from brain activity, or how someone feels).

In some embodiments, extracting comprises extracting one or more context-related features from the plurality of signals from the brain of the individual and one or more external context-related features from the external source.

Aspects of the present disclosure further include methods of decoding context-related features in an individual, the method comprising: contacting an optical device with the cortical region of the brain in the individual; conducting context perception training (e.g. via one or more external context-related cues) on the individual, wherein context perception training comprises at least one of: listening to a sound, responding to a sound, thinking about a sound (e.g. a speech event), thinking about a context-related event, reading, or a combination thereof; recording optical signals during context perception training; analyzing the optical signals in one or more regions of the brain; and decoding the optical signals into a context output. In some embodiments, the method further comprises decoding one or more external context-related features from an external source in the form of external signals during the context training on the individual or offline, into an external context output. In some embodiments, the method further comprises decoding a speech related-feature from a speech decoder, comprising at least one of: the context output and the external context output.

In some embodiments, methods of the present disclosure include a method of decoding contextual information, the method comprising: extracting one or more external context-related features; and decoding, with a context decoder, the one or more external context-related features into one or more context priors.

In some embodiments, the methods of the present disclosure comprise generating decoding constraints (e.g. by conducting one or more external context-related cues). In some embodiments, the one or more external context-related cues comprises listening to audible speech. In some embodiments, the one or more external context-related cues comprises reading. In some embodiments, the one or more external context-related cues comprises responding to audible speech. In some embodiments, responding comprises a verbal response. In some embodiments, the verbal response is a sound. In some embodiments, the sound is selected from the group consisting of: a phoneme, formant acoustics of a vowel, a diphone, a triphone, a consonant-vowel transition, a syllable, a word, a phrase, a sentence, and combinations thereof. In some embodiments, the external context-related cue comprises one or more of environmental objects in physical proximity to the individual, locational data of the individual, time of day, locational data decoded from the GPS, weather, heart rate, sound, or a combination thereof.

In some embodiments, the one or more external context-related features comprises the individual's thoughts while listening to a sound (e.g. audible speech) and/or reading. In some embodiments, sound is selected from the group consisting of: a phoneme, formant acoustics of a vowel, a diphone, a triphone, a consonant-vowel transition, a syllable, a word, a phrase, a sentence, and combinations thereof. In some embodiments, the one or more external context-related features comprises reading aloud one or more syllables, words, parts of words, phrases, utterances, paragraphs, sentences, and/or a combination thereof. In some embodiments, the one or more external context-related cues comprises reading, aloud, one or more scripts. In some embodiments, the one or more external context-related cues comprises responding to a sound (e.g. audible speech). In some embodiments, the one or more external context-related cues comprises verbally producing a set of responses after listening to the audible speech. In some embodiments, the one or more external context-related cues comprises listening to a sound. In some embodiments, the one or more external context-related cues comprises silently miming one or more syllables, words, parts of words, phrases, utterances, paragraphs, sentences, and/or a combination thereof by making the kinematic movements of a verbal response but without making sound. In some embodiments, the kinematic movements during the silently mimed speech is recorded (e.g. in the form of acoustic signals).

In some embodiments, the one or more context-related features comprises one or more cues from preceding language in the form of text, dialogue, exchanges, email, chats, texting, wherein these sources of the one or more context-related cues bear information about the context of intended decoded speech. In some embodiments, such language-related context refers to the semantics and other properties of language that are needed for understanding language. A non-limiting example includes, but is not limited to a subject receiving a text message: "what is your favorite musical instrument?" The speech decoder may confuse words that sound alike, for example, "fertilizer" and "synthesizer". But if the decoder knows the context of the question, then only "synthesizer" is the possible answer. Such a decoder in combination with the one or more context-related cues is configured to boost performance in speech decoding.

In some embodiments, the one or more external context-related cues comprises responding to audible speech or a sound. In some embodiments, responding to audible speech or a sound comprises a verbal response. In some embodiments, the verbal response is a sound.

In some embodiments, the method further comprises timing the individual during the one or more external context-related cues. In some embodiments, the method further comprises recording and/or analyzing acoustic signals during the context perception training (e.g. during one or more external context-related cues) on the individual.

In some embodiments, the one or more context-related features of the present methods comprises pain-related features in the individual. In some embodiments, the one or more context-related features of the present methods comprises language-related features in the individual. In some embodiments, the one or more context-related feature comprises the individual's thought. In some embodiments, the one or more context-related features comprises anxiety-related features in the individual. In some embodiments, the one or more context-related features comprises the individual's heart rate. In some embodiments, the one or more context-related features comprises mood-related features of the individual. In some embodiments, the one or more context-related features comprises the individual's thought during one or more external context-related cues. In some embodiments, the one or more context-related features comprises speech-related features when the individual is intended to produce a speech output.

In some embodiments, the one or more context-related features comprises speech perception. In some embodiments, the one or more context-related features comprises speech perception while listening to one or more external context-related cues.

In some embodiments, the method includes extracting the one or more context-related features from the plurality of signals and decoding the intended one or more context-related feature outputs occurs in real-time.

In some embodiments, the data produced (e.g. neural signals, optical signals, audio recordings) and analyzed into contextual data with or without the one or more external context-related cues serve as input to train speech detection and decoding models of the present disclosure.

Aspects of the present disclosure include detecting a plurality of neurophysiological signals from the cortical region of the brain. In some embodiments, the plurality of neurophysiological signals are neural signals. In some embodiments, the plurality of neurophysiological signals are optical signals.

In some embodiments, the neurophysiological signals are acquired by contacting 1 or more electrodes, 2 or more electrodes, or 3 or more electrodes that detect the plurality of signals with at least one region of the brain. In some embodiments, the neurophysiological signals are acquired by contacting 50 or more electrodes, 100 or more electrodes, 150 or more electrodes, 200 or more electrodes, 250 or more electrodes, 300 or more electrodes, 400 or more electrodes, 500 or more electrodes, 600 or more electrodes, 700 or more electrodes, 800 or more electrodes, 900 or more electrodes, 1000 or more electrodes, 1500 or more electrodes, 2000 or more electrodes, 2500 or more electrodes, 3000 or more electrodes, or 3500 or more electrodesthat detect the plurality of signals with at least one region of the brain. In some embodiments, the neurophysiological signals are acquired by contacting 1 or more electrodes per array, 2 or more electrodes per array, or 3 or more electrodes per array that detect the plurality of signals with at least one region of the brain. In some embodiments, the neurophysiological signals are acquired by contacting 50 or more electrodes per array, 100 or more electrodes per array, 150 or more electrodes per array, 200 or more electrodes per array, 250 or more electrodes per array, 300 or more electrodes per array, 400 or more electrodes per array, 500 or more electrodes per array, 600 or more electrodes per array, 700 or more electrodes per array, 800 or more electrodes per array, 900 or more electrodes per array, 1000 or more electrodes per array, 1500 or more electrodes per array, 2000 or more electrodes per array, 2500 or more electrodes per array, 3000 or more electrodes per array, or 3500 or more electrodes per array that detect the plurality of signals with at least one region of the brain. In some embodiments, the at least one region of the brain comprises the speech motor cortex of the brain. In some embodiments, the at least one region of the brain comprises the auditory cortex of the brain.

The neurophysiological signals are detected using at least three electrodes operably coupled to the speech motor cortex of the subject. By "operably coupled" is meant that one or more electrodes are of a suitable type and position so as to detect the desired neurophysiological signals in the motor cortex related to a context-related event. According to one embodiment, the one or more electrodes are operably coupled to the motor cortex by implantation on the surface of the motor cortex. In one aspect, an array of electrocorticography electrodes (ECoG array) is disposed on the surface of the motor cortex (e.g., the vSMC) for detection of ECoG neural signals (e.g., local field potentials) generated in the motor cortex. In some embodiments, the method comprises extracted context-related features from the neural or optical signals. In some embodiments, the context-related features comprise local field potentials generated in the motor cortex. In some embodiments, the context-related features comprise high gamma frequency signals (e.g. 70-200 Hz) generated in the motor cortex. In some embodiments, the context-related features comprise spectral features of the neural or optical signals. In some embodiments, the spectral features are Mel-frequency cepstral coefficients (MFCCs) extracted from the speech waveform (e.g. local field potentials generated in the motor cortex (e.g. speech motor cortex)). According to certain embodiments, the one or more electrodes are operably coupled to the motor cortex by insertion of the electrodes into the speech motor cortex (e.g., at a desired depth). According to certain embodiments, the neurophysiological electrode array is implantable. According to certain embodiments, the neurophysiological electrode array is implanted directly on the surface of the brain.

The specific location at which to position an electrode may be determined by identification of anatomical landmarks in the subject's brain, such as the pre-central and post-central gyri and the central sulcus. Identification of anatomical landmarks in a subject's brain may be accomplished by any convenient means, such as magnetic resonance imaging (MRI), functional magnetic resonance imaging (fMRI), and visual inspection of a subject's brain while undergoing a craniotomy. Once a suitable location for an electrode is determined, the electrode may be positioned (e.g., implanted) according to any convenient means. Suitable locations for positioning or implanting the at least three electrodes may include, but are not limited to, one or more regions of the ventral sensorimotor cortex (vSMC), including the pre-central gyrus, the post-central gyrus, the guenon (the gyral area directly ventral to the termination of the central sulcus), the superior temporal gyrus (STG), the inferior frontal gyrus (IFG), and any combination thereof. Correct placement of the at least three electrodes may be confirmed by any convenient means, including visual inspection or computed tomography (CT) scan. In some aspects, after electrode positions are confirmed, they may be superimposed on a surface reconstruction image of the subject's brain. In certain aspects, the electrodes are positioned such that the neurophysiological signals are detected from one or more regions of the vSMC, e.g., the neurophysiological signals are detected from a region of the vSMC selected from the pre-central gyrus, the post-central gyrus, the guenon, STG, IFG, and combinations thereof.

Methods of interest for positioning electrodes further include, but are not limited to, those described in U.S. Pat. Nos. 4,084,583; 5,119,816; 5,291,888; 5,361,773; 5,479,934; 5,724,984; 5,817,029; 6,256,531; 6,381,481; 6,510,340; 7,239,910; 7,715,607; 7,908,009; 8,045,775; and 8,019,142; the disclosures of which are incorporated herein by reference in their entireties for all purposes.

The number of electrodes operably coupled to the motor cortex may be chosen so as to provide the desired resolution and information about the neurophysiological neural or optical signals being generated in the motor cortex during one or more external context-related cues, as each electrode may convey information about the activity of a particular region (e.g., the vSMC, STG, or IFG as described in the examples below). By comparing differences between the signals of each electrode, neurophysiological neural signal patterns may be derived from the neural signals, or which electrodes responsive to the speech perception or speech production.

Accordingly, in certain embodiments, at least 10 electrodes (e.g., at least 20 electrodes) are employed. Between about 3 and 1024 electrodes, or more, may be employed. In some embodiments, the number of electrodes positioned is about 3 to 10 electrodes, about 10 to 20 electrodes, about 20 to 30 electrodes, about 30 to 40 electrodes, about 40 to 50 electrodes, about 60 to 70 electrodes, about 70 to 80 electrodes, about 80 to 90 electrodes, about 90 to 100 electrodes, about 100 to 110 electrodes, about 110 to 120 electrodes, about 120 to 130 electrodes, about 130 to 140 electrodes, about 140 to 150 electrodes, about 150 to 160 electrodes, about 160 to 170 electrodes, about 170 to 180 electrodes, about 180 to 190 electrodes, about 190 to 200 electrodes, about 200 to 210 electrodes, about 210 to 220 electrodes, about 220 to 230 electrodes, about 230 to 240 electrodes, about 240 to 250 electrodes, about 250 to 300 electrodes (e.g., a 16×16 array of 256 electrodes), about 300 to 400 electrodes, about 400 to 500 electrodes, about 500 to 600 electrodes, about 600 to 700 electrodes, about 700 to 800 electrodes, about 800 to 900 electrodes, about 900 to 1000 electrodes, or about 1000 to 1024 electrodes, or more. The electrodes may be homogeneous or heterogeneous.

Electrodes may be arranged in no particular pattern or any convenient pattern to facilitate detection of neural signals. For example, a plurality of electrodes may be placed in a grid pattern, in which the spacing between adjacent electrodes is approximately equivalent. Such spacing between adjacent electrodes may be, for example, about 2.5 cm or less, about 2 cm or less, about 1.5 cm or less, about 1 cm or less, about 0.5 cm or less, about 0.1 cm or less, or about 0.05 cm or less. Electrodes placed in a grid pattern may be arranged such that the overall plurality of electrodes forms a roughly geometrical shape. In certain embodiments, a grid pattern may be roughly square in overall shape, roughly rectangular, roughly trapezoidal, or roughly oval in shape, or roughly circular.

Electrodes may be pre-arranged into an array, such that the array includes a plurality of electrodes that may be placed on or in a subject's brain. Such arrays may be miniature- or micro-arrays, a non-limiting example of which may be a miniature neurophysiological array (e.g. ECoG array, microelectrode array, electroencephalography (EEG), array). For a general review of ECoG technology, see Ajmone-Marsan, C. Electrocorticography: Historical Comments on its Development and the Evolution of its Practical Applications, Electroencephalogr. Clin. Neurophysiol, Suppl. 1998, 48: 10-16; the disclosure of which is incorporated herein by reference.

Also of interest are electrodes that may receive electroencephalography (EEG) data. One or more wet or dry EEG electrodes may be used in practicing the subject methods. Electrodes and electrode systems of interest further include, but are not limited to, those described in U.S. Patent Publication Numbers 2007/0093706, 2009/0281408, 2010/0130844, 2010/0198042, 2011/0046502, 2011/0046503, 2011/0046504, 2011/0237923, 2011/0282231, 2011/0282232 and U.S. Pat. Nos. 4,709,702, 4,967,038, 5,038,782, 6,154,669; the disclosures of which are incorporated herein by reference.

An array may include, for example, about 5 electrodes or more, e.g., about 5 to 10 electrodes, about 10 to 20 electrodes, about 20 to 30 electrodes, about 30 to 40 electrodes, about 40 to 50 electrodes, about 50 to 60 electrodes, about 60 to 70 electrodes, about 70 to 80 electrodes, about 80 to 90 electrodes, about 90 to 100 electrodes, about 100 to 125 electrodes, about 125 to 150 electrodes, about 150 to 200 electrodes, about 200 to 250 electrodes, about 250 to 300 electrodes (e.g., a 256 electrode array in 16×16 format), about 300 to 400 electrodes, about 400 to 500 electrodes, or about 500 electrodes or more. In certain embodiments, the array may cover a surface area of about 1 $cm^2$, about 1 to 10 $cm^2$, about 10 to 25 $cm^2$, about 25 to 50 $cm^2$, about 50 to 75 $cm^2$, about 75 to 100 $cm^2$, or 100 $cm^2$ or more. Arrays of interest may include, but are not limited to, those described in U.S. Pat. Nos. USD565735; USD603051; USD641886; and USD647208; the disclosures of which are incorporated herein by reference.

Electrodes may be platinum-iridium electrodes or be made out of any convenient material. The diameter, length, and composition of the electrodes to be employed may be determined in accordance with routine procedures known to those skilled in the art. Factors which may be weighted when selecting an appropriate electrode type may include but not be limited to the desired location for placement, the type of subject, the age of the subject, cost, duration for which the electrode may need to be positioned, and other factors.

In certain aspects, an array of electrodes (e.g., an ECoG array, microelectrode array, EEG array) is positioned on the surface of the speech motor cortex such that the array covers the entire or substantially the entire region of the speech motor cortex corresponding to the somatotopic arrangement of articulatory kinematic representations of the subject. For example, the electrode array may be disposed on the surface of the speech motor cortex from −100 mm to +100 mm, from −80 mm to +80 mm, from −60 mm to +60 mm, from −40 mm to +40 mm, or from −20 mm to +20 mm relative to the central sulcus along the anterior-posterior axis. Alternatively, or additionally, the electrode array may be disposed on the surface of the speech motor cortex from a location at or proximal to the Sylvian fissure to a distance of 500 mm or less, 400 mm or less, 300 mm or less, 200 mm or less, 100 mm or less, 90 mm or less, 80 mm or less, 70 mm or less, 60 mm or less, 50 mm or less, or 40 mm or less from the Sylvian fissure along the dorsal-ventral axis. Non-limiting examples of an array and example positioning thereof can be found in U.S. Pat. No. 9,905,239, which is hereby incorporated by reference in its entirety.

In certain embodiments, a ground electrode or reference electrode may be positioned. A ground or reference electrode may be placed at any convenient location, where such locations are known to those of skill in the art. In certain embodiments, a ground electrode or reference electrode is a scalp electrode. A scalp electrode may be placed on a subject's forehead or in any other convenient location.

Aspects of the present disclosure comprise detecting a plurality of neural or optical signals for context-decoding. In some embodiments, the plurality of signals are acquired by any known neurophysiological recording device. In some embodiments, the plurality of signals are optical signals. In some embodiments, the plurality of signals are acquired through optical devices. Optical devices that can be used to acquire the plurality of signals include, but are not limited to: intrinsic optical signal (IOS) imaging, extrinsic optical signal (EOS) imaging, Doppler flowmetry (LDF), near-infrared (NIR) spectrometer, functional near-infrared spectroscopy (fNIRS), functional optical coherence tomography (fOCT), and surface plasmon resonance (SPR). Other techniques such as radioactive imaging can be used to acquire the plurality of signals. Non-limiting examples include radioactive imaging of changes in blood flow, magnetoencephalography (MEG), thermal imaging, positron-emission tomography (PET), functional magnetic resonance imaging (fMRI), and diffuse optical tomography (DOT).

Aspects of the present disclosure comprise detecting a plurality of neural or optical signals for context-decoding using non-invasive recording methods such as, but not limited to functional magnetic resonance imaging (fMRI), blood oxygen level-dependent (BOLD)-fMRI, diffusion tensor imaging (DTI), manganese-enhanced MRI (ME-MRI), multiphoton microscopy (MP), magnetoencephalographic imaging (MEGI), and the like.

In some embodiments, the plurality of signals are neural signals. In some embodiments, the method includes acquiring the plurality of signals by microelectrodes. In some embodiments, the method includes acquiring the plurality of signals by ECoG. In some embodiments, the method includes acquiring the plurality of signals by EEG. In some embodiments, the plurality of signals are neural signals. In some embodiments, the plurality of signals comprise local field potentials from the speech motor cortex of the brain. In some embodiments, the plurality of signals are intracranial spike recordings. In some embodiments, the plurality of signals and even non-invasive recording methods including fMRI signals. In some embodiments, the plurality of signals are optical signals.

In some embodiments, the method comprises extracting context-related features from the neural or optical signals. In some embodiments, extracting context-related features from the neural signals comprises filtering the plurality of signals in a high gamma frequency range to obtain neural signals in the auditory and sensorimotor brain regions. In some embodiments, plurality of signals are obtained from auditory and sensorimotor brain regions selected from the vSMC, STG, and IFG. In some embodiments, the plurality of signals comprise the high-gamma frequency component of the local field potentials. The high-gamma frequency component of the local field potential is a high-gamma frequency range of the plurality of signals associated with an intended speech output. In some embodiments, the high-gamma frequency range ranges from 70-200 Hz (e.g. 70-75 Hz, 75-80 Hz, 80-85 Hz, 95-90 Hz, 90-95 Hz, 95-100 Hz, 100-105 Hz, 105-110 Hz, 110-115 Hz, 115-120 Hz, 120-125 Hz, 125-130 Hz, 130-135 Hz, 135-140 Hz, 140-145 Hz, 145-150 Hz, 150-155 Hz, 155-160 Hz, 160-165 Hz, 165-170 Hz, 170-175 Hz, 175-180 Hz, 180-185 Hz, 185-190 Hz, 190-195 Hz, or 195-200 Hz). In some embodiments, the high-gamma frequency range ranges from 70-150 Hz. In some embodiments, the analytic amplitude of the high-gamma frequency component of the local field potentials was extracted with the Hilbert transform and down-sampled to 200 Hz. In some embodiments, the plurality of signals comprise a low frequency component (e.g. 1-30 Hz) extracted with a 5th order Butterworth bandpass filter and parallelly aligned with the high-gamma amplitude.

In some embodiments, electrodes for which neural signals are collected are from electrodes located on cortical areas related to a context-related feature, such as the vSMC, STG, and/or IFG.

In some embodiments, the one or more context-related features comprises the high-gamma amplitude frequency range that correlated with multi-unit firing rates within the neural signals.

In some embodiments, the method comprises detecting when the individual is intended to produce a context-related feature output. In some embodiments, said detecting comprises recording neural signals during one or more external context-related cues. In some embodiments, said detecting comprises extracting high frequency signals and/or low frequency signals from the raw neural signals of each electrode. In some embodiments, said detecting comprises extracting high-gamma amplitude signals and/or low frequency signals from the raw neural signals of each electrode.

In some embodiments, the method comprises extracting context-related features from the signals and decoding the context-related feature output in real-time.

In some embodiments, the method further comprises timing the individual during the context-related event. In some embodiments, the method further comprises timing the individual during the one or more external context-related cues.

In some embodiments, the method further comprises translating the context-related features into phonetic transcriptions or text. In some embodiments, the method further comprises computing phone likelihoods at each time point during the context-related event.

In some embodiments, decoding comprises predicting time segments of the neural or optical signals that that are associated with context-related events. In some embodiments, the time segment comprises at least 30 seconds, at least 1 minute, at least 5 minutes, at least 10 minutes, at least 20 minutes, at least 25 minutes, at least 30 minutes, at least 35 minutes, at least 40 minutes, at least 50 minutes, at least 55 minutes, or at least 60 minutes of a context-related event.

In some embodiments, decoding the context-related feature output comprises machine learning algorithms that identify spatiotemporal neural patterns associated with the context-related events (e.g. one or more external context-related cues). In some embodiments, the machine learning algorithms require context perception training data associated with a context-related feature. In some embodiments, the machine learning algorithm require at least 30 seconds, at least 1 minute, at least 5 minutes, at least 10 minutes, at least 20 minutes, at least 25 minutes, at least 30 minutes, at least 35 minutes, at least 40 minutes, at least 50 minutes, at least 55 minutes, or at least 60 minutes of speech training data. In some embodiments, the spatiotemporal neural patterns comprise rapid evoked responses in the STG during the speech events. In some embodiments, decoding the intended context-related feature output comprises predicting the temporal onsets and offsets of the speech events based on the rapid evoked responses in the STG.

In some embodiments, wherein the method further comprises displaying the decoded context-related feature output. In some embodiments, the context-related feature output is displayed on a screen. In some embodiments, the context-related feature output is displayed on a screen as one or more syllables, words, parts of words, phrases, utterances, paragraphs, sentences, and/or a combination thereof. In some embodiments, the context-related feature output is displayed on a screen as one or more sentences. In some embodiments, the context-related feature output is displayed on a computer, a tablet computer or smart phone, or any related computing device. In some embodiments, the tablet computer or smartphone runs an operating system selected from an iOS™ operating system, an Android™ operating system, a Windows™ operating system, or any other tablet- or smartphone-compatible operating system.

Aspects of the present disclosure include a non-transitory computer readable medium storing instructions that, when executed by one or more processors and/or computing devices, cause the one or more processors and/or computing devices to perform the steps for decoding context-related features in an individual, as provided herein.

Aspects of the present disclosure include a non-transitory computer readable medium storing instructions that, when executed by one or more processors and/or computing devices, cause the one or more processors and/or computing devices to perform the steps for decoding context-related predictions in an individual, as provided herein.

In some embodiments, the method of the present disclosure method is carried out using a receiver unit, comprising: a wireless receiver in communication with a wireless transmitter that receives the plurality of signals detected from at least three electrodes; one or more processors; a non-transient computer-readable medium comprising instructions that, when executed by the one or more processors, cause the one or more processors to: perform one or more filters on the plurality of signals; decode the plurality of neural or optical signals into a context-related feature output.

In some embodiments, the method comprises filtering the plurality of signals with one or more filters. In some embodiments, the one or more filters comprises one or more notch filters. In some embodiments, the one or more filters comprises one or more band-pass finish impulse response (FIR) filters. In some embodiments, the one or more processors is configured to extract analytic amplitude values across the one or more band-pass FIR filters applied to the plurality of signals. In some embodiments, the one or more processors is configured to average the analytic amplitude values across the one or more band-pass FIR filters to obtain one or more high gamma analytic amplitude signals (e.g. high gamma frequency range signals).

In some embodiments, the one or more processors is configured to normalize and store the one or more high gamma analytic amplitude signals in an event detector process. In some embodiments, the event detector process is configured to analyze the high gamma analytic signals. In some embodiments, the gamma analytic signals are analyzed at one or more time points to predict the onset and offset of context-related feature events. In some embodiments, the one or more time points comprises 10 or more ms time points, 20 or more ms time points, 30 or more ms time points, 40 or more ms time points, or 50 or more ms time points. In some embodiments, the one or more time points comprises 10 or more ms time points, 50 or more ms timepoints, 100 or more ms time points, 150 or more ms time points, 200 or more time points, 250 or more ms timepoints, 300 or more ms time points, 350 or more ms time points, 400 ms or more time points, 450 or more ms time points, or 500 or more ms time points.

In some embodiments, the one or more processors are configured to decode the one or more high gamma analytic amplitude signals into the context-related feature output.

In some embodiments, the one or more processors is a neural decoder. In some embodiments, the method comprises two or more processors, three or more processors, four or more processors, or five or more processors. In some embodiments, the one or more processors comprises a neural decoder comprising a bidirectional long short-term memory comprising an algorithm for decoding the context-related feature output. In some embodiments, the one or more processors is one or more (e.g. two or more, three or more, four or more, or five or more) stacked 3-layer bidirectional long short term memory (bLSTM) recurrent neural networks. In some embodiments, a first stacked 3-layer bLSTM is configured to learn the mapping between time point windows (e.g. 300 ms windows) of high-gamma and local field potential signals and the corresponding single time point of 32 articulatory features related to movement of the vocal tract. In some embodiments, the bLSTM decodes speech-related features from the neural signals. In some embodiments, a second bLSTM decodes acoustic features from the speech-related features of the neural signals.

In some embodiments, the one or more processors comprises an algorithm for decoding a context-related feature such as an intended speech output. In some embodiments, the one or more processors comprises a machine learning algorithm for estimating 32 dimensional articulatory kinematic trajectories (e.g. acoustically consequential movements of the vocal tract) using only produced acoustic and phonetic transcriptions. Dimensional articulatory kinematic trajectories are described in Chartier et al. (*Neuron* (2018) 98:5, pgs 1042-1054), which is hereby incorporated by reference in its entirety. In some embodiments, the dimensional articulatory kinematic trajectories are represented as place manner tuples (representations as continuous binary valued features) that incorporate physiological aspects in EMA, which include one or more of the tongue blade, tongue tip, jaw, upper lip, lower lip, velar stop, velar nasal, palatal approximant, palatal fricative, palatal affricate, labial stop, labial approximant, labial nasal, glottal fricative, dental fricative, labiodental fricative, alveolar stop, alveolar approximant, alveolar nasal, alveolar lateral, alveolar fricative, unconstructed, and voicing. In some embodiments, the machine learning algorithm comprises an existing annotated speech database (Wall Street Journal Corpus) and trained speaker independent deep recurrent network regression models to predict the place-manner tuple vectors from the acoustic signal of a speech event.

In some embodiments, the one or more processors comprises an autoencoder. In some embodiments, the autoencoder is a recurrent neural network encoder that is trained to convert phonological and acoustic features to the initialized 32 articulatory representations. In some embodiments, the one or more processor comprises a decoder, wherein the decoder converts the articulatory representation back to acoustic signals. In some embodiments, the one or more processors (e.g. stacked neural network) is re-trained optimizing the joint loss on acoustic and EMA parameters. After convergence, the encoder is used to estimate the final articulatory kinematic features that act as the intermediate to decode acoustics from neural signals.

Aspects of the present disclosure further include methods of decoding auditory perceived speech or verbal produced speech in an individual based on the context-related features (e.g. internal and/or external context-related features from the plurality of signals from the brain or from the external source).

In some embodiments, the method further comprises translating the time-aligned audio into phonetic transcriptions or text.

In some embodiments, decoding comprises computing context-related feature perception, context-related feature production, or context-related feature probabilities (e.g. internal and/or external context-related features from the plurality of signals and/or from the external source). In some embodiments, the decoding is computed with one or more processors as described in the present disclosure. In some embodiments, the method comprises a non-transient computer-readable medium comprising instructions that, when executed by the one or more processors, cause the one or more processors to perform its intended function as disclosed herein.

In some embodiments, the methods of the present disclosure are carried out using a receiver unit, comprising a wireless receiver in communication with a wireless transmitter that receives the plurality of signals. In some embodiments, the receiver unit includes one or more processors. In some embodiments, the receiver unit includes a non-transient computer-readable medium comprising instructions that, when executed by the one or more processors, cause the one or more processors to: perform one or more filters on the plurality of signals; and decode the plurality of signals into a context-dependent output.

In some embodiments, the methods of the present disclosure is carried out using a receiver unit, comprising: a receiver in communication with a transmitter that receives one or more of the plurality of signals detected from the at least three electrodes and the one or more external context-related features from the external source in the form of one or more external signals; one or more processors; a non-transient computer-readable medium comprising instructions that, when executed by the one or more processors, cause the one or more processors to: perform one or more filters on the plurality of signals and/or on the one or more external signals; decode the plurality of signals and/or the one or more external signals into one or more context priors.

In some embodiments, the non-transient computer-readable medium further comprises instructions that, when executed by the one or more processors, cause the one or more processors to compute conditional probability distributions of one or more of: the plurality of signals (e.g. neural signals or optical signals) and one or more external signals decoded from the external source.

Aspects of the present disclosure include a non-transient computer-readable medium comprising instructions that, when executed by the one or more processors, cause the one or more processors to: extract one or more of: one or more context-related features from a plurality of signals from the brain of an individual, and one or more external context-related features from an external source; and decode one or more of: the one or more context-related features from the plurality of signals, and the one or more external context-related features from the external source.

In some embodiments, the computer-readable medium further comprises instructions that, when executed by the one or more processors, cause the one or more processors to gather contextual information from one or more of: the plurality of signals and the external context-related features from the external source using a context integration predictive model.

In some embodiments, the context integration predictive model comprises context priors. In some embodiments, the context priors are conditional probabilities. In some embodiments, decoding the one or more context-related features from the plurality of signals and the one or more external context-related features from the external source comprises detection, utterance classification, and/or context integration models.

In some embodiments, the computer-readable medium comprises further instructions that, when executed by the one or more processors, cause the one or more processors to output the decoded context-related features and decoded external context-related features into a context-dependent output.

In some embodiments, decoding comprises machine learning algorithms that identify spatial, temporal, or a combination of spatial and temporal neural patterns associated with the context-related events.

In some embodiments, the one or more processors comprises a classification model to predict a context-related feature (e.g. internal or external context-related features from the plurality of signals from the brain or from the external source). In some embodiments, the classification model comprises a hidden Markov model (HMM).

In some embodiments, one or more processors further comprises a hyperparameter optimization model.

In some embodiments, the one or more processors comprises a context integration model. In some embodiments, the context integration model is configured to predict context-related features in the individual (e.g. internal or external context-related features from the plurality of signals from the brain or from the external source). In some embodiments, the context integration model is configured to receive predicted utterance log likelihoods from the classification model.

In some embodiments, the one or more processors comprises conditional probabilities in the form of context priors, wherein the context prior is the probability inferred by one or more of: one or more of the context-related features from the plurality of signals and the one or more external context-related features from the external source.

In some embodiments, the one or more processors comprises predicted context-related feature probabilities configured to detect onsets and offsets of context-related feature events.

In some embodiments, the one or more processors comprises classification models to predict the likelihood of context-related feature utterances within a detected time segment in the neural or optical signals.

In some embodiments, the one or more processors comprises a principal component analysis (PCA) model. In some embodiments, the one or more processors comprises a machine learning algorithm. In some embodiments, the one or more processors comprises a linear discriminant analysis (LDA) model. In some embodiments, the one or more processors comprises a principal component analysis (PCA) model and a linear discriminant analysis (LDA) model. In some embodiments, the PCA and LDA models are configured to extract the principal components of the context-related feature (e.g. internal or external context-related features from the plurality of signals from the brain or from the external source). In some embodiments, the PCA and LDA models are configured to predict the context-related feature (e.g. internal or external context-related features from the plurality of signals from the brain or from the external source). In some embodiments, the PCA and LDA models are configured to output the context-related feature (e.g. internal or external context-related features from the plurality of signals from the brain or from the external source). In some embodiments, the PCA and LDA models are configured to predict context-related feature probabilities (e.g. internal or external context-related features from the plurality of signals from the brain or from the external source).

In some embodiments, decoding the context-related features comprises machine learning algorithms that identify spatial and/or temporal neural patterns associated with the context-related feature events (e.g. internal or external context-related features from the plurality of signals from the brain or from the external source).

In some embodiments, decoding the context-related feature output comprises using a probability classification model. In some embodiments, the probability classification model comprises Viterbi decoding to compute question (or any speech targets, including single-word targets, and "continuous" sentences of arbitrary lengths with large vocabulary sizes) utterance likelihoods and context priors to decode the context-related feature output from the neural or optical signals and/or external context-related features.

In some embodiments, decoding comprises predicting time segments of the neural signals that that are associated with context-related events.

Methods—Speech Synthesis Decoding

Provided are methods of decoding speech from the brain of a subject. The methods include decoding neural signals detected from electrodes operably coupled to the speech motor cortex of an individual and extracting speech-related features from the neural signals when an individual is intended to produce a speech output in order to decode the intended speech output from the neural signals. The methods further include decoding articulatory movement features from one or more features of the neural signals into acoustic signals and decoding the acoustic signals into a speech output. The methods further include decoding auditory perceived speech or verbal produced speech in an individual into one or more syllables, words, parts of words, phrases, utterances, paragraphs, sentences, and/or a combination thereof. Speech decoding systems and devices for practicing the subject methods are also provided.

Aspects of the present disclosure include a method of decoding speech events in an individual. In some embodiments, the method includes extracting speech-related features from a plurality of signals from the brain of an individual when the individual is intended to produce a speech output; and decoding with one or more decoding constraints the intended speech output from the plurality of signals.

In some embodiments, silent speech comprises making mouthing movements without producing an audible sound.

Intended speech can include "perceived" or "attempted" speech production and is used interchangeably herein. In some embodiments, context priors can be used to for decoding perceived or produced speech. Non-limiting examples of "perceived" speech can include predicted speech before a speech output is produced from the vocal tract in the individual. Non-limiting examples of "perceived" speech can include attempted speech before a speech output is produced from the vocal tract in the individual. In some embodiments, the methods of the present disclosure provide for decoding predicted speech output before a produced speech output. In some embodiments, the methods of the present disclosure provide for decoding predicted speech output at approximately five seconds or more, approximately ten seconds or more, approximately thirty seconds or more, approximately forty seconds or more, approximately fifty seconds or more, approximately one minute or more, approximately two minutes or more, approximately three minutes or more, approximately four minutes or more, or approximately five minutes or more before a produced speech output. In some embodiments, the methods of the present disclosure provide for decoding predicted speech output at five seconds or more, ten seconds or more, twenty seconds or more, thirty seconds or more, forty seconds or more, fifty seconds or more, one minute or more, two minutes or more, three minutes or more, four minutes or more, or five minutes or more before a produced speech output. In some embodiments, "produced" speech comprises one or more syllables, words, parts of words, phrases, utterances, paragraphs, parts of paragraphs, sentences, parts of sentences, and/or a combination thereof that produce an audible sound. In some embodiments, the methods of the present disclosure provide for decoding a produced speech output at approximately five seconds or more, approximately ten seconds or more, approximately twenty seconds or more, approximately thirty seconds or more, approximately forty seconds or more, approximately fifty seconds or more, approximately one minute or more, approximately two minutes or more, approximately three minutes or more, approximately four minutes or more, or approximately five minutes or more after a produced speech output. In some embodiments, the methods of the present disclosure provide for decoding a produced speech output at five seconds or more, ten seconds or more, thirty seconds or more, forty seconds or more, fifty seconds or more, one minute or more, two minutes or more, three minutes or more, four minutes or more, or five minutes or more after a produced speech output.

Aspects of the present disclosure further include methods of decoding auditory perceived speech or verbal produced speech in an individual, the method comprising: contacting an electrode array with the cortical region of the brain in the individual; conducting speech perception training on the individual, wherein speech perception training comprises listening to pre-recorded questions; conducting speech production training on the individual, wherein speech production training comprises reading one or more answers on a screen; conducting speech testing on the individual, wherein speech testing comprises listening to pre-recorded questions and responding verbally with answers to the pre-recorded questions; recording a time-aligned audio of the speech perception training, speech production training, and speech testing on the individual; recording neurophysiological signals; analyzing the neurophysiological signals in the cortical region of the brain; and decoding the neurophysiological signals into a speech output.

In some embodiments, the methods of the present disclosure comprise generating decoding constraints by conducting one or more external context-related cues. In some embodiments, the one or more external context-related cues includes listening to one or more questions. In some embodiments, the one or more questions are pre-recorded questions. In some embodiments, the one or more external context-related cues comprises reading one or more answers on a screen. In some embodiments, the one or more external context-related cues comprises reading aloud one or more syllables, words, parts of words, phrases, utterances, paragraphs, sentences, and/or a combination thereof. In some embodiments, the one or more external context-related cues comprises reading, aloud, one or more scripts. In some embodiments, the one or more external context-related cues comprises verbally producing a set of answer responses after listening to the one or more questions. In some embodiments, the one or more external context-related cues comprises reading one or more answers on a screen. In some embodiments, the one or more external context-related cues comprises responding to one or more questions. In some embodiments, responding to one or more questions comprises a verbal response. In some embodiments, responding to one or more questions comprises a silently mimed response. In some embodiments, the one or more external context-related cues comprises silently mimed speech. In some embodiments, the one or more external context-related cues comprises silently miming one or more syllables, words, parts of words, phrases, utterances, paragraphs, sentences, and/or a combination thereof by making the kinematic movements of a verbal response but without making sound. In some embodiments, the kinematic movements during the silently mimed speech is recorded (e.g. in the form of acoustic signals). In some embodiments, the kinematic movements are correlated with recorded acoustic signals. In some embodiments, the one or more external context-related cues comprises a verbal response.

In some embodiments, the verbal response is a sound. In some embodiments, the sound is selected from the group consisting of: a phoneme, formant acoustics of a vowel, a diphone, a triphone, a consonant-vowel transition, a syllable, a word, a phrase, a sentence, and combinations thereof.

In some embodiments, the data produced (e.g. neural signals, optical signals, audio recordings) from the one or more external context-related cues serve as input to train speech detection and decoding models of the present disclosure.

Aspects of the present disclosure include detecting a plurality of neurophysiological signals from the cortical region of the brain. In some embodiments, the plurality of neurophysiological signals are neural signals. In some embodiments, the plurality of neurophysiological signals are optical signals. In some embodiments, the neurophysiological signals are acquired by contacting 1 or more electrodes, 2 or more electrodes, or 3 or more electrodes that detect the plurality of signals with at least one region of the brain. In some embodiments, the neurophysiological signals are acquired by contacting 50 or more electrodes, 100 or more electrodes, 150 or more electrodes, 200 or more electrodes, 250 or more electrodes, or 300 or more electrodes that detect the plurality of signals with at least one region of the brain. In some embodiments, the at least one region of the brain comprises the speech motor cortex of the brain.

The neurophysiological signals are detected using at least three electrodes operably coupled to the speech motor cortex of the subject. By "operably coupled" is meant that one or more electrodes are of a suitable type and position so as to detect the desired neurophysiological signals in the speech motor cortex related to a speech event. According to one embodiment, the one or more electrodes are operably coupled to the speech motor cortex by implantation on the surface of the speech motor cortex. In one aspect, an array of electrocorticography electrodes (ECoG array) is disposed on the surface of the speech motor cortex (e.g., the vSMC) for detection of ECoG neural signals (e.g., local field potentials) generated in the speech motor cortex. In some embodiments, the method comprises extracted speech-related features from the neural or optical signals. In some embodiments, the speech-related features comprise local field potentials generated in the speech motor cortex. In some embodiments, the speech-related features comprise high gamma frequency signals (e.g. 70-200 Hz) generated in the speech motor cortex. In some embodiments, the speech-related features comprise spectral features of the neural signals. In some embodiments, the spectral features are Mel-frequency cepstral coefficients (MFCCs) extracted from the speech waveform (e.g. local field potentials generated in the speech motor cortex). According to certain embodiments, the one or more electrodes are operably coupled to the speech motor cortex by insertion of the electrodes into the speech motor cortex (e.g., at a desired depth). According to certain embodiments, the neurophysiological electrode array is implantable. According to certain embodiments, the neurophysiological electrode array is implanted directly on the surface of the brain.

The specific location at which to position an electrode may be determined by identification of anatomical landmarks in the subject's brain, such as the pre-central and post-central gyri and the central sulcus. Identification of anatomical landmarks in a subject's brain may be accomplished by any convenient means, such as magnetic resonance imaging (MRI), functional magnetic resonance imaging (fMRI), and visual inspection of a subject's brain while undergoing a craniotomy. Once a suitable location for an electrode is determined, the electrode may be positioned (e.g., implanted) according to any convenient means. Suitable locations for positioning or implanting the at least three electrodes may include, but are not limited to, one or more regions of the ventral sensorimotor cortex (vSMC), including the pre-central gyrus, the post-central gyrus, the guenon (the gyral area directly ventral to the termination of the central sulcus), the superior temporal gyrus (STG), the inferior frontal gyrus (IFG), and any combination thereof. Correct placement of the at least three electrodes may be confirmed by any convenient means, including visual inspection or computed tomography (CT) scan. In some aspects, after electrode positions are confirmed, they may be superimposed on a surface reconstruction image of the subject's brain. In certain aspects, the electrodes are positioned such that the neurophysiological signals are detected from one or more regions of the vSMC, e.g., the neurophysiological signals are detected from a region of the vSMC selected from the pre-central gyrus, the post-central gyrus, the guenon, STG, IFG, and combinations thereof.

Methods of interest for positioning electrodes further include, but are not limited to, those described in U.S. Pat. Nos. 4,084,583; 5,119,816; 5,291,888; 5,361,773; 5,479,934; 5,724,984; 5,817,029; 6,256,531; 6,381,481; 6,510,340; 7,239,910; 7,715,607; 7,908,009; 8,045,775; and 8,019,142; the disclosures of which are incorporated herein by reference in their entireties for all purposes.

The number of electrodes operably coupled to the speech motor cortex may be chosen so as to provide the desired resolution and information about the neurophysiological neural signals being generated in the speech motor cortex during one or more external context-related cues, as each electrode may convey information about the activity of a particular region (e.g., the vSMC, STG, or IFG as described in the examples below). By comparing differences between the signals of each electrode, neurophysiological neural signal patterns may be derived from the neural signals, or which electrodes responsive to the speech perception or speech production.

Accordingly, in certain embodiments, at least 10 electrodes (e.g., at least 20 electrodes) are employed. Between about 3 and 1024 electrodes, or more, may be employed. In some embodiments, the number of electrodes positioned is about 3 to 10 electrodes, about 10 to 20 electrodes, about 20 to 30 electrodes, about 30 to 40 electrodes, about 40 to 50 electrodes, about 60 to 70 electrodes, about 70 to 80 electrodes, about 80 to 90 electrodes, about 90 to 100 electrodes, about 100 to 110 electrodes, about 110 to 120 electrodes, about 120 to 130 electrodes, about 130 to 140 electrodes, about 140 to 150 electrodes, about 150 to 160 electrodes, about 160 to 170 electrodes, about 170 to 180 electrodes, about 180 to 190 electrodes, about 190 to 200 electrodes, about 200 to 210 electrodes, about 210 to 220 electrodes, about 220 to 230 electrodes, about 230 to 240 electrodes, about 240 to 250 electrodes, about 250 to 300 electrodes (e.g., a 16×16 array of 256 electrodes), about 300 to 400 electrodes, about 400 to 500 electrodes, about 500 to 600 electrodes, about 600 to 700 electrodes, about 700 to 800 electrodes, about 800 to 900 electrodes, about 900 to 1000 electrodes, or about 1000 to 1024 electrodes, or more. The electrodes may be homogeneous or heterogeneous.

Electrodes may be arranged in no particular pattern or any convenient pattern to facilitate detection of neural signals. For example, a plurality of electrodes may be placed in a grid pattern, in which the spacing between adjacent electrodes is approximately equivalent. Such spacing between adjacent electrodes may be, for example, about 2.5 cm or less, about 2 cm or less, about 1.5 cm or less, about 1 cm or less, about 0.5 cm or less, about 0.1 cm or less, or about 0.05 cm or less. Electrodes placed in a grid pattern may be arranged such that the overall plurality of electrodes forms a roughly geometrical shape. In certain embodiments, a grid pattern may be roughly square in overall shape, roughly rectangular, roughly trapezoidal, or roughly oval in shape, or roughly circular.

Electrodes may be pre-arranged into an array, such that the array includes a plurality of electrodes that may be placed on or in a subject's brain. Such arrays may be miniature- or micro-arrays, a non-limiting example of which may be a miniature neurophysiological array (e.g. ECoG array, microelectrode array, electroencephalography (EEG), array). For a general review of ECoG technology, see Ajmone-Marsan, C. Electrocorticography: Historical Comments on its Development and the Evolution of its Practical Applications, Electroencephalogr. Clin. Neurophysiol, Suppl. 1998, 48: 10-16; the disclosure of which is incorporated herein by reference.

Also of interest are electrodes that may receive electroencephalography (EEG) data. One or more wet or dry EEG electrodes may be used in practicing the subject methods. Electrodes and electrode systems of interest further include, but are not limited to, those described in U.S. Patent Publication Numbers 2007/0093706, 2009/0281408, 2010/0130844, 2010/0198042, 2011/0046502, 2011/0046503, 2011/0046504, 2011/0237923, 2011/0282231, 2011/0282232 and U.S. Pat. Nos. 4,709,702, 4,967,038, 5,038,782, 6,154,669; the disclosures of which are incorporated herein by reference.

An array may include, for example, about 5 electrodes or more, e.g., about 5 to 10 electrodes, about 10 to 20 electrodes, about 20 to 30 electrodes, about 30 to 40 electrodes, about 40 to 50 electrodes, about 50 to 60 electrodes, about 60 to 70 electrodes, about 70 to 80 electrodes, about 80 to 90 electrodes, about 90 to 100 electrodes, about 100 to 125 electrodes, about 125 to 150 electrodes, about 150 to 200 electrodes, about 200 to 250 electrodes, about 250 to 300 electrodes (e.g., a 256 electrode array in 16×16 format), about 300 to 400 electrodes, about 400 to 500 electrodes, or about 500 electrodes or more. In certain embodiments, the array may cover a surface area of about 1 $cm^2$, about 1 to 10 $cm^2$, about 10 to 25 $cm^2$, about 25 to 50 $cm^2$, about 50 to 75 $cm^2$, about 75 to 100 $cm^2$, or 100 $cm^2$ or more. Arrays of interest may include, but are not limited to, those described in U.S. Pat. Nos. USD565735; USD603051; USD641886; and USD647208; the disclosures of which are incorporated herein by reference.

Electrodes may be platinum-iridium electrodes or be made out of any convenient material. The diameter, length, and composition of the electrodes to be employed may be determined in accordance with routine procedures known to those skilled in the art. Factors which may be weighted when selecting an appropriate electrode type may include but not be limited to the desired location for placement, the type of subject, the age of the subject, cost, duration for which the electrode may need to be positioned, and other factors.

In certain aspects, an array of electrodes (e.g., an ECoG array, microelectrode array, EEG array) is positioned on the surface of the speech motor cortex such that the array covers the entire or substantially the entire region of the speech motor cortex corresponding to the somatotopic arrangement of articulatory kinematic representations of the subject. For example, the electrode array may be disposed on the surface of the speech motor cortex from −100 mm to +100 mm, from −80 mm to +80 mm, from −60 mm to +60 mm, from −40 mm to +40 mm, or from −20 mm to +20 mm relative to the central sulcus along the anterior-posterior axis. Alternatively, or additionally, the electrode array may be disposed on the surface of the speech motor cortex from a location at or proximal to the Sylvian fissure to a distance of 500 mm or less, 400 mm or less, 300 mm or less, 200 mm or less, 100 mm or less, 90 mm or less, 80 mm or less, 70 mm or less, 60 mm or less, 50 mm or less, or 40 mm or less from the Sylvian fissure along the dorsal-ventral axis. Non-limiting examples of an array and example positioning thereof can be found in U.S. Pat. No. 9,905,239, which is hereby incorporated by reference in its entirety.

In certain embodiments, a ground electrode or reference electrode may be positioned. A ground or reference electrode may be placed at any convenient location, where such locations are known to those of skill in the art. In certain embodiments, a ground electrode or reference electrode is a scalp electrode. A scalp electrode may be placed on a subject's forehead or in any other convenient location.

Aspects of the present disclosure comprise detecting a plurality of signals when an individual is intended to produce a speech output. In some embodiments, the plurality of signals are acquired by any known neurophysiological recording device. In some embodiments, the plurality of signals are acquired through optical devices. Optical devices that can be used to acquire the plurality of signals include, but are not limited to: intrinsic optical signal (IOS) imaging, extrinsic optical signal (EOS) imaging, Doppler flowmetry (LDF), near-infrared (NIR) spectrometer, functional optical coherence tomography (fOCT), and surface plasmon resonance (SPR). Other techniques such as radioactive imaging can be used to acquire the plurality of signals. Non-limiting examples include radioactive imaging of changes in blood flow, magnetoencephalography (MEG), thermal imaging, positron-emission tomography (PET), functional magnetic resonance imaging (fMRI), and diffuse optical tomography (DOT). In some embodiments, the plurality of signals are acquired by microelectrodes. In some embodiments, the plurality of signals are acquired by ECoG. In some embodiments, the plurality of signals are acquired by EEG. In some embodiments, the plurality of signals are acquired by intracranial spike recordings. In some embodiments, the plurality of signals are neural signals. In some embodiments, the plurality of signals comprise local field potentials from the speech motor cortex of the brain. In some embodiments, the plurality of signals are acquired by functional magnetic resonance imaging (fMRI), blood oxygen level-dependent (BOLD)-fMRI, diffusion tensor imaging (DTI), manganese-enhanced MRI (ME-MRI), multiphoton microscopy (MP), magnetoencephalographic imaging (MEGI), and the like.

In some embodiments, the method comprises extracting speech-related features from the neural signals. In some embodiments, extracting speech-related features from the neural signals comprises filtering the plurality of signals in a high gamma frequency range to obtain neural signals in the auditory and sensorimotor brain regions. In some embodiments, plurality of signals are obtained from auditory and sensorimotor brain regions selected from the vSMC, STG, and IFG. In some embodiments, the plurality of signals comprise the high-gamma frequency component of the local field potentials. The high-gamma frequency component of the local field potential is a high-gamma frequency range of the plurality of signals associated with an intended speech output. In some embodiments, the high-gamma frequency range ranges from 70-200 Hz (e.g. 70-75 Hz, 75-80 Hz, 80-85 Hz, 95-90 Hz, 90-95 Hz, 95-100 Hz, 100-105 Hz, 105-110 Hz, 110-115 Hz, 115-120 Hz, 120-125 Hz, 125-130 Hz, 130-135 Hz, 135-140 Hz, 140-145 Hz, 145-150 Hz, 150-155 Hz, 155-160 Hz, 160-165 Hz, 165-170 Hz, 170-175 Hz, 175-180 Hz, 180-185 Hz, 185-190 Hz, 190-195 Hz, or 195-200 Hz). In some embodiments, the high-gamma frequency range ranges from 70-150 Hz. In some embodiments, the analytic amplitude of the high-gamma frequency component of the local field potentials was extracted with the Hilbert transform and down-sampled to 200 Hz. In some embodiments, the plurality of signals comprise a low frequency component (e.g. 1-30 Hz) extracted with a 5th order Butterworth bandpass filter and parallelly aligned with the high-gamma amplitude.

In some embodiments, electrodes for which neural signals are collected are from electrodes located on cortical areas related to speech, such as the vSMC, STG, and/or IFG.

In some embodiments, the one or more speech related features comprises the high-gamma amplitude frequency range that correlated with multi-unit firing rates within the neural signals. In some embodiments, the high gamma amplitude frequency range comprises the temporal resolution to resolve fine articulatory movements in the individual.

In some embodiments, the method further comprises recording acoustic signals (e.g. audio signals). In some embodiments, the method further comprises translating the recorded acoustic signals into phonetic transcriptions. In some embodiments, the method comprises aligning the time of the acoustic signals with one or more external context-related cues and/or speech events. In some embodiments, recording acoustic signals occurs during one or more external context-related cues. In some embodiments, the acoustic signals are recorded as acoustic waveforms. In some embodiments, the acoustic signals are represented as spectral features with the following parameters: a 25 mel-frequency cepstral coefficients (MFCCs), and/or 5 sub-band voicing strengths for glottal excitation modelling, pitch, and voicing (e.g. 32 features). In some embodiments, the acoustic parameters are configured to emphasize perceptually relevant acoustic features while maximizing audio reconstruction quality.

In some embodiments, the method further comprises one or more processors. In some embodiments, the one or more processors comprises one or more decoders. In some embodiments, the one or more decoders is configured to decode and/or synthesize neural signals. In some embodiments, the one or more decoders is configured to decode and/or synthesize acoustic signals. In some embodiments, the one or more decoders are configured to synthesize the neural signals into acoustic signals. In some embodiments, neural signals and acoustic signals are recorded simultaneously. In some embodiments, neural signals and acoustic signals are recorded simultaneously during one or more external context-related cues. In some embodiments, the method further comprises assessing and/or computing the spectral distortion between the recorded acoustic signals and the decoded acoustic signals synthesized from the neural signals. In some embodiments, the spectral distortion is computed using a Mel-cepstral distortion (MCD) metric (e.g. as shown in FIG. 1E-1*f*). The use of Mel-frequency bands as an acoustic parameter emphasizes the distortion of perceptually relevant frequency bands of the audio spectrogram.

In some embodiments, MCD of the synthesized speech is calculated when compared to original ground-truth audio recordings (e.g. recorded acoustic signals). MCD is an objective measure of error determined from MFCCs and is correlated to subjective perceptual judgments of acoustic quality. For reference acoustic features $mc^{(y)}$ and decoded features $mc^{(\hat{y})}$, $$MCD = \frac{10}{\ln(10)}\sqrt{\sum_{0<d<25}\left(mc_d^{(y)} - mc_d^{(\hat{y})}\right)^2} \quad (1)$$

In some embodiments, the method comprises quantifying one or more external context-related cues. In some embodiments, the one or more external context-related cues comprises silent speech. In some embodiments, the method comprises decoding silent speech. In some embodiments, the method comprises assessing decoding performance by decoding silent speech compared to the audible speech of a word, sentence, and/or paragraph uttered immediately prior to silent speech. In some embodiments, the method comprises dynamically time warping the decoded silent speech MFCCs to the MFCCs of the audible condition and computing Pearson's correlation coefficient and Mel-cepstral distortion.

In some embodiments, the method comprises detecting when the individual is intended to produce a speech output. In some embodiments, said detecting comprises recording neural signals during one or more external context-related cues. In some embodiments, said detecting comprises extracting high-gamma amplitude signals and/or low frequency signals from the raw neural signals of each electrode.

In some embodiments, the method comprises extracting speech-related features from the signals and decoding the intended speech output in real-time.

In some embodiments, the method further comprises timing the individual during the speech event. In some embodiments, the method further comprises timing the individual during the one or more external context-related cues. In some embodiments, the decoder synthesizes one or more external context-related cues based on the kinematic movements (e.g. articulatory kinematics) of the individual during a speech event and/or one or more external context-related cues. In some embodiments, the articulatory kinematics are configured to capture the physiological process by which speech is generated and/or encoded in the speech motor cortex (e.g. vSMC). In some embodiments where the one or more external context-related cues comprises silent mimes, the decoder synthesizes silent mimed speech based on the kinematic movements of the individual during the silent mimes. In some embodiments, the decoder synthesizes spectral features of silently mimed speech that are never audibly uttered. In some embodiments, the silently mimed speech is dynamically time-warped according to spectral features of the acoustic signals.

In some embodiments, the method further comprises translating the speech events into phonetic transcriptions or text. In some embodiments, the method comprises comparing median spectrograms of phonemes from original (e.g. recorded acoustic signals) and decoded (e.g. acoustic signals decoded from neural signals) audio. In some embodiments, the acoustic signals decoded from neural signals closely resemble original speech. In some embodiments, the method further comprises computing phone likelihoods at each time point during the speech event.

In some embodiments, decoding comprises predicting time segments of the neural signals that that are associated with speech events. In some embodiments, the time segment comprises at least 30 seconds, at least 1 minute, at least 5 minutes, at least 10 minutes, at least 20 minutes, at least 25 minutes, at least 30 minutes, at least 35 minutes, at least 40 minutes, at least 50 minutes, at least 55 minutes, or at least 60 minutes of speech.

In some embodiments, decoding the intended speech output comprises machine learning algorithms that identify spatiotemporal neural patterns associated with the speech events. In some embodiments, the machine learning algorithms require speech training data associated with a speech event. In some embodiments, the machine learning algorithm require at least 30 seconds, at least 1 minute, at least 5 minutes, at least 10 minutes, at least 20 minutes, at least 25 minutes, at least 30 minutes, at least 35 minutes, at least 40 minutes, at least 50 minutes, at least 55 minutes, or at least 60 minutes of speech training data. In some embodiments, the spatiotemporal neural patterns comprise rapid evoked responses in the STG during the speech events. In some embodiments, decoding the intended speech output comprises predicting the temporal onsets and offsets of the speech events based on the rapid evoked responses in the STG.

In some embodiments, wherein the method further comprises displaying the decoded speech output. In some embodiments, the speech output is displayed on a screen. In some embodiments, the speech output is displayed on a screen as one or more syllables, words, parts of words, phrases, utterances, paragraphs, sentences, and/or a combination thereof. In some embodiments, the speech output is displayed on a screen as one or more sentences. In some embodiments, the speech output is displayed on a computer, a tablet computer or smart phone, or any related computing device. In some embodiments, the tablet computer or smartphone runs an operating system selected from an iOS™ operating system, an Android™ operating system, a Windows™ operating system, or any other tablet- or smartphone-compatible operating system.

Aspects of the present disclosure include a non-transitory computer readable medium storing instructions that, when executed by one or more processors and/or computing devices, cause the one or more processors and/or computing devices to perform the steps for decoding speech events in an individual, as provided herein.

Aspects of the present disclosure include a non-transitory computer readable medium storing instructions that, when executed by one or more processors and/or computing devices, cause the one or more processors and/or computing devices to perform the steps for decoding auditory perceived speech or verbal produced speech in an individual, as provided herein.

In some embodiments, the method of the present disclosure method is carried out using a receiver unit, comprising: a wireless receiver in communication with a wireless transmitter that receives the plurality of signals detected from at least three electrodes; one or more processors; a non-transient computer-readable medium comprising instructions that, when executed by the one or more processors, cause the one or more processors to: perform one or more filters on the plurality of signals; decode the plurality of signals into articulatory movement representations; and output the plurality of acoustic signals into a speech output.

In some embodiments, the method comprises filtering the plurality of signals with one or more filters. In some embodiments, the one or more filters comprises one or more notch filters. In some embodiments, the one or more filters comprises one or more band-pass finish impulse response (FIR) filters. In some embodiments, the one or more processors is configured to extract analytic amplitude values across the one or more band-pass FIR filters applied to the plurality of signals. In some embodiments, the one or more processors is configured to average the analytic amplitude values across the one or more band-pass FIR filters to obtain one or more high gamma analytic amplitude signals (e.g. high gamma frequency range signals).

In some embodiments, the one or more processors is configured to normalize and store the one or more high gamma analytic amplitude signals in an event detector process. In some embodiments, the event detector process is configured to analyze the high gamma analytic signals. In some embodiments, the gamma analytic signals are analyzed at one or more time points to predict the onset and offset of auditory perceived or verbal produced speech events. In some embodiments, the one or more time points comprises 10 or more ms time points, 20 or more ms time points, 30 or more ms time points, 40 or more ms time points, or 50 or more ms time points. In some embodiments, the one or more time points comprises 10 or more ms time points, 50 or more ms timepoints, 100 or more ms time points, 150 or more ms time points, 200 or more time points, 250 or more ms timepoints, 300 or more ms time points, 350 or more ms time points, 400 ms or more time points, 450 or more ms time points, or 500 or more ms time points.

In some embodiments, the one or more processors are configured to decode the one or more high gamma analytic amplitude signals into the speech output.

In some embodiments, the one or more processors is a neural decoder. In some embodiments, the method comprises two or more processors, three or more processors, four or more processors, or five or more processors. In some embodiments, the one or more processors comprises a neural decoder comprising a bidirectional long short-term memory comprising an algorithm for decoding the plurality of acoustic signals into the speech output. In some embodiments, the one or more processors is one or more (e.g. two or more, three or more, four or more, or five or more) stacked 3-layer bidirectional long short term memory (bLSTM) recurrent neural networks. In some embodiments, a first stacked 3-layer bLSTM is configured to learn the mapping between time point windows (e.g. 300 ms windows) of high-gamma and local field potential signals and the corresponding single time point of 32 articulatory features related to movement of the vocal tract. In some embodiments, a second stacked 3-layer bLSTM is configured to learn the mapping between the output of decoded articulatory features and 32 acoustic parameters for decoding an intended speech output (e.g. one or more syllables, words, parts of words, phrases, utterances, paragraphs, sentences, and/or a combination thereof). In some embodiments, the first and/or second stacked 3-layer bLSTM is trained with a learning rate of 0.001.

In some embodiments, the bLSTM decodes speech-related features from the neural signals. In some embodiments, the speech-related features are articulatory kinematic features from the neural or optical signals. In some embodiments, the speech-related features comprises articulatory movement representations. In some embodiments, the one or more processors decodes the articulatory movement representations into acoustic signals. In some embodiments, the speech-related features comprises articulatory kinematic features. In some embodiments, the one or more processors decodes the articulatory kinematic features into acoustic signals. In some embodiments, the one or more processors decodes the articulatory movement representations and the articulatory kinematic features into acoustic signals. In some embodiments, a second bLSTM decodes acoustic features from the speech-related features of the neural or optical signals. In some embodiments, the bLSTM decodes acoustic features from the decoded articulatory kinematic features from the neural signals. In some embodiments, the bLSTM decodes acoustic features from the articulatory movement features. In some embodiments, the articulatory movement features comprise recorded acoustic signals during a speech event.

In some embodiments, the one or more processors comprises an algorithm for decoding an intended speech output. In some embodiments, the algorithm is an articulatory kinematics inference model. In some embodiments, the articulatory inference model comprises a stacked deep encoder-decoder. In some embodiments, the encoder combines phonological and acoustic representations into a latent articulatory representation that is then decoded to reconstruct the original acoustic signal during a speech event. In some embodiments, the latent representation is initialized with inferred articulatory movement from Electromagnetic Midsagittal Articulography (EMA) and appropriate manner features.

In some embodiments, the one or more processors comprises a machine learning algorithm for estimating 32 dimensional articulatory kinematic trajectories (e.g. acoustically consequential movements of the vocal tract) using only produced acoustic and phonetic transcriptions. Dimensional articulatory kinematic trajectories are described in Chartier et al. (*Neuron* (2018) 98:5, pgs 1042-1054), which is hereby incorporated by reference in its entirety. In some embodiments, the dimensional articulatory kinematic trajectories are represented as place manner tuples (representations as continuous binary valued features) that incorporate physiological aspects in EMA, which include one or more of the tongue blade, tongue tip, jaw, upper lip, lower lip, velar stop, velar nasal, palatal approximant, palatal fricative, palatal affricate, labial stop, labial approximant, labial nasal, glottal fricative, dental fricative, labiodental fricative, alveolar stop, alveolar approximant, alveolar nasal, alveolar lateral, alveolar fricative, unconstructed, and voicing. In some embodiments, the machine learning algorithm comprises an existing annotated speech database (Wall Street Journal Corpus) and trained speaker independent deep recurrent network regression models to predict the place-manner tuple vectors from the acoustic signal of a speech event.

In some embodiments, the one or more processors comprises an autoencoder. In some embodiments, the autoencoder is a recurrent neural network encoder that is trained to convert phonological and acoustic features to the initialized 32 articulatory representations. In some embodiments, the one or more processor comprises a decoder, wherein the decoder converts the articulatory representation back to acoustic signals. In some embodiments, the one or more processors (e.g. stacked neural network) is re-trained optimizing the joint loss on acoustic and EMA parameters. After convergence, the encoder is used to estimate the final articulatory kinematic features that act as the intermediate to decode acoustics from neural signals.

In some embodiments, the one or more processors further comprises an autoencoder configured to convert phonological and acoustic features of the audible speech or silent speech acoustic signals into one or more articulatory representations. In some embodiments, the one or more processors further comprises a decoder configured to convert the one or more articulatory representations to audible speech or silent speech acoustic signals. In some embodiments, the one or more processors further comprises an encoder configured to estimate final articulatory kinematic features, wherein the final articulatory kinematic features are used in an algorithm to decode articulatory movement features from the neural signals.

In some embodiments, the one or more processors comprises a deep neural network comprising an algorithm for decoding the audible speech or silent speech acoustic signal as mel frequency cepstral coefficients. In some embodiments, the deep neural network comprises an algorithm for decoding the audible speech or silent speech acoustic signals as 25 dimensional mel frequency cepstral coefficients.

In some embodiments, the one or more processors comprises a hidden Markov model based acoustic model configured to perform sub-phonetic alignment.

In some embodiments, the one or more processors comprises a Kullback-Leibler (KL) divergence model configured to compare the distribution of a decoded phoneme of the neural signals to a distribution of a ground-truth phoneme.

Aspects of the present disclosure further include methods of decoding auditory perceived speech or verbal produced speech in an individual, the method comprising: contacting an electrode array with the cortical region of the brain in the individual; conducting speech perception training on the individual, wherein speech perception training comprises listening to pre-recorded questions; conducting speech production training on the individual, wherein speech production training comprises reading one or more answers on a screen; conducting speech testing on the individual, wherein speech testing comprises listening to pre-recorded questions and responding verbally with answers to the pre-recorded questions; recording a time-aligned audio of the speech perception training, speech production training, and speech testing on the individual; recording neural signals; analyzing the neural signals in the cortical region of the brain; and decoding the neural signals into a speech output.

In some embodiments, the method further comprises translating the time-aligned audio into phonetic transcriptions or text.

In some embodiments, the method further comprises determining time points at which the recorded neural signals is associated with speech perception, speech production, speech testing, or silence.

In some embodiments, the method further comprises determining which electrodes in the electrode array are responsive to the speech perception training, speech production training, or speech testing.

In some embodiments, the electrode array comprises 3 or more electrodes.

In some embodiments, decoding comprises computing speech perception, speech production, or silence probabilities. In some embodiments, the decoding is computed with one or more processors as described in the present disclosure. In some embodiments, the method comprises a non-transient computer-readable medium comprising instructions that, when executed by the one or more processors, cause the one or more processors to perform its intended function as disclosed herein.

In some embodiments, the methods of the present disclosure include methods of decoding intended speech events in an individual, the method comprising extracting speech-related features from a plurality of signals from the brain of the individual when the individual is intended to produce a speech output; and decoding, with one or more decoding constraints, the intended speech output from the plurality of signals.

In some embodiments, the plurality of signals comprises neural signals acquired by electrocorticography (ECoG), electroencephalography (EEG), or microelectrodes.

In some embodiments, the plurality of signals comprises optical signals, wherein the optical signals are fast optical signals (FOS) or event-related optical signals (EROS) or BOLD signals in functional magnetic resonance imaging (fMRI).

In some embodiments, said acquiring comprises contacting at least three electrodes that detect the plurality of signals with at least one region of the brain. In some embodiments, the at least one region of the brain comprises the speech motor cortex of the brain. In some embodiments, the at least one region of the brain is selected from the sensorimotor cortex (SMC), superior temporal gyrus (STG), and inferior frontal gyrus (IFG).

In some embodiments, contacting comprises implantation on the surface of the speech motor cortex of the brain. In some embodiments, the plurality of signals comprise local field or action potentials from the at least one region of the brain. In some embodiments, the plurality of signals comprise the high-gamma frequency or other frequency components of the local field potentials.

In some embodiments, the method further comprises detecting when the individual is intended to produce a speech output.

In some embodiments, wherein extracting speech-related features from the signals and decoding the intended speech output occurs in real-time. In some embodiments, where the one or more external context-related cues comprises listening to pre-recorded questions. In some embodiments, the one or more external context-related cues comprises reading one or more answers on a screen. In some embodiments, wherein the one or more external context-related cues comprises responding to pre-recorded questions. In some embodiments, wherein responding to pre-recorded questions comprises a verbal response. In some embodiments, wherein the verbal response is a sound. In some embodiments, wherein the sound is selected from the group consisting of: a phoneme, formant acoustics of a vowel, a diphone, a triphone, a consonant-vowel transition, a syllable, a word, a phrase, a sentence, and combinations thereof. In some embodiments, wherein the one or more external context-related cues comprises visually responding to pre-recorded questions.

In some embodiments, wherein the method further comprises timing the individual during the speech event. In some embodiments, wherein the one or more external context-related cues comprises silently mimed speech.

In some embodiments, wherein the method further comprises translating the speech events into phonetic transcriptions or text. In some embodiments, wherein the method further comprises computing phone likelihoods at each time point during the speech event.

In some embodiments, wherein said extracting speech-related features comprises filtering the plurality of signals in a high gamma frequency range to obtain neural signals in the auditory and sensorimotor brain regions. In some embodiments, wherein the plurality of signals are obtained from auditory and sensorimotor brain regions selected from the vSMC, STG, and IFG.

In some embodiments, wherein the high gamma frequency ranges from 70 to 200 Hz.

In some embodiments, wherein decoding comprises predicting time segments of the neural signals that that are associated with speech events. In some embodiments, wherein the intended speech output is decoded before the produced speech output.

In some embodiments, wherein the neural signals comprise rapid evoked responses in the one or more regions in the brain during the speech events.

In some embodiments, wherein decoding comprises predicting the temporal onsets and offsets of the speech events based on the rapid evoked responses in the one or more regions of the brain.

In some embodiments, wherein the method further comprises displaying the decoded speech output. In some embodiments, wherein the speech output is displayed on a screen as one or more words. In some embodiments, wherein the speech output is displayed on a screen as one or more sentences.

In some embodiments, wherein the method is carried out using a receiver unit, comprising: a receiver (e.g. wireless or non-wireless) in communication with a transmitter that receives the plurality of signals detected from the at least three electrodes; one or more processors; a non-transient computer-readable medium comprising instructions that, when executed by the one or more processors, cause the one or more processors to: perform one or more filters on the plurality of signals; decode the plurality of signals into articulatory movement representations; and output the plurality of acoustic signals into a speech output.

In some embodiments, wherein the one or more processors is a neural decoder. In some embodiments, wherein the one or more processors decodes the articulatory movement representations into acoustic signals. In some embodiments, wherein the one or more filters comprises one or more notch filters. In some embodiments, wherein the one or more processors is further configured to stream the plurality of signals onto a computer. In some embodiments, wherein the one or more filters comprises one or more band-pass finish impulse response (FIR) filters. In some embodiments, wherein the one or more processors is configured to extract analytic amplitude values across the one or more band-pass FIR filters applied to the plurality of signals. In some embodiments, wherein the one or more processors is configured to average the analytic amplitude values across the one or more band-pass FIR filters to obtain one or more gamma (e.g. high) analytic amplitude signals. In some embodiments, wherein the one or more processors is configured to normalize and store the one or more gamma (e.g. high) analytic amplitude signals. In some embodiments, wherein the one or more processors comprises an event detector process configured to analyze the gamma (e.g. high) analytic signals.

In some embodiments, wherein the gamma (e.g. high) analytic signals are analyzed at one or more time points to predict the onset and offset of auditory perceived or verbal produced speech events. In some embodiments, wherein the one or more processors are configured to decode the one or more high gamma analytic amplitude signals into the speech output.

In some embodiments, wherein the neural decoder comprises a bidirectional long short-term memory recurrent neural network comprising an algorithm for decoding the plurality of acoustic signals into the speech output.

Aspects of the present disclosure include a method of decoding auditory perceived speech or verbal produced speech in an individual, the method comprising: a) contacting an electrode array with the cortical region of the brain in the individual; b) conducting at least one of: speech perception training on the individual, wherein speech perception training comprises listening to a sound; speech production training on the individual, wherein speech production training comprises reading; speech testing on the individual, wherein speech testing comprises listening to a sound and responding verbally to the sound; e) recording a time-aligned audio of the speech perception training, speech production training, and speech testing on the individual; f) recording a plurality of signals in step b); g) analyzing the neural signals in the cortical region of the brain; and i) decoding the neural signals into a speech output.

In some embodiments, wherein the plurality of signals are neural signals. In some embodiments, wherein the method further comprises translating the time-aligned audio in step e) into phonetic transcriptions or text. In some embodiments, wherein the method further comprises determining time points at which the recorded neural signals is associated with speech perception, speech production, speech testing, or silence.

In some embodiments, the method further comprises determining which electrodes in the electrode array are responsive to the speech perception training, speech production training, or speech testing. In some embodiments, the electrode array comprises three or more electrodes. In some embodiments, decoding comprises computing speech perception, speech production, or silence probabilities.

Systems—Decoding Contextual Information

Also provided are systems for performing the methods of the present disclosure. Such systems include decoding contextual information from brain activity in the individual and/or from external context-related features.

Aspects of the present disclosure include a context decoding system comprising: one or more processors comprising a context decoder configured to decode context related features from one or more of: a plurality of signals from the brain of an individual, and one or more external context-related features from an external source.

Aspects of the present disclosure include a context decoding system comprising: an electrode array in contact with the cortical region of the brain in the individual; one or more processors; a non-transient computer-readable medium comprising instructions that, when executed by the one or more processors, cause the one or more processors to: extract one or more of: one or more context-related features from a plurality of signals from the brain of an individual, and one or more external context-related features from an external source; and decode one or more of: the one or more context-related features from the plurality of signals, and the one or more external context-related features from the external source. In some embodiments, the external source decodes the one or more external context-related features into one or more external signals.

In some embodiments, the external source comprises a natural language text analyzer, an acoustic device, an imaging device, a time tracking device, a heart monitoring device, a computer, a telecommunication device, a GPS, a radio, a television, or a combination thereof. In some embodiments, the time tracking device is a clock. In some embodiments, an imaging device is a charge-coupled device. In some embodiments, the charge-coupled device is a camera.

In some embodiments, the one or more external context-related features comprises semantics or other linguistics attributes from text or language, visual environmental objects in physical proximity to the individual, locational data of the individual, the time of day, weather, heart rate, sound, or a combination thereof. In some embodiments, the external context-related features are decoded from the external source. For example, in a clinical speech decoding application, a camera could be used to provide information about nearby objects that the patient would like to interact with (light switches, water, computers, etc.). The emotional state of the patient could also be inferred and used to influence the speech decoder. The time of day can be used to inform the decoder too (e.g. one would be far more likely to say 'good morning' if it is, in fact, morning time and not evening time). Therefore, speech decoding of the present invention is not limited to decoding speech from brain activity, but also using all available information to inform and assist the decoder. This meta-data can be explicit (eg. time, location, etc) vs implicit (e.g. what someone heard, as inferred from brain activity, or how someone feels).

Aspects of the present disclosure include a contextual decoding system comprising an electrical array in contact with the cortical region of the brain in the individual, wherein the electrode array comprises a plurality of electrodes; an electrical recording device configured to record neural signals in the brain, one or more processors, a non-transient computer-readable medium comprising instructions that, when executed by the processor, cause the processor to perform one or more filters on one or more of: the plurality of signals, and one or more external context-related features from an external source; decode one or more of: the plurality of signals into context-related features, and output context-related features and the external context-related features into a speech output. In some embodiments, the external context-related features is decoded by the external source into external signals.

In some embodiments, the one or more context-related features comprises language-related features, pain-related features, anxiety-related features, mood-related features, thoughts, sounds, or a combination thereof, from the individual from the plurality of signals.

In some embodiments, the neural array comprises a plurality of electrodes. In some embodiments, the plurality of electrodes comprises 50 or more electrodes, 100 or more electrodes, 150 or more electrodes, 200 or more electrodes, 250 or more electrodes, 300 or more electrodes, 350 or more electrodes, 400 or more electrodes, 450 or more electrodes, or 500 or more electrodes.

In some embodiments, the system comprises an electrical recording device configured to record neural signals in the brain. In some embodiments, the electrical recording device is a 16-channel recording device. In some embodiments, the electrical recording device is a 32-channel recording device. In some embodiments, the electrical recording device is a 64-channel recording device. 128-channel recording device. In some embodiments, the electrical recording device is a 256-channel recording device. In some embodiments, the electrical recording device is implantable. In some embodiments, the electrical recording device is wireless.

In some embodiments, the electrical recording device is an EEG device. In some embodiments, the electrical recording device is an ECoG device. In some embodiments, the electrical recording device is microelectrodes.

In some embodiments, the plurality of signals are ECoG signals or EEG signals. In some embodiments, the ECoG signals or EEG signals are neural signals.

In some embodiments, the system includes an optical device for configured to acquire optical signals associated with one or more context-related features. In some embodiments, the plurality of signals are acquired by any known neurophysiological recording device. In some embodiments, the plurality of signals are optical signals. In some embodiments, the plurality of signals are acquired through optical devices. Optical devices that can be used to acquire the plurality of signals include, but are not limited to: intrinsic optical signal (IOS) imaging, extrinsic optical signal (EOS) imaging, Doppler flowmetry (LDF), near-infrared (NIR) spectrometer, functional optical coherence tomography (fOCT), and surface plasmon resonance (SPR). Other techniques such as radioactive imaging can be used to acquire the plurality of signals. Non-limiting examples include radioactive imaging of changes in blood flow, magnetoencephalography (MEG), thermal imaging, positron-emission tomography (PET), functional magnetic resonance imaging (fMRI), and diffuse optical tomography (DOT).

In some embodiments, the system comprises one or more processors. In some embodiments, the system comprises a non-transient computer-readable medium comprising instructions that, when executed by the processor, cause the one or more processors to: perform one or more filters on the plurality of signals; decode the plurality of signals into context-related features; and output the plurality of signals into a context-related output.

In some embodiments, the one or more processors is configured to output the decoded context-related feature and/or external context-related features into a context-dependent output. In some embodiments, the one or more processors is configured to decode one or more of: the context-related feature and external context-related feature using a probability classification model. In some embodiments, the probability classification model computes question utterance likelihoods in order to decode the one or more of: context-related feature output from the plurality of signals and the external context-related feature output from the external source. In some embodiments, the probability classification model computes context priors to decode one or more of: the context-related feature output from the plurality of signals, and the external context-related feature output from the external source. In some embodiments, the probability classification model comprises Viterbi decoding. Inn some embodiments, the probability classification model comprises an artificial intelligence algorithm.

In some embodiments, the one or more processors is configured to compute conditional probability distributions of the plurality of signals.

In some embodiments, the one or more processors comprises a principal component analysis (PCA) model.

In some embodiments, the non-transient computer-readable medium further comprises instructions that, when executed by the one or more processors, cause the one or more processors to compute conditional probability distributions of one or more of: the plurality of signals (e.g. neural signals or optical signals), and the external context-related feature from the external source (e.g. in the form of external signals).

In some embodiments, decoding comprises machine learning algorithms that identify spatial, temporal, or a combination of spatial and temporal neural patterns associated with the context-related features (e.g. internal context-related features from the plurality of signals and/or the external context-related features from the external source).

In some embodiments, the one or more processors comprises a classification model to predict a context-related feature. In some embodiments, the classification model comprises a hidden Markov model (HMM).

In some embodiments, one or more processors further comprises a hyperparameter optimization model.

In some embodiments, the one or more processors comprises a context integration model. In some embodiments, the context integration model is configured to predict context-related features (e.g. internal context-related features from the plurality of signals and/or the external context-related features from the external source). In some embodiments, the context integration model is configured to receive predicted utterance log likelihoods from the classification model.

In some embodiments, the one or more processors comprises conditional probabilities in the form of context priors, wherein the context prior is the probability inferred by one or more of: the one or more context-related features and the one or more external context-related features from the external source.

In some embodiments, the one or more processors comprises predicted context-related feature probabilities configured to detect onsets and offsets of context-related feature events (e.g. internal context-related features from the plurality of signals and/or the external context-related features from the external source).

In some embodiments, the one or more processors comprises classification models to predict the likelihood of context-related feature utterances within a detected time segment in the neural or optical signals.

In some embodiments, the one or more processors comprises a principal component analysis (PCA) model. In some embodiments, the one or more processors comprises a machine learning algorithm. In some embodiments, the one or more processors comprises a linear discriminant analysis (LDA) model. In some embodiments, the one or more processors comprises a principal component analysis (PCA) model and a linear discriminant analysis (LDA) model. In some embodiments, the PCA and LDA models are configured to extract the principal components of the context-related feature (e.g. internal context-related features from the plurality of signals and/or the external context-related features from the external source). In some embodiments, the PCA and LDA models are configured to predict the context-related feature (e.g. internal context-related features from the plurality of signals and/or the external context-related features from the external source). In some embodiments, the PCA and LDA models are configured to output the context-related feature (e.g. internal context-related features from the plurality of signals and/or the external context-related features from the external source). In some embodiments, the PCA and LDA models are configured to predict context-related feature (e.g. internal context-related features from the plurality of signals and/or the external context-related features from the external source) probabilities.

In some embodiments, decoding the context-related features comprises machine learning algorithms that identify spatial and/or temporal neural patterns associated with the context-related feature events (e.g. internal context-related features from the plurality of signals and/or the external context-related features from the external source).

In some embodiments, decoding the context-related feature output comprises using a probability classification model. In some embodiments, the probability classification model comprises Viterbi decoding to compute question utterance likelihoods and context priors to decode the context-related feature output from the neural or optical signals and/or external context-related feature output from the external source.

In some embodiments, the non-transient computer-readable medium comprising instructions further cause the one or more processors to perform one or more filters on the plurality of signals and/or the external context-related features from the external source (e.g. in the form of external signals). In some embodiments, the one or more filters comprises one or more low-pass filters (e.g. low frequency component ranging from 1-30 Hz). In some embodiments, the one or more filters comprises one or more notch filters.

In some embodiments, neural signals are filtered at a high gamma frequency ranging from 70 to 200 Hz. In some embodiments, the neural signals are filtered at a low frequency ranging from 1-30 Hz. In some embodiments, the neural signals are filtered at other frequencies ranging from 1-200 Hz.

In some embodiments, the one or more processors is configured to stream the signals onto a computer, tablet, smartphone, and/or related devices.

wherein the one or more processors is configured to apply one or more band-pass finish impulse response (FIR) filters to the neural signals. In some embodiments, the one or more FIT filters are configured to band-pass the neural signals in one or more different sub-bands in the high gamma band frequency range. In some embodiments, the one or more processors is configured to extract analytic amplitude values (e.g. high gamma analytic amplitude values) across the one or more band-pass FIR filters applied to the neural signals. In some embodiments, the one or more processors is configured to average the analytic amplitude values across the one or more band-pass FIR filters to obtain one or more high gamma analytic amplitude signals.

In some embodiments, the one or more processors is configured to decode the one or more high gamma analytic amplitude signals into an intended context-related feature output. In some embodiments, the one or more processors is configured to decode the one or more external context-related signals into an intended external context-related feature output.

In some embodiments, the intended context-related feature (e.g. intended context-related feature from the plurality of signals and/or from the external context-related feature from the external source) is configured to output text associated with the context-related feature as one or more syllables, words, parts of words, phrases, utterances, paragraphs, sentences, and/or a combination thereof.

Aspects of the present disclosure include a system comprising: an electrode array positioned on a brain of an individual; one or more processors; a non-transient computer-readable medium comprising instructions that, when executed by the one or more processors, cause the one or more processors to: record and/or detect a plurality of signals associated with cortical activity in the brain; extract one or more context-related features from the plurality of signals of the brain; and decode a context-related feature output from the plurality of signals. In some embodiments, the computer-readable medium comprises further instructions that, when executed by the one or more processors, cause the one or more processors to: decode one or more external context-related features from an external source. In some embodiments, the context-related feature output and the external context-related feature output is text comprising one or more syllables, words, parts of words, phrases, utterances, paragraphs, sentences, and/or a combination thereof.

In some embodiments, the electrode array is contacted with the cortical region of the brain. In some embodiments, the electrode array is positioned on a cap that is placed on the surface of the cortical region of the brain. In some embodiments, said contacting comprises implanting the electrode array in the cortical region of the brain. In some embodiments, wherein said contacting comprises operably coupling a neurosensor comprising the electrode array to the cortical region of the brain.

In some embodiments, the neural signals are recorded during an audible speech event, a silent speech event, and/or one or more external context-related cues (e.g. listening to a sound, responding to a sound, reading etc.). In some embodiments, the one or more processors is further configured to record the plurality of signals when the individual hears a sound, when the individual is reading, and/or when the individual is thinking.

In some embodiments, the one or more features of the neural signals comprises high-gamma amplitude signals in a frequency ranging from 70-200 Hz. In some embodiments, the one or more features of the neural signals comprises low frequency amplitude signals in a frequency ranging from 1-30 Hz. In some embodiments, the one or more features of the neural signals comprises other frequency components ranging from 1-200 Hz.

In some embodiments, the electrode array is operably connected to the sensorimotor cortext (SMC), the ventral sensorimotor cortex (vSMC), superior temporal gyrus (STG), and/or the inferior frontal gyrus (IFG) of the brain.

Systems—Speech Synthesis Decoding

Also provided are systems for performing the methods of the present disclosure. Such systems include speech decoding systems.

Aspects of the present disclosure include a system comprising an electrode array positioned on the brain of an individual; one or more processors; a non-transient computer-readable medium comprising instructions that, when executed by the one or more processors, cause the one or more processors to: record neural signals associated with cortical activity in the brain; extract one or more neural signals of the brain; and decode a speech output from the neural signals.

Aspects of the present disclosure include a speech neural decoding system comprising an electrode array in contact with the cortical region of the brain in the individual, wherein the electrode array comprises a plurality of electrodes; an electrical recording device configured to record neural signals in the brain; one or more processors; a non-transient computer-readable medium comprising instructions that, when executed by the processor, cause the one or more processors to: perform one or more filters on the plurality of signals; decode the plurality of signals into articulatory movement representations; and output the plurality of acoustic signals into a speech output.

Aspects of the present disclosure include a speech neural decoding system comprising: an electrode array in contact with the cortical region of the brain in the individual; one or more processors; a non-transient computer-readable medium comprising instructions that, when executed by the one or more processors, cause the one or more processors to: record neural or optical signals associated with cortical activity in the brain; extract one or more features associated with cortical activity in the brain; decode articulatory movement features from the one or more features of the neural signals; decode acoustic signals from the articulatory movement features, and decode a speech output from the acoustic signals.

In some embodiments, the neural array comprises a plurality of electrodes. In some embodiments, the plurality of electrodes comprises 50 or more electrodes, 100 or more electrodes, 150 or more electrodes, 200 or more electrodes, 250 or more electrodes, 300 or more electrodes, 350 or more electrodes, 400 or more electrodes, 450 or more electrodes, or 500 or more electrodes.

In some embodiments, the system comprises an electrical recording device configured to record neural signals in the brain. In some embodiments, the electrical recording device is a 16-channel recording device. In some embodiments, the electrical recording device is a 32-channel recording device. In some embodiments, the electrical recording device is a 64-channel recording device. In some embodiments, the electrical recording device is a 128-channel recording device. In some embodiments, the electrical recording device is an 256-channel recording device. In some embodiments, the electrical recording device is implantable. In some embodiments, the electrical recording device is wireless.

In some embodiments, the electrical recording device is an ECoG recording device. In some embodiments, the electrical recording device is an EEG recording device. In some embodiments, the electrical recording device comprises a plurality of microelectrodes. In some embodiments, the electrical recording device is any known electrical recording device configured to record a plurality of neural signals in the brain.

In some embodiments, the system comprises one or more processors. In some embodiments, the system comprises a non-transient computer-readable medium comprising instructions that, when executed by the processor, cause the one or more processors to: perform one or more filters on the plurality of signals; decode the plurality of signals into articulatory movement representations; and output the plurality of acoustic signals into a speech output.

In some embodiments, the plurality of signals comprise ECoG signals or EEG signals. In some embodiments, the ECoG signals or EEG signals are neural signals.

In some embodiments, the one or more filters comprises one or more low-pass filters (e.g. low frequency component ranging from 1-30 Hz). In some embodiments, the one or more filters comprises one or more notch filters.

In some embodiments, neural signals are filtered at a high gamma frequency ranging from 70 to 200 Hz. In some embodiments, the neural signals are filtered at a low frequency ranging from 1-30 Hz.

In some embodiments, the one or more processors is configured to stream the signals onto a computer, tablet, smartphone, and/or related devices.

wherein the one or more processors is configured to apply one or more band-pass finish impulse response (FIR) filters to the neural signals. In some embodiments, the one or more FIT filters are configured to band-pass the neural signals in one or more different sub-bands in the high gamma band frequency range. In some embodiments, the one or more processors is configured to extract analytic amplitude values (e.g. high gamma analytic amplitude values) across the one or more band-pass FIR filters applied to the neural signals. In some embodiments, the one or more processors is configured to average the analytic amplitude values across the one or more band-pass FIR filters to obtain one or more high gamma analytic amplitude signals.

In some embodiments, the one or more processors is configured to normalize and store the one or more high gamma analytic amplitude signals in an event detector process, wherein the event detector process analyzes the high gamma analytic signals at one or more time points. In some embodiments, the event detector process is configured to analyze the high gamma analytic signals at one or more time points to predict the onset and offset of auditory perceived speech or verbal produced speech events.

In some embodiments, the one or more processors is configured to decode the one or more high gamma analytic amplitude signals into an intended speech output.

In some embodiments, the electrode array is contacted with the cortical region of the brain. In some embodiments, the electrode array is positioned on a cap that is placed on the surface of the cortical region of the brain. In some embodiments, said contacting comprises implanting the electrode array in the cortical region of the brain. In some embodiments, wherein said contacting comprises operably coupling a neurosensor comprising the electrode array to the cortical region of the brain.

In some embodiments, the intended speech output is configured to output text as one or more syllables, words, parts of words, phrases, utterances, paragraphs, sentences, and/or a combination thereof.

Aspects of the present disclosure include a system comprising: an electrode array positioned on a brain of an individual; one or more processors; a non-transient computer-readable medium comprising instructions that, when executed by the one or more processors, cause the one or more processors to: record and/or detect neural signals associated with cortical activity in the brain; extract one or more features from the neural signals of the brain; decode articulatory movement features from the one or more features of the neural signals; decode acoustic signals from the articulatory movement features; and decode a speech output from the acoustic signals. In some embodiments, the speech output is text comprising one or more syllables, words, parts of words, phrases, utterances, paragraphs, sentences, and/or a combination thereof.

Aspects of the present disclosure include a system comprising an electrode array positioned on the brain of an individual; one or more processors; a non-transient computer-readable medium comprising instructions that, when executed by the one or more processors, cause the one or more processors to: record neural signals associated with cortical activity in the brain; extract one or more neural signals of the brain; and decode a speech output from the neural signals.

Aspects of the present disclosure include a speech neural decoding system comprising an optical device configured to record optical signals from a cortical region of the brain in the individual; one or more processors; a non-transient computer-readable medium comprising instructions that, when executed by the processor, cause the one or more processors to: perform one or more filters on the plurality of signals; decode the plurality of optical signals into articulatory movement representations; and output the plurality of optical signals into a speech output.

Aspects of the present disclosure include a speech neural decoding system comprising: an optical device configured to record optical signals from a cortical region of the brain in the individual; one or more processors; a non-transient computer-readable medium comprising instructions that, when executed by the one or more processors, cause the one or more processors to: record optical signals associated with cortical activity in the brain; extract one or more features associated with cortical activity in the brain; decode articulatory movement features from the one or more features of the optical signals; decode optical signals from the articulatory movement features, and decode a speech output from the optical signals.

In some embodiments, the system includes an optical device for configured to acquire optical signals associated with one or more context-related features. In some embodiments, the plurality of signals are acquired by any known neurophysiological recording device. In some embodiments, the plurality of signals are optical signals. In some embodiments, the plurality of signals are acquired through optical devices. Optical devices that can be used to acquire the plurality of signals include, but are not limited to: intrinsic optical signal (IOS) imaging, extrinsic optical signal (EOS) imaging, Doppler flowmetry (LDF), near-infrared (NIR) spectrometer, functional optical coherence tomography (fOCT), and surface plasmon resonance (SPR). Other techniques such as radioactive imaging can be used to acquire the plurality of signals. Non-limiting examples include radioactive imaging of changes in blood flow, magnetoencephalography (MEG), thermal imaging, positron-emission tomography (PET), functional magnetic resonance imaging (fMRI), and diffuse optical tomography (DOT).

In some embodiments, the one or more processor comprises one or more BLSTM neural networks. In some embodiments, the one or more bidirectional long short-term memory comprises an algorithm for decoding articulatory movement features from the neural or optical signals. In some embodiments, the one or more bidirectional long short-term memory or other recurrent neural networks comprises an algorithm for decoding the acoustic signals, neural signals, and/or optical signals into text. In some embodiments, the one or more bidirectional long short-term memory neural networks comprising an algorithm for decoding articulatory movement features from the neural signals or optical signals is a first bidirectional long short-term memory neural network. In some embodiments, the one or more bidirectional long short-term memory neural networks comprising an algorithm for decoding the acoustic signals into text is a second bidirectional long short-term memory neural network. In some embodiments, the neural signals are electrocorticography (ECoG) neural signals. In some embodiments, the neural signals are EEG signals.

In some embodiments, the one or more processors comprises a second bidirectional long short-term memory neural network comprising an algorithm for decoding acoustic signals from the articulatory movement features. In some embodiments, the articulatory movement features comprise kinematic representations of articulation from the one or more features from the neural or optical signals. In some embodiments, the one or more processors comprises a second neural network (e.g. a bidirectional long short-term memory) comprising an algorithm for decoding the audible speech and/or silent speech acoustic signals from the individual.

In some embodiments, the neural signals are recorded during an audible speech event, a silent speech event, and/or one or more external context-related cues from the individual. In some embodiments, the one or more processors is further configured to record the audible speech or silent speech signals from the individual.

In some embodiments, the one or more processors is further configured to record audible and silent speech signals simultaneously during recording of the neural signals.

In some embodiments, the one or more features of the neural signals comprises high-gamma amplitude signals in a frequency ranging from 70-200 Hz. In some embodiments, the one or more features of the neural signals comprises low frequency amplitude signals in a frequency ranging from 1-30 Hz.

In some embodiments, the one or more processors is configured to estimate vocal kinematic trajectories associated with the audible speech or silent speech signals.

In some embodiments, the one or more processors further comprises an autoencoder configured to convert phonological and acoustic features of the audible speech or silent speech acoustic signals into one or more articulatory representations. In some embodiments, the one or more processors further comprises a decoder configured to convert the one or more articulatory representations to audible speech or silent speech acoustic signals. In some embodiments, the one or more processors further comprises an encoder configured to estimate final articulatory kinematic features, wherein the final articulatory kinematic features are used in an algorithm to decode articulatory movement features from the neural signals.

In some embodiments, the electrode array is operably connected to the ventral sensorimotor cortex (vSMC), superior temporal gyrus (STG), and/or the inferior frontal gyrus (IFG) of the brain.

In some embodiments, the one or more processors comprises a deep neural network comprising an algorithm for decoding the audible speech or silent speech acoustic signal as mel frequency cepstral coefficients. In some embodiments, the deep neural network comprises an algorithm for decoding the audible speech or silent speech acoustic signals as 25 dimensional mel frequency cepstral coefficients.

In some embodiments, the one or more processors comprises a hidden Markov model based acoustic model configured to perform sub-phonetic alignment.

In some embodiments, the one or more processors comprises a Kullback-Leibler (KL) divergence model configured to compare the distribution of a decoded phoneme of the neural signals to a distribution of a ground-truth phoneme.

Aspects of the present disclosure include a speech neural decoding system comprising: an electrode array in contact with the cortical region of the brain in the individual, wherein the electrode array comprises a plurality of electrodes; an electrical recording device configured to record neural signals in the brain; one or more processors; a non-transient computer-readable medium comprising instructions that, when executed by the processor, cause the one or more processors to: perform one or more filters on the plurality of signals; decode the plurality of signals into articulatory movement representations; and output the plurality of acoustic signals into a speech output. In some embodiments, the one or more filters comprises one or more low-pass filters.

In some embodiments, wherein the one or more filters comprises one or more notch filters.

In some embodiments, wherein the one or more processors is configured to stream the signals onto a real-time computer.

In some embodiments, wherein the neural signals are neural signals.

In some embodiments, wherein the one or more processors is configured to apply one or more band-pass finish impulse response (FIR) filters to the neural signals.

In some embodiments, wherein the one or more FIT filters are configured to band-pass the ECoG signals in one or more different sub-bands in the high gamma band frequency range.

In some embodiments, wherein the one or more processors is configured to extract analytic amplitude values across the one or more band-pass FIR filters applied to the neural signals.

In some embodiments, wherein the one or more processors is configured to average the analytic amplitude values across the one or more band-pass FIR filters to obtain one or more high gamma analytic amplitude signals.

In some embodiments, wherein the one or more processors is configured to normalize and store the one or more high gamma analytic amplitude signals in an event detector process, wherein the event detector process analyzes the high gamma analytic signals at one or more time points.

In some embodiments, wherein the event detector process analyzes the high gamma analytic signals at one or more time points to predict the onset and offset of auditory perceived speech or verbal produced speech events.

In some embodiments, wherein the one or more processors is configured to decode the one or more high gamma analytic amplitude signals into an intended speech output.

In some embodiments, wherein said contacting comprises implanting the electrode array in the cortical region of the brain.

In some embodiments, wherein said contacting comprises operably coupling a neurosensor comprising the electrode array to the cortical region of the brain.

In some embodiments, wherein the intended speech output is configured to output text as one or more syllables, words, parts of words, phrases, utterances, paragraphs, sentences, and/or a combination thereof.

In some embodiments, wherein the neural signals are filtered at a frequency ranging from 70 to 200 Hz.

In some embodiments, wherein the one or more processor comprises one or more bidirectional long short-term memory (BLSTM) neural networks.

A system comprising: an electrode array positioned on a brain of an individual; one or more processors; a non-transient computer-readable medium comprising instructions that, when executed by the one or more processors, cause the one or more processors to: record neural signals associated with cortical activity in the brain; extract one or more features from the neural signals of the brain; decode articulatory movement features from the one or more features of the neural signals; decode acoustic signals from the articulatory movement features; and decode a speech output from the acoustic signals.

In some embodiments, wherein the one or more processors comprises a recurrent neural network (RNN).

In some embodiments, wherein the RNN is one or more bidirectional long short-term memory (BLSTM) neural networks.

In some embodiments, wherein the bidirectional long short-term memory comprises an algorithm for decoding articulatory movement features from the neural signals.

In some embodiments, wherein the one or more bidirectional long short-term memory neural networks comprises an algorithm for decoding the acoustic signals into text.

In some embodiments, wherein the speech output is text comprising one or more syllables, words, parts of words, phrases, utterances, paragraphs, sentences, and/or a combination thereof.

In some embodiments, wherein the one or more processors comprises a second neural network (e.g. bidirectional long short-term memory) comprising an algorithm for decoding acoustic signals from the articulatory movement features In some embodiments, wherein the articulatory movement features comprise kinematic representations of articulation from the one or more features from the neural signals.

In some embodiments, wherein the neural signals are recorded during:

audible speech from the individual;

silent or intended speech from the individual; and/or a sound heard from the individual.

In some embodiments, wherein the one or more processors is further configured to record audible or silent speech signals simultaneously during recording of the neural signals.

In some embodiments, wherein the neural signals are electrocorticography (ECoG) neural signals.

In some embodiments, wherein the one or more features of the neural signals comprises high-gamma amplitude signals in a frequency ranging from 70-200 Hz.

In some embodiments, wherein the one or more features of the neural signals comprises low frequency amplitude signals in a frequency ranging from 1-30 Hz.

In some embodiments, wherein the one or more processors is further configured to record the audible speech or silent speech signals from the individual.

In some embodiments, wherein the one or more processors comprises a second neural network (e.g. bidirectional long short-term memory) comprising an algorithm for decoding the audible speech or silent speech acoustic signals from the individual.

In some embodiments, wherein the one or more processors is configured to estimate vocal kinematic trajectories associated with the audible speech or silent speech signals.

In some embodiments, wherein the one or more processors further comprises an autoencoder configured to convert phonological and acoustic features of the audible speech or silent speech acoustic signals into one or more articulatory representations.

In some embodiments, wherein the one or more processors further comprises a decoder configured to convert the one or more articulatory representations to audible speech or silent speech acoustic signals.

In some embodiments, wherein the one or more processors further comprises an encoder configured to estimate final articulatory kinematic features, wherein the final articulatory kinematic features are used in an algorithm to decode articulatory movement features from the neural signals.

In some embodiments, wherein the electrode array is operably connected to the ventral sensorimotor cortex (vSMC), superior temporal gyrus (STG), and the inferior frontal gyrus (IFG) of the brain.

In some embodiments, wherein the one or more processors comprises a deep neural network comprising an algorithm for decoding the audible speech or silent speech acoustic signal as mel frequency cepstral coefficients.

In some embodiments, wherein the deep neural network comprises an algorithm for decoding the audible speech or silent speech acoustic signals as 25 dimensional mel frequency cepstral coefficients.

In some embodiments, wherein the one or more processors comprises a hidden Markov model based acoustic model configured to perform sub-phonetic alignment.

In some embodiments, wherein the one or more processors comprises a Kullback-Leibler (KL) divergence model configured to compare the distribution of a decoded phoneme of the ECoG signals to a distribution of a ground-truth phoneme.

A system comprising: an electrode array positioned on a brain of an individual; one or more processors; a non-transient computer-readable medium comprising instructions that, when executed by the one or more processors, cause the one or more processors to: record neural signals associated with cortical activity in the brain; extract one or more features from the neural signals of the brain; and decode a speech output from the neural signals.

In some embodiments, wherein the processor further decodes articulatory movement features from the one or more features of the neural signals.

In some embodiments, wherein the processor further decodes acoustic signals from the articulatory movement features.

In some embodiments, wherein the processor further decodes a speech output from the acoustic signals.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: Speech Synthesis from Neural Decoding of Spoken Sentences

A neural decoder was designed that explicitly leverages kinematic and sound representations encoded in human cortical activity to synthesize audible speech. Recurrent neural networks first decoded directly recorded cortical activity into articulatory movement representations, and then transformed those representations into speech acoustics. In closed vocabulary tests, listeners could readily identify and transcribe neurally synthesized speech. Intermediate articulatory dynamics enhanced performance even with limited data. Decoded articulatory representations were highly conserved across speakers, enabling a component of the decoder be transferrable across participants. Furthermore, the decoder could synthesize speech when a participant silently mimed sentences. These findings advance the clinical viability of speech neuroprosthetic technology to restore spoken communication.

A biomimetic approach that focuses on vocal tract movements and the sounds they produce can achieve the high communication rates of natural speech, and also likely the most intuitive for users to learn. In patients with paralysis, for example from ALS or brainstem stroke, high fidelity speech control signals may only be accessed by directly recording from intact cortical networks.

The feasibility of a neural speech prosthetic was demonstrated by translating brain signals into intelligible synthesized speech at the rate of a fluent speaker. High-density electrocorticography (ECoG) signals were recorded from five participants undergoing intracranial monitoring for epilepsy treatment as they spoke several hundred sentences aloud. A recurrent neural network was designed that decoded cortical signals with an explicit intermediate representation of the articulatory dynamics to synthesize audible speech.

Speech Decoder Design

Figure 1B:
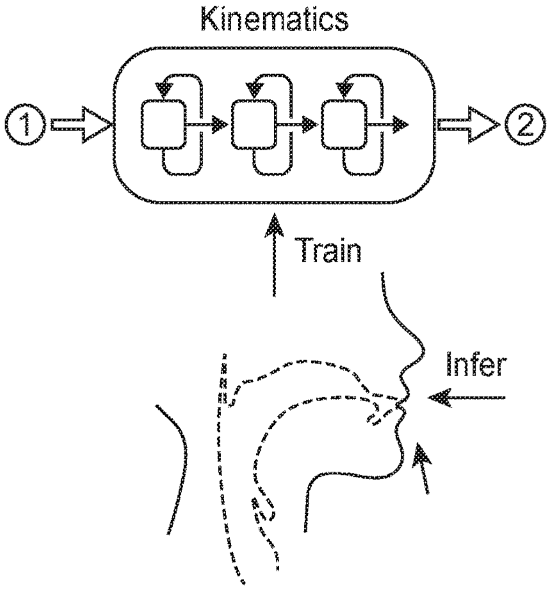
Figure 1C:
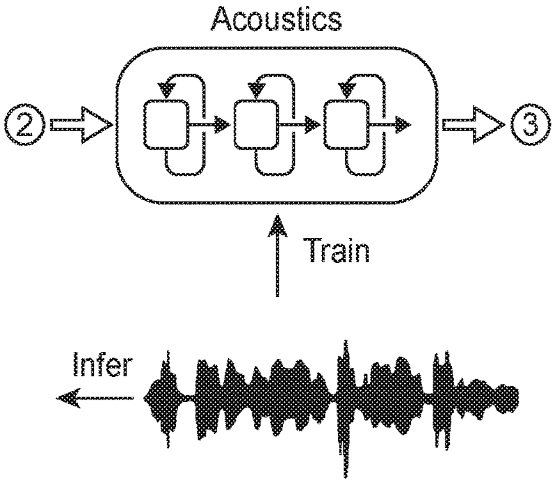
Figure 1D:
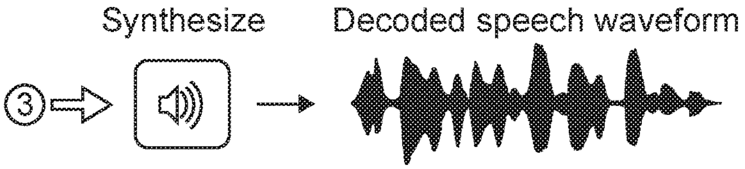
Figure 1E:
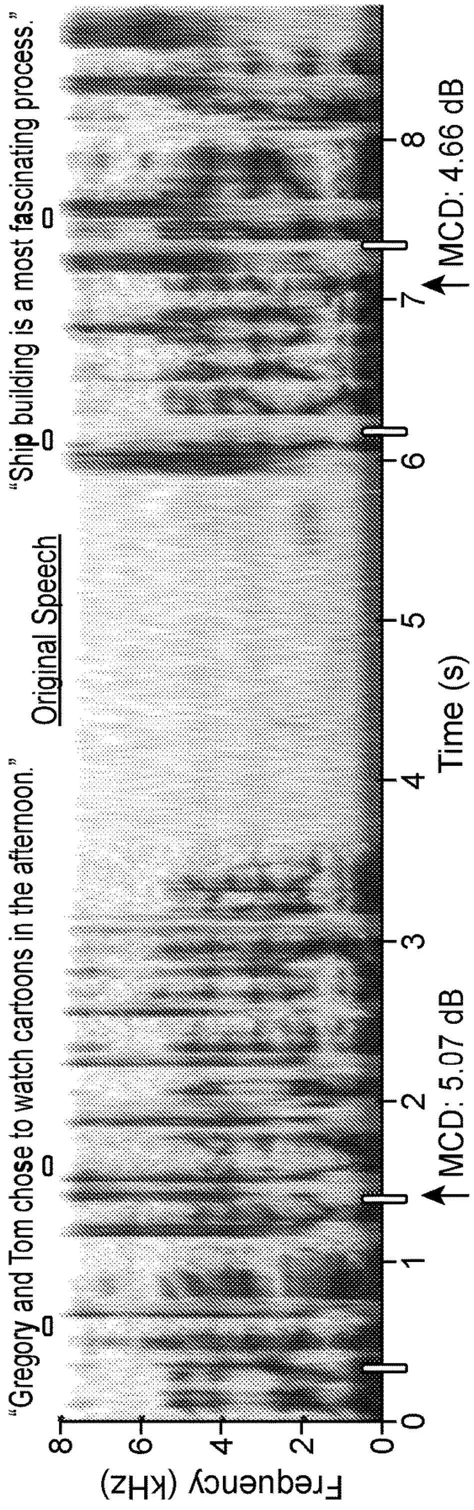
Figure 1F:
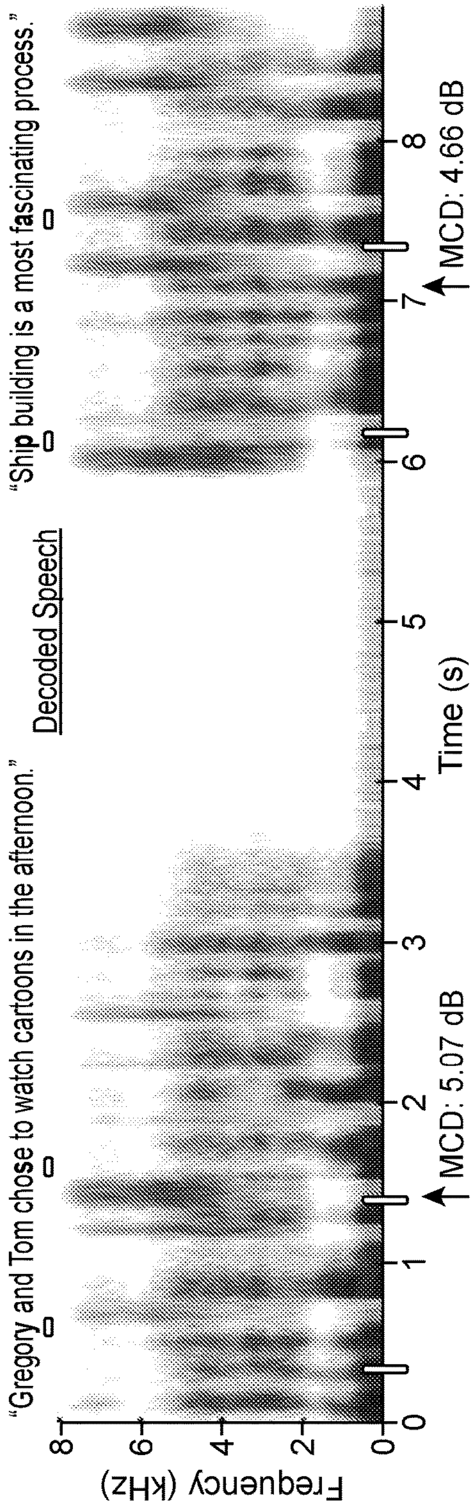
Figures 1G, 1H:
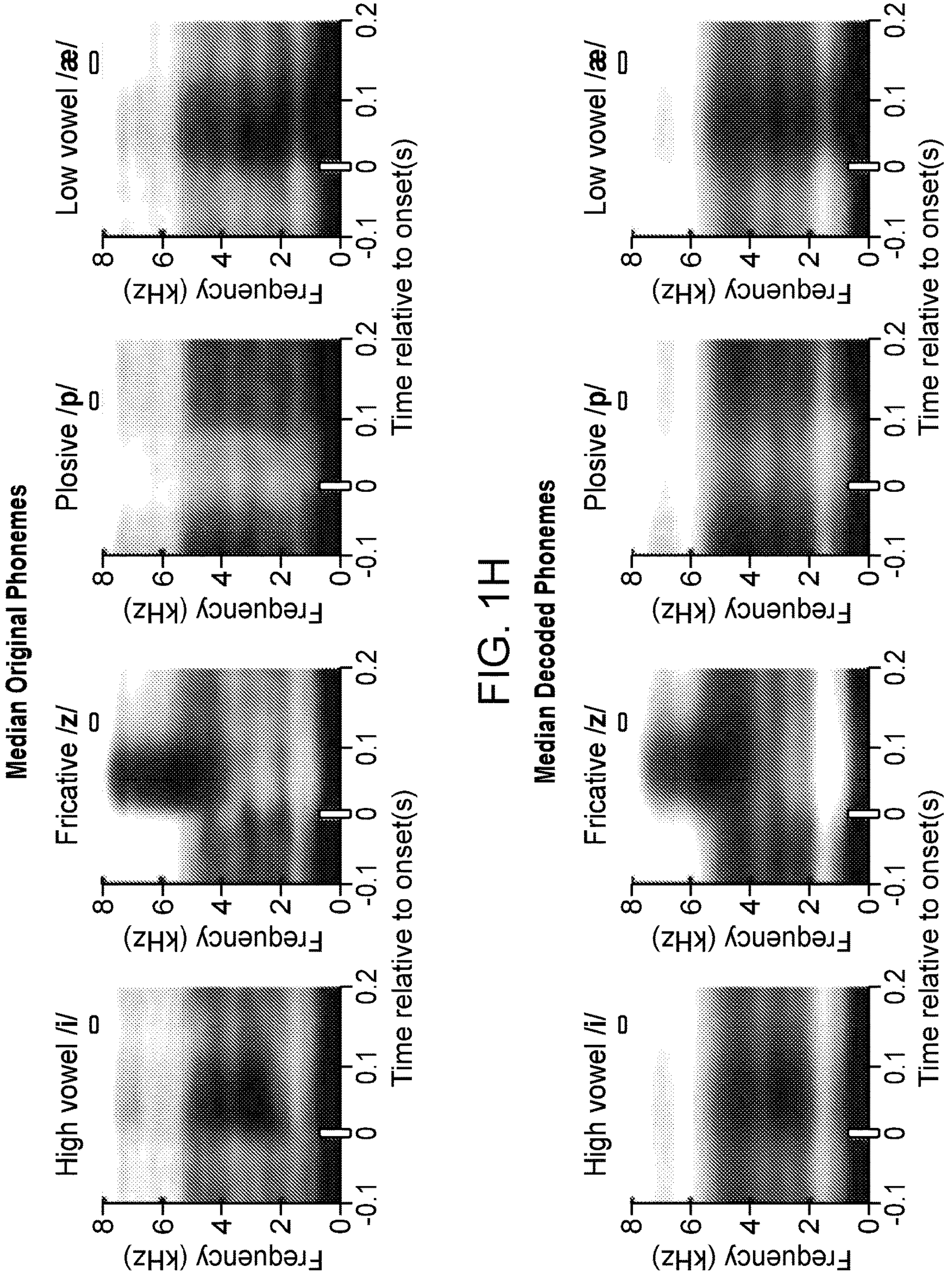

The two-stage decoder approach is shown in FIG. 1A-1D. Stage 1: a bidirectional long short-term memory (bLSTM) recurrent neural network decodes articulatory kinematic features from continuous neural activity (high-gamma amplitude envelope and low frequency component) recorded from ventral sensorimotor cortex (vSMC), superior temporal gyrus (STG), and inferior frontal gyrus (IFG) (FIG. 1A-1B). Stage 2: a separate bLSTM decodes acoustic features ($F_0$, mel-frequency cepstral coefficients (MFCCs), voicing and glottal excitation strengths) from the decoded articulatory features from Stage 1 (FIG. 1C). The audio signal is then synthesized from the decoded acoustic features (FIG. 1D). To integrate the two stages of the decoder, Stage 2 (articulation-to-acoustics) was trained directly on output of Stage 1 (brain-to-articulation) so that it not only learns the transformation from kinematics to sound, but can correct articulatory estimation errors made in Stage 1.

A component of the decoder of the present disclosure is the intermediate articulatory representation between neural activity and acoustics (FIG. 1B). The vSMC exhibits robust neural activations during speech production that predominantly encode articulatory kinematics. A statistical approach was used to estimate vocal tract kinematic trajectories (movements of the lips, tongue, and jaw) and other physiological features (e.g. manner of articulation) from audio recordings. These features initialized the bottleneck layer within a speech encoder-decoder that was trained to reconstruct a participant's produced speech acoustics. The encoder was then used to infer the intermediate articulatory representation used to train the neural decoder. With this decoding strategy, it was possible to accurately reconstruct the speech spectrogram.

Synthesis Performance

Figure 5A:
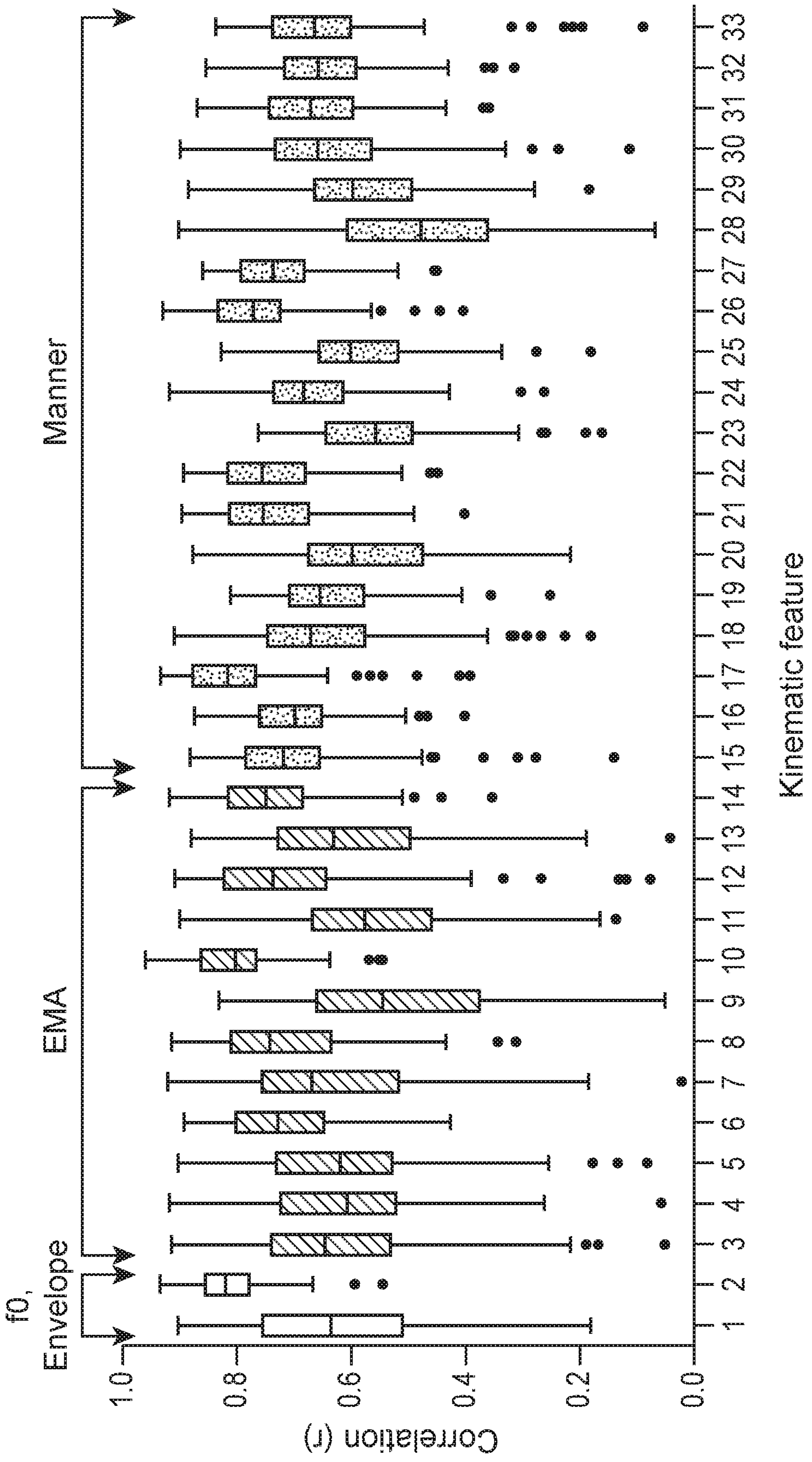
FIGS. 5A-5B: Decoding performance of kinematic and spectral features.
Figure 5B:
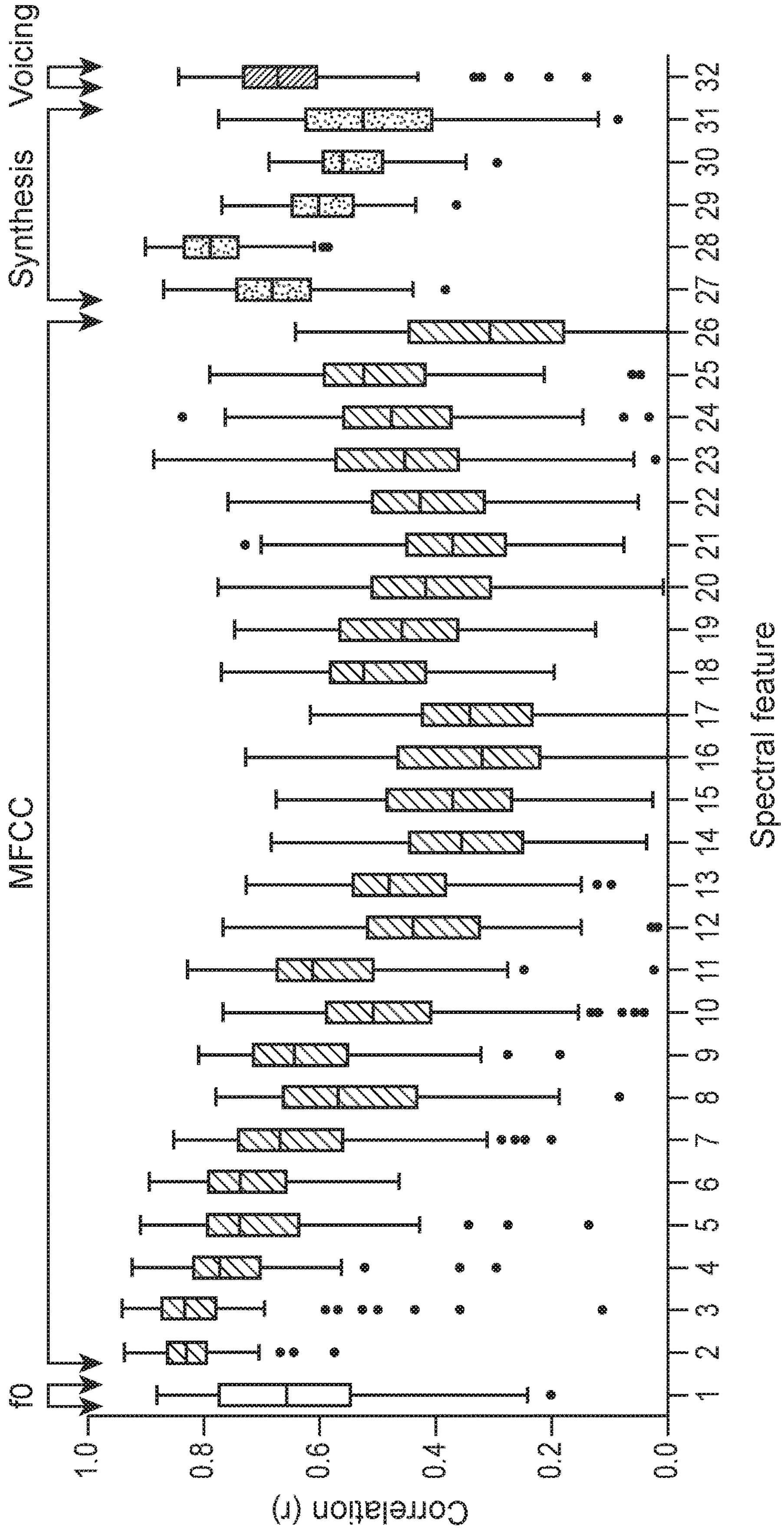

Overall, detailed reconstructions of speech synthesized from neural activity alone was observed. FIGS. 1E-1F shows the audio spectrograms from two original spoken sentences plotted above those decoded from brain activity. The decoded spectrogram retained salient energy patterns present in the original spectrogram and correctly reconstructed the silence in between the sentences when the participant was not speaking. FIGS. 5A-5B, illustrates the quality of reconstruction at the phonetic level. Median spectrograms of original and synthesized phonemes showed that the typical spectrotemporal patterns were preserved in the decoded exemplars (e.g. formants F1-F3 in vowels /i:/ and /x/; and key spectral patterns of mid-band energy and broadband burst for consonants /z/ and /p/, respectively).

To understand to what degree the synthesized speech was perceptually intelligible to naïve listeners, two listening tasks were conducted that involved single-word identification and sentence-level transcription, respectively. The tasks were run on Amazon Mechanical Turk, using all 101 synthesized sentences from the test set for participant P1.

For the single-word identification task, 325 words were evaluated that were spliced from the synthesized sentences. The effect of word length (number of syllables) and the number of choices (10, 25, and 50 words) on speech intelligibility were quantified, since these factors inform optimal design of speech interfaces. It was found that listeners were more successful at word identification as syllable length increased, and number of word choices decreased, consistent with natural speech perception.

For sentence-level intelligibility, a closed vocabulary, free transcription task was designed. Listeners heard the entire synthesized sentence and transcribed what they heard by selecting words from a defined pool (of either 25 or 50 words) that included the target words and random words from the test set. The closed vocabulary setting was necessary because the test set was a subset of sentences from MOCHA-TIMIT which was primarily designed to optimize articulatory coverage of English but contains highly unpredictable sentence constructions and low frequency words.

Figure 6:
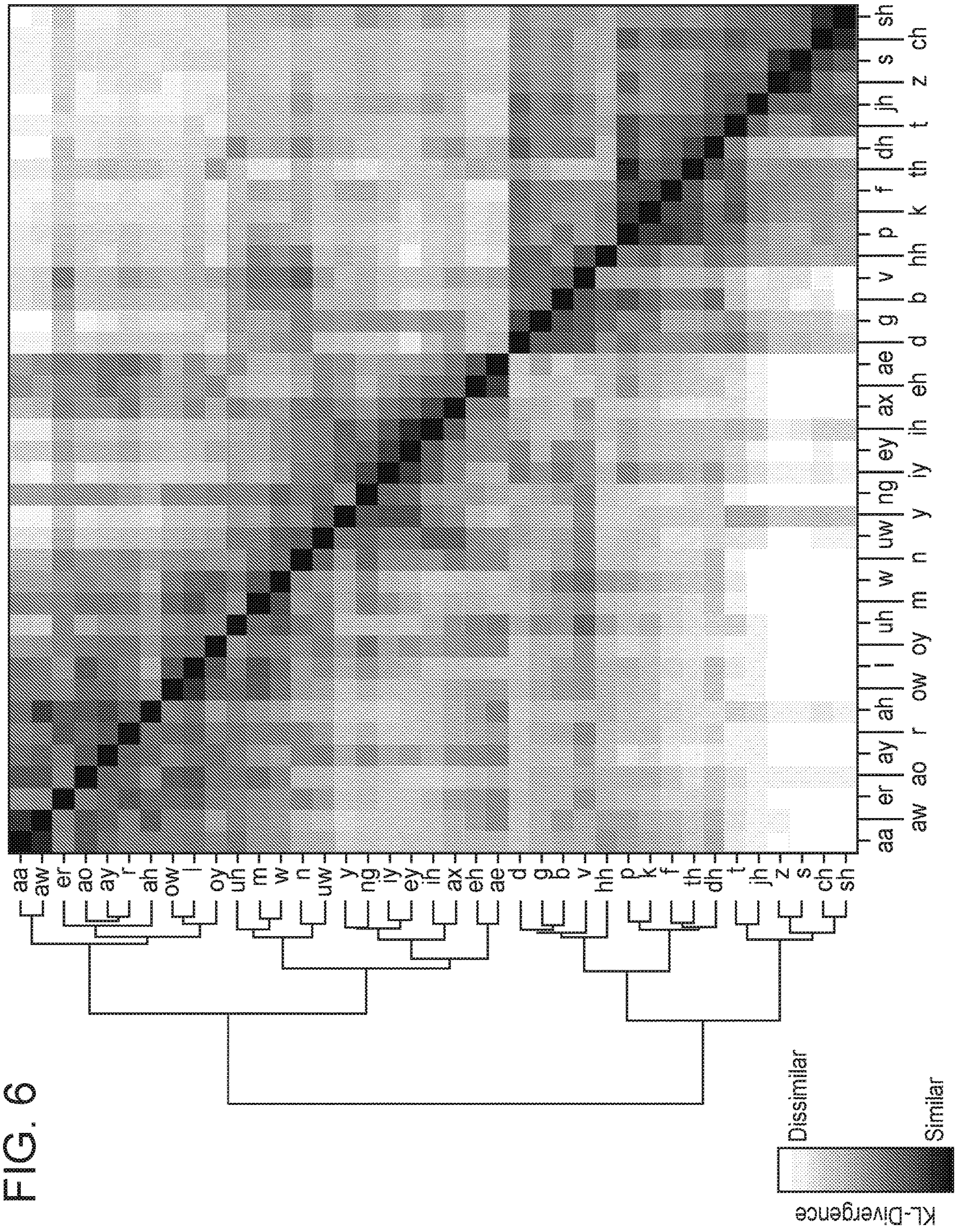
FIG. 6: Ground-truth acoustic similarity matrix. Compares acoustic properties of ground-truth spoken phonemes with one another. Similarity is computed by first estimating a gaussian kernel density for each phoneme and then computing the Kullback-Leibler (KL) divergence between a pair of a phoneme distributions. Each row compares the acoustic properties of a two ground-truth spoken phonemes. Hierarchical clustering was performed on the resulting similarity matrix.

Listeners were able to transcribe synthesized speech well. Of the 101 synthesized trials, at least one listener was able to provide a perfect transcription for 82 sentences with a 25-word pool and 60 sentences with a 50-word pool. Of all submitted responses, listeners transcribed 43% and 21% of the total trials perfectly, respectively (FIG. 6). Transcribed sentences had a median 31% WER with a 25-word pool size and 53% WER with a 50-word pool size. Table 1 shows listener transcriptions for a range of WERs. Median level transcriptions still provided a fairly accurate, and in some cases legitimate transcription (eg., "mum" transcribed as "mom" etc.). The errors suggest that the acoustic phonetic properties of the phonemes are still present in the synthesized speech, albeit to the lesser degree (eg., "rabbits" transcribed as "rodents"). This level of intelligibility for neurally synthesized speech would already be immediately meaningful and practical for real world application.

Figure 2A:
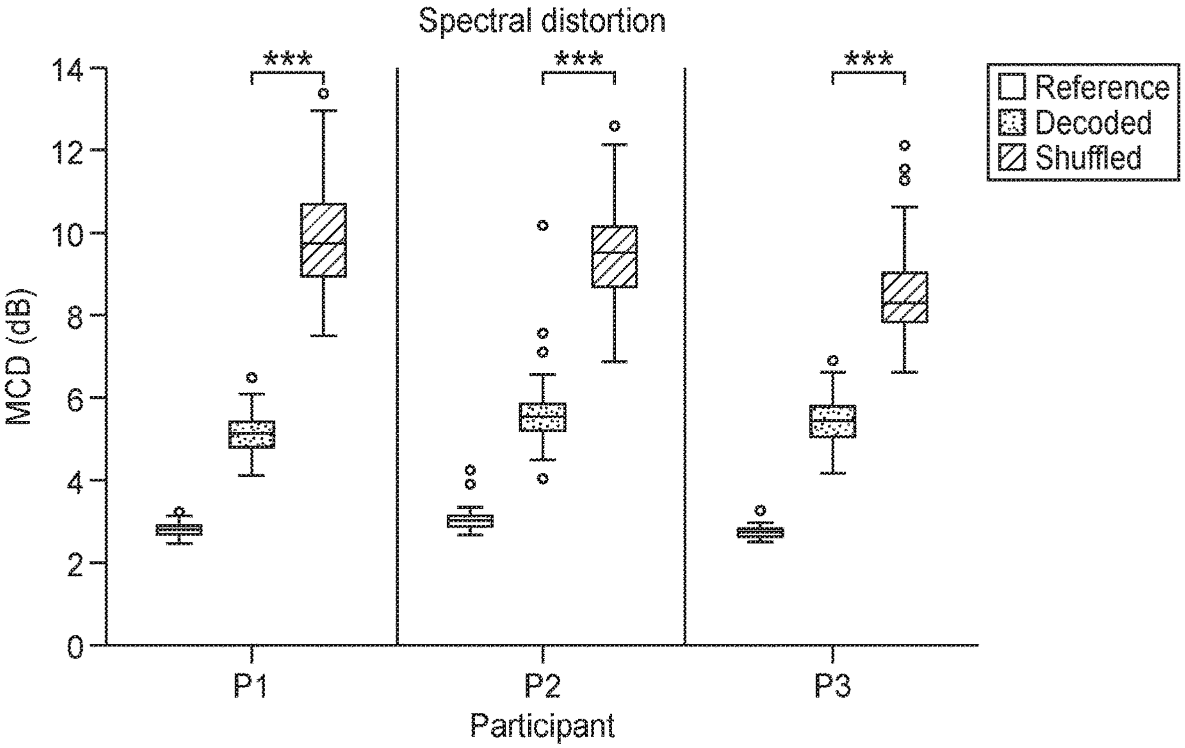
FIGS. 2A-2D: Decoded speech intelligibility and feature-specific performance.

The decoding performance was then quantified at a feature level for all participants. In speech synthesis, the spectral distortion of synthesized speech from ground-truth is commonly reported using the mean Mel-Cepstral Distortion (MCD). Mel-Frequency bands emphasize the distortion of perceptually relevant frequency bands of the audio spectrogram. In FIG. 2A, the MCD of neurally synthesized speech was compared to a reference synthesis from articulatory kinematics and chance-level decoding (lower MCD is better). The reference synthesis acts as a bound for performance as it simulated what perfect neural coding of the kinematics would achieve. For the five participants (P1-5), the median MCD scores of decoding speech ranged from 5.14 dB, 5.55 dB, and 5.49 dB, all better than chance-level decoding ($p<1e-18$, n=100 sentences, Wilcoxon signed-rank test (WSRT), for each participant).

The correlations between original and decoded acoustic features were computed. For each sentence and feature, the Pearson's correlation coefficient was computed using every sample (at 200 Hz) for that feature. The sentence correlation of the mean decoded acoustic features (intensity+MFCCs+excitation strengths+voicing) and inferred kinematics across participants are plotted. Prosodic features such as pitch (F0), speech envelope, and voicing were decoded well above chance-level ($r>0.6$, except F0 for P2: $r=0.49$ and all features for P5, $p<1e-10$, WSRT, for all participants and features).

Figure 2B:
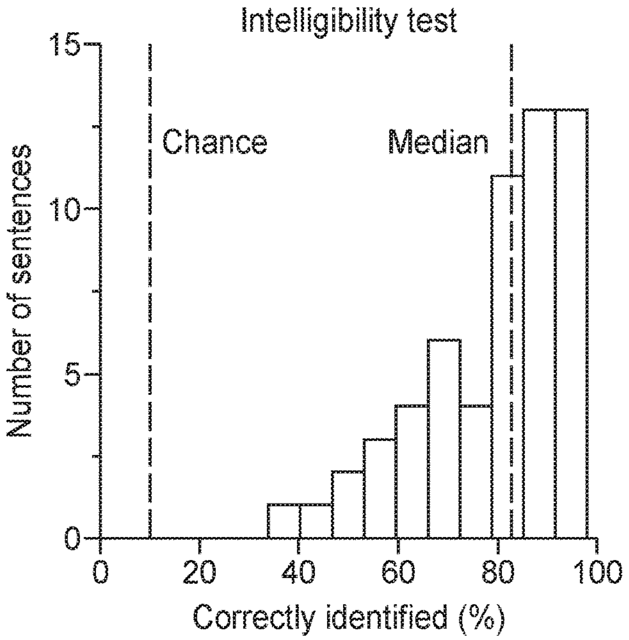

To assess perceptual intelligibility of the decoded speech, Amazon Mechanical Turk was used to evaluate naive listener's ability to understand the neurally decoded trials. 166 people were asked to identify 10 sentences (written on screen) corresponded to the decoded audio they heard. The median percentage of participants who correctly identified each sentence was 83%, significantly above chance (10%) (FIG. 2B).

Figure 2C:
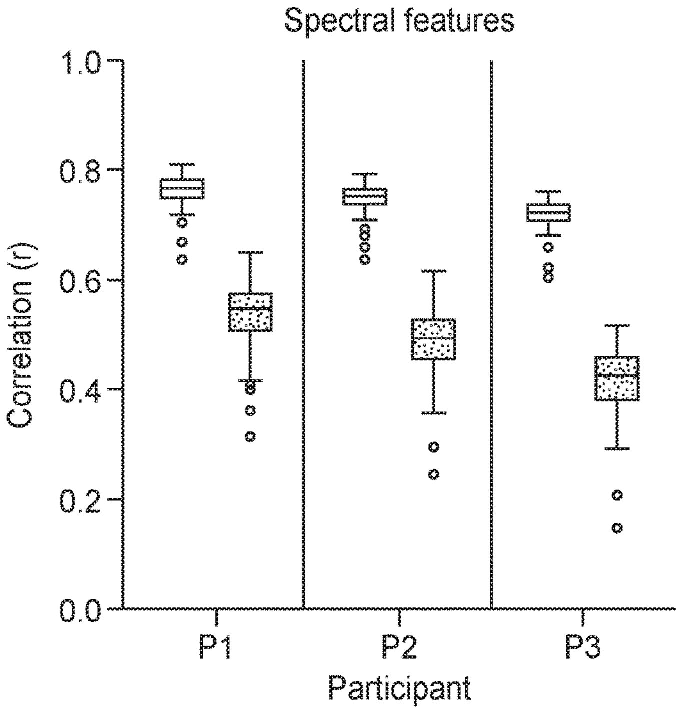

In addition to spectral distortion and intelligibility, the correlations between original and decoded spectral features were also examined. The median correlations (of sentences, Pearson's r) of the mean decoded spectral feature (pitch+25 MFCCs+excitation strengths+voicing) for each participant were 0.55, 0.49, and 0.42 (FIG. 2C).

Figure 2D:
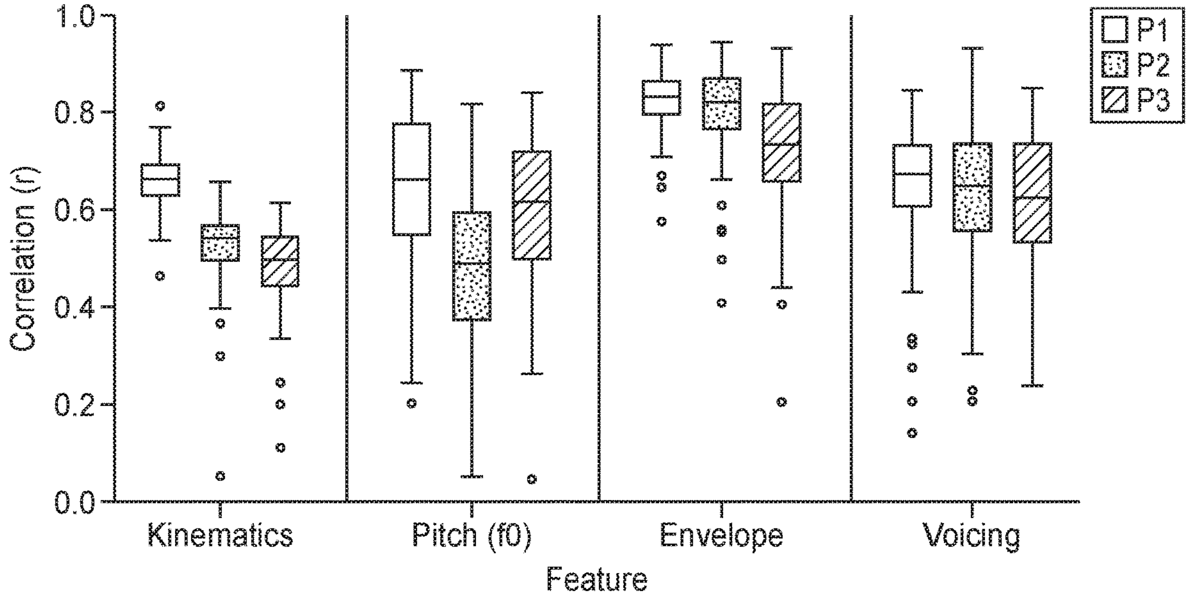

Similarly, for decoded kinematics (the intermediate representation), the median correlations were 0.66, 0.54, and 0.50 (FIG. 2D). Finally, three key aspects of prosody were examined for intelligible speech: pitch (f0), speech envelope, and voicing (FIG. 2D). For all participants, these features were decoded well above chance-level correlations ($r>0.6$, except f0 for P2: $r=0.49$, $p<1e-10$, n=100, WSRT, for all participants and features in FIGS. 2C-2D). Correlation decoding performance for all other features is shown in FIGS. 5A-5B.

Effects of Model Design Decisions

The following analyses were performed on data from P1. In designing a neural decoder for clinical applications, there are several key considerations that determine model performance. First, in patients with severe paralysis or limited speech ability, training data may be very difficult to obtain. Therefore, the amount of data necessary was assessed to achieve a high level of performance. A clear advantage was found in explicitly modeling articulatory kinematics as an intermediate step over decoding acoustics directly from the ECoG signals. The motivation for including articulatory kinematics was to reduce the complexity of the ECoG-to-acoustic mapping because it captures the physiological process by which speech is generated and is encoded in the vSMC. The "direct" decoder was a bLSTM recurrent neural network optimized for decoding acoustics (MFCCs) directly from same ECoG signals as employed in articulatory decoder.

Figure 3A:
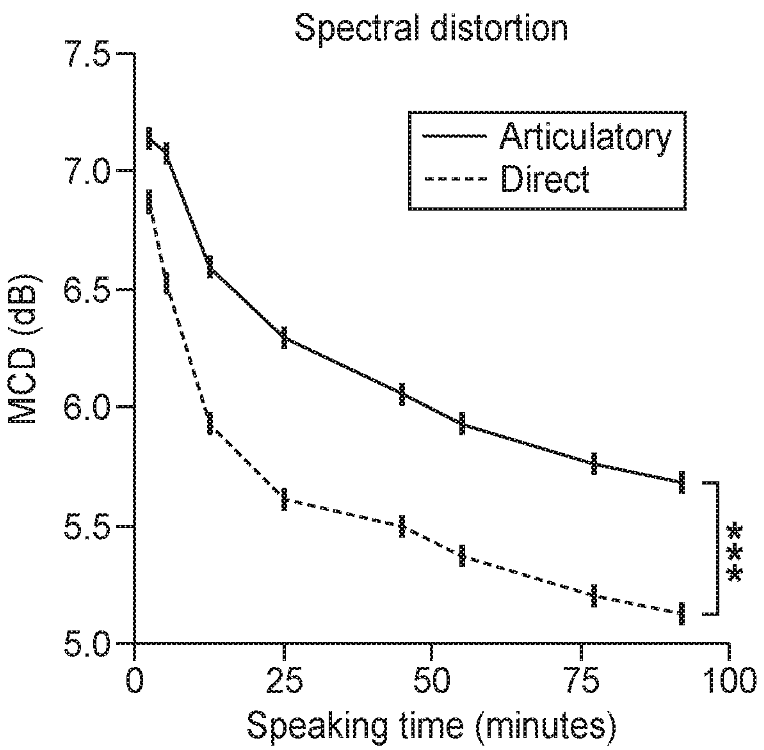
FIGS. 3A-3F: Effects of model design decisions.
Figure 3B:
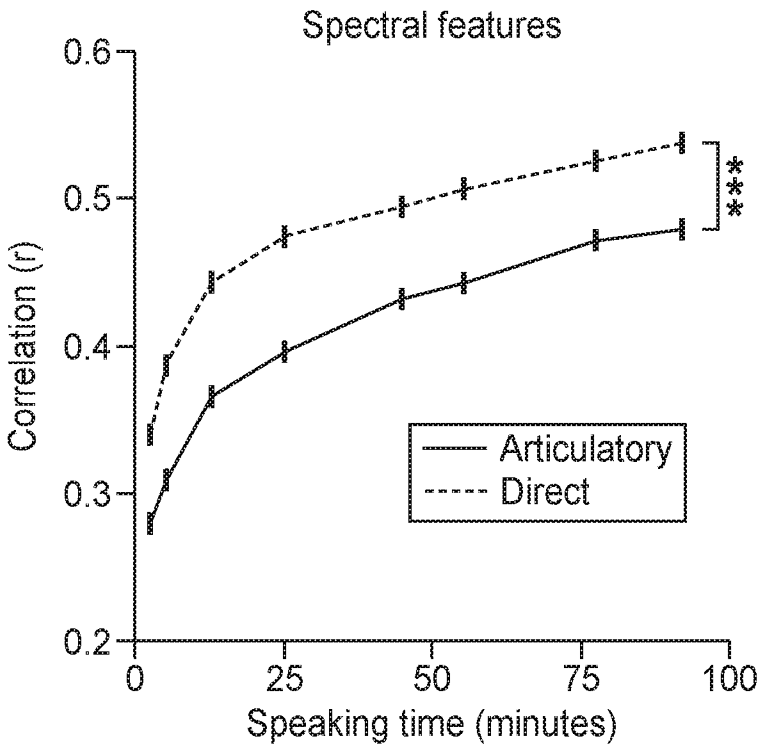

It was found that a robust performance could be achieved with as little as 25 minutes of speech, but performance continued to improve with the addition of data (FIG. 3A-3B). Without the articulatory intermediate step, the direct ECoG to acoustic decoding MCD was offset by 0.54 dB (0.2 dB is perceptually noticeable) using the full data set (FIG. 3A) ($p=1e^{-17}$, n=101, WSRT), a substantial difference given that a change in MCD as small as 0.2 dB is perceptually noticeable The biomimetic approach using an intermediate articulatory representation requires less training data.

Figure 3C:
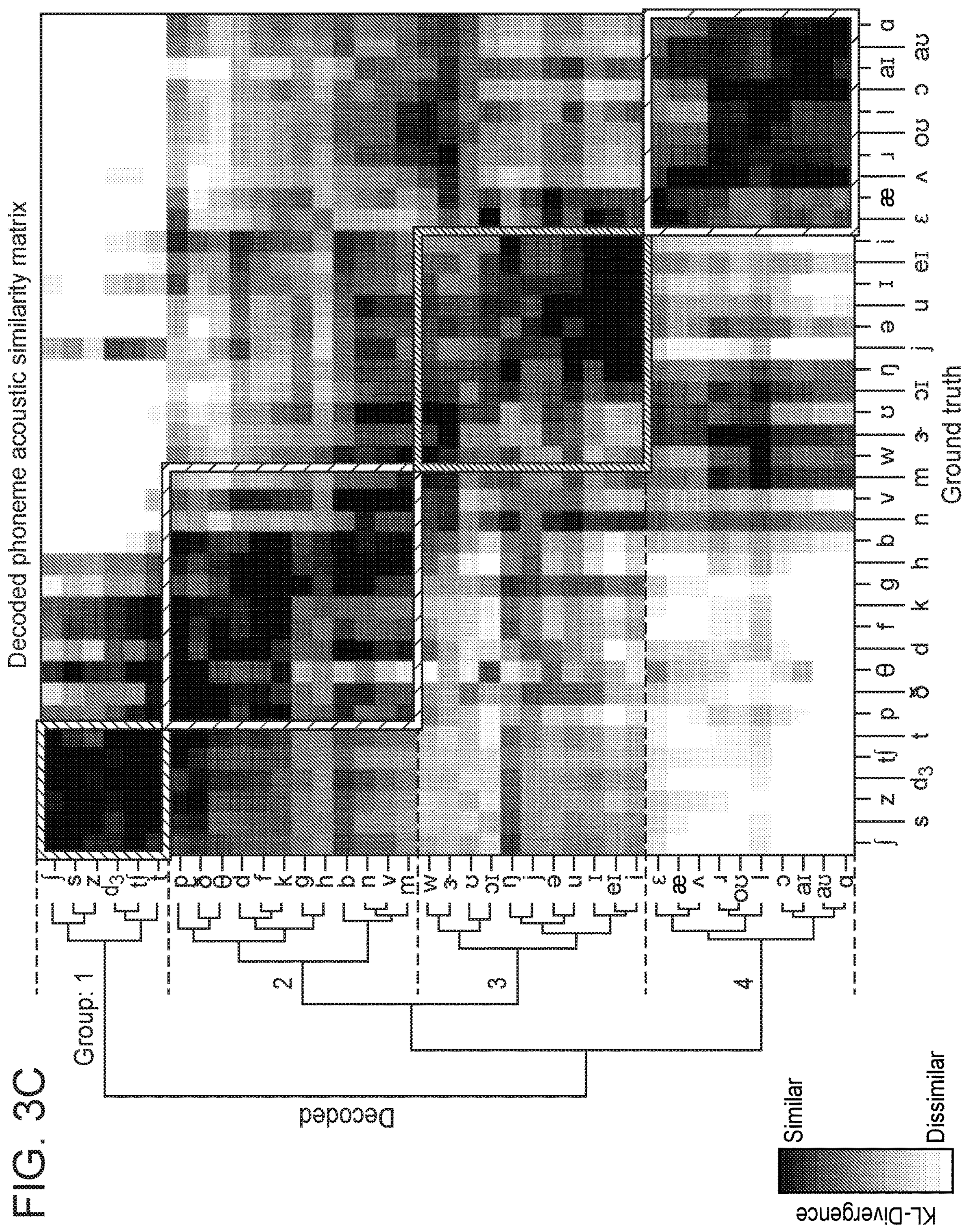

To understand the acoustic-phonetic properties that were preserved in decoded speech important for relative phonetic discrimination, the distribution of spectral features of each decoded phoneme to those of each ground-truth was compared by constructing a statistical distribution of the spectral feature vectors for each phoneme. Using the Kullback-Leibler (KL) divergence, the distribution of each decoded phoneme was compared to the distribution of each ground-truth phoneme to determine how similar they were (FIG. 3C). From the acoustic similarity matrix of only ground-truth phoneme pairs (FIG. 6), it was hypothesized that in addition to the same decoded and ground-truth phoneme being similar to one another, phonemes with shared acoustic properties would also be characterized as similar to one another. For example, two fricatives will be more acoustically similar to one another than to a vowel.

Hierarchical clustering on the KL-divergence of each phoneme pair demonstrated that phonemes were clustered into four main groups. Group 1 contained consonants with an alveolar place of constriction. Group 2 contained almost all other consonants. Group 3 contained mostly high vowels. Group 4 contained mostly mid and low vowels. The difference between groups tended to correspond to variations along acoustically significant dimensions (frequency range of spectral energy for consonants, and formants for vowels). Indeed, these groupings explain some of the confusions reflected in listener transcriptions of these stimuli. This hierarchical clustering was also consistent with the acoustic similarity matrix of only ground-truth phoneme-pairs (FIG. 6) (cophenetic correlation=0.71, $p=1e^{10}$).

Figure 3D:
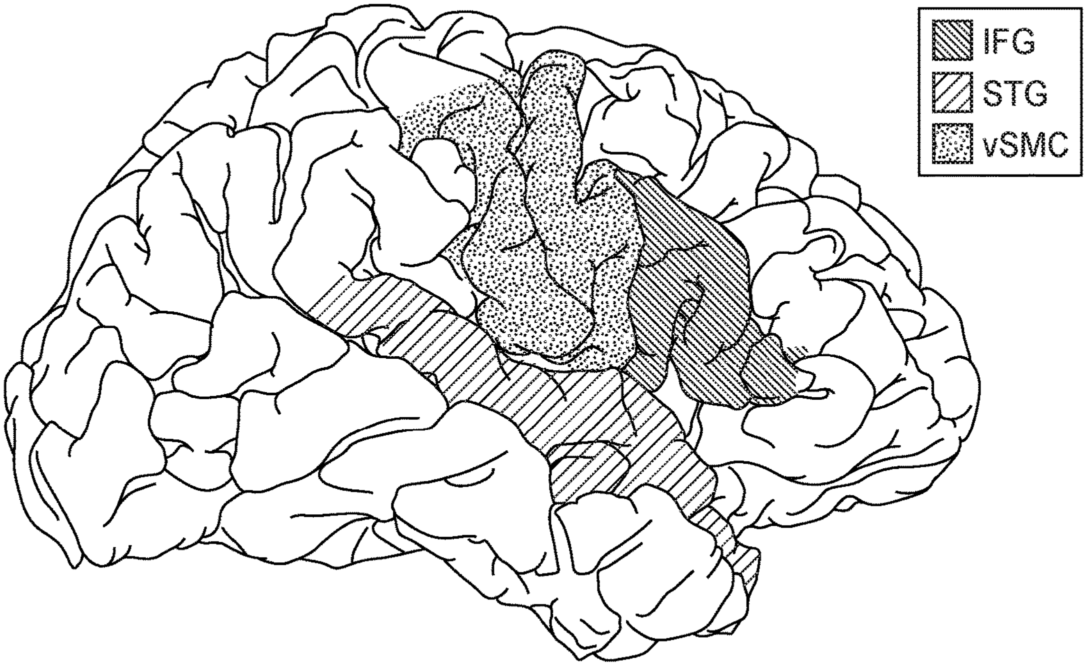
Figure 3E:
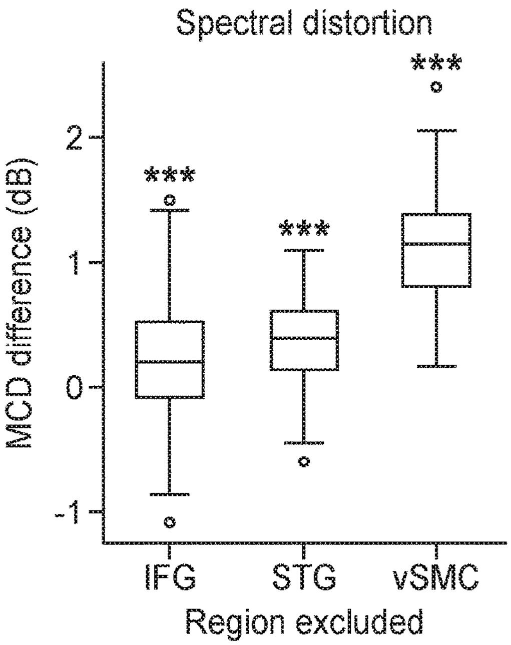
Figure 3F:
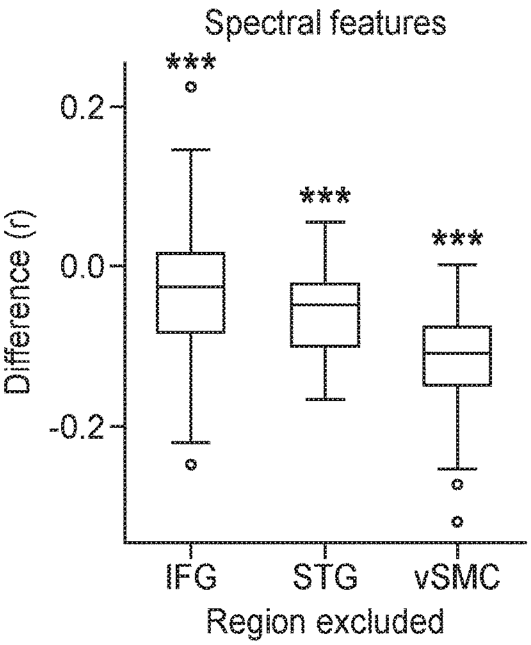

Third, since the success of the decoder depends on the initial electrode placement, the contribution of several anatomical regions (vSMC, STG, and IFG) that are involved in continuous speech production was quantified. Decoders were trained in a leave-one-region-out fashion where all electrodes from a particular region were held out (FIG. 3D) and performance was compared. Removing any region led to some decreased decoder performance (FIGS. 3E-3F) ($p=3e^{-4}$, n=100, WSRT). However, excluding vSMC resulted in the largest decrease in performance (1.13 dB MCD increase).

Fourth, it was investigated whether the decoder generalized to novel sentences that were never seen in the training data. Since P1 produced some sentences multiple times, two decoders were compared: one that was trained on all sentences (not the particular instances in the test set), and one that was trained excluding every instance of the sentences in the testing set. No significant difference was found in decoding performance of the sentences for both MCD and correlations of spectral features (p=0.36, p=0.75, n=51, WSRT). As a result, the decoder can generalize to arbitrary words and sentences that the decoder was never trained on.

Silently Mimed Speech Decoding

Figure 4A:
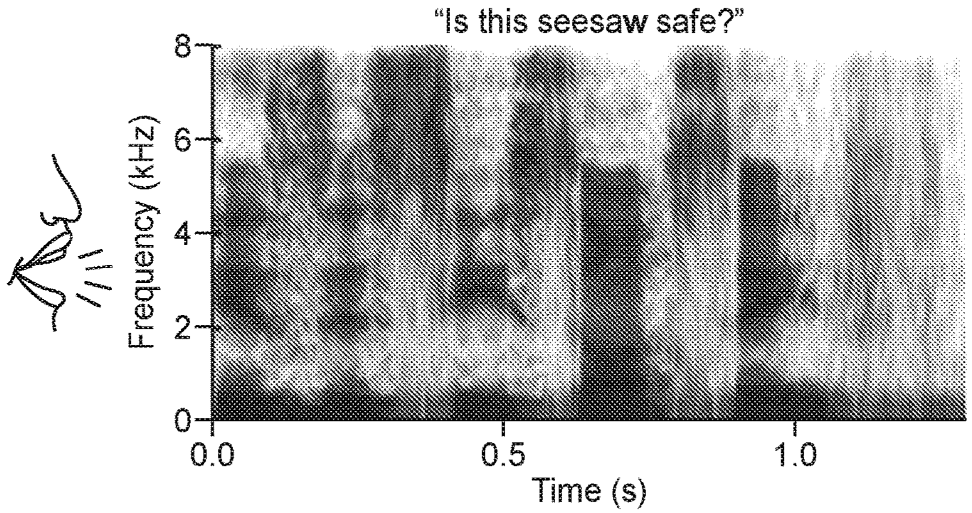
FIGS. 4A-4E: Speech synthesis from neural decoding of silently mimed speech.
Figure 4B:
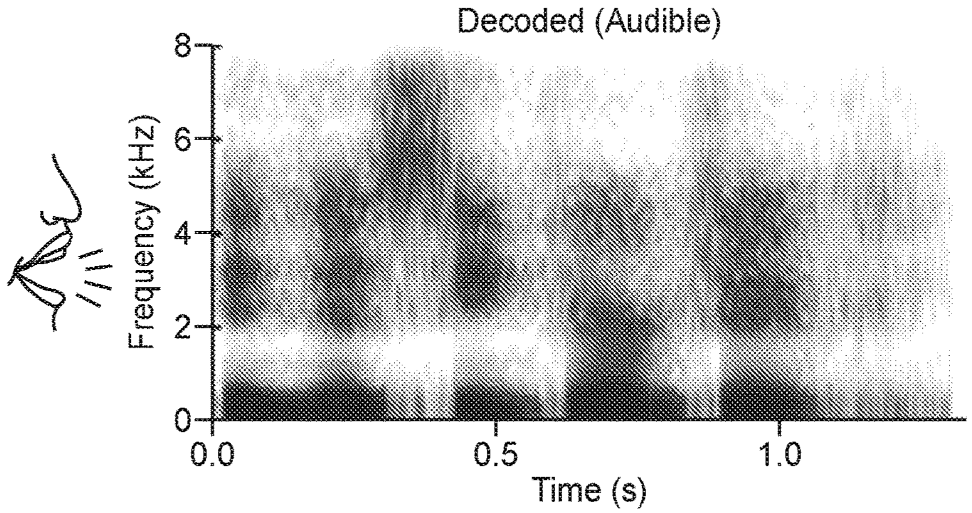
Figure 4C:
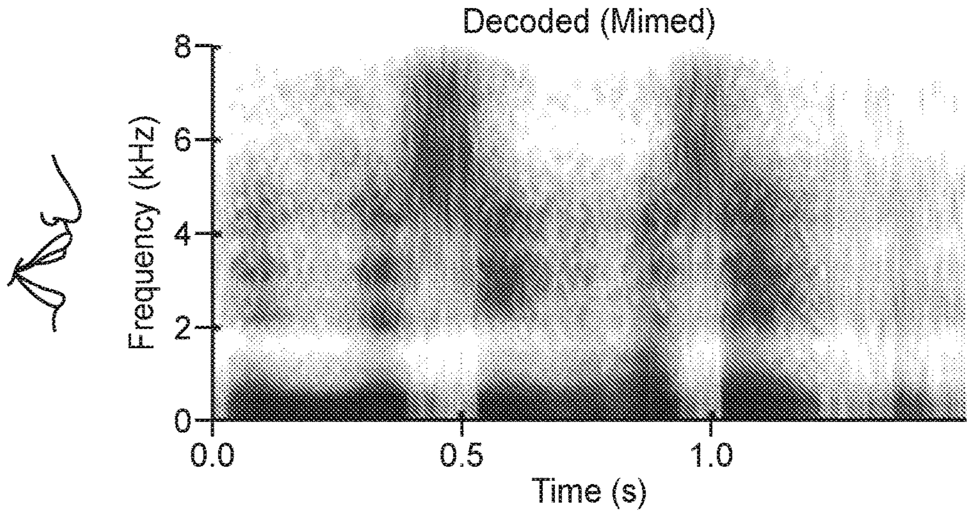
Figure 4D:
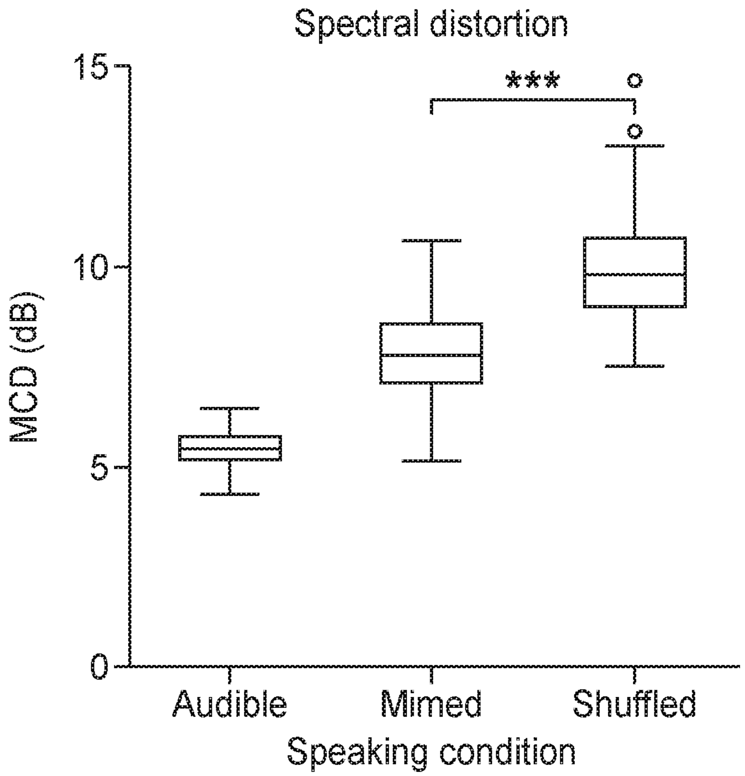
Figure 4E:
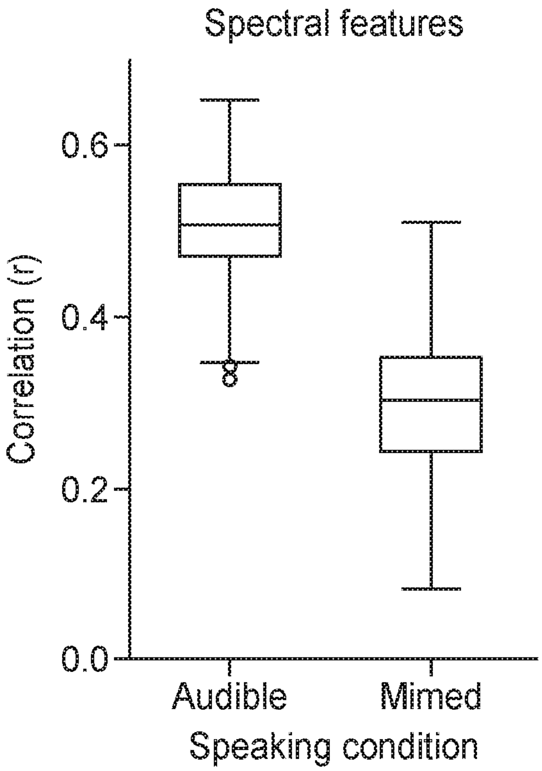

To rule out the possibility that the decoder is relying on the auditory feedback of participants' vocalization, and to simulate a setting where subjects do not overtly vocalize, the decoder was tested on silently mimed speech. A decoder with a held-out set of 58 sentences was tested in which the participant (P1) audibly produced each sentence and then mimed the same sentence, making the same kinematic movements but without making sound. Even though the decoder was not trained on mimed sentences, the spectrograms of synthesized silent speech demonstrated similar spectral patterns to synthesized audible speech of the same sentence (FIGS. 4A-4C). With no original audio to compare, performance of the synthesized mimed sentences was quantified with the audio from the trials with spoken sentences. The spectral distortion and correlation of the spectral features was calculated by first dynamically time-warping the spectrogram of the synthesized mimed speech to match the temporal profile of the audible sentence (FIGS. 4D-4E) and then comparing performance. Performance on mimed speech was inferior to that of audible/spoken speech (30% MCD difference), and demonstrates that it is possible to decode important spectral features of speech that were never audibly uttered ($p<1e^{-11}$, compared to chance, n=58; Wilcoxon signed-rank test).

State-Space of Decoded Speech Articulation

Modeling the underlying kinematics enhances the decoding performance. Low-dimensional kinematic state-space trajectories were examined, by computing the state-space projection via principal components analysis (PCA) on the articulatory kinematic features. The first ten principal components (PCs) (of 33 total) captured 85% of the variance and the first two PCs captured 35%.

The state-space trajectories appeared to manifest the dynamics of syllabic patterns in continuous speech. When examining transitions of specific phonemes, it was found that PC1 and PC2 retained their biphasic trajectories of vowel/consonant states, but showed specificity toward particular phonemes indicating that PC1 and PC2 are not necessarily just describing jaw opening and closing, but rather global opening and closing configurations of the vocal tract. These findings are consistent with theoretical accounts of human speaking behavior, which postulate that high-dimensional speech acoustics lie on a low-dimensional articulatory state-space.

To evaluate the similarity of the decoded state-space trajectories, productions of the same sentence across participants that were projected into their respective kinematic state-spaces were correlated (only P1, P2, and P4 had comparable sentences). The state-space trajectories were highly similar (r>0.8, FIG. 40, demonstrating that the decoder is likely relying upon a shared representation across speakers, a critical basis for generalization.

A shared kinematic representation across speakers could be very advantageous for someone who cannot speak as it may be more intuitive and faster to first learn to use the kinematics decoder (Stage 1), while using an existing kinematics-to-acoustics decoder (stage 2) trained on speech data collected independently.

Discussion

The results demonstrate intelligible speech synthesis from ECoG during both audible and silently mimed speech production. The present disclosure demonstrates speech synthesis using high-density, direct cortical recordings from human speech cortex. The decoder of the present disclosure explicitly incorporated the knowledge to simplify the translation of neural activity to sound by first decoding the primary physiological correlate of neural activity and then transforming to speech acoustics. This statistical mapping permits generalization with limited amounts of training.

The results show that cortical activity at vSMC electrodes provided for decoding (FIGS. 3E-3F) because it encodes the underlying articulatory physiology that produces speech. This knowledge was incorporated to simply the complex mapping from neural activity to sound by first decoding the physiological correlate of neural activity and then transforming to speech acoustics. Therefore, statistical mapping permits generalization with limited amounts of training.

The present disclosure represents one step forward for addressing a major challenge posed by paralyzed patients who cannot speak. The results demonstrate that speakers share a similar kinematic state-space representation (speaker-independent), and it is possible to transfer model knowledge about the mapping of kinematics to sound across subjects. Tapping into this emergent, low-dimensional representation from coordinated population neural activity in the intact cortex may be a critical for bootstrapping a decoder, as well facilitating BCI learning.

TABLE 1

Listener transcriptions of neurally synthesized speech. Examples shown at several word error rate levels. The original text is indicated by "o" and the listener transcriptions are indicated by "t".

| Word Error Rate | Original sentences (o) and transcriptions of synthesized speech (t) |
|---|---|
| 0% | o: is this seesaw safe |
| | t: is this seesaw safe |
| ~10% | o: bob bandaged both wounds with the skill of a doctor |
| | t: bob bandaged full wounds with the skill of a doctor |
| ~20% | o: those thieves stole thirty jewels |
| | t: thirty thieves stole thirty jewels |
| | o: help celebrate brother's success |
| | t: help celebrate his brother's success |
| ~30% | o: get a calico cat to keep the rodents away |
| | t: the calico cat to keep the rabbits away |
| | o: carl lives in a lively home |
| | t: carl has a lively home |
| ~50% | o: mum strongly dislikes appetizers |
| | t: mom often dislikes appetizers |
| | o: etiquette mandates compliance with existing regulations |
| | t: etiquette can be made with existing regulations |
| >70% | o: at twilight on the twelfth day we'll have Chablis |
| | t: i was walking through chablis |

Methods

Participants and experimental task. Three human participants (30 F, 31 F, 34 M) underwent chronic implantation of high-density, subdural electrode array over the lateral surface of the brain as part of their clinical treatment of epilepsy (right, left, and right hemisphere grids, respectively). Participants gave their written informed consent before the day of the surgery. All participants were fluent in English. All protocols were approved by the Committee on Human Research at UCSF and experiments/data in this study complied with all relevant ethical regulations. Each participant read and/or freely spoke a variety of sentences. P1 read aloud two complete sets of 460 sentences from the MOCHA-TIMIT database. Additionally, P1 also read aloud passages from the following stories: Sleeping Beauty, Frog Prince, Hare and the Tortoise, The Princess and the Pea, and Alice in Wonderland. P2 read aloud one full set of 460 sentences from the MOCHA-TIMIT database and further read a subset of 50 sentences an additional 9 times each. P3 read 596 sentences describing three picture scenes and then freely described the scene resulting in another 254 sentences. P3 also spoke 743 sentences during free response interviews. In addition to audible speech, P1 also read 10 sentences 12 times each alternating between audible and silently mimed (i.e. making the necessary mouth movements) speech. Microphone recordings were obtained synchronously with the ECoG recordings.

Data acquisition and signal processing. Electrocorticography was recorded with a multi-channel amplifier optically connected to a digital signal processor (Tucker-Davis Technologies). Speech was amplified digitally and recorded with a microphone simultaneously with the cortical recordings. ECoG electrodes were arranged in a 16×16 grid with 4 mm pitch. The grid placements were decided upon purely by clinical considerations. ECoG signals were recorded at a sampling rate of 3,052 Hz. Each channel was visually and quantitatively inspected for artifacts or excessive noise (typically 60 Hz line noise). The analytic amplitude of the high-gamma frequency component of the local field potentials (70-200 Hz) was extracted with the Hilbert transform and down-sampled to 200 Hz. The low frequency component (1-30 Hz) was also extracted with a 5th order Butterworth bandpass filter, down-sampled to 200 Hz and parallelly aligned with the high-gamma amplitude. Finally, the signals were z-scored relative to a 30 second window of running mean and standard deviation, so as to normalize the data across different recording sessions. High-gamma amplitude was studied because it correlates well with multi-unit firing rates and has the temporal resolution to resolve fine articulatory movements. A low frequency signal component was also included due to the decoding performance improvements note for reconstructing perceived speech from auditory cortex. Decoding models were constructed using all electrodes from vSMC, STG, and IFG except for electrodes with bad signal quality as determined by visual inspection.

Phonetic and phonological transcription. For the collected speech acoustic recordings, transcriptions were corrected manually at the word level so that the transcript reflected the vocalization that the participant actually produced. Given sentence level transcriptions and acoustic utterances chunked at the sentence level, hidden Markov model based acoustic models were built for each participant so as to perform sub-phonetic alignment within the Festvox framework. Phonological context features were also generated from the phonetic labels, given their phonetic, syllabic and word contexts.

Cortical surface extraction and electrode visualization. The electrodes were localized on each individual's brain by co-registering the preoperative T1 MRI with a postoperative CT scan containing the electrode locations, using a normalized mutual information routine in SPM12. Pial surface reconstructions were created using Freesurfer. Final anatomical labeling and plotting was performed using the img pipe python package.

Inference of articulatory kinematics. The articulatory kinematics inference model comprises a stacked deep encoder-decoder, where the encoder combines phonological and acoustic representations into a latent articulatory representation that is then decoded to reconstruct the original acoustic signal. The latent representation is initialized with inferred articulatory movement from Electromagnetic Midsagittal Articulography (EMA) and appropriate manner features. A statistical subject-independent approach to acoustic-to-articulatory inversion which estimates 12 dimensional articulatory kinematic trajectories (x and y displacements of tongue dorsum, tongue blade, tongue tip, jaw, upper lip and lower lip, as would be measured by EMA) using only the produced acoustics and phonetic transcriptions is known. Since, EMA features do not describe all acoustically consequential movements of the vocal tract, complementary speech features were appended that improve reconstruction of original speech. In addition to voicing and intensity of the speech signal, place manner tuples were added (represented as continuous binary valued features) to bootstrap the EMA with what was determined were missing physiological aspects in EMA. There were 18 additional values to capture the following place-manner tuples: 1) velar stop, 2) velar nasal, 3) palatal approximant, 4) palatal fricative, 5) palatal affricate, 6) labial stop, 7) labial approximant, 8) labial nasal, 9) glottal fricative, 10) dental fricative, 11) labiodental fricative, 12) alveolar stop, 13) alveolar approximant, 14) alveolar nasal, 15) alveolar lateral, 16) alveolar fricative, 17) unconstructed, 18) voicing. For this purpose, an existing annotated speech database (Wall Street Journal Corpus) was used and trained speaker independent deep recurrent network regression models to predict these place-manner vectors only from the acoustics, represented as 25-dimensional Mel Frequency Cepstral Coefficients (MFCCs). The phonetic labels were used to determine the ground truth values for these labels (e.g., the dimension "labial stop" would be 1 for all frames of speech that belong to the phonemes /p/, /b/ and so forth). However, with a regression output layer, predicted values were not constrained to the binary nature of the input features. In all, these 32 combined feature vectors form the initial articulatory feature estimates.

Finally, to ensure that the combined 32 dimensional representation has the potential to reliably reconstruct speech, an autoencoder was designed to optimize these values. Specifically, a recurrent neural network encoder is trained to convert phonological and acoustic features to the initialized 32 articulatory representations and then a decoder converts the articulatory representation back to the acoustics. The stacked network is re-trained optimizing the joint loss on acoustic and EMA parameters. After convergence, the encoder is used to estimate the final articulatory kinematic features that act as the intermediate to decode acoustics from ECoG.

Neural decoder. The decoder maps ECoG recordings to MFCCs via a two stage process by learning intermediate mappings between ECoG recordings and articulatory kinematic features, and between articulatory kinematic features and acoustic features. All data (ECoG, kinematics, and acoustics) are sampled and processed by the model at 200 Hz. This model was implemented using TensorFlow in python. In the first stage, a stacked 3-layer bLSTM learns the mapping between 300 ms (60 time points) window of high-gamma and LFP signals and a corresponding single time point (sampled at 200 Hz) of the 32 articulatory features. In the second stage, an additional stacked 3-layer bLSTM learns the mapping between the output of the first stage (decoded articulatory features) and 32 acoustic parameters (200 Hz) for full sentences sequences. These parameters are 25 dimensional MFCCs, 5 sub-band voicing strengths for glottal excitation modelling, log(F0), voicing. At each stage, the model is trained to with a learning rate of 0.001 to minimize mean-squared error of the target. Dropout rate is set to 50% to suppress overfitting tendencies of the model. A bLSTM was used because of their ability to retain temporally distant dependencies when decoding a sequence.

During testing, a full sentence sequence of neural activity (high-gamma and low-frequency components) is processed by the decoder. The first stage processes 300 ms of data at a time, sliding over the sequence sample by sample, until it has returned a sequence of kinematics that is equal length to the neural data. The neural data is padded with an additional 150 ms of data before and after the sequence to ensure the result is the correct length. The second stage processes the entire sequence at once, returning an equal length sequence of acoustic features. These features are then synthesized into an audio signal.

At each stage, the model is trained using the Adam optimizer to minimize mean-squared error. The optimizer was initialized with learning rate=0.001, beta1=0.9, beta2=0.999, epsilon=1e−8. Models were stopped from training after the validation loss no longer decreased. Dropout rate is set to 50% in stage 1 and 25% in stage 2 to suppress overfitting tendencies of the models. There are 100 hidden units for each LSTM cell. Each model employed 3 stacked bLSTMs with an additional linear layer for regression. A bLSTM was used because of their ability to retain temporally distant dependencies when decoding a sequence.

In the first stage, the batch size for training is 256, and in the second stage the batch size is 25. Training and testing data were randomly split based off of recording sessions, meaning that the test set was collected during separate recording sessions from the training set. The training and testing splits in terms of total speaking time (minutes: seconds) are as follows: P1—training: 92:15, testing: 4:46 (n=101); P2—training: 36:57, testing: 3:50 (n=100); P3—training: 107:42, testing: 4:44 (n=98); P4—training: 27:39, testing 3:12 (n=82); P5—training 44:31, testing 2:51 (n=44). n=number of sentences in test set.

The "direct" ECoG to acoustics decoder a similar architecture as the stage 1 articulatory bLSTM except with an MFCC output. Originally the direct acoustic decoder was trained as a 6-layer bLSTM that mimics the architecture of the 2 stage decoder with MFCCs as the "intermediate layer" and as the output. However, it was found that performance was better with a 4-layer bLSTM (no intermediate layer) with 100 hidden units for each layer, 50% dropout and 0.005 learning rate using Adam optimizer for minimizing mean-squared error. Models were coded using Python's version 1.9 of Tensorflow.

Speech synthesis from acoustic features. An implementation of the Mel-log spectral approximation algorithm with mixed excitation within Festvox was used to generate the speech waveforms from estimates of the acoustic features from the neural decoder.

Model training procedure. As described, simultaneous recordings of ECoG and speech are collected in short blocks of approximately 5 minutes. To partition the data for model development, 2-3 blocks were allocated for model testing, 1 block for model optimization, and the remaining blocks for model training. The test sentences 432 for P1 and P2 each spanned 2 recording blocks and comprised 100 sentences read aloud. The test sentences for P3 were different because the speech comprised 100 sentences over three blocks of freely and spontaneously speech describing picture scenes. For shuffling the data to test for significance, the order of the electrodes were shuffled that were fed into the decoder. This method of shuffling preserved the temporal structure of the neural activity.

Mel-Cepstral Distortion (MCD). To examine the quality of synthesized speech, the Mel-Cepstral Distortion (MCD) of the synthesized speech was calculated when compared the original ground-truth audio. MCD is an objective measure of error determined from MFCCs and is correlated to subjective perceptual judgments of acoustic quality. For reference acoustic features $mc^{(y)}$ and decoded features $mc^{(\hat{y})}$, $$MCD = \frac{10}{\ln(10)}\sqrt{\sum_{0<d<25}\left(mc_d^{(y)} - mc_d^{(\hat{y})}\right)^2} \quad (1)$$

Intelligibility Assessment. Listening tests using crowd-sourcing are a standard way of evaluating the perceptual quality of synthetic speech. To comprehensively assess the intelligibility of the neurally synthesized speech, a series of identification and transcription tasks was conducted on the Amazon Mechanical Turk. A set of 60 sentences (6 trials of 10 unique sentences) were evaluated int his assessment. These trials, also held out during training the decoder, were used in place of the 100 unique sentences tested throughout the rest of FIG. 2 because the listeners always had the same 10 sentences to chose from. Each trial sentence was listened to by 50 different listeners. In all, 166 unique listeners took part in the evaluations.

To assess the amount of training data affects decoder performance, the data was partitioned by recording blocks and trained a separate model for an allotted number of blocks. In total, 8 models were trained, each with one of the following block allotments: [1, 2, 5, 10, 15, 20, 25, 28]. Each block comprised an average of 50 sentences recorded in one continuous session.

For the word level identification tasks, several cohorts of words grouped by the number of syllables within were created. Using the time boundaries from the ground truth phonetic labelling, audio was extracted from the neurally synthesized speech into four classes of 1-syllable, 2-syllable, 3-syllable and 4-syllable words. Tests were conducted on each of these groups of words that involve identification of the synthesized audio from a group of i) 10 choices, ii) 25 choices, and iii) 50 choices of what they think the word is. The presented options included the true word and the remaining choices randomly drawn from the other words within the class. All words within the word groups were judged for intelligibility without any further sub-selection.

Since the content words in the MOCHA-TIMIT data are largely low frequency words to assess sentence-level intelligibility, along with the neurally synthesized audio file, the listeners were presented with a pool of words that may be in the sentence. This makes it task a limited vocabulary free response transcription. Two experiments were conducted where the transcriber is presented with pool of i) 25 word choices, and ii) 50 word choices that may be used the sentence. The true words that make up the sentence are included along with randomly drawn words from the entire test set and displayed in alphabetical order. Given that the median sentence is only 7 words long (std=21, min=4, max=13), this task design allows for reliable assessment of intelligibility. Each trial was judged by 10-20 different listeners. Each intelligibility task was performed by 47-187 unique listeners (a total of 1755 listeners across 16 intelligibility tasks making all reported analyses statistically reliable. All sentences from the test set were sent for intelligibility assessment without any further selection. The listeners were required to be English speakers located in the United States, with good ratings (>98% rating from prior tasks on the platform). For the sentence transcription tasks, an automatic spell checker was employed to correct misspellings.

No further spam detection, or response rejection was done in all analyses reported. Word Error Rate (WER) metric computed on listener transcriptions is used to judge the intelligibility of the neurally synthesized speech. Where I is the number of word insertions, D is the number of word deletions and S is the number of word substitutions for a reference sentence with N words, WER is computed as $$WER = \frac{I + D + S}{N} \tag{2}$$

Data limitation analysis. To assess the amount of training data affects decoder performance, the data was partitioned by recording blocks and trained a separate model for an allotted number of blocks. In total, 8 models were trained, each with one of the following block allotments: [1, 2, 5, 10, 15, 20, 25, 28]. Each block comprised an average of 50 sentences recorded in one continuous session.

Quantification of silent speech synthesis. By definition, there was no acoustic signal to compare the decoded silent speech. In order to assess decoding performance, decoded silent speech was evaluated in regards to the audible speech of the same sentence uttered immediately prior to the silent trial. This was done so dynamically time-warping the decoded silent speech MFCCs to the MFCCs of the audible condition and computing Pearson's correlation coefficient and Mel-cepstral distortion.

Phoneme acoustic similarity analysis. The acoustic properties of decoded phonemes were compared to ground-truth to better understand the performance of the decoder of the present disclosure. To do this, all time points were sliced for which a given phoneme was being uttered and used the corresponding time slices to estimate its distribution of spectral properties. With principal components analysis (PCA), the 32 spectral features were projected onto the first 4 principal components before fitting the gaussian kernel density estimate (KDE) model. This process was repeated so that each phoneme had two KDEs representing either its decoded and or ground-truth spectral properties. Using Kullback-Leibler divergence (KL divergence), each decoded phoneme KDE was compared to every ground-truth phoneme KDE, creating an analog to a confusion matrix used in discrete classification decoders. KL divergence provides a metric of how similar two distributions are to one another by calculating how much information is lost when one distribution was approximated with another. Lastly, Ward's method was used for agglomerative hierarchical clustering to organize the phoneme similarity matrix.

To understand whether the clustering of the decoded phonemes was similar to the clustering of ground-truth phoneme pairs, the cophenetic correlation (CC) was used to assess how well the hierarchical clustering determined from decoded phonemes preserved the pairwise distance between original phonemes, and vice versa[24]. For the decoded phoneme dendrogram, the CC for preserving original phoneme distances was 0.71 as compared to 0.80 for preserving decoded phoneme distances. For the original phoneme dendrogram, the CC for preserving decoded phoneme distances was 0.64 as compared to 0.71 for preserving original phoneme distances. $p < 1e-10$ for all correlations.

State-space kinematic trajectories. For state-space analysis of kinematic trajectories, principal components analysis (PCA) was performed on the 33 kinematic features using the training data set from P1. FIGS. 4A-4B shows kinematic trajectories (original, decoded (audible and mimed) projected onto the first two principal components (PCs). The example decoded mimed trajectory occurred faster in time by a factor of 1.15 than the audible trajectory so the trajectory was uniformly temporally stretched for visualization. The peaks and troughs of the decoded mimed trajectories were similar to the audible speech trajectory (r=0.65, r=0.55) although the temporal locations are shifted relative to one another, likely because the temporal evolution of a production, whether audible or mimed, is inconsistent across repeated productions. To quantify the decoding performance of mimed trajectories, the dynamic time-warping approach described above was used, although in this case, temporally warping with respect to the inferred kinematics (not the state-space).

For analysis of state-space trajectories across participants, the correlations of productions of the same sentence were measured, but across participants. Since the sentences were produced at different speeds, they were dynamically time-warped to match and compared against correlations of dynamically time-warped mismatched sentences.

Example 2: Real-Time Decoding of Question-and-Answer Speech Dialogue Using Human Cortical Activity Although this work shows a very simple demonstration by decoding the context based priors on brain activity evoked while the patient listened to a question, the approach can be generalized to include more complex contexts. In addition, the decoding targets don't need to be limited to answer responses to questions; they can be any speech targets, including single-word targets and "continuous" sentences of arbitrary lengths with large vocabulary sizes. Additionally, neural signals can be generalized beyond ECoG to modalities such as intracranial spike recordings and even non-invasive recording methods including fMRI or optical sensing methods (such as fNIRS).

Figure 7A:
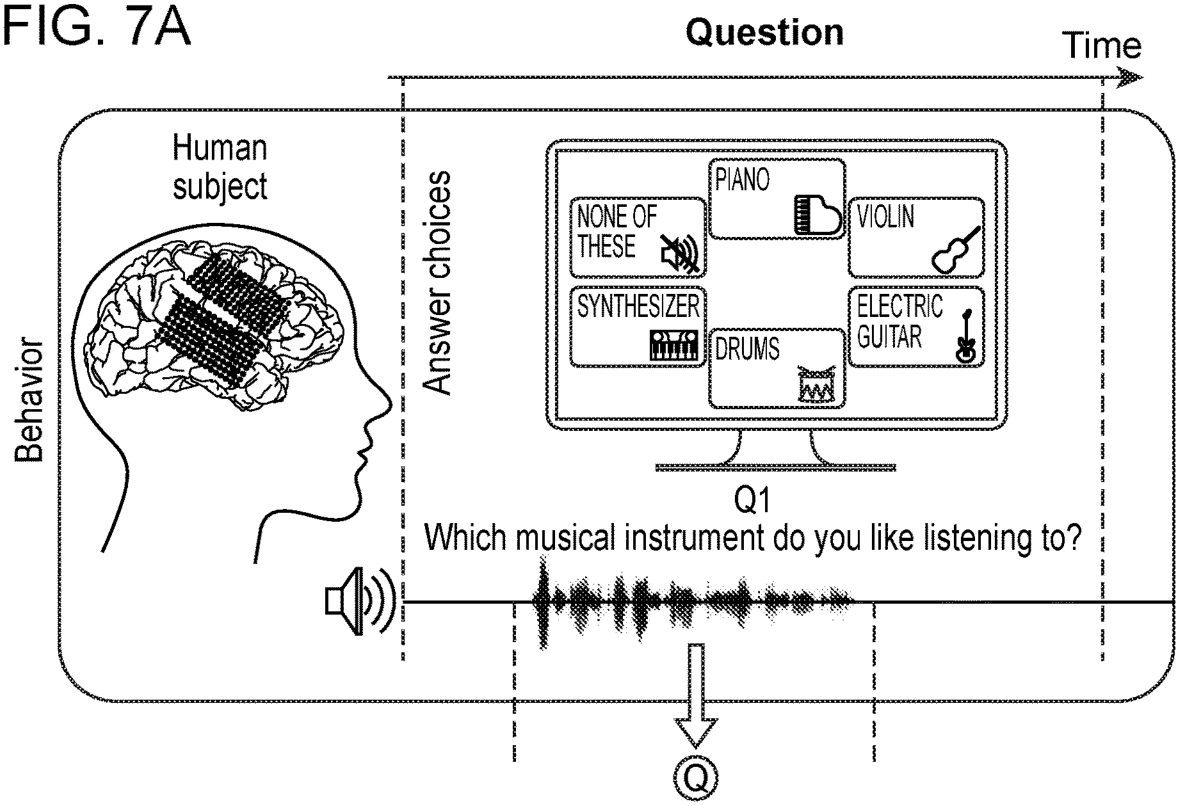
FIGS. 7A-7K: Schematic of real-time speech decoding during a question (blue) and answer (red) task.
Figure 7B:
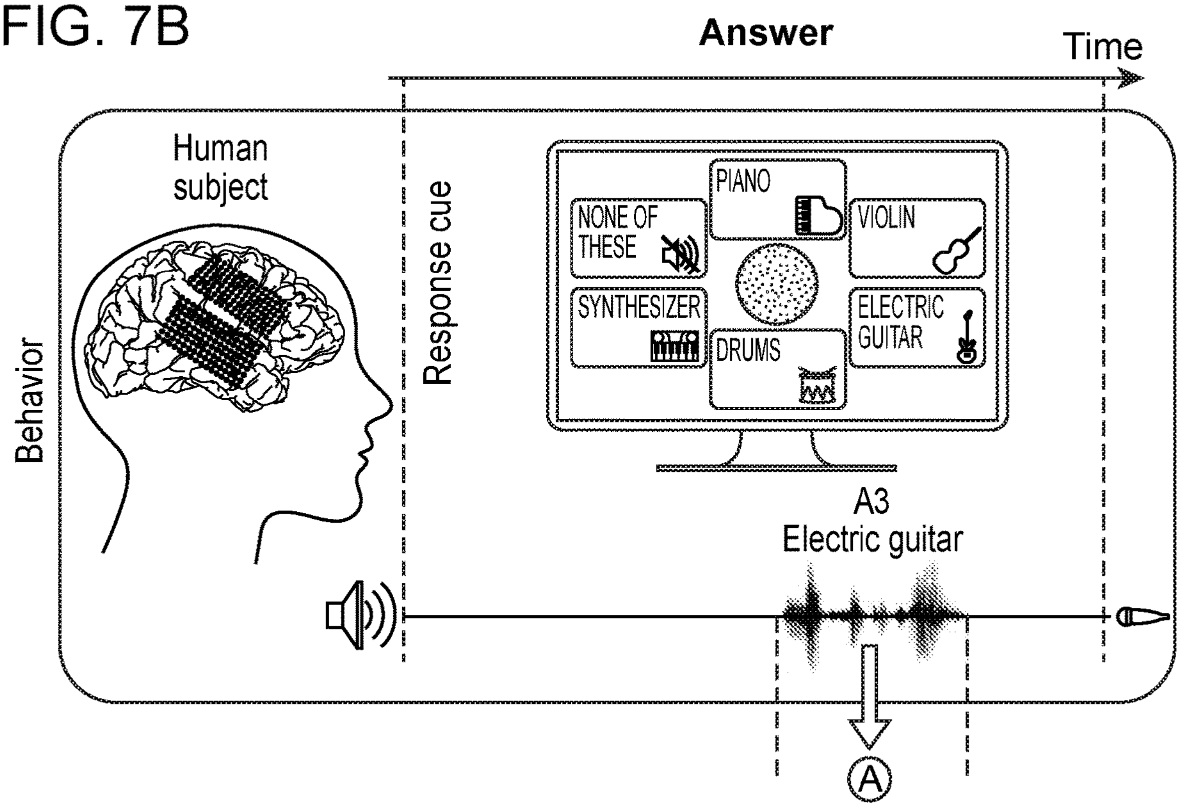
Figure 7C:
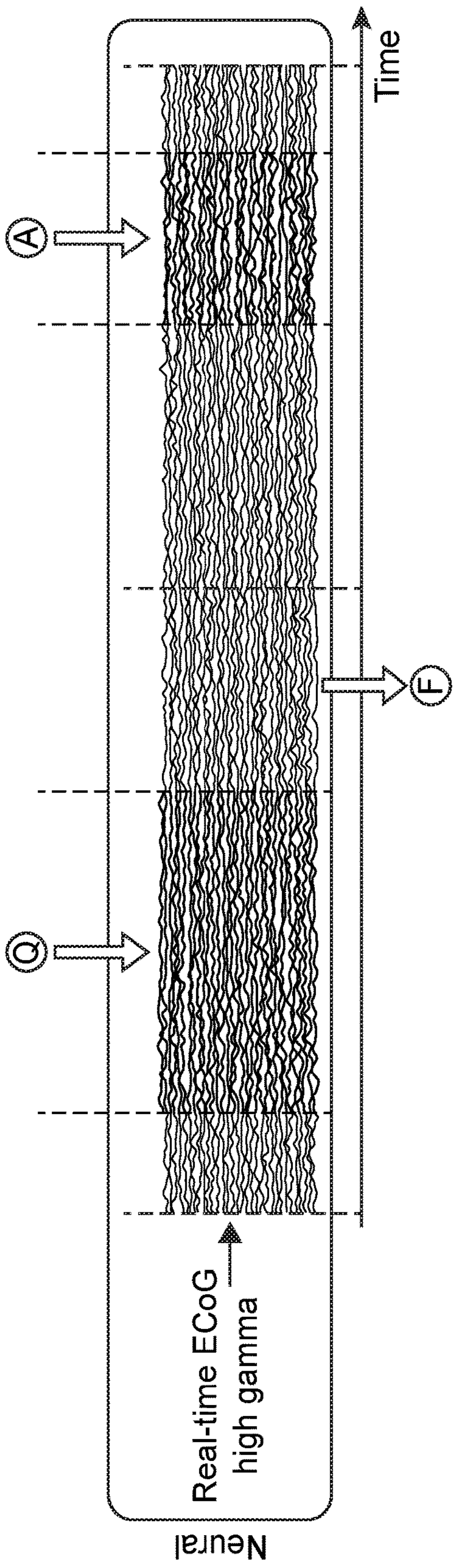
Figure 7D:
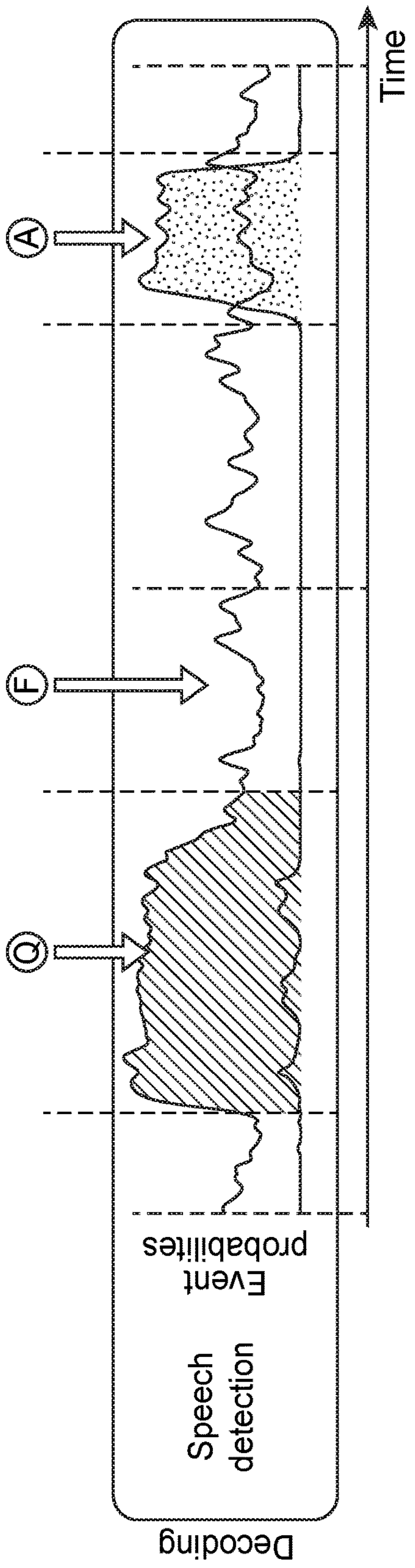
Figure 7E:
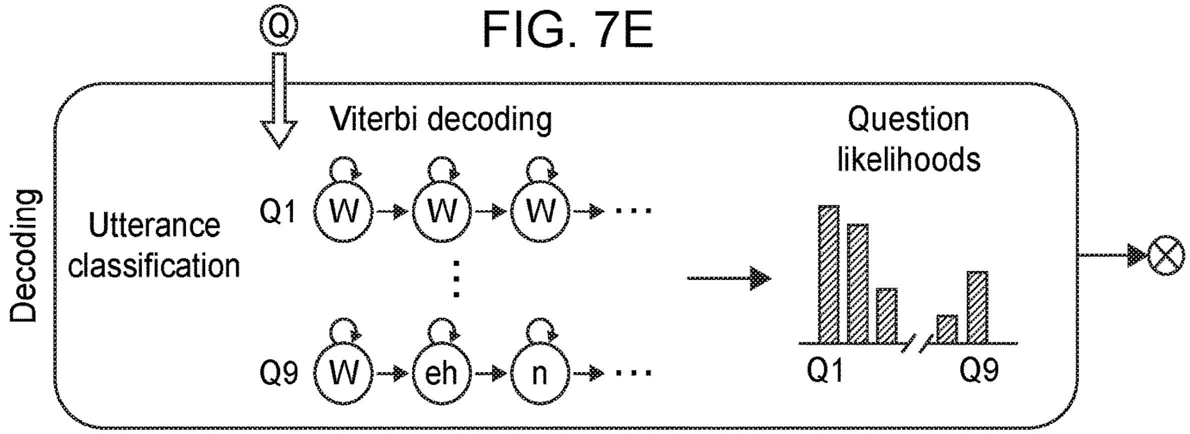
Figure 7F:
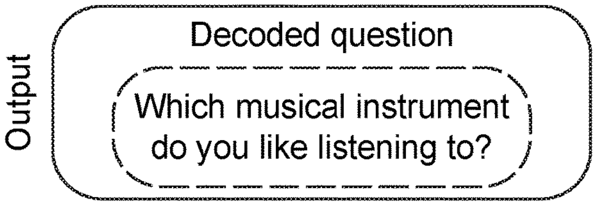
Figure 12:
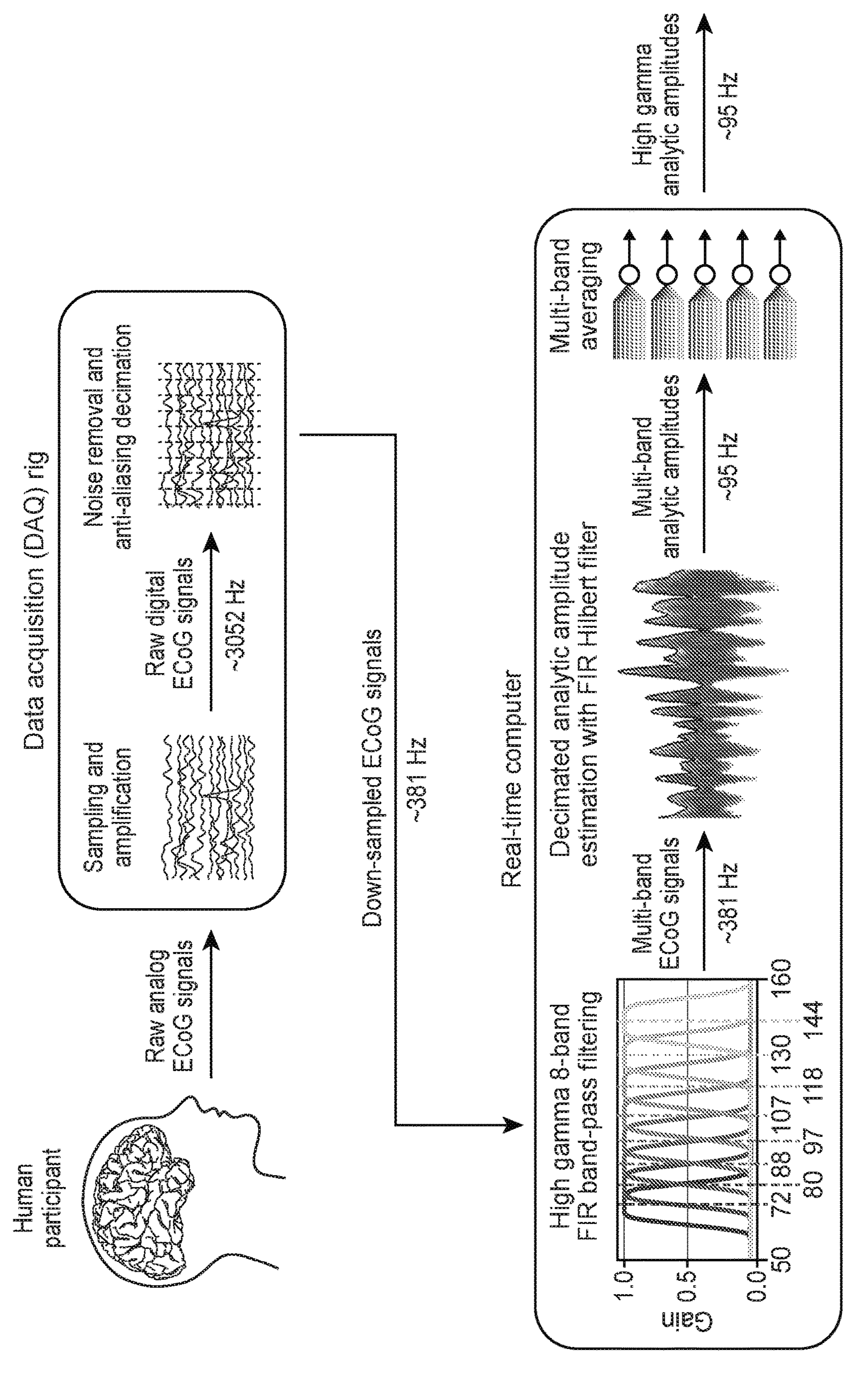
FIG. 12: Real-time neural signal preprocessing with the rtNSR system 14. In the DAQ rig, ECoG signals are sampled from the participant's brain at ~3052 Hz, quantized, notch filtered at 60, 120, and 180 Hz, and decimated (with anti-aliasing) to ~381 Hz. The resulting signals are streamed into the real-time computer and, within rtNSR, band-passed using eight FIR filters with center frequencies in the high gamma band (filter responses shown in the bottom-left plot). The analytic amplitude is then estimated for each of the eight band-passed signals for each channel at ~95 Hz using an FIR filter designed to approximate the Hilbert transform. The analytic amplitudes for the eight bands associated with each channel are averaged to yield a high gamma analytic amplitude signal for each channel.

While participants performed a question-and-answer natural speech perception (FIG. 7A) and production (FIG. 7B) task, neural activity was acquired from high-density ECoG arrays that covered auditory and sensorimotor cortical regions. In real-time, neural activity was altered to extract signals in the high gamma frequency range (70-150 Hz; FIG. 7C, FIG. 12), which correlate with multiunit activity and have been previously used to decode speech signals from auditory and sensorimotor brain regions. These high gamma signals were used to perform real-time speech event detection, predicting which time segments of the neural activity occurred during question perception (FIG. 7D, blue curve) or answer production (FIG. 7D, red curve). The speech event detector was trained to identify spatiotemporal neural patterns associated with these events, such as rapid evoked responses in STG during question perception or causal activity patterns in vSMC during answer production, which were used during real-time decoding to predict the temporal onsets and offsets of detected speech events For each time segment that was labeled as a question event, a classification model was used to analyze the high gamma activity and compute question likelihoods using phone-level Viterbi decoding29 (FIG. 7E). In this approach, a hidden Markov model (HMM) was used to represent each question utterance and estimate the probability of observing a time segment of high gamma activity assuming that the participant was hearing the sequence of phones that comprise the utterance. The most likely question was output as the decoded question (FIG. 7F).

Figure 7G:
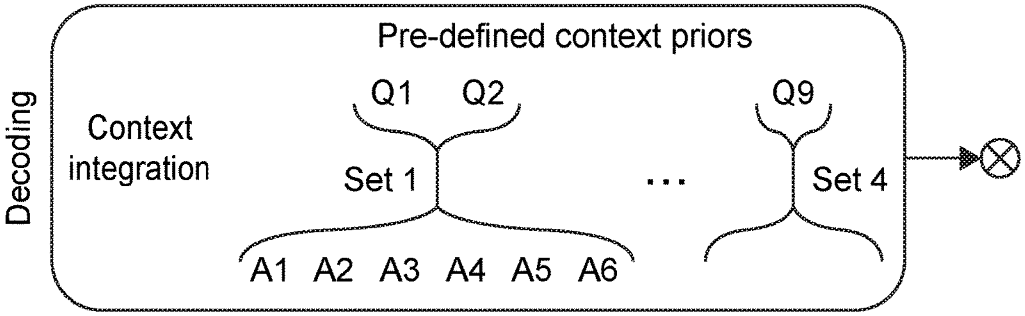
Figure 7H:
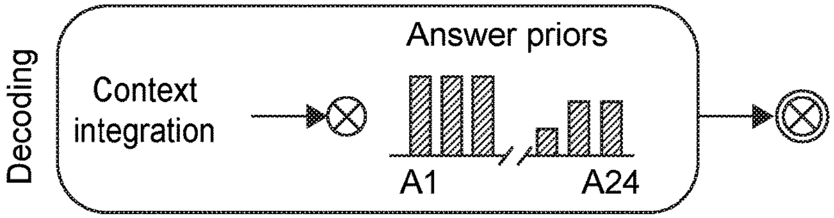

It was hypothesized that answer decoding could be improved by utilizing knowledge about the previously decoded question. A question-and-answer task was designed such that specific answer responses were only valid for certain questions (Table 2). For example, if a participant heard the question "How is your room currently?", there were five valid answers ("Bright", "Dark", "Hot", "Cold", and "Fine"). The relationship between each question and the valid answers was used to define context priors (FIG. 7G), which were represented by a at probability distribution for within-question answers and zero probability for out-of-question answers. A context integration model combined these context priors with decoded question likelihoods to compute answer prior probabilities (FIG. 7H). This context integration model was used during online real-time decoding and offline analysis (except where specifically indicated).

TABLE 2

The question/answer sets.

| QA set number | Question | Answer |
|---|---|---|
| 1 | Which musical instrument do you like listening to? | Piano |
| | Which musical instrument do you dislike hearing? | Violin |
| | | Electric guitar |
| | | Drums |
| | | Synthesizer |
| | | None of these |
| 2 | How is your room currently? | Bright |
| | | Dark |
| | | Hot |
| | | Cold |
| | | Fine |
| 3 | From 0 to 10, how much pain are you in? | Zero |
| | From 0 to 10, how nauseous are you? | One |
| | From 0 to 10, how happy do you feel? | Two |
| | From 0 to 10, how stressed are you? | Three |
| | From 0 to 10, how comfortable are you? | Four |
| | | Five |
| | | Six |
| | | Seven |
| | | Eight |
| | | Nine |
| | | Ten |
| 4 | When do you want me to check back on you? | Today |
| | | Tomorrow |

Figure 7I:
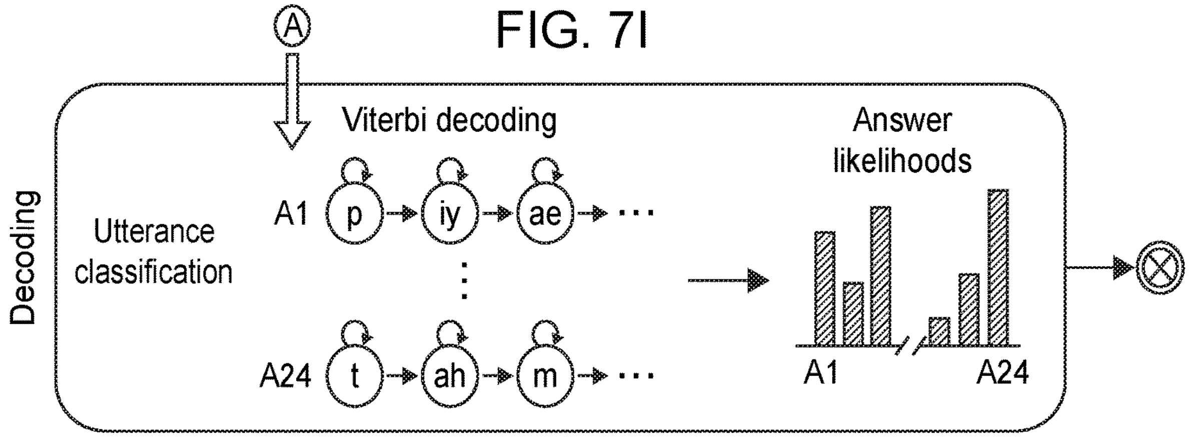
Figure 7J:
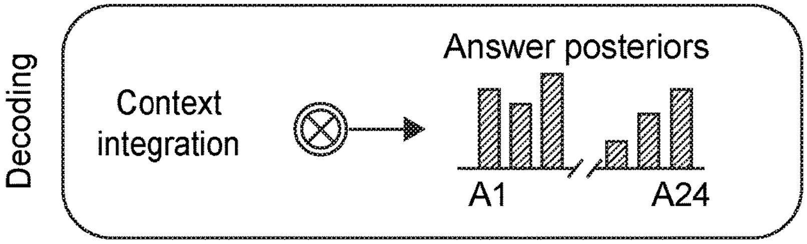
Figure 7K:
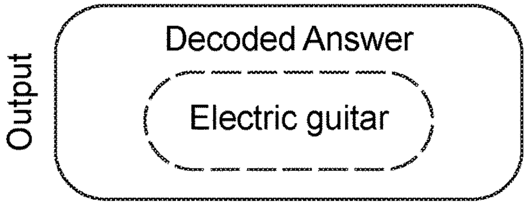

As with question decoding, for each time segment that was labeled as an answer event, a classification model was used to analyze the high gamma activity and compute answer likelihoods using phone-level Viterbi decoding (FIG. 7I). The context integration model combined these answer likelihoods with the answer priors to obtain answer posterior probabilities (FIG. 7J), and the answer with the highest posterior probability was output as the decoded answer (FIG. 7K). A participant performing this task during online decoding was recorded. The question and answer (with and without context integration) likelihoods were stored for later offline comparisons.

Prior to testing, models were fit using data collected during separate training task blocks. The question classification models were fit using data collected while participants listened to multiple repetitions of each of the question stimuli, and the answer classification models were fit using data collected while participants read each answer aloud multiple times. The speech detection models were fit using both of these types of training task blocks. Information about the amount of data collected for training and testing with each participant is provided in Table 3.

Question and Answer Decoding Performance

In offline analysis using the real-time decoding approach, decoding accuracy was evaluated for questions, answers without context integration, and answers with context integration. The primary performance evaluation metric was decoding accuracy rate, which was defined as 1 minus the utterance error rate using the actual and predicted utterances for each prediction type. Here, an utterance refers to one of the question stimuli or answer choices. The utterance error rate was defined as the edit (Levenshtein) distance between the actual and predicted utterance sequences across all test blocks for a participant. This value measures the minimum number of deletions, insertions, and substitutions (at the utterance level) required to convert the predicted utterance sequence into the actual utterance sequence, which is analogous to the word error rate metric commonly used in automatic speech recognition (ASR) systems to assess word-level decoding performance. Thus, the decoding accuracy rate describes the performance of the full decoding approach, including contributions from the speech event detection, utterance classification, and context integration models.

Figure 8A:
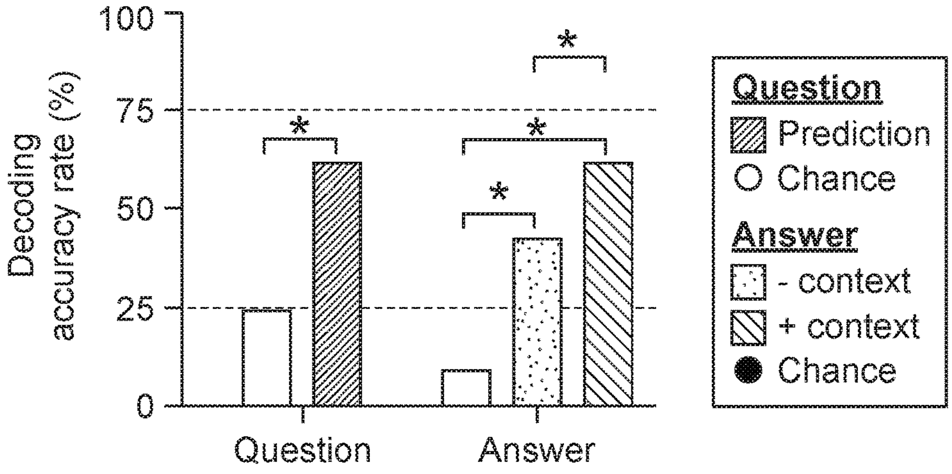
FIGS. 8A-8G: Speech decoding and classification results for one participant.

For all participants, accuracy rate for decoding of each prediction type (questions, answers without context, and answers with context) was significantly above chance (P<0: 05, one tailed bootstrap test, 4-way Holm-Bonferroni correction; FIG. 8A for participant 1, FIG. 14A for other participants; Table 4). Chance accuracy rate was computed using bootstrapped sequences of randomly-sampled utterances. Overall, the accuracy rates for questions (participant 1: 2.6, participant 2: 3.1, participant 3: 2:1 times the chance level) and answers with context (participant 1: 7.2, participant 2: 3.5, participant 3: 3.7 times the chance level) demonstrate that the full system (event detection, utterance classification, and context integration) achieves reliable decoding of perceived and produced speech from ECoG signals. Importantly, a significant increase was observed in decoding accuracy rate during answer decoding when context was integrated compared to when it was not integrated (participant 1: $P=1.9\times10^{-3}$, participant 2: $P=7.9\times10^{-5}$, participant 3: P=0.029, one-tailed permutation test, 4-way Holm-Bonferroni correction). These results indicate that the context integration model was able to leverage the question predictions to improve decoding of the subsequent answer responses for each participant.

Figure 8B:
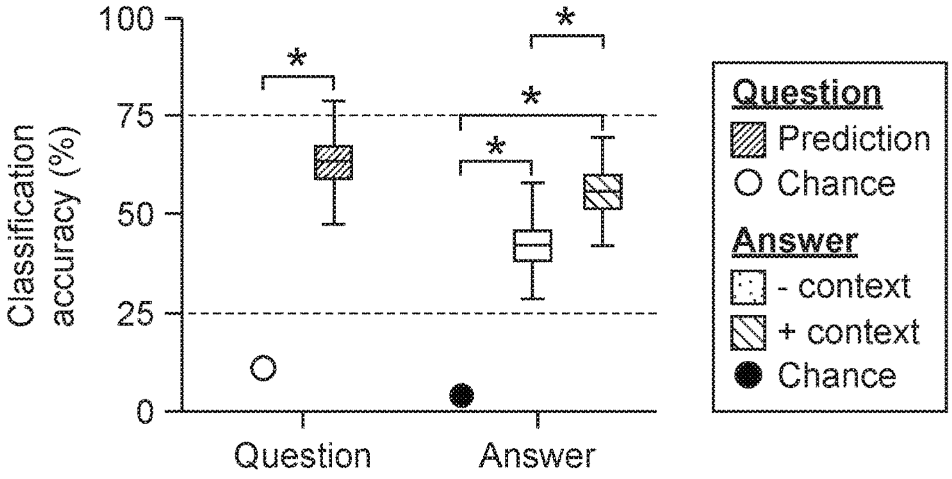
Figure 8C:
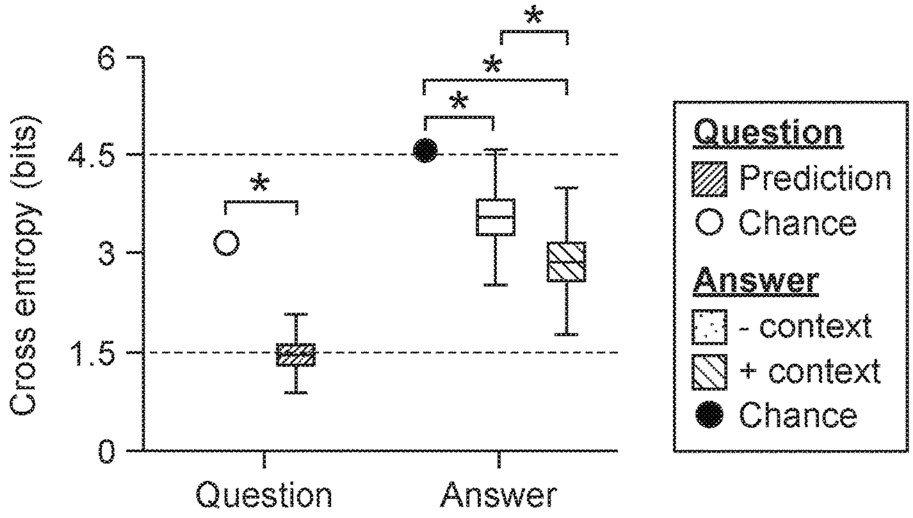
Figure 14B:
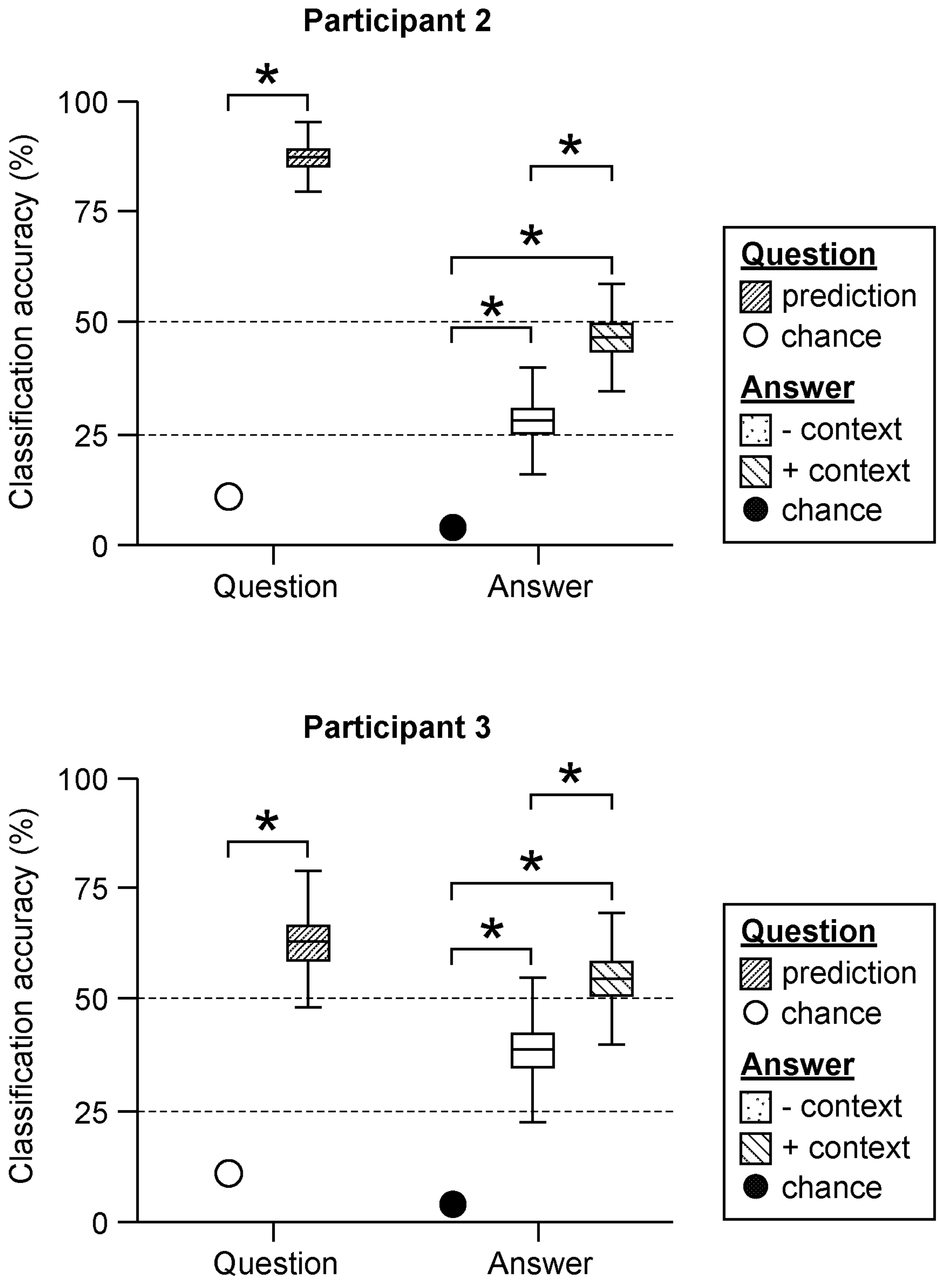

To better understand how each of the components contributed to the overall performance of the full system, the utterance classification and context integration models were examined separately from the speech detection model. In this work, "classification" and "decoding" were explicitly differentiated: Given a set of features (such as a time window of neural signals), classification refers to the prediction of a single label from these features, and decoding refers to the prediction of an arbitrary-length label sequence from these features. To evaluate classification performance, true event times were used determined from acoustic transcriptions of the test blocks, ensuring that the appropriate time window of neural signals was associated with each classification target (each test trial). Using these true event times, question and answer classification accuracy was calculated, defined as the proportion of correct utterance classifications in the test blocks. These classification accuracy values directly measure the efficacy of the utterance classifiers and can be compared to the decoding accuracy rates to assess the efficacy of the speech detectors. This metric directly measures the performance of the utterance classifiers and can be compared to the decoding accuracy rate For all participants, classification accuracy was above chance for each prediction type (P<0.05, one-tailed bootstrap test, 4-way Holm-Bonferroni correction; FIG. 8B, FIG. 14B). Similar to the full system decoding accuracy rate, answer classification accuracy was higher when integrating context (participant 1: P=0.033, participant 2: P=1.9e−6, participant 3: P=9.2e−4, one-tailed exact McNemar's test, 4-way Holm-Bonferroni correction).

Next, these classification results were used to measure the information transfer rate (ITR) of the answer classifiers. The ITR metric quantifies the amount of information that a system communicates per unit time and is commonly used to evaluate brain-computer interfaces. ITRs were observed as high as 1.4 bits per second for the answer classifications with context (all computed ITRs are given in Table 5).

Classification performance was also assessed using cross entropy, a metric that compares the predicted utterance likelihoods and the actual utterance identities for each trial across all test blocks for a participant. Given utterance log likelihoods predicted by a classification model for trials in the test blocks, cross entropy measures the average number of bits required to correctly classify those utterances. These values provide further insight into the performance of the utterance classification and context integration models by considering the predicted probabilities of the utterances (not just which utterance was most likely in each trial). Lower cross entropy indicates better performance. For all participants, cross entropy was better than chance (P<0.05, one-tailed bootstrap test, 4-way Holm-Bonferroni correction; FIG. 8A for participant 1, FIG. 14A for other participants; Table 4) and was significantly better for the answer predictions when integrating context (participant 1: P=7.6e−06, participant 2: P=2.6e−17, participant 3: P=3.1e−11, one-tailed Wilcoxon signed-rank test, 4-way Holm-Bonferroni correction).

Figure 8D:
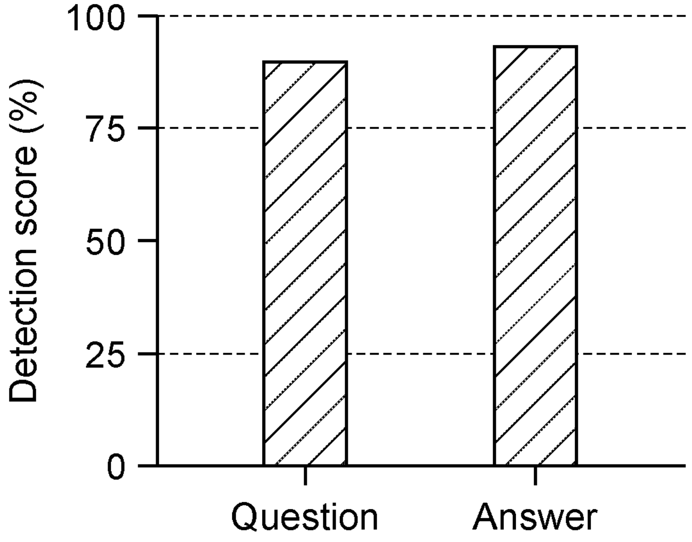
Figure 14D:
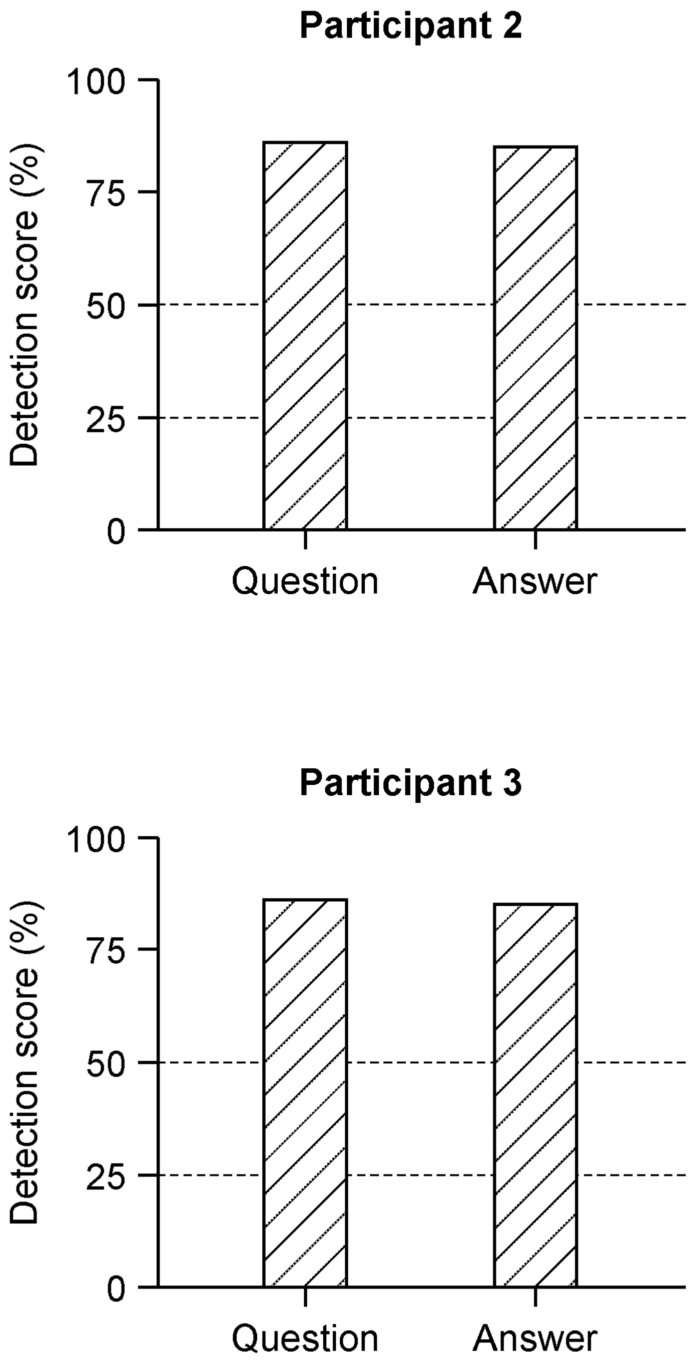

To evaluate the performance of the event detector, a detection score was computed that incorporates frame-by-frame detection accuracy and a comparison between the number of detected and actual utterances (FIG. 8D, FIG. 14D). For all participants, detection scores for questions and answers were high (above 85%) but not perfect. This result is consistent with the observation of decoding accuracy rates that were slightly lower than their corresponding classification accuracies.

Figure 8E:
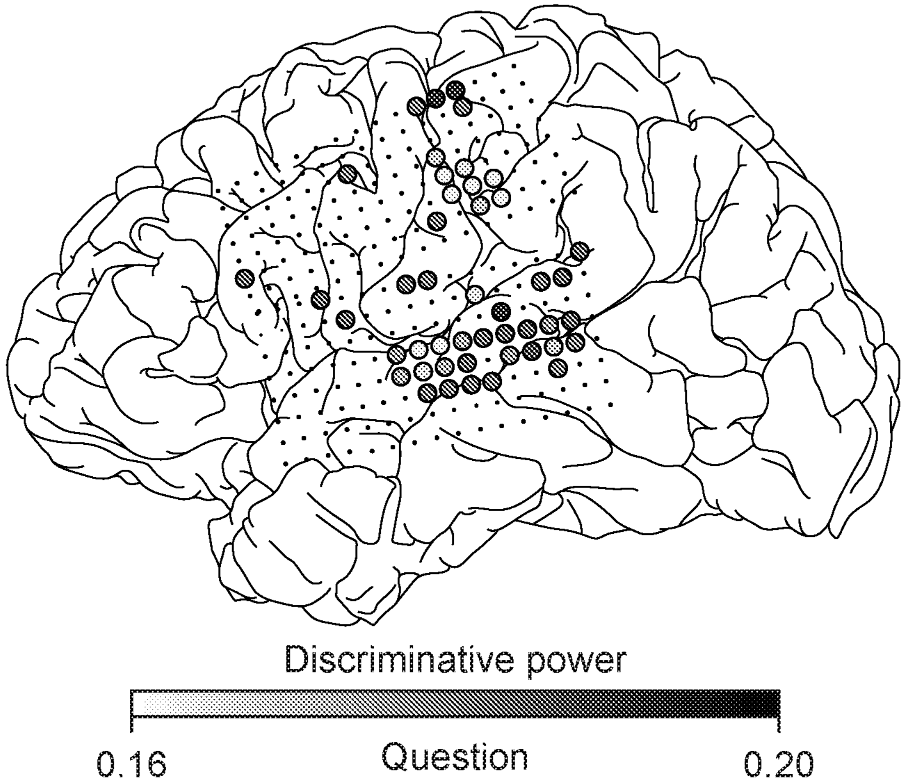
Figure 8F:
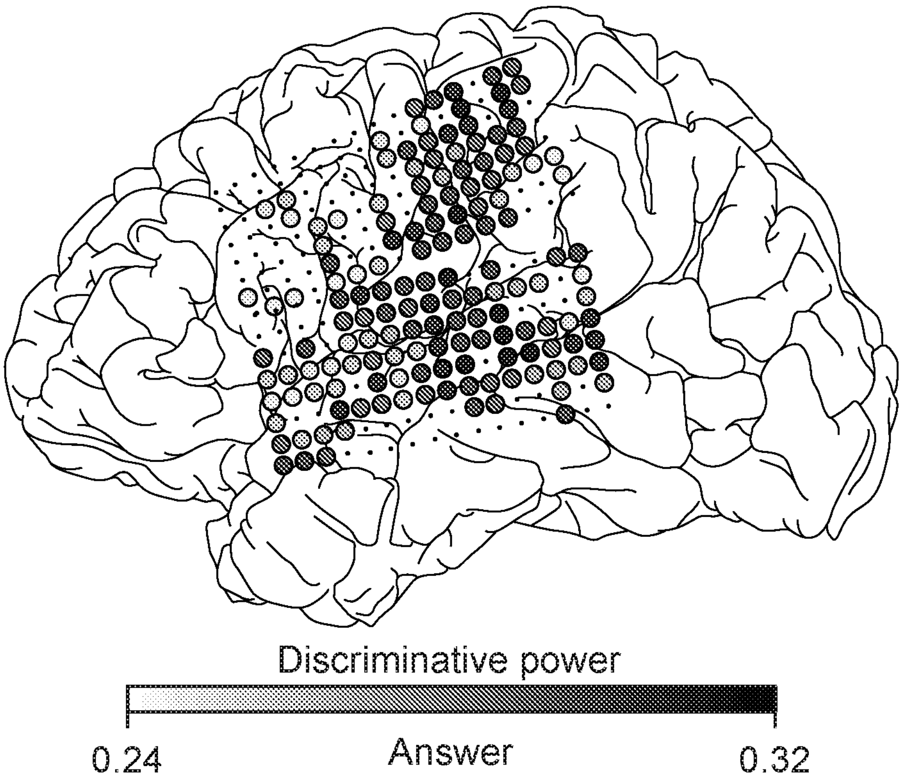
Figure 8G:
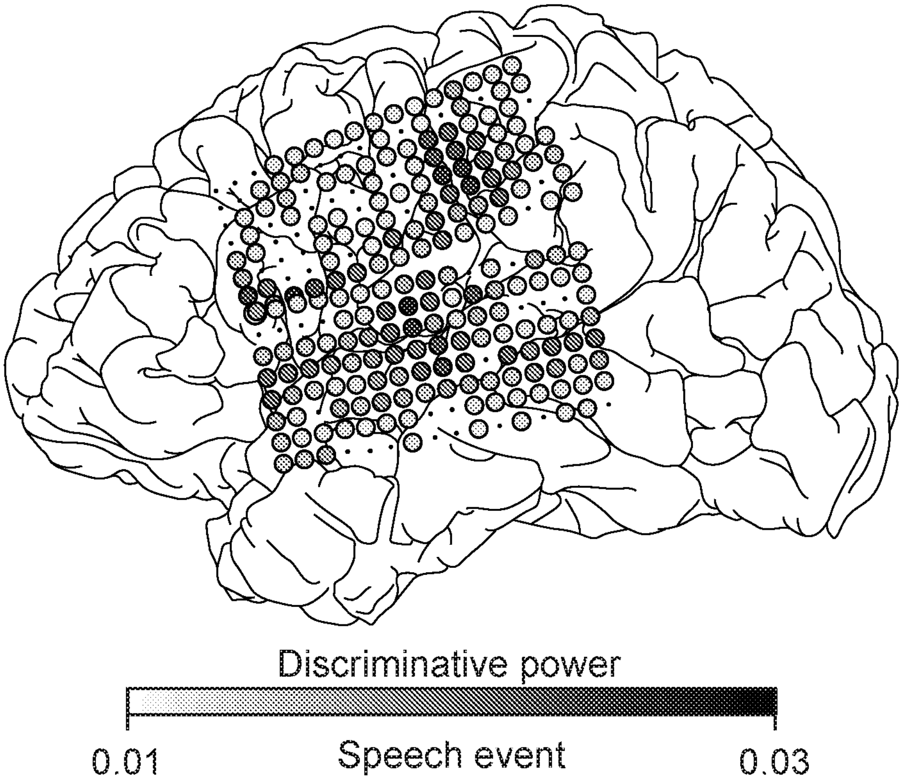

Finally, to characterize the contribution of individual electrodes during utterance classification and speech detection, the discriminative power of each ECoG electrode was calculated. Here, discriminative power provides an estimate of how much each electrode contributes to a model's ability to discriminate between utterances or speech events. It was found that for question decoding, discriminative power was highest across STG electrodes FIG. 8E, FIG. 14E), consistent with auditory responses to heard speech observed in this region. Clusters of discriminative power for question decoding were also observed in vSMC, although the relevant electrodes in this region were sparser and more variable across participants. The electrodes that contributed most to answer decoding were located in both vSMC and STG (FIG. 8F, FIG. 14F), reflecting activity related both to speech production and perception of self-produced speech. Lastly, electrodes that contributed to speech detection were distributed throughout sensorimotor and auditory regions (FIG. 8G, FIG. 14G).

Effects of Data Limitations, Hyperparameter Selection, and Spatial Resolution

Overall, the reliable decoding performance that was observed may reflect certain idiosyncrasies of the neural data and recording constraints associated with each participant. To understand the limitations of the decoding models used in this task, their performance was assessed as a function of three factors that can vary across participants: amount of data used during model fitting, specific model hyperparameters used during testing, and spatial resolution of the cortical signals.

Figure 16:
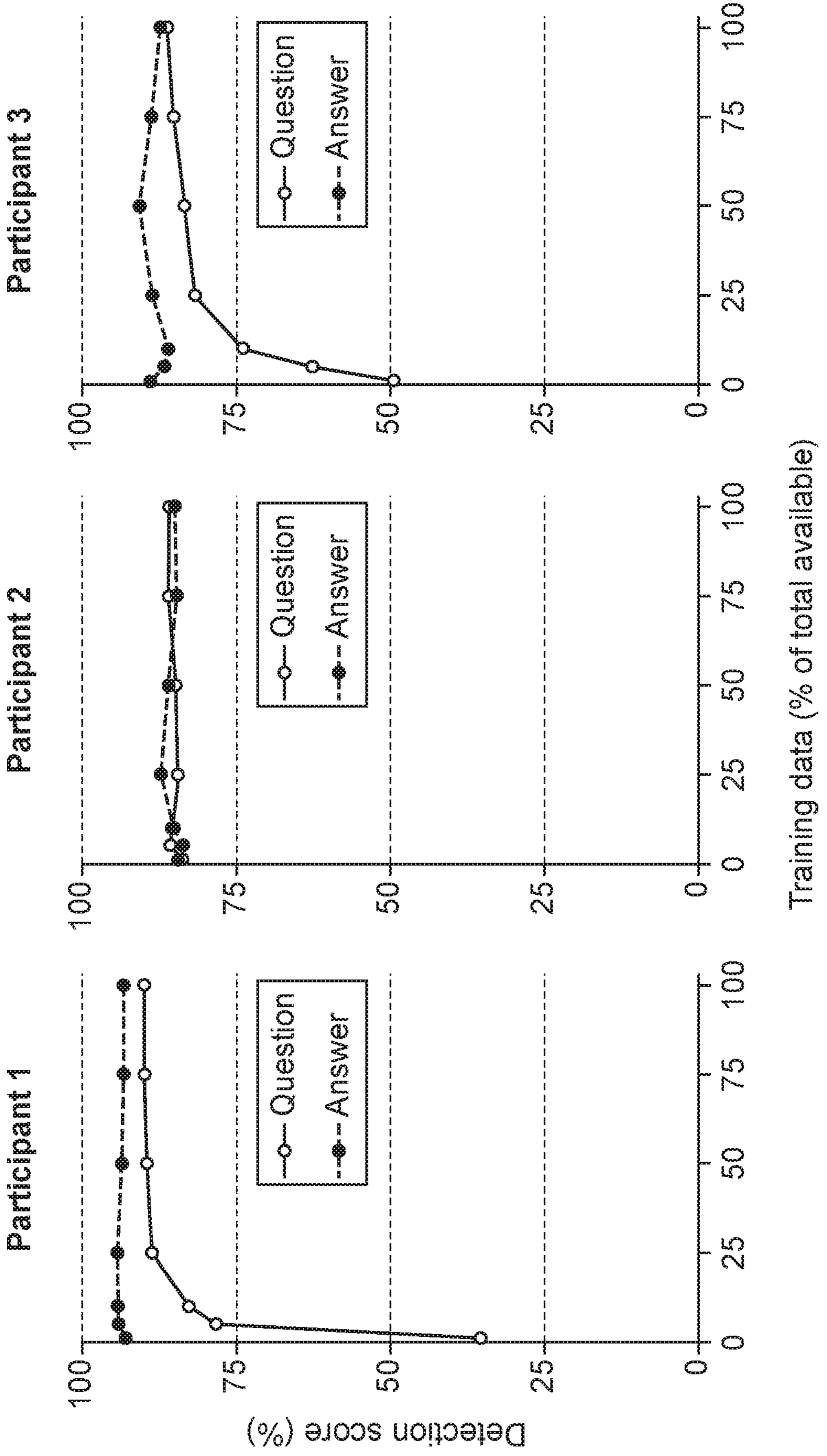
FIG. 16: Effects of amount of training data on speech detection for each participant. Each plot shows question and answer detection scores (mean with standard error) after fitting the speech detection models with various percents of the available speech and silence data points. The percents in these plots are relative to the total amounts of available training data for each participant (shown in Table 3). The error bars in this plot were typically too small to be seen alongside the circular markers.

First, it was analyzed how the amount of neural data used during training affects decoder performance. For each participant, fit utterance classification models was fit with neural data recorded during perception and production of an iteratively increasing number of randomly drawn samples (perception or production trials during training blocks) of each utterance. These models were then evaluated on all test block trials for that participant. It was found that classification accuracy and cross entropy improved over approximately 10-15 training samples (FIG. 9, FIG. 10). After this point, performance began to improve more slowly, although it never completely plateaued (except for the answer classifier for participant 2, where 30 training samples were acquired; FIG. 10). These findings suggest that reliable classification performance can be achieved with only 5 minutes of speech data, but it remains unclear how many training samples would be required before performance no longer improves. A similar analysis was also performed with the detection models to assess speech detection performance as a function of the amount of training data used. It was found that detection performance plateaus with about 25% of the available training data (as little as 4 minutes of data, including silence) for each participant (FIG. 16).

Next, the impact that hyperparameter selection had on classification performance was investigated. Hyperparameters are model parameters that are set before training a model on a dataset and are not learned directly from the dataset. Examples of physiologically relevant hyperparameters include a temporal offset shift between perceived and produced phones and the neural data (which could account for neural response delays or speech production planning), the duration of the spatiotemporal neural feature vectors used during model training and testing, and a P-value threshold used when deciding which electrodes should be considered relevant and included in the analyses. Prior to evaluating performance offline with real-time simulations, a cross-validated hyperparameter optimization was performed on the models used during decoding. Using an iterative optimization algorithm, different sets of hyperparameter values were evaluated for each test block using a leave-one-block-out cross-validation procedure. 250 optimization epochs were performed for each test block (each epoch evaluated one unique set of hyperparameter values). During the primary performance evaluation for each test block, the hyperparameter values that produced the best performance on the held-out validation set associated was used with that block.

Figure 15A:
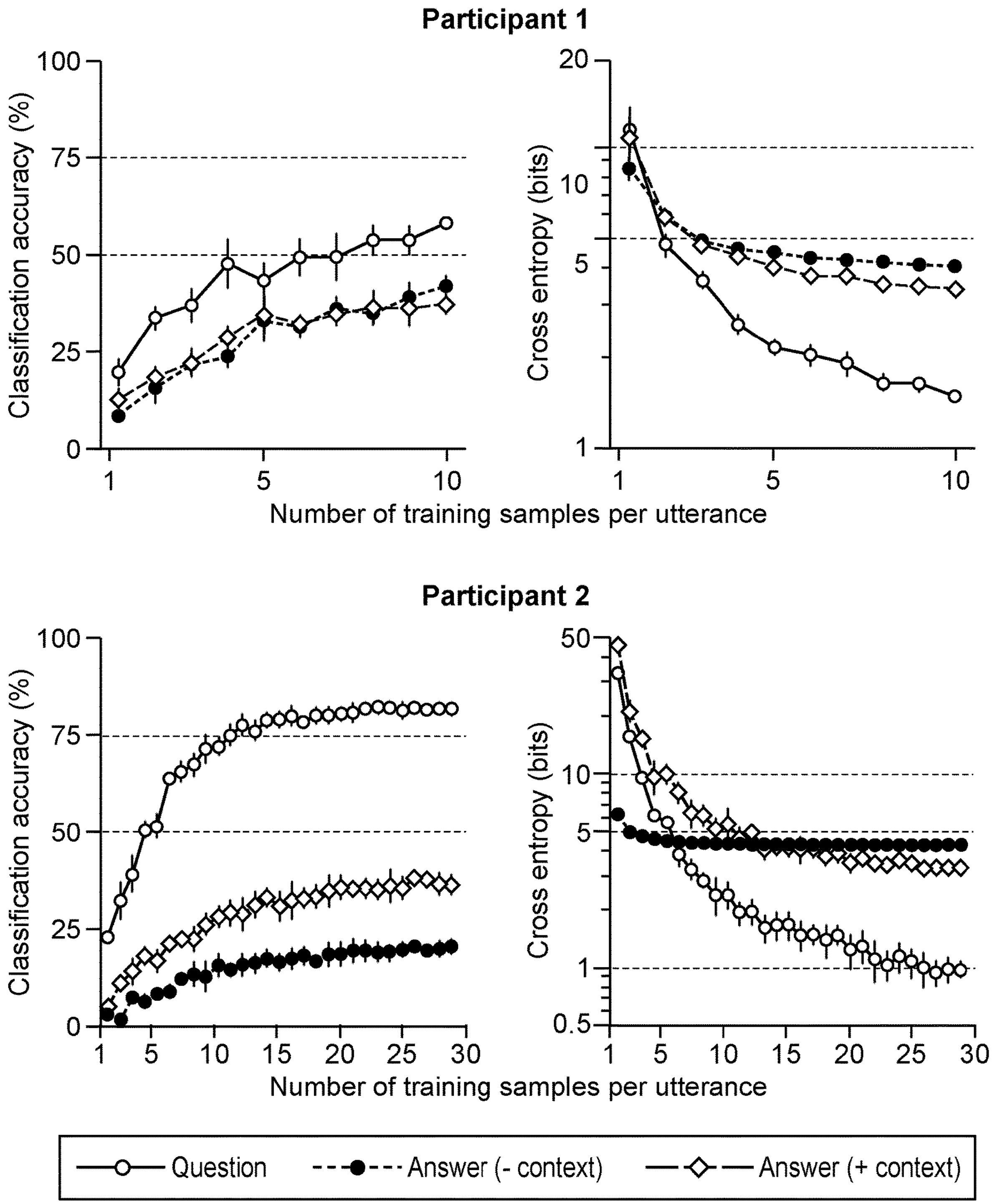
FIGS. 15A-15B: Effects of amount of training data and hyperparameter optimization on speech classification for participants 1 and 2 (participant 3 shown in FIG. 9).
Figure 15B:
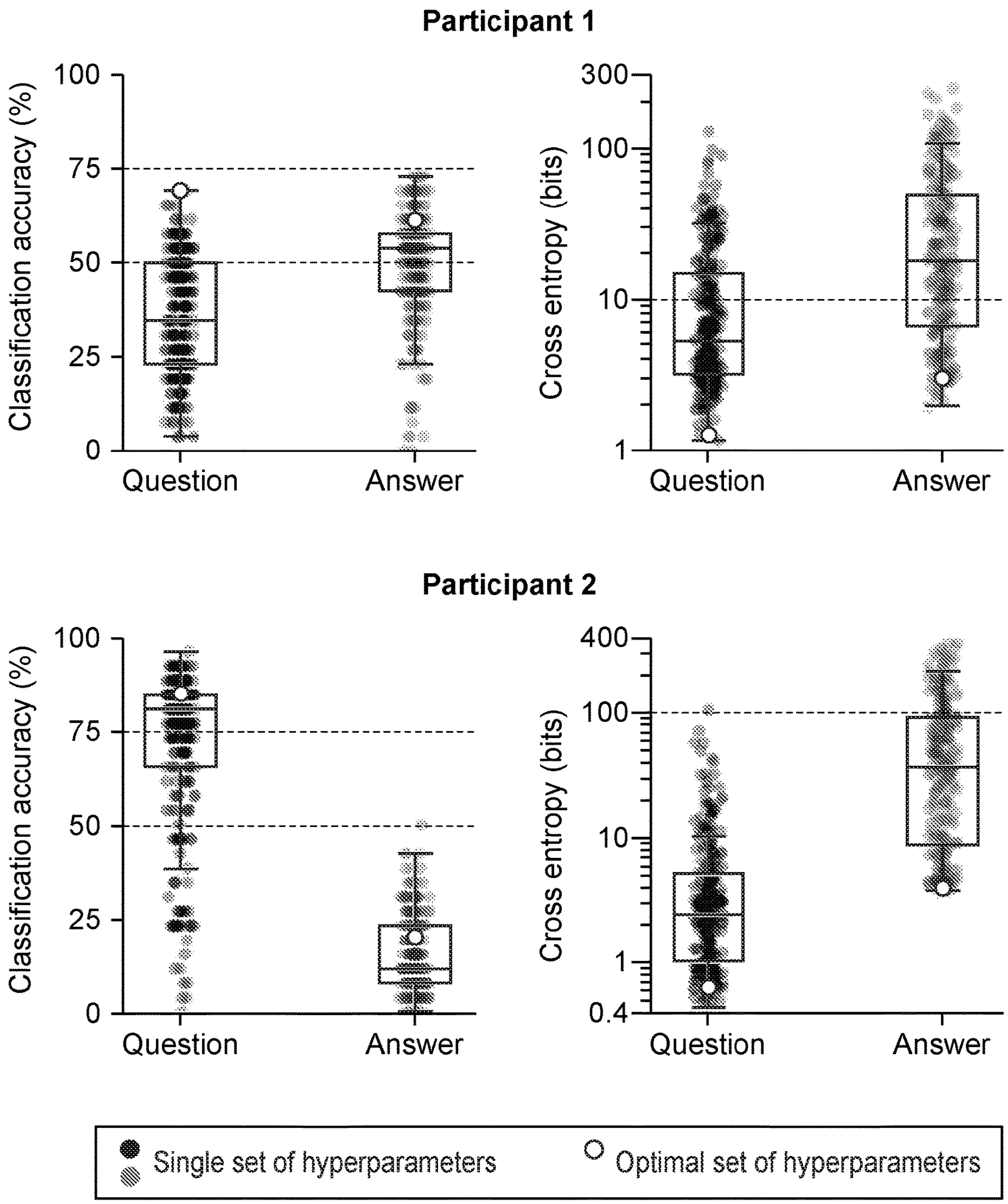

To understand how hyperparameter selection affected performance, classification performance on one test block was compared for each participant across the 250 hyperparameter sets that were evaluated for each utterance type (without using the context integration model) during optimization on the associated validation set. For each participant, large variability in classification accuracy and cross entropy was observed across the different hyperparameter sets, suggesting that hyperparameter values can have a large impact on performance (FIG. 9B, FIG. 15B). For each participant and metric, it was also found that the optimal hyperparameters on the validation set were always better than the median performance observed across all hyperparameter sets. This finding demonstrates that the optimizer successfully chose high-performing hyperparameter values to use during testing and also that hyperparameter values that performed well in certain test blocks are generalizable to other test blocks.

The impact was also assessed for the high spatial resolution of the ECoG arrays used with the participants had on performance. To simulate a low-resolution ECoG array, the electrodes were sub-divided for participant 1 into four distinct sets: one set containing the electrodes spatially located in the odd-numbered rows and odd-numbered columns of the ECoG grid, another set containing the electrodes located in the odd-numbered rows and even-numbered columns, and two more sets determined similarly except with even-numbered rows (refer to FIG. 8A-8G for the electrode locations for this participant). For each of these four sets, the performance of the system was evaluated while restricting models to only have access to the electrodes in the current set during training and testing (hyperparameter values from the high resolution models were used here). It was found that performance was significantly worse for the low-resolution models compared to the high-resolution ones for each prediction type and performance metric ($P<0.05$, one-tailed one-sample t-test; FIG. 10) except for the answer detection score ($P=0.12$). These findings emphasize the importance of high spatial resolution when using cortical features to decode speech.

Viterbi Classification and Phonetic Modeling

To gain a more intuitive understanding of the neural and stimulus-dependent features that drove decoding performance, the specific phone-level decisions made by the answer classification models (independently from the context integration model) during testing (FIG. 11) was examined. These classifiers represented each utterance as a hidden Markov model (HMM), with phones as hidden states and neural data as observed states. During testing, phone likelihoods were computed at each time point during a detected utterance. Viterbi decoding was then performed on the HMM associated with each utterance to compute the most likely path through the hidden states (phones) given the observed sequence of neural data.

Figure 11A:
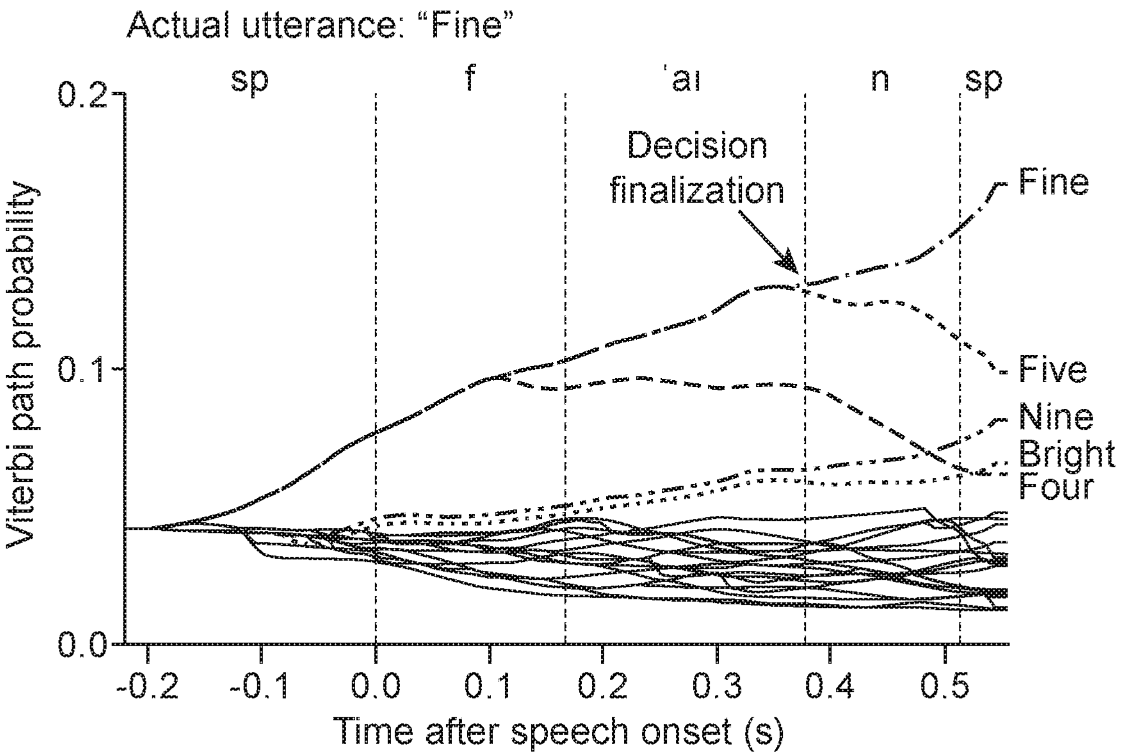
FIGS. 11A-11C: Within-trial temporal characteristics and phone-based performance of the answer (speech production) classification model.

How estimated phone likelihoods affected the probability of each utterance across time was examined. For example, when a participant produced the answer “Fine” (in response to the question “How is your room currently?”), an answer classifier used the sequence of phone likelihood estimates (predicted from neural data) to update the predicted probabilities of each possible answer at each time point during the utterance (FIG. 11). The pattern of the answer probabilities illustrates how phonetic similarity drives the classifier predictions. For example, the utterances “Fine”, “Five”, and “Four” remain equally likely until the decoder receives neural activity associated with production of the /a/ phone, at which point “Four” becomes less likely. Subsequently, “Fine” and “Five” are equally likely until the decoder receives neural activity associated with the /n/ phone, at which point “Fine” becomes and remains the most likely utterance. Similarly, there is a brief increase in the probability of “Bright” about halfway through the utterance, consistent with the presence of the /a/ phone (after which the probability decreases). At the end of the utterance, the presence of the /a/ and /n/ phones is associated with an increase in the probability of “Nine”.

To understand how much phonetic information the answer classifiers required before finalizing an utterance prediction, for each test trial the earliest time point during Viterbi decoding at which the utterance that was most likely at the end of decoding became and remained more likely than the other utterances was computed. The decision finalization time was defined as the percent of time into the utterance when this time point was reached (using the actual speech onset and offset times from the transcriptions). These decision finalization times were computed for each trial in which the answer classification models correctly predicted the produced answer (94 trials total across all participants and test blocks).

Figure 11B:
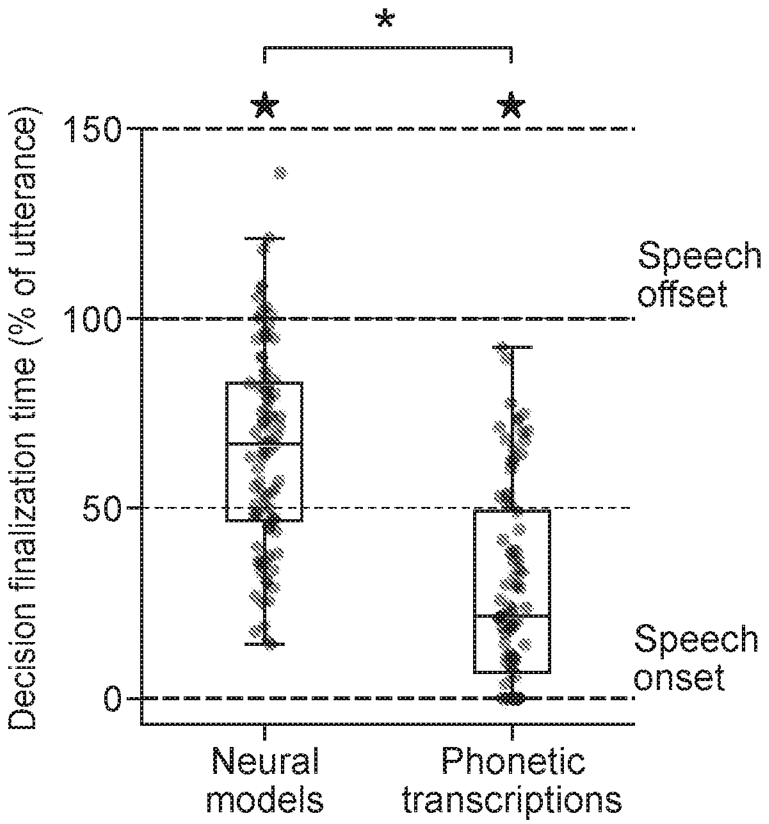
Figure 11C:
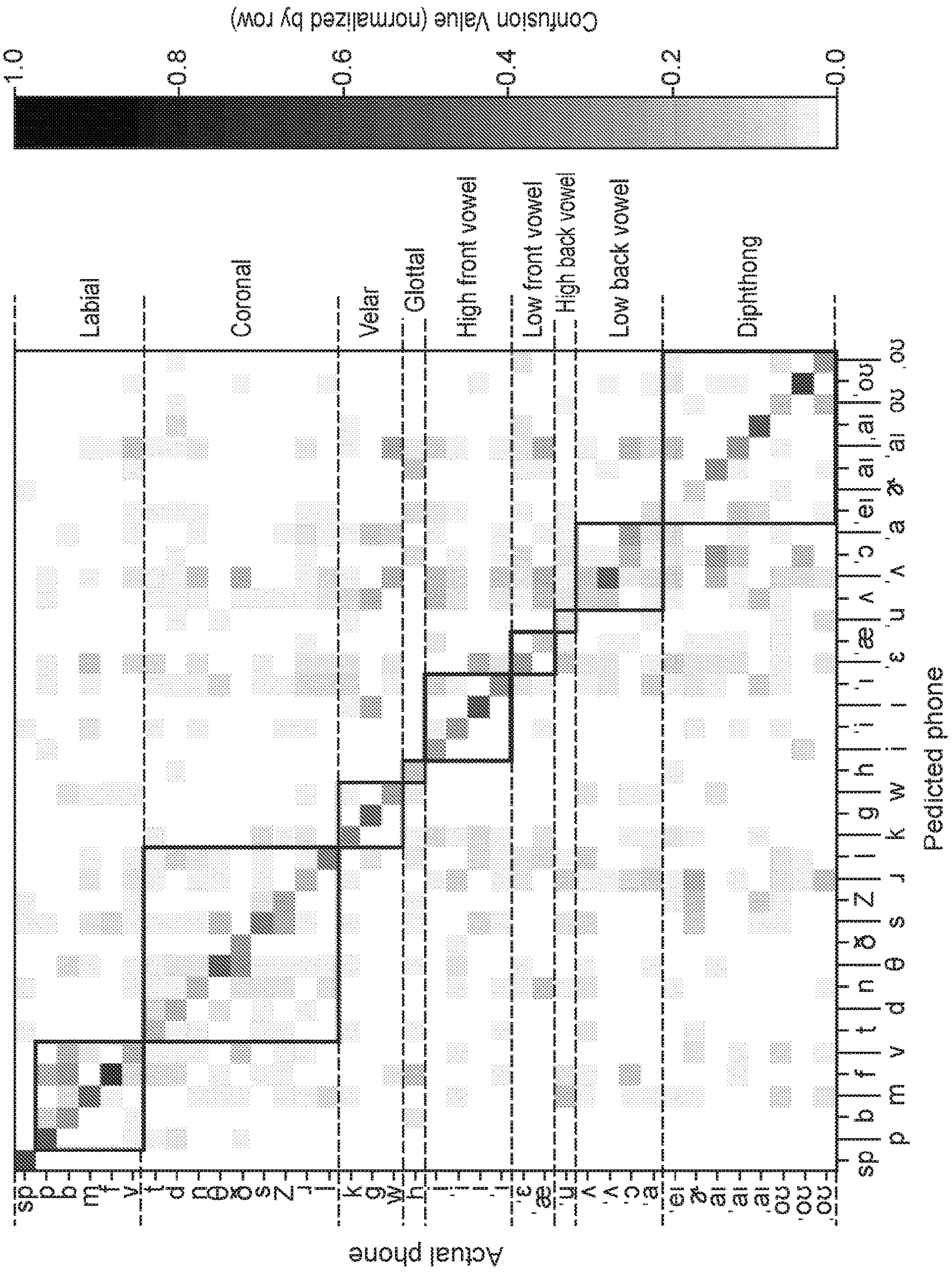

It was found that the decision finalization times typically occurred before all of the neural data from an utterance was seen ($P=2.1e^{-15}$, one-tailed single-sample Wilcoxon signed-rank test; FIG. 11*b*). Because some utterances began with the same phones (e.g., the phones /s "I/ at the start of “Six” and “Synthesizer”), the lower bound was expected for the finalization times to occur after speech onset even if the actual phone identity at each time point was known. To compute this lower bound, the finalization times were recalculated for these trials using phone likelihoods constructed directly from the phonetic transcriptions. Because no two utterances had the exact same phonetic content, these transcription-based finalization times always occurred before the speech offset ($P=1.6e^{-16}$, one-tailed single-sample Wilcoxon signed-rank test). The neural-based finalization times were significantly later than the transcription-based finalization times ($P=1.2e^{-10}$, one-tailed Wilcoxon signed-rank test), which is expected when using imperfect phone likelihoods from neural data. Overall, these results demonstrate that the answer classifiers were able to finalize classification decisions before the offset of speech using estimated phone likelihoods. Furthermore, this observation cannot be explained entirely by the phonetic separability of the utterances themselves.

The performance of the answer phone likelihood models were also characterized that were used during utterance classification. Across all participants and test blocks, the answer phone likelihood models were used to classify which phone was being produced at each time point. In total, there were 10585 time points that occurred during speech production, and the overall phone classification accuracy across these blocks was 25.12% (the chance level was 2.70% if choosing randomly from the 37 different phones produced during testing). When silence data points were included, the number of time points was 165804 and the overall phone classification accuracy was 50.97%. This ability of the phone likelihood models to discriminate between phones was a major factor in the success of the utterance classification models during testing.

Based on recent findings suggesting that the clustering of neural encoding of phonemes in vSMC during speech production is largely driven by place of articulation, it was hypothesized that the phone confusions observed in this analysis would be organized by place of articulation. To assess this hypothesis, the set of phone labels were divided into 9 disjoint sets according to place of articulation (excluding the silence token /sp/). Each actual and predicted phone label was then collapsed from the phone classification results into one of these 9 phonetic category labels. It was found that the mutual information between the actual and predicted labels using this categorization was significantly higher than randomized phonetic categorizations ($P=0.0012$, one-tailed bootstrap test), supporting the hypothesis that phone confusions during production can be partially explained by place of articulation. The resulting confusion matrix visually illustrates these findings (FIG. 11C), with a prominent diagonal (indicating good overall classification performance) and confusions that are consistent with this hypothesis (such as the confusions between the alveolar fricatives /s/ and /z/ and between many of the labial phones).

Context Integration Effects

Finally, how manipulations to the context integration approach affects answer classification performance were assessed. It was shown that context integration improves decoder performance for each participant. This context integration approach involves using "soft" context priors, which refers to the fact that "soft" classification is performed for each question utterance to obtain a probability distribution over the possible questions, which are then used to compute the answer priors. An alternative approach is to use "hard" context priors, which force the decoded answer in any trial to be the most likely answer utterance within the same question/answer set as the predicted question. To assess the efficacy of using hard priors during context integration, the context integration step was repeated using hard priors for each participant and measured the resulting classification accuracies. It was found that answer classification accuracy was always lower when using hard priors instead of soft priors, although this effect was not significant in any participant (participant 1: P=0.25, participant 2: P=0.50, participant 3: P=0.063, one-tailed exact McNemar's test; Table 6). These findings suggest that the decoding system would not benefit from greater constraints on which answer utterances are allowed in each trial based on the predicted questions.

Using "true", determined from the actual presented questions, were evaluated to determine how they affected performance. In this approach, the decoded answer is the most likely answer utterance within the same question/answer set as the actual question. To obtain an upper bound on the performance of the context integration models, the context integration step was repeated using true priors for each participant. It found that answer classification accuracy was significantly higher for participant 1, identical for participant 2, and slightly higher (but not significant) for participant 3 when using true priors instead of soft priors (participant 1: P=0.016, participant 2: P=1.0, participant 3: P=0.063, one-tailed exact McNemar's test; Table 6). This finding is supported by the relatively high question classification accuracy for participant 2 compared to the other participants, suggesting that the context integration model was performing at its upper bound only for participant 2 and not for the other participants.

Discussion

High-resolution recordings directly from the cortical surface was demonstrated to show that the high-resolution recordings can be used to decode both perceived and produced speech in real-time. By integrating what participants hear and say, an interactive question-and-answer behavioral paradigm was leveraged that can be used in a real-world assistive communication setting. Together, these results represent an important step in the development of a clinically viable speech neuroprosthesis.

The present results demonstrate the use of neural signals to decode speech. A novel behavioral paradigm was used that mimics the turn-taking and conversational aspects of natural speech communication. By designing the question/answer sets to contain stimuli that would be challenging and meaningful to decode successfully while leveraging the established functional speech representations in auditory and sensorimotor cortical areas, evaluating the ability to decode a type of speech that is useful for individuals who could benefit from neuroprosthetic technology was possible. Specifically, conversational speech consists of utterances by both speakers that tend to be related to the same topic. Here, it was demonstrated that predicting which question was heard improves the ability to decode the subsequent answer, with the question serving as a constraining context. Also, a performance improvement was not observed when restricting the possible answer predictions based on the predicted question. Using true question identities as context resulted in increased answer classification accuracy for one participant.

In practice, it may be sufficient to use a microphone to recognize heard speech; however, there are several potential advantages to detecting and decoding speech using neural signals. First, speech is often ambiguous; sentences containing the same words in the same order can have completely different meanings depending on the way in which they are spoken.

Additionally, speech in natural environments is often masked by irrelevant noise. Both of these issues are challenging for many automatic speech recognition (ASR) systems. Second, in more complex conversational settings, decoding heard speech from the brain provides important additional information that a microphone signal would not, including whether the listener is attending to the speaker.

Finally, there are both scientific and technical advantages to a fully-contained and generalizable speech decoding system that can distinguish among multiple speech sources and use each of them as context for the others. Nevertheless, the context integration approach could be improved by incorporating various input sources as context for large-vocabulary decoding, including video, kinematic, and acoustic sensors placed around the user, and video processing and ASR algorithms could be applied directly to these inputs to improve context decoding.

In general, the observed decoding accuracy rates are approaching the range that would be useful to patients relying on this technology to communicate. Importantly, these rates reflect decoding of produced utterances that participants chose to say voluntarily (as opposed to specific cued utterances that were read or repeated on each trial). Here, a greater emphasis was placed on task naturalness than on maximization of ITR.

The results were achieved with Viterbi decoding with hidden Markov models (HMMs), except neural activity were used herein as features during decoding instead of acoustic signals. An HMM model architecture was selected for several reasons, including its inherent robustness to certain kinds of variability in the structure of speech. During Viterbi decoding, the answer classifiers were robust to variability in the exact duration and pronunciations of the produced answers because the amount of time each HMM could spend in each phone state was flexible. Similarly, both the question and answer classifiers were robust to slight inaccuracies in the detected speech onsets and offsets because each HMM started and ended with a silence state. The phone likelihood models underlying these utterance classifiers relied on discriminable phonetic encoding in the neural activity. The demonstrated methodologies allow for robust decoding of continuous speech from neural activity, including in data-limited settings such as clinical recordings with epilepsy patients.

Additionally, it was found that it is both possible and practical to determine which time segments of continuous neural signals are associated with perceived and produced speech events directly from the neural activity itself. By training models to detect speech events from neural activity, reliable detection accuracy for perception and production events were achieved even though they occurred intermittently throughout testing blocks that lasted on the order of minutes.

Several participant-specific and practical factors that influenced speech decoding performance were identified. First, it is generally true (in many types of modeling applications) that more training data leads to improved decoder performance.

Third, the high spatial resolution of the ECoG arrays used in this work played a major role in the ability to reliably decode speech from cortical activity. The results show that low-resolution neural signals could be used to successfully detect speech production events.

Phonetic features were shown to be a driver of classification for produced utterances by characterizing how the answer classifiers incorporated information across time within individual trials and discriminated between the possible utterances. The HMM-based models learned to recognize neural activity patterns associated with phonetic features (such as coronal articulation and vowel height) and adjusted their online utterance probability estimates depending on the presence of these features at each time point. The phonetic confusions exhibited by the classifiers were partially explained by place of articulation features, suggesting that the phone likelihood models struggled to discriminate between within-category speech sounds during decoding. Although these phonetic representations are only an approximation of the underlying kinematic and articulatory representations of speech in vSMC, the use of simple phonetic labels to describe behavior enabled the classifiers to leverage standard ASR techniques during decoding.

Nevertheless, the present results demonstrate that produced speech can be detected and decoded from neural activity in real-time while integrating dynamic information from the surrounding context.

Method

Participants

Three human epilepsy patients undergoing treatment at the UCSF Medical Center participated in this study. For the clinical purpose of localizing seizure foci, ECoG arrays were surgically implanted on the cortical surface of one hemisphere for each participant. All participants were right-handed with left hemisphere language dominance determined by their clinicians.

The research protocol was approved by the UCSF Committee on Human Research. Prior to surgery, each patient gave his or her written informed consent to participate in this research.

Neural Data Acquisition

Participants 1 and 2 were each implanted with two 128-channel ECoG arrays (PMT Corp.) and participant 3 was implanted with a 256-channel ECoG array (Ad-Tech, Corp.). Participants 1 and 3 had left hemisphere coverage and participant 2 had right hemisphere coverage. Each implanted array contained disc electrodes with 1.17 mm exposure diameters arranged in a square lattice formation with a 4 mm center-to-center electrode spacing. The open source img_pipe package was used to generate MRI brain reconstruction images with electrode locations for each participant (FIG. 8A-8G, FIG. 14).

Online speech decoding with Participant 2 portrays real-time decoding of perceived questions and produced answers. In each trial, the participant listened to a pre-recorded question, and a set of valid answers to that question are displayed on a screen visible to the participant. When a green "go" circle appears in the center of that screen, the participant responds verbally with one of the answers. During this process, the raw ECoG activity is acquired and processed within the rtNSR software. A separate screen facing the camera (not visible to the participant) is used to display the decoding results. Decoded questions are displayed on the top half of this screen, and decoded answers are displayed on the bottom half. Animated ellipses appear on this screen when a perceived question or produced answer onset is detected from the neural activity. When the associated speech offset is detected, the neural data is used to decode the question or answer and display the prediction on this screen.

A data acquisition (DAQ) rig was used to process the local field potentials recorded from these arrays at multiple cortical sites from each participant. These analog ECoG signals were amplified and quantized using a pre-amplifier (PZS, Tucker-Davis Technologies). Anti-aliasing (low-pass filtering at 1500 Hz) and line noise removal (notch filtering at 60, 120, and 180 Hz) was performed on a digital signal processor (RZ2, Tucker-Davis Technologies). On the DAQ rig, these neural data was stored (at 3051.76 Hz) along with the time-aligned microphone and speaker audio channels (at 24414.06 Hz). These neural data were anti-aliased again (low-pass filtered at 190 Hz) and streamed at a sampling rate of 381.47 Hz to a real-time computer, which was a Linux machine (64-bit Ubuntu 14.04, Intel Core i7-4790K processor, 32 GB of RAM) implementing a custom software package called real-time Neural Speech Recognition (rtNSR).

High Gamma Feature Extraction

The rtNSR package implemented a filter chain comprising three processes to measure high gamma activity in real-time (FIG. 7 High gamma band activity (70-150 Hz) was used in this work because previous research has shown that activity in this band is correlated with multi-unit firing processes in the cortex and can be used as an effective representation of cortical activity during speech processing.

The first of these three processes applied eight band-pass finite impulse response (FIR) filters to the ECoG signals acquired from the DAQ rig (at 381.47 Hz). The logarithmically increasing center frequencies of these filters were 72.0, 79.5, 87.8, 96.9, 107.0, 118.1, 130.4, and 144.0 (in Hz, rounded to the nearest decimal place). The filters each had an order of 150 and were designed using the Parks-McClellan algorithm.

The second process in the filter chain estimated the analytic amplitude values for each band and channel using the signals obtained from the band-passing process. An 80th-order FIR filter was designed using the Parks-McClellan algorithm to approximate the Hilbert transform. For each band and channel, this process estimated the analytic signal using the original signal (delayed by 40 samples, which was half of the filter order) as the real component and the FIR Hilbert transform approximation of the original signal as the imaginary component. The analytic amplitudes were then computed as the magnitudes of these analytic signals. This filtering approach was applied to every fourth sample of the received signals, effectively decimating the signals to 95.37 Hz.

The final process in the filter chain averaged analytic amplitude values across the eight bands, yielding a single high gamma analytic amplitude measure for each channel.

After filtering, the high gamma signals were z-scored using Welford's method with a 30-second sliding window. To mitigate signal artifacts such as channel noise and epileptic activity, the z-score values were clipped to lie within the range of [−3.5, 3.5]. The resulting z-scores were used as the representation of high gamma activity in all subsequent analyses and real-time testing.

Experimental Task Design

The overall goal of this task was to demonstrate real-time decoding of perceived and produced speech while leveraging contextual relationships between the content of the two speech modalities. To achieve this, a question-and-answer task was designed in which participants listen to questions and respond verbally to each question with an answer. There were 9 pre-recorded acoustic question stimuli and 24 possible answers (Table 2). Questions were recorded by a female speaker at 44.1 kHz and were presented to each participant aurally via loudspeakers. Each visual answer choice was represented as a small rectangle containing the text prompt and a small image depicting the text (FIG. 7B; images were included to increase participant engagement). The stimuli were divided into four question/answer sets (QA sets 1-4). The answers in each QA set represented the answer choices that would appear on the screen for each of the questions in that set.

Three types of task blocks were used: (1) question (perception) training, in which participants heard each question 10 times in a random order (stimulus length varied from 1.38-2.42 seconds in duration with an onset-to-onset interval of 3 seconds); (2) answer (production) training, in which participants read each possible answer choice aloud 10 times in a random order (each answer appeared on the screen with a gray background for 0.5 seconds, was changed to a green background for 1.5 seconds to represent a "go" cue for the participant to read the answer, and removed from the screen for 0.5 seconds before the next answer was displayed); and (3) testing, in which participants heard questions and responded verbally with answers (choosing a response from the possible options presented on the screen after each question). During the testing blocks, a green circle appeared on the screen after each question was presented to cue participants to respond aloud with an answer of their choosing. The participants were encouraged to choose different answers when they encountered the same questions, although they were free to respond with any of the presented answer choices during each trial. There was 2-3 seconds of silence and a blank screen between each trial. In each block, the questions played to the participant were chosen based on how many questions and answers are in each QA set (questions with more valid answers had a greater chance of being played in each trial). Trials in which the participant failed to respond or responded with an invalid choice (less than 0.5% of trials) were excluded from further analysis. There were 26 question-and-answer trials in each testing block.

During each block, time-aligned behavioral and neural data were collected and stored. The data collected during training blocks were used to fit the decoding models. The data collected during testing blocks were used to decode the perceived questions and produced answers in real-time and were also used offline during hyperparameter optimization.

Phonetic Transcription

After data collection, both questions and answers were phonetically transcribed from the time-aligned audio using the p2fa package which uses the Hidden Markov Model Toolkit and the Carnegie Mellon University Pronouncing Dictionary. The phone boundaries were manually fine-tuned using the Praat software package. Including a silence phone token /sp/, there were a total of 38 unique phones in the question stimuli and 38 unique phones in the produced answer utterances, although these two phone sets were not identical.

Modeling

After collecting training data for a participant, models were fit using the time-aligned high gamma z-score neural data and phonetic transcriptions. Model fitting was performed offline, and the trained models were saved to the real-time computer to be used during online testing. The values for many model parameters that were not learned directly from the training data were set using hyperparameter optimization. Three types of models were used in this work: speech detection models, utterance classification models, and context integration models.

Speech Detection

Before using the neural data to train speech detection models, the collected data was analyzed to identify electrodes that were responsive to speech events. For each time point in the neural data, the phonetic transcriptions were used to determine if that time point occurred during speech perception, speech production, or silence. Welch's analysis of variance (ANOVA) was performed on each electrode to identify channels that were significantly modulated by the different types of speech events. Channels that had a Welch's ANOVA P-value less than a threshold hyperparameter were included in the feature vectors used to train and test the speech detection models.

Figure 17:
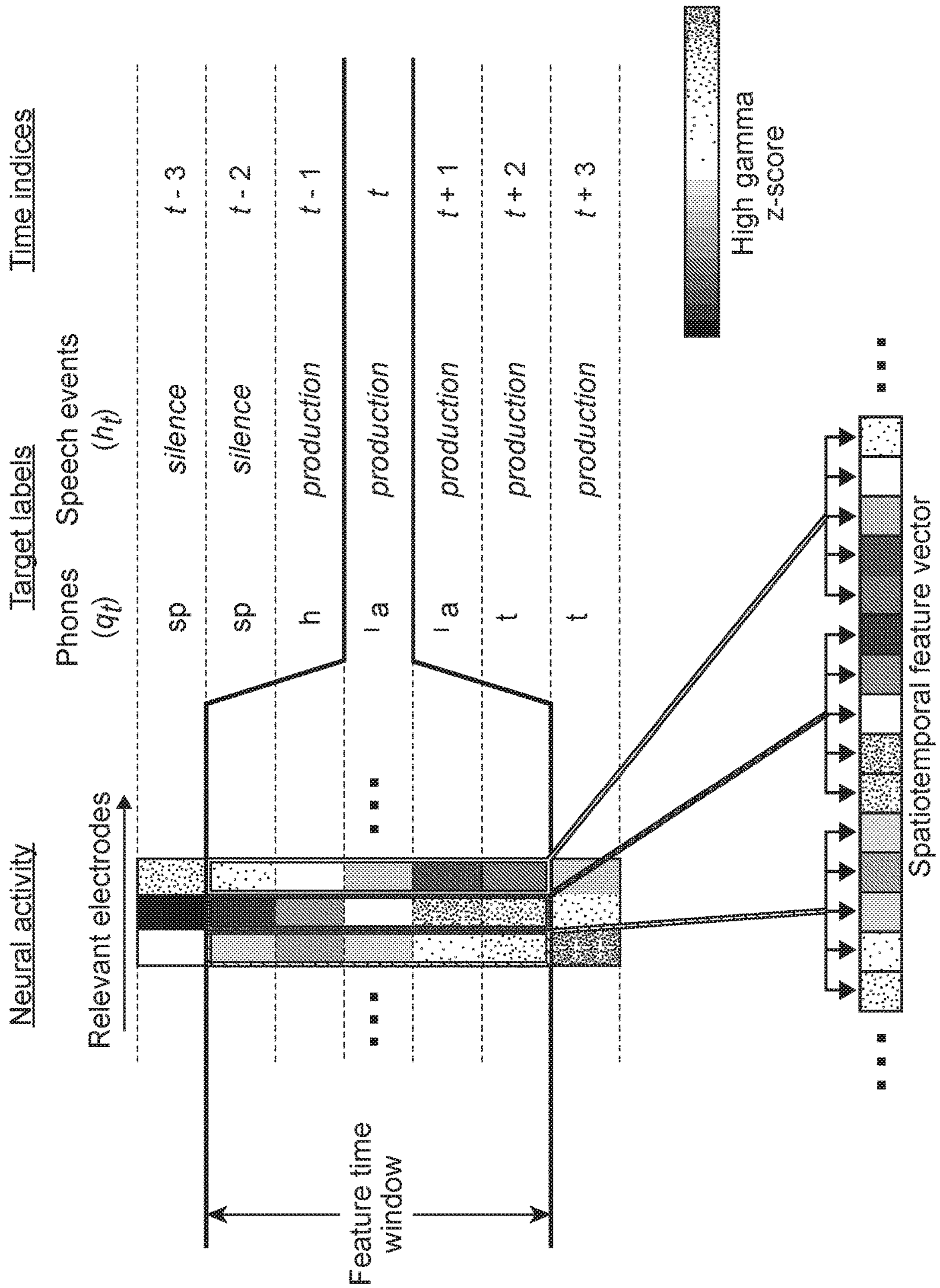
FIG. 17: Spatiotemporal neural feature vectors and associated target labels during training of the speech detection and utterance classification models. In this example, a participant produces the answer utterance \Hot" (with phonetic transcription /h "A t/). Speech onset occurs at time index t−1. The phone labels qt at each time point t are obtained from phonetic transcriptions. The speech event labels $h_t$, which are either silence, perception, or production at every time point, are determined from these phonetic transcriptions. The feature vector at time t contains the high gamma z-score value at every relevant electrode for every time point within some feature time window relative to t. The feature vector and target label for each time index are used to train the speech event probability and phone likelihood models. During testing, the neural feature vectors $y_t$ are constructed in a similar fashion and used within the speech detection model to compute the speech event probabilities p $(h_t|y_t)$ and within the utterance classification models to compute the phone likelihoods p $(y_t|q_t)$.

Speech events were modeled discriminatively as conditional probability distributions of the form. Here, represents the speech event at time t and is one of the values in the class set, and is the spatiotemporal neural feature vector at time t. The labels were determined from the phonetic transcriptions: for any given time index t, was perception if the participant was listening to a phone at time t, production if the participant was producing a phone at time t, or silence otherwise. Each of these feature vectors was constructed by concatenating high gamma z-score values for relevant electrodes across all of the time points in a time window relative to the target time point, capturing both spatial (multiple electrodes) and temporal (multiple time points) dynamics of the cortical activity (FIG. 17). Specifically, a feature vector associated with the speech event label at some time index t consisted of the neural data at the time indices within the closed interval, where and represent the window onset shift and window duration, respectively, and were determined using hyperparameter optimization.

To compute the speech event probabilities at each time point, a principal component analysis (PCA) model was fit with the constraint that the dimensionality of the projected feature vectors would be reduced to the minimum number of principal components required to explain a certain fraction of the variance across the features (this fraction was a hyperparameter determined during optimization). The new projected feature vectors and the speech event labels were used to fit a linear discriminant analysis (LDA) model implementing the least-squares solution with automatic shrinkage described by the Ledoit-Wolf lemma. After training, these PCA-LDA models could be used during testing to extract the principal components from a previously unseen spatiotemporal feature vector and predict speech event probabilities from the resulting projection (the LDA model assumed flat class priors when computing these probabilities). A Python package scikit-learn was used to implement the PCA and LDA models.

Figure 13A:
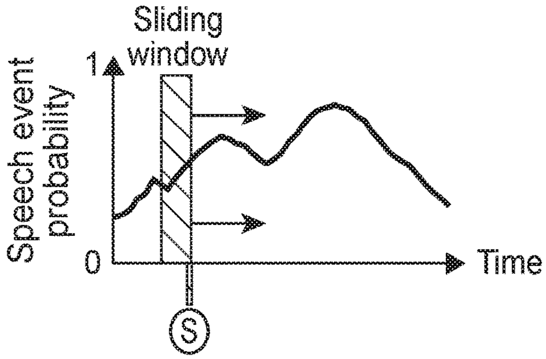
FIGS. 13A-13E: Speech event detection during real-time decoding.
Figure 13B:
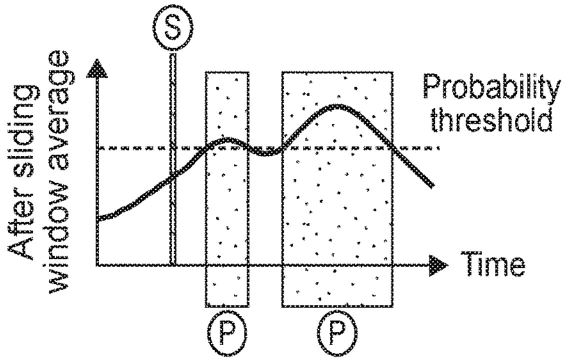
Figure 13C:
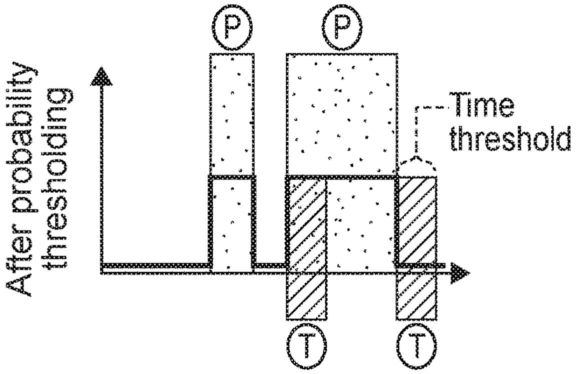
Figure 13D:
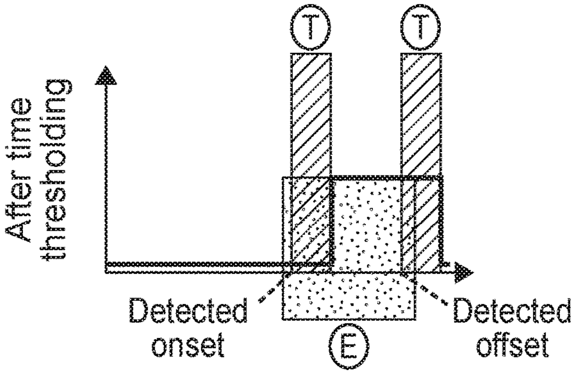
Figure 13E:
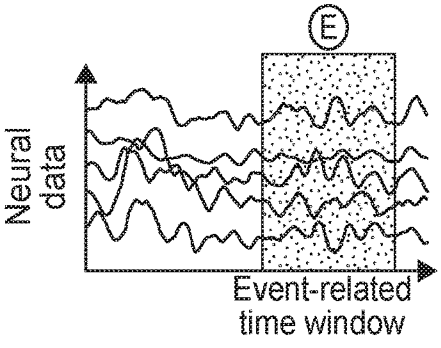

During testing, the predicted speech event probabilities were used to detect the onsets and offsets of speech events (FIG. 13) with a multi-step approach. For every time point t, the probabilities were computed using the speech event probability model (FIG. 8A-8G). For perception and production, these probabilities were smoothed using a sliding window average (FIG. 13B). Next, these smoothed probabilities were discretized to be either 1 if the detection model assigned time point t to the associated speech event type or 0 otherwise (FIG. 13C). These probability-thresholded binary values were then thresholded in time (debounced); a speech onset (or offset) was only detected if this binary value changed from 0 to 1 and remained 1 for a certain number of time points (or the opposite for offsets; FIG. 13D). Whenever a speech event offset was detected (which could only occur after an onset had been detected), the neural data in the detected window were passed to the appropriate utterance classification model (FIG. 13E). The number of recent time points used during probability averaging, probability threshold value, time threshold duration, and onset and offset index shifts (integers added to the predicted onset and offset time indices before segmenting the neural data) were all treated as hyperparameters and set via optimization (with separate parameters for perception and production).

Utterance Classification

For each participant and utterance type (questions and answers), classification models were used to predict the likelihood of each utterance given a detected time segment of neural activity. For each utterance, a hidden Markov model (HMM) was constructed to represent that utterance, with phones as hidden states and spatiotemporal neural feature vectors as observed states at each time index t. Each of these HMMs was created using the representative phone sequence for the associated utterance (determined from the phonetic transcriptions). The transition matrix for each HMM, which specified the transition probabilities, was defined such that each hidden state was one of the phones in the associated representative sequence and could only self-transition (with some probability) or transition to the next phone in the sequence (with probability). A self-transition probability of 1 was used for the final state. The silence phone token /sp/ was used as the initial and final states for each HMM. Given a time series of high gamma z-score values, each of these HMMs yielded the likelihood of observing those neural features during perception or production of the underlying phone sequence. These likelihoods are robust to natural variability in the durations of the phones in the sequence, which is a key motivation for using HMMs in this approach (even with a single speaker producing the same utterance multiple times, phone durations will vary).

Similar to the relevant electrode selection procedure used for the speech detection models, certain channels were identified that should be considered relevant to the type of speech processing associated with each utterance type. Using the three previously described data subsets (perception, production, and silence), two-tailed Welch's t-tests was performed for each channel between the appropriate subsets for each utterance type (perception vs. silence for questions and production vs. silence for answers). Channels with a P-value less than a threshold hyperparameter value were considered relevant for the current utterance type and were used during subsequent phone likelihood modeling.

PCA-LDA models were then trained to compute the phone emission likelihoods at each time point t. The hyperparameters associated with these models, including the feature time window parameters and the PCA minimum variance fraction, were optimized separately from the parameters in the speech event model.

Figure 18:
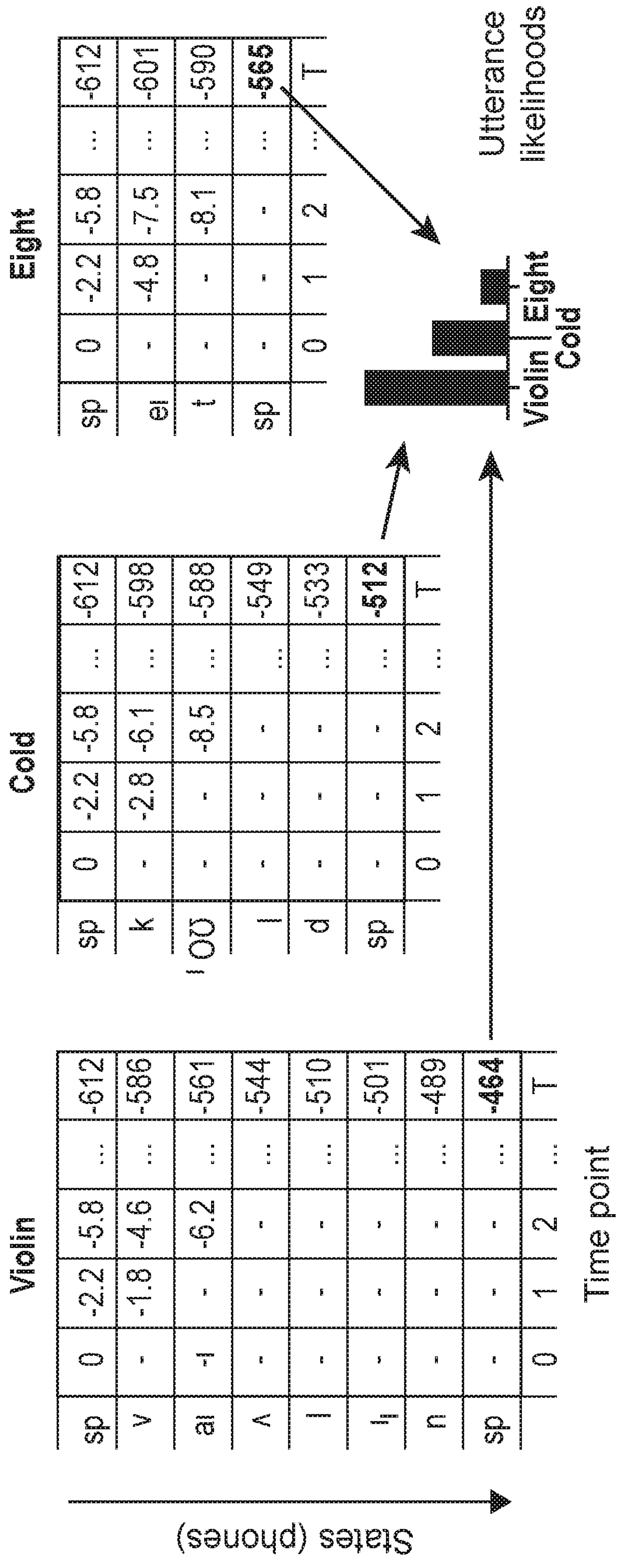
FIG. 18: Schematic example of Viterbi decoding in the utterance classification models. In this example, a classification model computes the likelihoods of the utterances "Violin" (/v aɪ Λ1 'ɪ n/), "Cold" (/k 'oʊ 1 d/), and "Eight" (/"e ɪ t/). Each utterance is represented as an HMM with phones (obtained from the phonetic transcriptions) as hidden states and spatiotemporal neural feature vectors as observations. Each HMM is forced to have /sp/ as the first and last states. The transition matrix of each HMM is defined such that a phone state can only transition to itself or, if it is not the last phone, the next phone in the sequence. Given feature vectors for time indices t ε{0, 1, . . . , T}, Viterbi decoding is performed on each HMM, updating the values in the Viterbi trellis for each HMM (shown here as tables of log likelihoods) at each time index. The log likelihood of the most likely Viterbi path at the final state of each HMM (the value for the final /sp/ state at time T) is used as the log likelihood of that utterance. The classifier then smooths and normalizes these log likelihood values to obtain a final estimate for the utterance likelihoods.

During testing, Viterbi decoding was used on each HMM to determine the likelihood of each utterance given a detected time segment of high gamma z-scores (FIG. 18). The log likelihood of each utterance was computed using the following recursive formula:

$$v_{(t,s)} = w_e \log p(y_t \mid s) + \max_{i \in S}[v_{(t-1,i)} + \log p(s \mid i)], \quad (3)$$

where $v_{(t,s)}$ is the log probability of the most likely Viterbi path that ends in phone (state) s at time t, p $(y_t|s)$ is the phone emission likelihood (the probability of observing the neural feature vector if the current phone is s), (s|i) is the phone transition probability (the probability of transitioning from phone i to phone s), $w_e$ is an emission probability scaling factor (a model hyperparameter) to control the weight of the emission probabilities relative to the transition probabilities, and S is the set of all possible phones. To initialize the recursion, each Viterbi decoding procedure was forced to start with a Viterbi path log probability of zero for the first state (the initial silence phone /sp/) and negative infinity for every other state.

After decoding for each HMM, the Viterbi path log probability at the final state and time point for that HMM represents the log likelihood of the corresponding utterance u given the neural data. Log probabilities are used here and in later computations for numerical stability and computational efficiency.

The computed log likelihoods for each utterance were then smoothed and normalized using the following formula:

$$\ell_u^* := \omega\ell_u - \log\left[\sum_{j \in U} \exp(\omega\ell_j)\right], \quad (4)$$

where $l^*_u$ is the smoothed and normalized log likelihood for utterance u, ω is the smoothing hyperparameter, and U is the set of all valid utterances (for the current utterance type). Because differences in utterance log likelihoods can be large (e.g., in the hundreds), the smoothing hyperparameter, which lay in the closed interval, was included to allow the model to control how confident its likelihood predictions were. The closer w is to zero, the smoother the log likelihoods are (less sample variance among the log likelihoods). The final log term in Eq. 4 represents the Log SumExp function and was used to compute the normalization constant for the current smoothed log likelihoods. After computing this constant and subtracting it from the smoothed log likelihoods, the $l^*_u$ values satisfied the following equality:

$$\sum_{j \in U} \exp(\ell_j^*) = 1. \quad (5)$$

These $l^*_u$ values were used as the utterance classification model's estimate of the utterance log likelihoods given the corresponding neural data.

Context Integration

Because each answer was only valid for specific questions and an answer always followed each question, a context integration model was developed that used predicted question likelihoods to update the predicted answer probabilities during testing.

Prior to testing, the relationships between questions and answers in the form of conditional probabilities was defined. These probabilities, referred to as the context priors, were computed using the following formula:

$$p(u_a \mid U_q) = \begin{cases} \frac{1}{N_{A,q}} & \text{if } u_a \text{ and } u_q \text{ are in same } QA \text{ set,} \\ 0 & \text{otherwise,} \end{cases} \quad (6)$$

where $p(U_a|U_q)$ is the context prior specifying the probability of responding to the question $U_a$ with the answer $U_q$ and $N_{a,q}$ is the number of answers in the same question-and-answer (QA) set as $U_q$ (the number of valid answers to $U_q$; Table 2). These context priors assume that the valid answers to any question are equally likely.

During testing, the context integration model receives predicted utterance log likelihoods from both the question and answer classification models. Each time the model receives predicted question log likelihoods (denoted $1^*_{Uq}$, containing the log likelihoods $1^*_{Uq}$ for each question utterance $U_q$), it computes prior log probabilities for the answer utterances from these question likelihoods and the pre-defined context priors using the following formula:

$$\log p_Q(u_a) = \log\left\{\sum_{u_q \in U_Q} \exp\left[\log p(u_a \mid u_q) + \ell^*_{u_q}\right]\right\} + c, \quad (7)$$

where $P_q(U_a)$ is defined as the prior probability of the answer utterance $U_a$ computed using $1^*_{Uq}$, $U_q$, is the set of all question utterances, and c is a real-valued constant. Each time the model receives predicted answer log likelihoods (the $1^*_{Ua}$ values for each answer utterance $U_a$), it computes posterior log probabilities for the answer utterances from these answer likelihoods and the answer priors. The unnormalized log posterior probabilities $\emptyset_{ua}$ were computed for each answer utterance $U_a$ using the following formula:

$$\phi_{u_a} := m \log p_Q(u_a) + \ell^*_{u_a} + d, \quad (8)$$

where m is the context prior scaling factor and d is a real-valued constant. Here, m is a hyperparameter that controls the weight of the answer priors relative to the answer likelihoods (a larger m causes the context to have a larger impact on the answer posteriors). These answer log posterior values were then normalized using the following formula:

$$\phi^*_{u_a} := \phi_{u_a} - \log\left[\sum_{j \in U_A} \exp(\phi_j)\right], \quad (9)$$

where $\emptyset^*_{ua}$ is the normalized log posterior probability of $u_a$ and $U_A$ is the set of all answer utterances. The constants c and d do not need to be computed in practice because they are canceled out during the normalization step in Eq. 9. These $\emptyset^*_{ua}$ values satisfy the following equality:

$$\sum_{j \in U_A} \exp(\phi^*_j) = 1. \quad (10)$$

Finally, the predicted utterance identities are computed as:

$$\hat{u}_q = \underset{u_q \in U_Q}{\operatorname{argmax}} \ell^*_{u_q}, \quad (11)$$

-continued $$\hat{u}_{a-} = \underset{u_a \in U_A}{\operatorname{argmax}} \ell^*_{u_a}, \quad (12)$$

$$\hat{u}_{a+} = \underset{u_a \in U_A}{\operatorname{argmax}} \phi^*_{u_a}, \quad (13)$$

where $\hat{u}_q$, $\hat{u}_{a-}$, and $\hat{u}_{a+}$, are the system's predictions for questions, answers without context, and answers with context, respectively. The $\hat{u}_g$ and $\hat{u}_{a+}$ predictions are the system outputs during decoding, and the $u_{a-}$ predictions are used in offline analyses. For a more thorough mathematical description of the context integration procedure.

Although an answer followed each question during testing, it was possible for the speech detector to fail to detect question or answer events (or to detect false positives). Because of this, the context integration model was not forced to always expect answer likelihoods after receiving question likelihoods or vice versa. Instead, during each test block, a set of values was maintained for the answer priors that were only updated when a new set of question likelihoods was received. When a new set of answer likelihoods was received, the current answer prior values were used to compute the posteriors. If answer likelihoods were received before receiving any question likelihoods, answer posteriors and answer with context predictions would not be computed from those likelihoods (although this did not actually occur in any test blocks).

Hyperparameter Optimization

Each type of model (speech detection, utterance classification, and context integration) had one or more parameters that could not be learned directly from the training data. Instead of manually selecting values for these hyperparameters, cross-validated hyperparameter optimization was performed using the hyperopt Python package. This package uses a Bayesian-based optimization algorithm called the Tree-structured Parzen Estimator to explore a hyperparameter space across multiple epochs. Briefly, this optimization approach samples hyperparameter values from pre-defined prior distributions, uses a loss function to evaluate the current hyperparameters, and then repeats these steps using knowledge gained from the evaluations it has already performed. After a desired number of epochs, the hyperparameter set associated with the minimal loss value across all epochs is chosen as the optimal hyperparameter set.

Hyperparameter optimization was performed for each participant, model type, and test block. A leave-one-block-out cross-validation scheme was used for each test block. Specifically, during an optimization run for any given test block, the hyperparameters were evaluated on a held-out validation set comprising all of the other test blocks available for the current participant. 250 epochs were used for each optimization run. All of the hyperparameters that were set via optimization are described in Table 7

Evaluation Methods and Statistical Analyses

Primary Evaluation Metrics

The following metrics were used during the primary evaluations of the system: decoding accuracy rate, classification accuracy, cross entropy, speech detection score, and electrode discriminative power (FIG. 8A-8G). The decoding accuracy rate metric represented the full performance of the system (the combined performance of the speech detection, utterance classification, and context integration models). When computing the accuracy rates for each prediction type (questions, answers without context, and answers with context) and participant, overall actual and predicted sequences were obtained by concatenating the actual and predicted utterances across all of the test blocks. An utterance error rate was then calculated using these sequences, which is an analog of the commonly-used word error rate metric and is a measure of the edit (Levenshtein) distance between the actual and decoded utterance label sequences in a given test block. The accuracy rate was then computed as 1 minus the utterance error rate (or 0 if this difference would be negative).

Classification accuracy and cross entropy metrics were computed for each participant by using only the utterance classification and context integration models (and not the speech detection models). In this approach, decoding on the test blocks was performed using the actual speech event times and the previously trained utterance classification models. Because the HMMs used to represent the utterances were designed to start and end the Viterbi decoding process during silence, 300 ms of silence time points were padded before and after the utterance in each speech-related time window of neural data passed to the classifiers. Context integration model optimization was then performed with these new classification results and applied the optimized context integration models to the results. After this step, all of the pairs of actual and predicted utterance labels were pooled for each prediction type across all of the test blocks for each participant.

Classification accuracy was defined as the proportion of trials in which the utterance classification model correctly predicted the identity of the utterance. To obtain the mean and variance of the classification accuracy, classification accuracies were used computed on bootstrapped resamples of the trials (one million resamples). To measure information transfer rate, these classification accuracy values, speech durations from the test blocks, and the number of possible answer responses were used.

The cross entropy metric quantified the amount of predictive information provided by the utterance classification and context integration models during testing and hyperparameter optimization. Cross entropies were computed using the surprisal values for each classification trial, prediction type, and participant. For a given trial and prediction type, the relevant surprisal value for that trial is equal to the negative of the predicted log probability associated with the actual utterance label. The cross entropy is equal to the mean of these surprisal values. To obtain the mean and variance of the cross entropy, cross entropies computed on bootstrapped resamples of the trials were used (one million resamples). Lower cross entropy indicates better performance.

To evaluate and optimize the speech detector, a score metric was created that computes a weighted combination of a frame-by-frame accuracy and a general event detection accuracy. The frame-by-frame accuracy measures the performance of the speech detector using the detected presence or absence of a speech event at each time point. This measure is analogous to sensitivity and specificity analyses commonly used for binary prediction. Phonetic transcriptions were used to determine the actual times of the speech events and compute true positives, true negatives, false positives, and false negatives. When using these transcribed speech times, each speech onset time was incremented and incremented each speech offset time by 300 ms to label some silence time points before and after each utterance as positive frames. This modification was performed to encourage the optimizer to select hyperparameters that would include silence before and after each utterance in the detected neural feature time windows, which is useful during utterance classification. The frame-by-frame accuracy measure was calculated using the following formula:

$$a_{frame} := \frac{w_P N_{TP} + (1 - w_P) N_{TN}}{w_P N_P + (1 - w_P) N_N}, \tag{14}$$

where $w_p$ is the positive weight fraction, $N_{TP}$ is the number of true positives detected, $N_{TN}$ is the number of true negatives detected, NP is the total number of positive frames in the test data, and $N_N$ is the total number of negative frames in the test data. The positive weight fraction was included to allow control over how important true positive detection was relative to true negative detection. In practice, $w_p$=0.75 was used, meaning that correctly detecting positive frames was three times as important as correctly detecting negative frames. This value was used to encourage the optimizer to select hyperparameters that would prefer to make more false positive errors than false negative errors, since the performance of the utterance classifiers should diminish more if a few speech-relevant time points were excluded from the detected time window than if a few extra silence time points were included. The general event detection accuracy, which measures how well the speech events were detected without considering which time points were associated with each event, was computed using the following formula:

$$a_{event} := 1 - \min\left(1, \frac{|N_{DE} - N_{AE}|}{N_{AE}}\right), \tag{15}$$

where $N_{DE}$ and $N_{AE}$ are the number of detected and actual speech events in the current test block, respectively. To compute the speech detection score, these two measures were combined using the following formula:

$$s_{detection} = \omega_F a_{frame} + (1 - \omega_F) a_{event}, \tag{16}$$

where $w_F$ is the frame-by-frame accuracy weight fraction, which allows control over how much impact the frame-by-frame accuracy measure has on the speech detection score relative to the general event detection accuracy. In practice, $w_F$=0.5 was let for an equal weighting between the two measures.

To assess the importance of each electrode during phone and speech event likelihood modeling, the discriminative power of each electrode within the trained PCA-LDA models was estimated. A test block for each participant was arbitrarily selected and obtained the trained and optimized utterance classification and speech detection models associated with that test block. For each of these models, the learned parameters were examined within the LDA model. For each feature in the LDA model (which is a principal component), the between-class variance was measured for that feature by computing the variance of the corresponding class means. The values along the diagonal of the shared covariance matrix was used as a measure of the within-class variance of each feature (because diagonal covariance matrices were not forced in the LDA models, this is only an approximation of the true within-class variances). Similar to a coefficient of determination ($R^2$) calculation, the discriminative power for each LDA feature was then estimated as a ratio of the between-class variance to the total variance using the following formula:

$$\eta_i = \frac{\sigma_{b,i}^2}{\sigma_{w,i}^2 + \sigma_{b,i}^2}, \tag{17}$$

where $n_i$, $\sigma^2_{b,i}$, and $\sigma^2_{w,i}$, are the estimated discriminative power, between-class variance, and within-class variance, respectively, for the ith LDA feature. To obtain the discriminative powers for each original feature in the spatiotemporal neural feature vectors (the inputs to the PCA model), the absolute values of the PCA component weights were used to project the LDA feature discriminative powers back into the original feature space. Finally, the discriminative power for each electrode was set equal to the maximum discriminative power value observed among the original features associated with that electrode (that is, the maximum function was used to aggregate the discriminative powers across time for each electrode within the spatiotemporal feature vectors). The resulting discriminative power values were used to quantify the relative contributions of each electrode during phone or speech event discrimination.

Auxiliary Decoding Analyses

Figure 9A:
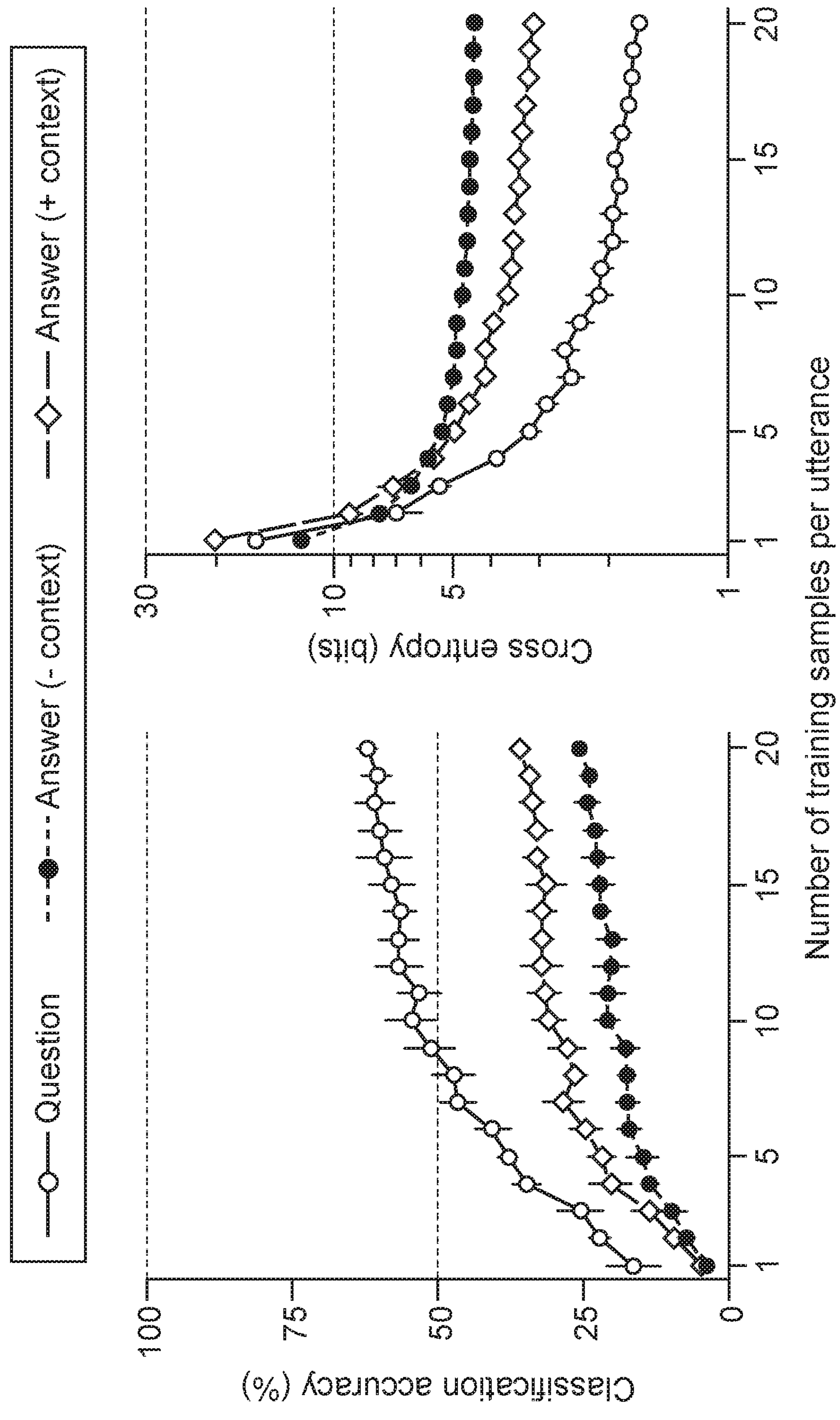
FIGS. 9A-9B: Effects of amount of training data and hyperparameter optimization on speech classification for one participant.
Figure 9B:
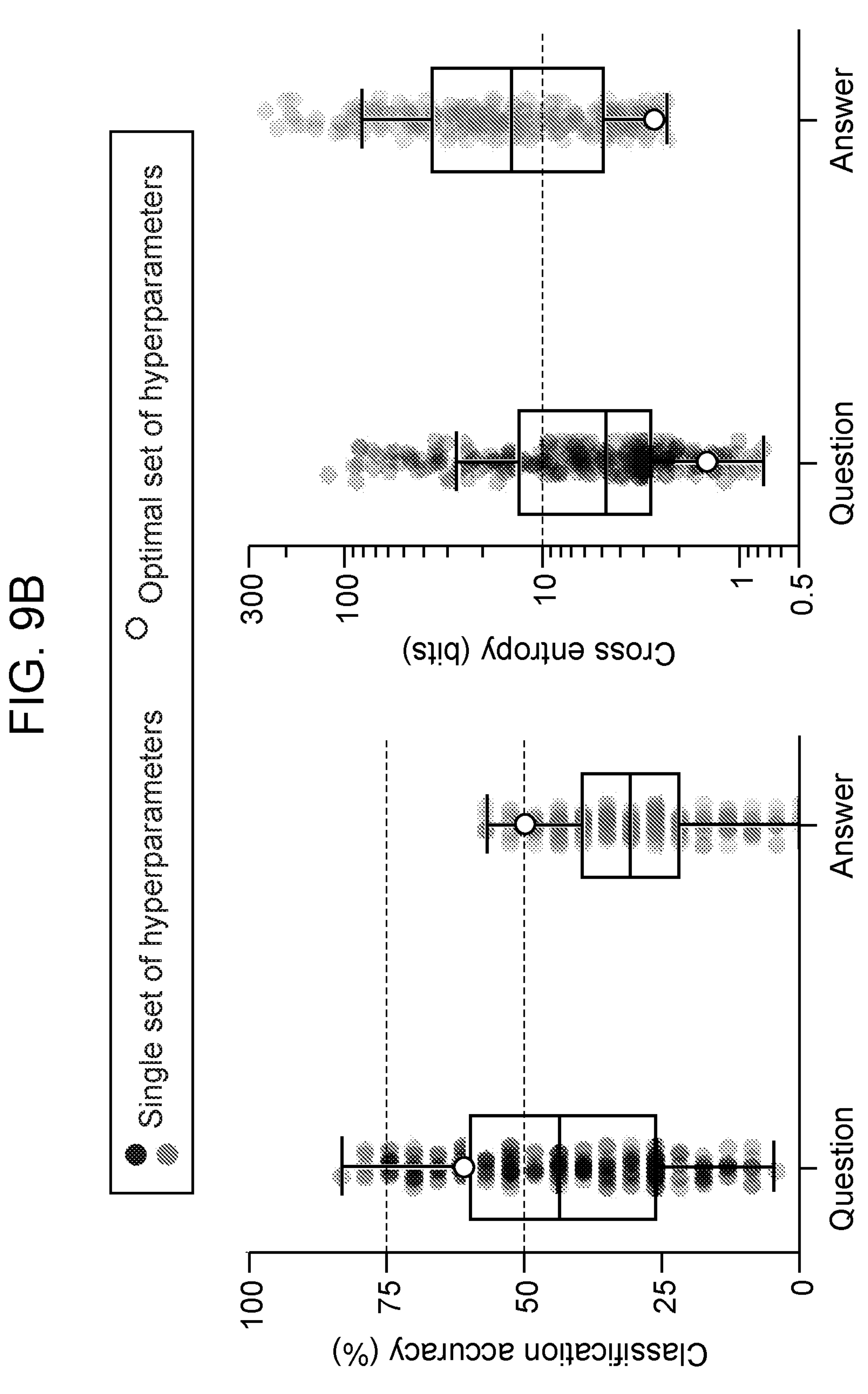
Figure 10A:
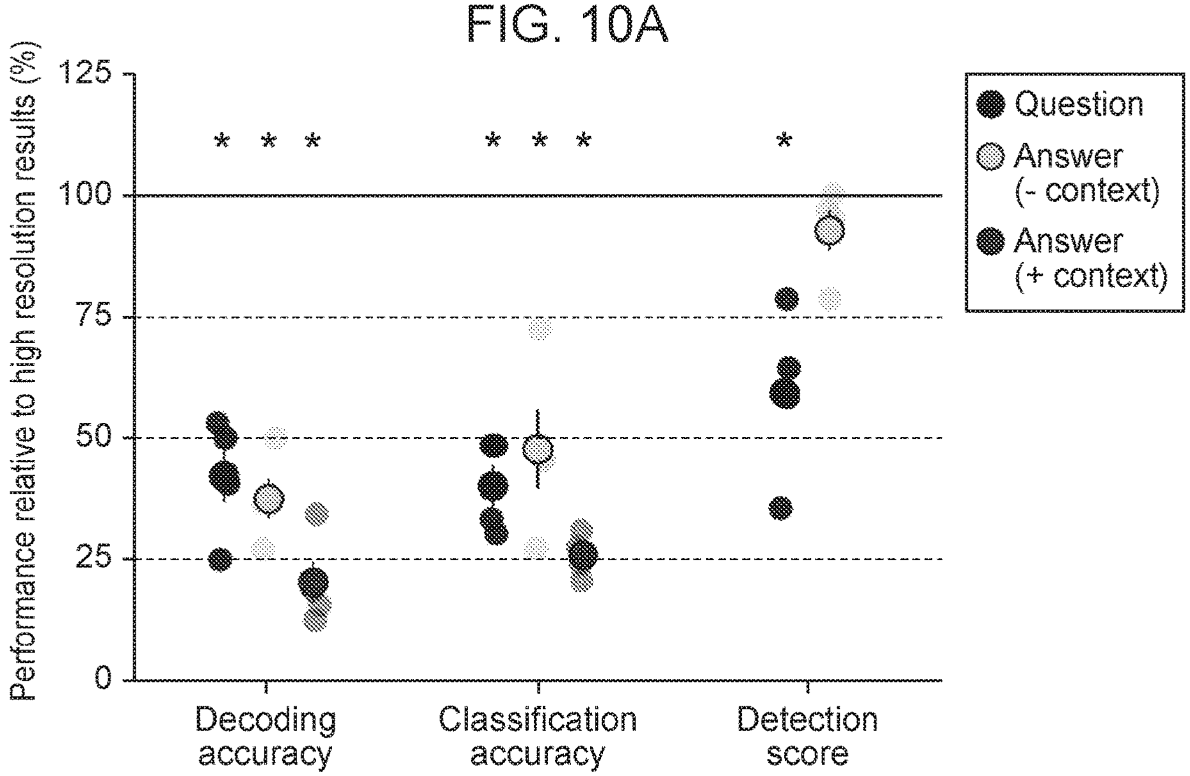
FIGS. 10A-10B: Performance evaluation using simulated low-resolution spatial coverage with participant 1. All values are presented as percents of the corresponding high-resolution result value. Each dark dot (with black outline) depicts the mean performance (with standard error) across the four low-resolution simulation results (shown as light dots with no outline). Except for the answer detection score, performance is significantly worse with the low-resolution signals than with the high-resolution signals (*$P<0:05$).
Figure 10B:
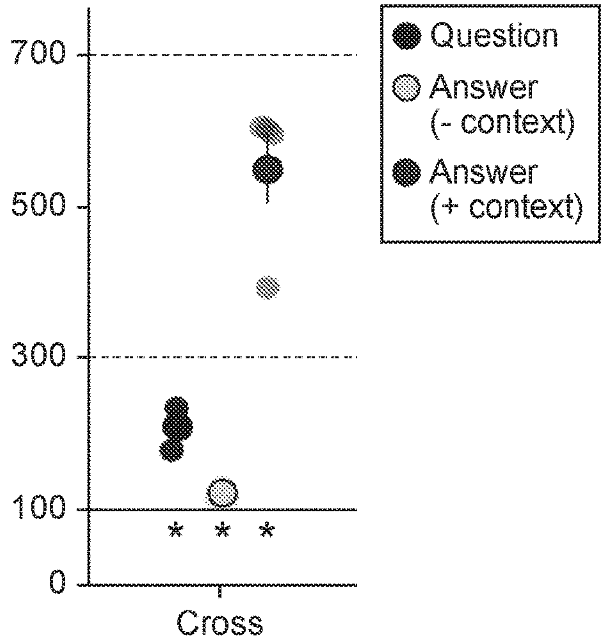

The sensitivity of the decoding models was investigated to limited data availability, sub-optimal hyperparameter configurations, and spatial resolution (FIG. 9A-9B and FIG. 10).

Additional analyses on the Viterbi decoding and phone likelihood modeling approaches used by the answer classifiers (FIG. 11C) was performed. When performing answer classification with hard or true priors instead of soft priors, the question likelihoods in each trial were modified prior to context integration. For hard priors, the likelihood of the most likely question was set to 1 and the likelihoods of the other questions were set to 0. For true priors, the likelihood of the question that was actually presented to the participant was set to 1 and the likelihoods of the other questions were set to 0. After this modification, the context integration procedure was performed normally to obtain the answer predictions.

Statistical Testing

For all tests, P-values less than 0.05 were considered as significant. A 4-way Holm-Bonferroni correction was used for the chance comparisons with the three prediction types (questions, answers without context, and answers with context) and the answer with vs. without context comparison because the neural data used during these analyses were not independent of each other.

Real-Time Decoding

Figure 19:
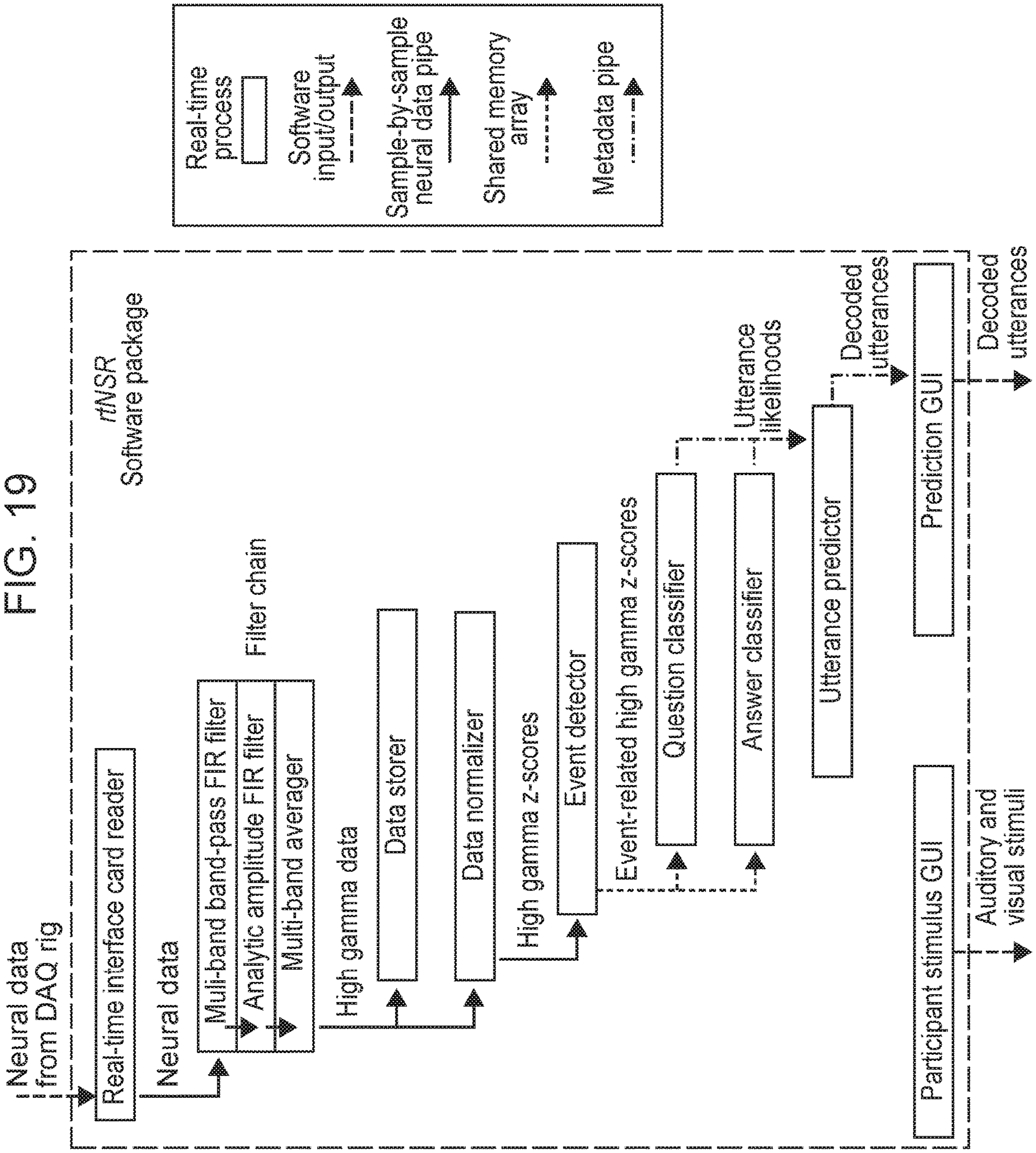
FIG. 19: Schematic depiction of the rtNSR system used during real-time decoding. The solid rectangles represent real-time process classes and arrows represent the passing of information between the processes. The Real-time interface card reader process reads neural data acquired from the DAQ rig and streamed through the real-time interface card (PO8e, Tucker-Davis Technologies). The neural data are processed in a filter chain comprising three processes: the Multi-band band-pass FIR filter process that band-passes the signals for each channel in eight different sub-bands in the high gamma band range (between 70{150 Hz), the Analytic amplitude FIR filter process that extracts the analytic amplitude for each band and each channel, and the Multi-band averager process that averages the analytic amplitude values across the bands for each channel to obtain the desired measure of that channel's high gamma activity. These high gamma signals are written to disk in the data storer process (along with metadata from other processes, not depicted here) and normalized and clipped in the Data normalizer process. The normalized neural data are piped to the Event detector process, which analyzes the data at each time point to predict the onsets and offsets of speech events. When an event is detected, the high gamma z-scores are stored in a shared memory array that can be accessed by either the Question classifier or Answer classifier process to predict the utterance likelihoods associated with that event. The Utterance predictor process uses these likelihoods to update the answer priors and predict which question was heard or which answer was said by the participant. The Prediction GUI process displays the decoded utterances on a screen. Throughout the task, the Participant stimulus GUI process presents the auditory and visual stimuli to the participant.

An rtNSR software package was used. Written in Python, this package is flexible and efficient due to its modular structure and utilization of software pipelining. With further development, rtNSR was used here to present the audio and visual stimuli, process the neural signals, and perform speech decoding in real-time (FIG. 19). It was also used for offline model training and data analysis.

Due to clinical time constraints, hyperparameter optimization was not performed prior to real-time testing with the participants. All of the results reported in this work were computed using offline simulations of the data with the rtNSR system. During the offline simulations, the real-time process that reads samples from the real-time interface card is replaced with a process that simulates input samples from a dataset on disk. The remainder of the decoding pipeline remains the same. During online testing at the patient's bedside, the system performed decoding without experiencing systematic/runtime errors and with negligible latency using hyperparameter values chosen via trial and error on datasets that were previously collected. Therefore, it can be reasonably expected that the decoding results that was observed in the offline simulations would have been identical to those in the online setting with the patients, since the only relevant differences between the online and offline tests were the specific values of the hyperparameters.

Example 3: Decoding Speech from the Human Cortex

The present disclosure shows spoken speech from cortical activity, an enterprise with both scientific and practical implications. Taking a cue from recent advances in machine translation and automatic speech recognition, a recurrent neural network (RNN) was trained to map ECoG signals directly to sentences.

In particular, an encoder-decoder framework was used that first encodes a sequence of neural activity into an abstract sentence representation, and then decodes this representation, word by word, into an English sentence. Each element of the input sequence is a vector, corresponding to a single sample of the envelope of the high-frequency (70-150-Hz) component of the ECoG signal at each of about 250 electrodes distributed over peri-Sylvian speech cortices. Each element of the output sequence is a single word from a small (~200-2000-word) vocabulary, the entire sequence composing the sentence that coincided with the ECoG input sequence. Across a corpus of several hundred such ECoG-sentence pairs, the RNN is trained end-to-end with back-propagation to predict the next word in the sentence, given its current internal state and the previous word. In the evaluation phase, a held-out sequence of ECoG data is fed to the network, which then emits words conditioned on its current internal state and the previous predicted word, until an end-of-sequence token is emitted. For the best subjects, average word error rates across validation sets ~50 sentences) are just 4-8%.

Finally, the present disclosure shows how to use transfer learning to overcome limitations on data availability. In fine, certain components of the network are trained under all subjects' data, while other (e.g., the first hidden layer) are "proprietary." This scheme was shown to improve decoding performance, despite very different electrode coverage across subjects.

Figure 25:
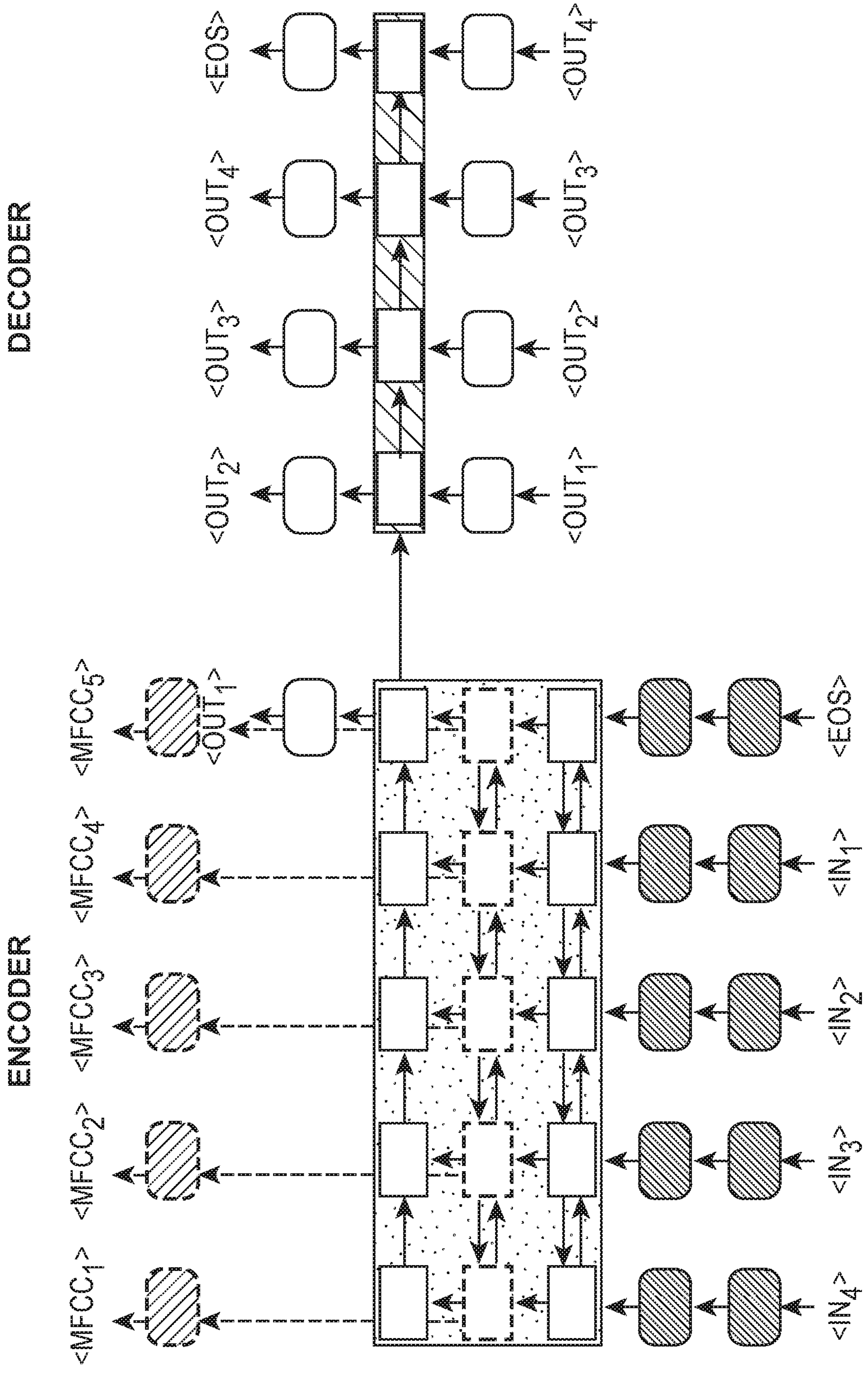
FIG. 25: Encoder-decoder network with encoder targeting. The RNNs are unfolded across time, or more precisely, across sequence elements. In this modification of the encoder-decoder network, the encoder, as well as the decoder, is targeted, in this case, with the mel-frequency cepstral coefficients (MFCCs) that temporally coincide with the input ECoG (high-y) data. Feed-forward layers have rounded corners, recurrent layers have angular corners; temporal-convolution layers are shaded a darker gray. Bidirectional RNNs are indicated with pairs of opposing arrows. Each "unit" in the recurrent layer is an LSTM cell.
Figure 26:
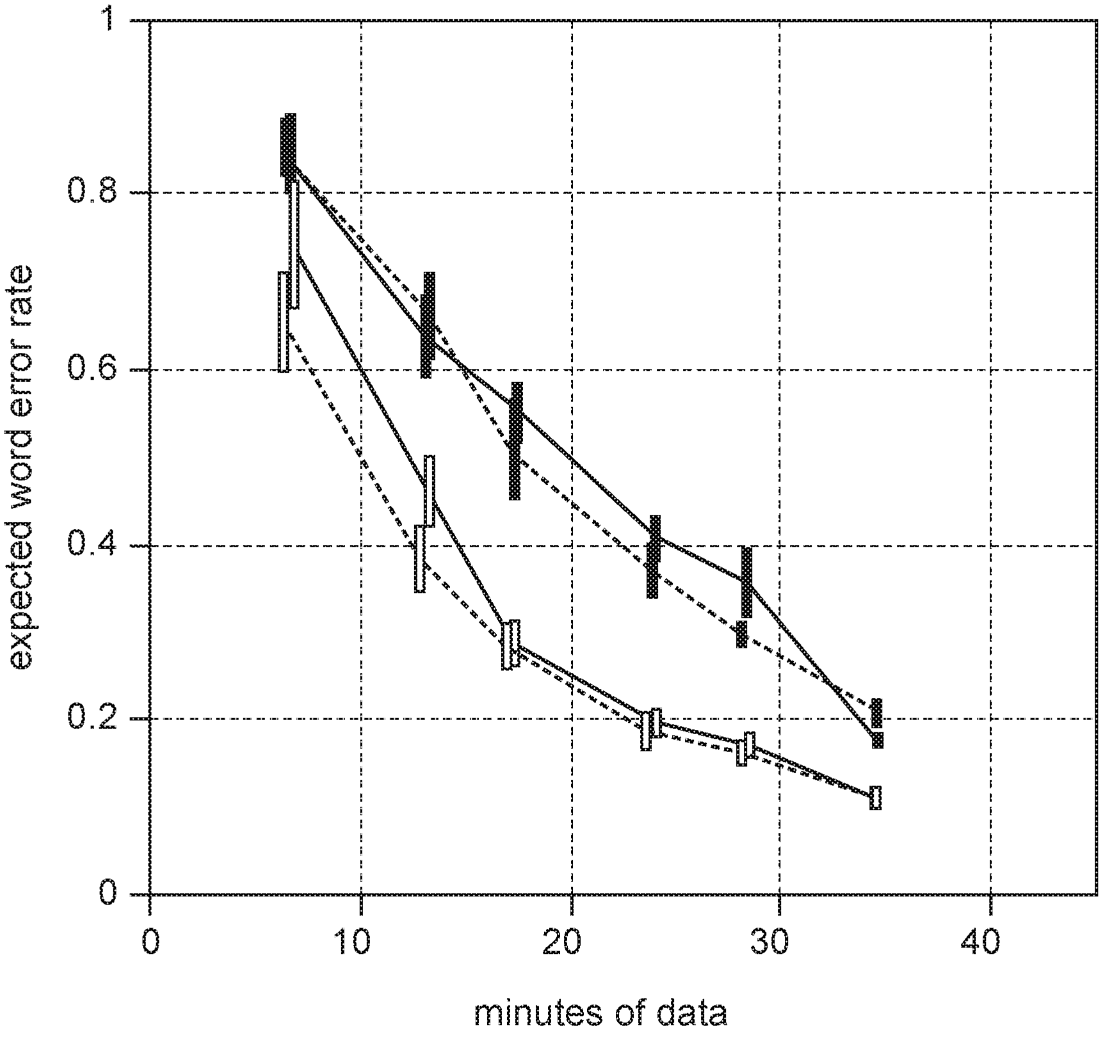
FIG. 26: Word error rate as a function of number of minutes of training data. One participant. Without transfer learning-dashed; without MFCC targeting, green.
Figure 27A:
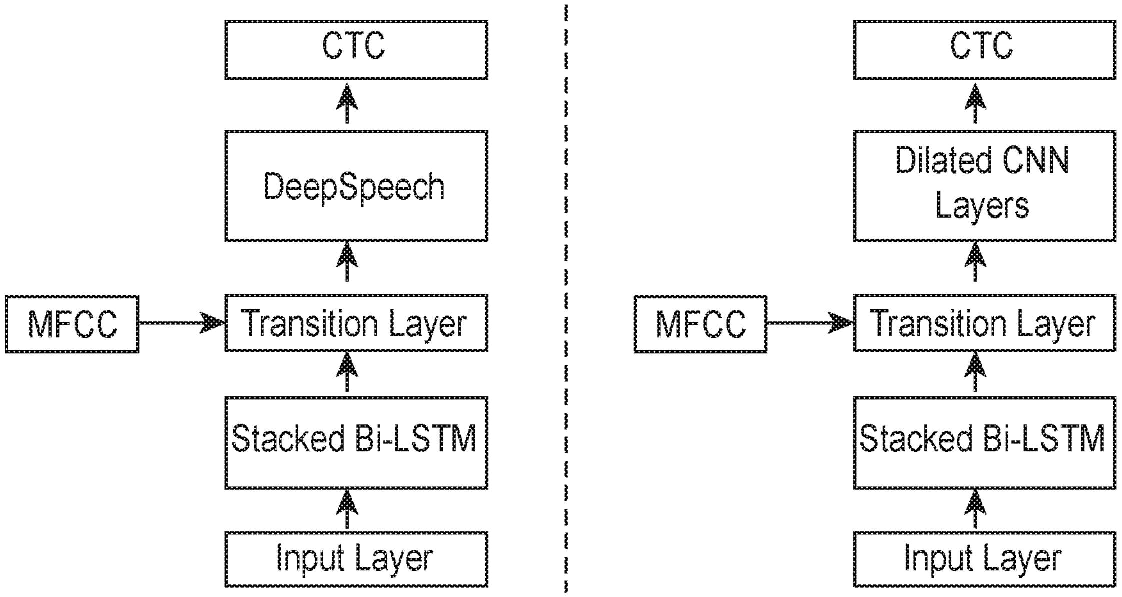
Figure 27B:
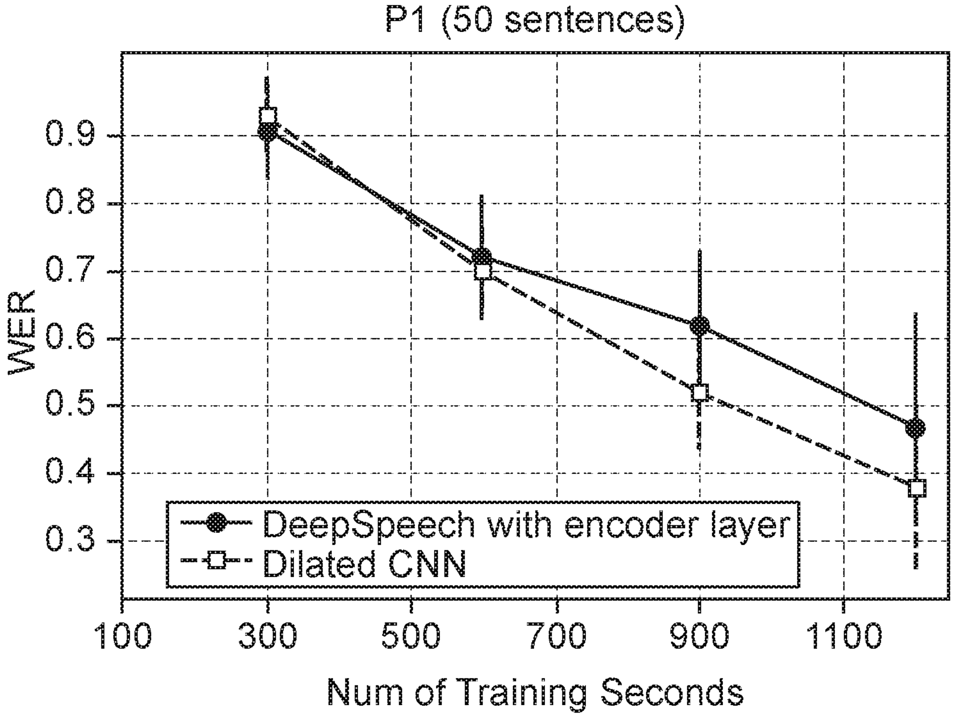
Figure 28:
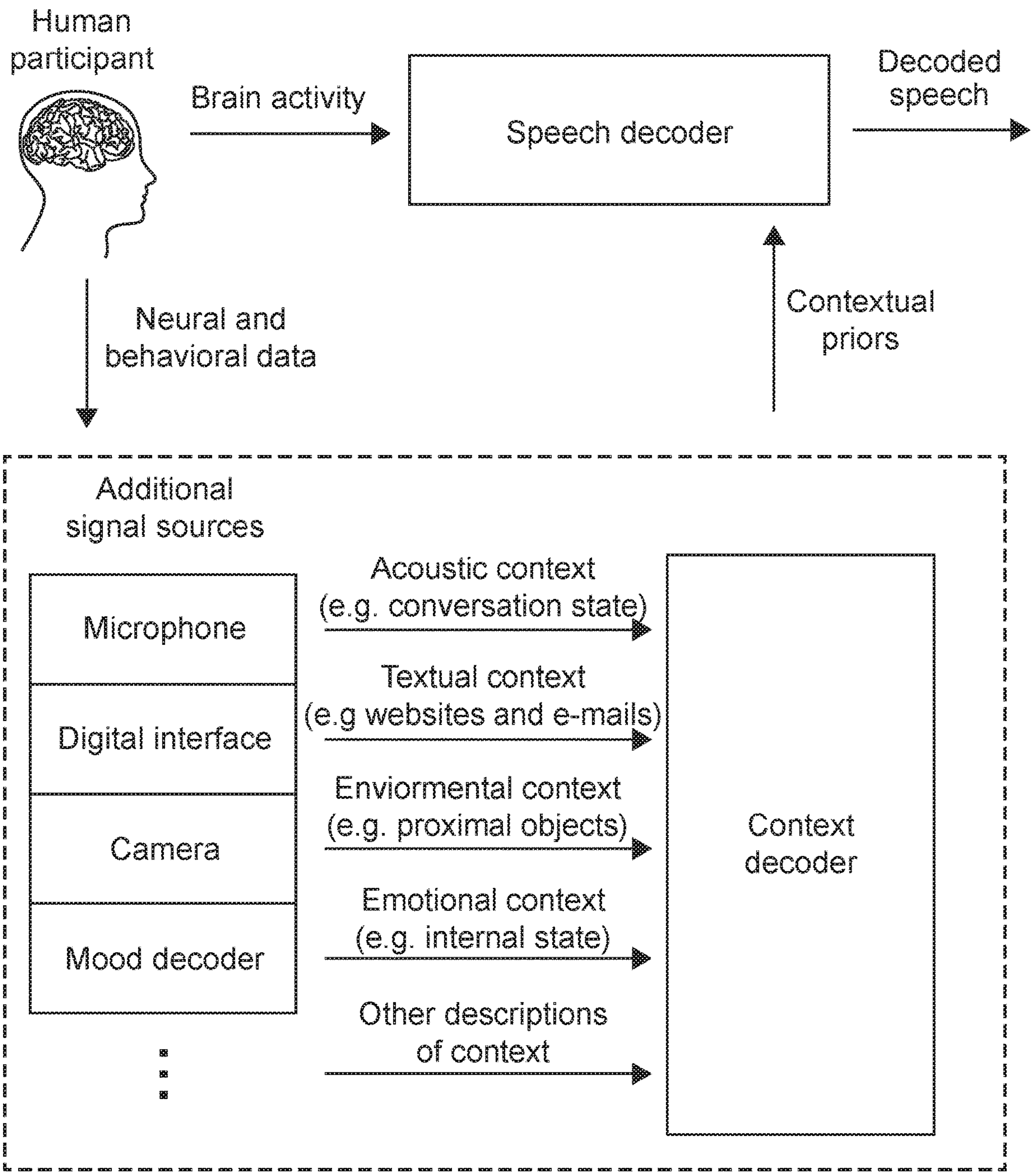
FIG. 28 shows use of context decoding (e.g. context-related events from signals in the brain or alternative signal sources of information such as external context-related events from an external source) in improving speech decoding.

The basic architecture of the encoder-decoder network is described in FIG. 25. The objective function to be minimized is a weighted sum of cross entropies: one (based on a multivariate Gaussian) penalizing the encoder outputs' deviation from the current MFCCs; the other (based on a categorical distribution) penalizing the decoder out-puts in proportion as they fail to assign all their probability to the target (true) word. The objective is minimized with stochastic gradient descent via backpropagation, with dropout applied to all layers.

Input sequences consist of the high-signal sampled at about 100 Hz, each corresponding to a single sentence and therefore variable in length. Before passing into the RNN, they pass through two layers of temporal convolution, with widths and strides of about 4 samples, effectively downsampling the signal. The data sets (two subjects) were created by asking subjects to read one of about 450 sentences (MOCHA-TIMIT), with repeats as time permitted; or alternatively (two subjects), one of about 30 sentences. The same sentence types (but not, obviously, tokens) generally appeared in both the training and validation sets.

Example 4: Decoding Text from Neural Activity During Speaking Using Electrocorticography The goal of this study was to decode spoken text from only from the recorded neural activity during speech production. A 2-stage process was used where regress from neural data to acoustic features that are then decoded to text using an acoustic feature recognizer. Neural data were collected from three human participants (patients with medically refractory epilepsy), implanted with high-density subdural ECoG arrays, as they spoke fluent sentences. For the first stage of neural-to-acoustic feature regression we used stacked multiple neural network layers to reduce the high density input neural signals into the low dimensional acoustic feature manifold. For the second stage of acoustic feature decoder, two candidate models were evaluated: 1) an off-the shelf LSTM based ASR system (Baidu's DeepSpeech), and 2) a dilated CNN system (similar architecture as Wavenet). These text decoding networks are stacked above the front end feature extraction networks (i.e., four layer networks). These effectively end-to-end network structures require least interference on priors. However, considering that the speech associated neural signals have large variance, our intermediate target of acoustic features—Mel-frequency cepstral coefficients (MFCCs) acts as a regularizer. The mean squared error on the latent features (MFCCs here) imposes additional constraints on both feature extraction and projection.

The joint CTC loss and MSE loss in terms of output logits and latent features speed up the convergence of the models while converging on reasonable optima for the end-to-end networks.

Using these tandem models, new state-of-the-art Word Error Rates (WER) were set on neural speech decoding on a constrained vocabulary task. Importantly, the success of these ASR style decoder architectures implies the possibility for future extension to large vocabulary neural speech decoding.

1) Neural Recordings: All neural data was preprocessed to reject artifacts and extract local field potentials bandpassed in the high gamma range (70-150 Hz). Sampling rate of 200 Hz was used both for neural and behavioral data. 2) Model Training: Both learning rate and weight value of MFCC loss are applied decay coefficient, and batch size is 1. For dilated CNN, batch normalization is applied on the outputs of each layer. The reduced features are padded into the same sequence length with MFCC components. In order to achieve robust decoding, this padding is randomly set either at the beginning of the sequence or at the end of the sequence. A n-gram language model incorporated beam search will be applied to the outputs of CTC 3) Language Model: Either 3-gram or 4-gram language models were used which are obtained by using KenLM. LM1: general purpose English language model in deepspeech based on librispeech dataset; LM2: An LM based on 1300 word task vocabulary; LM3: A constrained 150 word vocabulary.

Utility

The subject methods and systems find use in any application in which it is desirable to decode contextual information and perceived and/or produced speech from the brain of a subject (e.g., a human subject). Subjects of interest include those in which the ability to communicate via spoken language is lacking or impaired. Examples of such subjects include, but are not limited to, subjects who may be suffering from paralysis, locked-in syndrome, dystonia, Lou Gehrig's disease, aphasia, dysarthria, stuttering, laryngeal dysfunction/loss, vocal tract dysfunction, tinnitus epilepsy, traumatic brain injury, stroke, Parkinson's disease, OCD, depression, chronic pain, and the like. An example application in which the subject methods and systems find use is providing a speech impaired individual with a speech communication neuroprosthetic system which detects and decodes neural signals correlated to speech and/or patterns thereof from the speech motor cortex of the subject and produces fluent and intelligible speech in text format, enabling the subject to communicate with others without using speech articulators or writing/typing the speech for display to others. The methods and systems of the present disclosure also find use in diagnosing speech motor disorders (e.g., aphasia, dysarthria, stuttering, and the like). In addition, the subject methods and systems find use, e.g., in enabling individuals to communicate via mental telepathy.

In certain aspects, methods and systems of the present disclosure utilize population neural or optical analyses to decode individual speech sounds (phonemes, including consonants and vowels), silent mimes (e.g. kinematic movements without making a sound), and/or contextual information such as hearing sounds, thoughts, language-related features, pain-related features, anxiety-related features, mood-related features, and the like. These speech sounds are the building block units of human speech. Phonemes can be concatenated into syllables, words, phrases and sentences to provide the full combinatorial potential of spoken language. This approach based on the natural neurophysiologic mechanisms of speech production has distinct advantages over present technologies for, e.g., communication neuroprostheses, which either focus on purely acoustic parameter control (e.g. formant) or spelling devices, neither of which are robust or efficient for communication.

In certain aspects, the methods and systems of the present disclosure are capable of decoding spontaneous, natural speech controlled by a patient's volition. For example, perceived or produced speech can be detected and decoded from neural activity in real-time while integrating dynamic information from the surrounding context. Such "dynamic information" can include, but is not limited to, heart-rate, global positioning system (GPS), and the like.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112 (f) or 35 U.S.C. § 112(6) is not invoked.

What is claimed is:

1. A method of decoding events, the method comprising:

receiving, via a neural recording device, a plurality of signals from the brain of an individual;

processing the plurality of signals to detect an event associated with the individual's attempt or act of performing an action;

extracting one or more context-related features from a time window of the plurality of signals from the brain of the individual preceding, during, or following the event using an artificial neural network having two or more layers, wherein the artificial neural network has been trained on context perception data to identify spatiotemporal neural patterns associated with context-related features; and decoding, using the one or more context-related features, the event from the plurality of signals.

2. The method of claim 1, wherein the one or more context-related features comprises anxiety-related features in the individual, language-related features, pain-related features in the individual, the individual's thought, and/or the individuals emotional state.

3. The method of claim 1, wherein decoding the event from the plurality of signals includes decoding a produced or intended speech output.

4. The method of claim 1, wherein the one or more context-related features comprises one or more cues from preceding language in the form of text, dialogue, discourse, exchanges, email, chats, texting, wherein said one or more cues bear information about the context of intended decoded speech.

5. The method of claim 4, wherein the one or more context-related features comprises speech perception while listening to one or more external context-related cues.

6. The method of claim 5, wherein the one or more external context-related cues comprises a sound.

7. The method of claim 6, wherein the sound is selected from the group consisting of: a phoneme, formant acoustics of a vowel, a diphone, a triphone, a consonant-vowel transition, a syllable, a word, a phrase, a sentence, and combinations thereof.

8. The method of claim 1, further comprising determining context likelihoods from the context-related features.

9. The method of claim 8, wherein the one or more external context-related cues comprises reading.

10. The method of claim 8, wherein the one or more external context-related cues comprises responding to audible speech.

11. The method of claim 10, wherein responding to audible speech comprises a verbal response.

12. The method of claim 11, wherein the verbal response is a sound.

13. The method of claim 1, wherein said extracting occurs in real-time or offline.

14. The method of claim 1, wherein the method is carried out using a receiver unit, comprising:

a receiver in communication with the neural recording device; one or more processors; and a non-transient computer-readable medium comprising instructions that, when executed by the one or more processors, cause the one or more processors to:

perform one or more filters on the plurality of signals and/or on the one or more external signals;

decode the event from the plurality of signals.

15. The method of claim 14, wherein the one or more processors comprises a principal component analysis (PCA) model.

16. The method of claim 14, wherein the one or more processors comprises a machine learning algorithm.

17. The method of claim 1, wherein the event is a speech event, the speech event being an attempted or intended production of a speech or textual output.

18. The method of claim 1, further comprising: decoding, from the one or more context-related features, one or more context priors, the decoding the event from the neural signal data including decoding the event using the one or more context priors.

19. The method of claim 18, wherein the context-related features include a perceived question, and the one or more context priors include predetermined answers to the perceived question, the decoding the event from the neural signal data including decoding an answer to the perceived question from the neural signal data.

20. The method of claim 1, wherein the decoding the event from the neural signal data includes decoding the neural signal data using an artificial neural network that is configured to transform the neural signal data into one or more intermediate representations and decode the one or more intermediate representations into one or more words or sentences.

21. The method of claim 20, wherein the artificial neural network uses a recurrent neural network (RNN).

22. The method of claim 1, wherein the processing the plurality of signals to detect an event includes extracting from the plurality of signals high frequency signals and low frequency signals, and the decoding the event from the plurality of signals includes decoding the event using information from the high frequency signals and the low frequency signals.

23. The method of claim 22, wherein the high frequency signal are 70-200 Hz.

24. The method of claim 22, wherein the low frequency signals are 1-30 Hz.

* * * * *